US008383657B2

(12) United States Patent
Faghih et al.

(10) Patent No.: US 8,383,657 B2
(45) Date of Patent: *Feb. 26, 2013

(54) THIAZOLYLIDINE UREA AND AMIDE DERIVATIVES AND METHODS OF USE THEREOF

(75) Inventors: Ramin Faghih, Lake Forest, IL (US); Gregory A. Gfesser, Lindenhurst, IL (US); Kathleen H. Mortell, Chicago, IL (US); Murali Gopalakrishnan, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 244 days.

This patent is subject to a terminal disclaimer.

(21) Appl. No.: 12/338,849

(22) Filed: Dec. 18, 2008

(65) Prior Publication Data

US 2009/0163470 A1   Jun. 25, 2009

Related U.S. Application Data

(60) Provisional application No. 61/015,996, filed on Dec. 21, 2007.

(51) Int. Cl.
*A61K 31/427* (2006.01)
*C07D 277/04* (2006.01)
*C07D 277/12* (2006.01)
(52) U.S. Cl. .................................... 514/370; 548/195
(58) Field of Classification Search .............. 548/195
See application file for complete search history.

(56) References Cited

U.S. PATENT DOCUMENTS

| | | | |
|---|---|---|---|
| 5,244,863 | A | 9/1993 | Kawamura et al. |
| 5,312,798 | A | 5/1994 | Kawamura et al. |
| 5,914,328 | A | 6/1999 | Lin et al. |
| 5,948,793 | A | 9/1999 | Abreo et al. |
| 6,165,943 | A | 12/2000 | Mayer et al. |
| 6,538,003 | B1 | 3/2003 | Galli et al. |
| 6,720,328 | B2 | 4/2004 | Aslanian et al. |
| 6,809,105 | B2 | 10/2004 | Schrimpf et al. |
| 6,833,370 | B1 | 12/2004 | Schrimpf et al. |
| 2003/0149315 | A1 | 8/2003 | Klauck-Jacobs et al. |
| 2005/0065178 | A1 | 3/2005 | Basha et al. |
| 2005/0137184 | A1 | 6/2005 | Ji et al. |
| 2005/0137204 | A1 | 6/2005 | Ji et al. |
| 2005/0171181 | A1 | 8/2005 | Wager et al. |
| 2005/0182045 | A1 | 8/2005 | Nagase et al. |
| 2005/0245531 | A1 | 11/2005 | Ji et al. |
| 2005/0282811 | A1 | 12/2005 | Howard et al. |
| 2007/0066588 | A1 | 3/2007 | Cowart et al. |
| 2007/0184490 | A1 | 8/2007 | Verlinden et al. |
| 2008/0027041 | A1 | 1/2008 | Hudkins et al. |
| 2008/0176925 | A1 | 7/2008 | Butler et al. |
| 2008/0242653 | A1 | 10/2008 | Liu et al. |
| 2009/0221648 | A1 | 9/2009 | Rueter et al. |

FOREIGN PATENT DOCUMENTS

| | | |
|---|---|---|
| EP | 446802 B1 | 6/1995 |
| EP | 0 446 802 | 7/1995 |
| EP | 694523 A1 | 1/1996 |
| EP | 0694523 B1 | 1/1996 |
| EP | 1595881 A1 | 5/2004 |
| EP | 1795527 A1 | 6/2007 |
| JP | 08081449 A | 3/1996 |
| JP | 8081449 A2 | 3/1996 |
| WO | WO9640682 A1 | 12/1996 |
| WO | 98/42703 | 10/1998 |
| WO | WO9842703 A1 | 10/1998 |
| WO | WO9910338 A2 | 3/1999 |
| WO | WO9932480 A1 | 7/1999 |
| WO | WO9965876 A1 | 12/1999 |
| WO | WO0071534 A1 | 11/2000 |
| WO | WO0075110 A1 | 12/2000 |
| WO | 01/10853 | 2/2001 |
| WO | WO0110853 A1 | 2/2001 |
| WO | WO0132619 A1 | 5/2001 |
| WO | WO0132620 A1 | 5/2001 |
| WO | WO0132622 A1 | 5/2001 |
| WO | WO0162736 A1 | 8/2001 |
| WO | WO0206223 A1 | 1/2002 |
| WO | WO0240461 A2 | 5/2002 |
| WO | WO02074758 A2 | 9/2002 |
| WO | WO03059341 A1 | 7/2003 |
| WO | WO2004016608 A1 | 2/2004 |
| WO | WO2004018607 A2 | 3/2004 |
| WO | WO2004022556 A1 | 3/2004 |
| WO | 2004/029053 | 4/2004 |
| WO | WO2004029053 A1 | 4/2004 |
| WO | WO2004043458 A1 | 5/2004 |
| WO | WO2004052894 A1 | 6/2004 |
| WO | WO2004056369 A1 | 7/2004 |
| WO | WO2004085433 A2 | 10/2004 |
| WO | WO2004098600 A1 | 11/2004 |
| WO | WO2005028477 A1 | 3/2005 |
| WO | WO2005066166 A2 | 7/2005 |
| WO | WO2005066167 A2 | 7/2005 |
| WO | WO2005066168 A1 | 7/2005 |
| WO | WO2005077899 A2 | 8/2005 |

(Continued)

OTHER PUBLICATIONS

Document No. 111:57603, CAPLUS retrieved on Jul. 2010.*
Document No. 140:4964, CAPLUS retrieved on Jul. 2010.*
Adler, L. E., et al., "Schizophrenia, Sensory Gating, and Nicotinic Receptors", Schizophrenia Bulletin, 24(2):189-202 (1998).
Albuquerque, E.X., et al., "Modulation of Nicotinic Receptor Activity in the Central Nervous System: A Novel Approach to the treatment of Alzheimer Disease", Alzheimer Dis. & Assoc. Disorders, 15(Suppl. 1):S19-S25 (2001).
Alkondon, M. & Albuquerque, E. X., "The nicotinic acetylcholine receptor subtypes and their function in the hippocampus and cerebral cortex", Prog. in Brain Res., 145:109-120 (2004).

(Continued)

*Primary Examiner* — Shawquia Young
(74) *Attorney, Agent, or Firm* — Lisa V. Mueller; Michael Best & Friedrich LLP

(57) ABSTRACT

The invention relates to novel thiazolylidine urea and amide derivatives that are PAMs of neuronal nicotinic receptors, compositions comprising the same, processes for preparing such compounds, and methods for using such compounds and compositions.

7 Claims, 3 Drawing Sheets

FOREIGN PATENT DOCUMENTS

| | | |
|---|---|---|
| WO | WO2006028239 A1 | 3/2006 |
| WO | WO2006051410 A1 | 5/2006 |
| WO | WO2006132914 A2 | 12/2006 |
| WO | WO2007038074 A1 | 4/2007 |
| WO | WO2007063385 A2 | 6/2007 |
| WO | WO2007084535 A2 | 7/2007 |
| WO | WO2007100990 A2 | 9/2007 |
| WO | WO2008005338 A1 | 1/2008 |
| WO | WO2008058096 A2 | 5/2008 |
| WO | WO2008076685 A2 | 6/2008 |
| WO | WO2008083442 A1 | 7/2008 |
| WO | WO2008137087 A1 | 11/2008 |
| WO | WO2009082698 A1 | 7/2009 |

OTHER PUBLICATIONS

Balbani, A.P.S. & Montovani, J.C., "Recent developments for smoking cessation and treatment of nicotine dependence", Exp. Opin. Ther. Patents, 13(7):289-297 (2003).

Broad, L.M., et al., "Selective alpha7 nicotinic acetylcholine receptor ligands for the treatment of neuropsychiatric diseases", Drugs of the Future, 32(2):161-170 (2007).

Bunnelle, W.H. & Decker, M.W., "Neuronal nicotinic acetylcholine receptor ligands as potential analgesics", Expert Opin. Ther. Patents, 13(7):1003-1021 (2003).

Cordero-Erausquin, M. & Changeux, J-P., "Tonic nicotinic modulation of serotoninergic transmission in the spinal cord", PNAS, 98(5):2803-2807 (2001).

Couturier, S., et al., "A Neuronal Nicotinic Acetylcholine Receptor Subunit (alpha7) Is Developmentally Regulated and forms a Homo-Oligomeric Channel Blocked by alpha-BTX", Neuron, 5:847-856 (1990).

Dajas-Bailador, F. & Wonnacott, S., "Nicotinic acetylcholine receptors and the regulation of neuronal signalling", TRENDS in Pharm. Sci., 25(6):317-324 (2004).

D'Andrea, M.R. & Nagele, R.G., "targeting the Alpha 7 Nicotinic Acetylcholine Receptor to Reduce Amyloid Accumulation in Alzheimer's Disease Pyramidal Neurons", Curr. Pharm. Des., 12:677-684 (2006).

Decker, M.W., et al., "The therapeutic potential of nicotinic acetylcholine receptor agonists for pain control", Expert Opin. Investig. Drugs, 10(10):1819-1830 (2001).

De Luca, V., et al., "Regulation of alpha7-nicotinic receptor subunit and alpha7-like gene expression in the prefrontal cortex of patients with bipolar disorder and schizophrenia", Acta Psychiatr. Scand., 114:211-215 (2006).

Faghih, R., et al., "Advances in the Discovery of Novel Positive Allosteric Modulators of the alpha7 Nicotinic Acetylcholine Receptor", Recent patent on CNS Drug Disc., 2:99-106 (2007).

Friedman, J.I., et al., "A Double Blind Placebo Controlled Trial of Donepezil Adjunctive Treatment to Risperidone for the Cognitive Impairment of Schizophrenia", Biol. Psychiatry, 51:349-357 (2002).

Furnis, B.S., et al., Vogel's Testbook of Practical Organic Chemistry, 5th Ed.:TOC (1989).

Gotti, C. & Clementi, F., "Neuronal nicotinic receptors: from structure to pathology", Prog. in Neurobiol., 74:363-396 (2004).

Gotti, C., et al., "Brain Neuronal Nicotinic Receptors as New Targets for Drug Discovery", Curr. Pharm. Des., 12:407-428 (2006).

Green, T.W. & Wuts, P.G., Protective Groups in Organic Synthesis, 3rd Ed.:TOC (1999).

Gundish, D., "Nicotinic acetylcholine receptor ligands as potential therapeutics", Expert Opin. Ther. Patents, 15 (9):1231-1239 (2005).

Gurwitz, D., "The therapeutic potential of nicotine and nicotinic agonists for weight control", Exp. Opin. Invest. Drugs, 8(6):747-760 (1999).

Hajos, M., et al., "The Selective alpha7 Nicotinic Acetylcholine Receptor Agonist PNU-282987 [N-{(3R)-1-Azabicyclo [2.2.2]oct-3-yl]-4-chlorobenzamide Hydrochloride] Enhances GABAergic Synaptic Activity in Brain Slices and Restores Auditory Gating Deficits in Anesthetized Rats", J. of Pharmacol. & Exp. Ther., 312(3):12-13-1222 (2005).

Hevers, W. & Luddens, H., "The Diversity of GABAA Receptors", Mol. Neurobiol., 18:35-86 (1998).

Higuchi, T. & Stella, V., "Pro-drugs as Novel Drug Delivery Systems", ACS Symposium Series 14, TOC (1987).

Hogg, R.C., et al., "Nicotinic acetylcholine receptors: from structure to brain function", Rev. Physiol. Biochem. Pharmacol., 147:1-46 (2003).

Hunter, B.E., et al, "A novel nicotinic agonist facilitates inductionof long-term potentiation in the rat hippocampus", Neurosci. Ltrs., 168:130-134 (1994).

Hurst, R.S., et al., "A Novem Positive Allosteric Modulator of the alpha7 Neuronal Nicotinic Acetylcholine Receptor: In Vitro and In Vivo Characterization", J. of Neurosci., 25(17):4396-4405 (2005).

IUPAC 1974, "Rules for the Nomenclature of Organic Chemistry—Section E: Stereochemistry", Pure Appl. Chem., 45:13-30 (1976).

Jonnala, R.R. & Buccafusco, J.J., "Relationship Between the Increased Cell Surface alpha7 Nicotinic Receptor Expression and Neuroprotection Induced by Several Nicotinic Receptor Agonists", J. of Neurosci. Res., 66:565-572 (2001).

Keller, J.J., et al., "Performance of alpha7 nicotinic receptor null mutants is impaired in appetitive learning measured in a signaled nose poke task", Behav. Br. Res., 162:143-152 (2005).

Kihara, T., et al., "Alpha7 Nicotinic receptor transduces Signals to Phosphatidylinositol 3-Kinase to Block A beta-Amyloid-induced Neurotoxicity", J. of Biol. Chem., 276(17):13541-13546 (2001).

Korolkovas, A., Essentials of Medicinal Chemistry, 2nd Ed.:92-136 (1988).

Leonard, S., et al., "Smoking and schizophrenia: abnormal nicotinic receptor expression", Eur. J. of Pharm., 393:237-242 (2006).

Levin, E.D., "Nicotinic receptor Subtypes and Cognitive Function", J. of Neurobiol., 53:633-640 (2002).

Liu, Q-s, et al., "Beta-Amyloid peptide blocks the response of alpha7-contianing nicotinic receptors on hippocampal neurons", PNAS, 98(8):4734-4739 (2001).

Martin, L.F., "Alpha-7 nicotinic receptor agonists: potential new candidates for the treatment of schizophrenia", Psychopharmacology, 174:54-64 (2004).

Paterson, D. & Nordberg, A., "Neuronal nicotinic receptors in the human brain", Progress in Neurobiol., 61:75-111 (2000).

Pichat, P., et al., "SSR180711A, a novel selective alpha-7 nicotinic receptor partial agonist III Effects in models predictive of therapeutic activity on cognitive symptoms of schizophrenia", Soc. for Neurosci., Abstract #583.3 (2004).

Romanelli, M.N. & Gualtieri, F., "The quest for the treatment of cognitive impairment: alpha7 nicotinic and alpha5 GABAA receptor modulators", Expert Opin. Ther. Patents, 17(11):1365-1377 (2007).

Rowley, M., et al., "Current and Novem Approaches to the Drug Treatment of Schizophrenia", J. of Medicinal Chem., 44(4):477-501 (2001).

Shimohama, S., "Nicotinic alpha7 receptors protect against glutamate neurotoxicity and neuronal ischemic damage", Br. Res., 779:359-363 (1998).

Stevens, K. E., et al., "Selective alpha7-nicotinic agaonists normalize inhibition of auditory response in DBA mice", Psychopharmacology, 136:320-327 (1998).

Van Kampen M., et al., "AR-R 17779 improves social recognition in rate by activation of nicotinic alpha7 receptors", Psychopharmacology, 172:375-383 (2004).

Vincler, M., "Neuronal nicotinic receptors as targets for novel analgesics", Expert Opin. Investig. Drugs, 14 (10):1191-1198 (2005).

Vincler, M. & Mcintosh, J.M., "Targeting the alpha9alpha10 nicotinic acetylcholine receptor to treat severe pain", Expert Opin. Ther. Targets, 11(7):891-897 (2007).

Wang, H., et al., "Nicotinic acetylcholine receptor alpha7 subunit is an essential regulator of inflammation", Nature, 421:384-388 (2003).

PCT Search Report and Written Opinion mailed Jul. 9, 2009 for PCT/US2008/087774 (9243WOO1).

Adler, et al., "Schizophrenia, Sensory Gating, and Nicotinic Receptors," Schizophrenia Bulletin, 1998, vol. 24 (2), pp. 189-202.

Albuquerque, et al., "Modulation of Nicotinic Receptor Activity in the Central Nervous System: A Novel Approach to the Treatment of Alzheimer Disease," Alzheimer Disease and Associated Disorders, 2001, vol. 15 (1), pp. s19-25.

Alkondon, et al., "The Nicotinic Acetylcholine Receptor Subtypes and Their Function in the Hippocampus and Cerebral Cortex," Progress in Brain Research, 2004, vol. 145, pp. 109-120.

Balbani, et al., "Recent Developments for Smoking Cessation and Treatment of Nicotine Dependence," Expert Opinion on Therapeutic Patents, 2007, vol. 17 (3), pp. 287-297.

Broad, et al., "Selective alpha7 Nicotinic Acetylcholine Receptor Ligands for the Treatment of Neuropsychiatric Diseases," Drugs of the Future, 2007, vol. 32 (2), pp. 161-170.

Bundgaard, "Design of Pro Drugs," 1985, pp. 1-6.

Bunnelle, et al., "Neuronal Nicotinic Acetylcholine Receptor Ligands as Potential Analgesics," Expert Opinion on Therapeutic Patents, 2003, vol. 13 (7), pp. 1003-1021.

Cordero-Erausquin, et al., "Tonic Nicotinic Modulation of Serotoninergic Transmission in the Spinal Cord," Proceedings of the National Academy of Sciences, 2001, vol. 98 (5), pp. 2803-2807.

Couturier, et al., "A Neuronal Nicotinic Acetylcholine Receptor Subunit (alpha7) Is Developmentally Regulated and Forms a Homo-Oligomeric Channel Blocked by Alpha-BTX," Neuron, 1990, vol. 5 (6), pp. 847-856.

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Dajas-Bailsdor, et al., "Nicotinic Acetylcholine Receptors and the Regulation of Neuronal Signaling," Trends in Pharmacological Sciences, 2004, vol. 25 (6), pp. 317-324.

D'Andrea, et al., "Targeting the Alpha 7 Nicotinic Acetylcholine Receptor to Reduce Amyloid Accumulation in Alzheimer's Disease Pyramidal Neurons," Current Pharmaceutical Design, 2006, vol. 12 (6), pp. 677-684.

De, et al., "Unraveling Alzheimer's Disease," The FASEB Journal, 2010, vol. 22, pp. 246-260.

Deluca, et al., "Regulation of Alpha7-Nicotinic Receptor Subunit and Alpha7—Like Gene Expression in the Prefrontal Cortex of Patients with Bipolar Disorder and Schizophrenia," Acta Psychiatrica Scandinavia, 2006, vol. 114 (3), pp. 211-215.

Decker, et al., "The Therapeutic Potential of Nicotinic Acetylcholine Receptor Agonists for Pain Control," Expert Opinion on Investigational Drugs, 2001, vol. 10 (10), pp. 1819-1830.

Faghih, et al., "Advances in the Discovery of Novel Positive Allosteric Modulators of the Alpha7 Nicotinic Acetylcholine Receptor," Recent Patent on CNS Drug Disc, 2007, vol. 2 (2), pp. 99-106.

Fox, et al., "Effects of Histamine H3 Receptor Ligands GT2331 and Ciproxifan in a Repeated Acquisition Response in the Spontaneously Hypertensive Rat Pup," Behavioural Brain Research, 2002, vol. 131 (1-2), pp. 151-161.

Fox, et al., "Pharmacological Properties of ABT-239 [4-(2-{2-[(2R)-2-Methylpyrrolidinty]ethyl}- benzofuran-5-yl)benzonitrile]- : II Neurophysiological Characterization and Broad Preclinical Efficacy in Cognition and Schizophrenia of a Potent and Selective Histamine H3 R," Journal of Pharmacology and Experimental Therapeutics, 2005, vol. 313 (1), pp. 176-190.

Friedman, et al., "A Double Blind Placebo Controlled Trial of Donepezil Adjunctive Treatment to Risperidone for the Cognitive Impairment of Schizophrenia," Biological Psychiatry, 2002, vol. 51, pp. 349-357.

Furniss, et al., Vogel's Textbook of Practical Organic Chemistry, 5th Edition, Longman Scientific & Technical, 1989, Table of Contents.

Gottic, et al., "Brain Neuronal Nicotinic Receptors as New Targets for Drug Discovery," Current Pharmaceutical Design, 2006, vol. 12 (4), pp. 407-428.

Gottic, et al., "Neuronal Nicotinic Receptors: from Structure to Pathology," Progress in Neurobiology, 2004, vol. 74 (6), pp. 363-396.

Greene, et al., "Protection for the Amino group," Protective Groups in Organic Synthesis, 1999, Third Edition, pp. 494-653.

Gundish, "Nicotinic Acetylcholine Receptor Ligands as Potential Therapeutics," Expert Opinion on Therapeutic Patents, 2005, vol. 15 (9), pp. 1221-1239.

Gurwitz, "The Therapeutic Potential of Nicotine and Nicotinic Agonists for Weight Control," Expert Opinion on Investigational Drugs, 1999, vol. 8 (6), pp. 747-760.

Hajos M, et al., "The Selective Alpha7 Nicotinic Acetylcholine Receptor Agonist PNU- 282987 [N-{(3R)-1-Azabicyclo }2.2.2) oct-3-yl)-4-Chlorobenzamide Hydrochloride) Enhances GABAergic Synaptic Activity in Brain Slices and Restores Auditory Gating Deficits in Anesthetized," Journal of Pharmacology and Experimental Therapeutics, 2005, vol. 312 (3), pp. 1213-1222.

Hevers, et al., "The Diversity of GABA, Receptors. Pharmacological and Electrophysiological Properties of GABAA Channel Subtypes," Molecular Neurobiology, 1998, vol. 18 (1), pp. 35-86.

Higuchi, et al., eds., Pro-drugs as Novels Delivery Systems, vol. 14, ACS Symposium Series, 1975, Table of Contents.

Hogg, et al., "Nicotinic Acetylcholine Receptors: From Structure to Brain Function," Reviews of Physiology, Biochemistry and Pharmacology, 2003, vol. 147, pp. 1-46.

Hunter, et al., "A Novel Nicotinic Against Facilitates Induction of Long-Term Potentiation in the Rat Hippocampus," Neuroscience Letters, 1994, vol. 168 (1-2), pp. 130-134.

Hurst, et al., "A Novel Positive Allosteric Modulator of the Alpha7 Neuronal Nicotinic Acetylcholine Receptor: in vitro and in vivo Characterization," Journal of Neuroscience, 2005, vol. 25 (17), pp. 4396-4405.

International Search Report and Written Opinion for PCT/US2008/087774, mailed 13 Jul. 2009, 10 pages.

International Search Report for Application No. PCT/US2008/087729, mailed on Feb. 25, 2009, 3 pages.

Jonnala, et al., "Relationship between the Increased Cell Surface .alpha.7 nicotinic Receptor Expression and Neuroprotection Induced by Several Nicotinic Receptor Agonists," Journal of Neuroscience Research, 2001, vol. 66 (4), pp. 565-572.

Keller, et al., "Performance of Alpha7 Nicotinic Receptor Null Mutants is Impaired in Appetitive Learning Measured in a Signaled Nose Poke Task," Behavioural Brain Research, 2005, vol. 162 (1), pp. 143-152.

Kihara, et al., "Alpha.7 Nicotinic Receptor Transduces Signals to Phosphatidylinositol 3- kinase to Block A .beta.-amyloid-induced Neurotoxicity," Journal of Biological Chemistry, 2001, vol. 276 (17), pp. 13541-13546.

Kirk-Othmer., Encyclopedia of Chemical Technology, 3rd Edition, Third Edition, John Wiley & Sons, 1984, Table of Contents.

Korolkovas, "Development of Drugs" in: Essentials of Medicinal Chemistry, Second Edition, John Wiley and Sons, 1988, pp. 97-118.

Leonard, et al., "Smoking and Schizophrenia: Abnormal Nicotinic Receptor Expression," European Journal of Pharmacology, 2000, vol. 393 (1-3), pp. 237-242.

Levin, "Nicotinic Receptor Subtypes and Cognitive Function," Journal of Neurobiology, 2002, vol. 53 (4), pp. 633-640.

Liu, et al., "Alpha-Amyloid Peptide Blocks the Response of Alpha. 7—Containing Nicotinic Receptors on Hippocampal Neurons," Proceedings of the National Academy of Sciences, 2001, vol. 98 (8), pp. 4734-4739.

March, "Reactions, Mechanisms, and Structure", in: Advanced Organic Chemistry, 3rd Edition, John Wiley & Sons, Inc, 1985, Table of Contents.

Martin, et al., "Alpha-7 Nicotinic Receptor Agaonists Potential New Candidates for the Treatment of Schizophrenia," Psychopharmacology, 2004, vol. 174 (1), pp. 54-64.

Paterson, et al., "Neuronal Nicotinic Receptors in the Human Brain," Progress in Neurobiology, 2000, vol. 61 (1), pp. 75-111.

Pichat, et al., "SSR180711A, A Novel Selective Alpha-7 Nicotinic Receptor Partial Agonist III Effects in Models Predictive of Therapeutic Activity on Cognitive Symptoms of Schizophrenia," Society for Neuroscience, 2004.

Reeves, et al., "Pharmacological Management of Attention-Deficit Hyperactivity Disorder," Expert Opinion on Pharmacotherapy, 2004, vol. 5 (6), pp. 1313-1320.

Rezvani, et al., "Effect of R3487/MEM3454, a Novel Nicotinic a7 Receptor Partial Agonist and 5-HT3 Antagonist on Sustained Attention in Rats," Progress in Neuro-Psychopharmacology & Biological Psychiatry, 2009, vol. 33 (2), pp. 269-275.

Romanelli, et al., "The Quest for the Treatment of Cognitive Impairment: Alpha7 Nicotinic and Alpha5 GABAA Receptor Modulators," Expert Opinion on Therapeutic Patents, 2007, vol. 17 (11), pp. 1365-1377.

Rowley, et al., "Current and Novel Approaches to The Drug Treatment of Schizophrenia," Journal of Medicinal Chemistry, 2001, vol. 44 (4), pp. 477-501.

Shimohama, et al., "Nicotinic Alpha 7 Receptors Protect Against Glutamate Neurotoxicity and Neuronal Ischemic Damage," Brain Research, 1998, vol. 779 (1-2), pp. 359-363.

Stevens, et al., "Selective A7-Nicotinic Agonists Normalize Inhibition of Auditory Response in Dba Mice," Psychopharmacology, 1998, vol. 136 (4), pp. 320-327.

Tietje, et al., "Preclinical Characterization of A-582941: A Novel alpha7 Neuronal Nicotinic Receptor Agonist with Broad Spectrum Cognition-Enhancing Properties,"CNS Neuroscience and Therapeutics, 2008, vol. 14 (1), pp. 65-82.

U.S. Office Action for U.S. Appl. No. 12/338,865 mailed Apr. 4, 2011.

Van Kampen, et al., "Ar-R 17779 Improves Social Recognition in Rate by Activation of Nicotinic Alpha7 Receptors," Psychopharmacology, 2004, vol. 172 (4), pp. 375-383.

Vincler, et al., "Targeting the Alpha9alpha10 Nicotinic Acetylcholine Receptor to Treat Severe Pain," Expert Opinion on Therapeutic Targets, 2007, vol. 11 (7), pp. 891-897.

Vincler, "Neuronal Nicotinic Receptors As Targets for Novel Analgesics," Expert Opinion on Investigational Drugs, 2005, vol. 14 (10), pp. 1191-1198.

Wang, et al., "Nicotinic Acetylcholine Receptor Alpha7 Subunit is an Essential Regulator of Inflammation," Nature, 2003, vol. 421 (6921), pp. 384-388.

\* cited by examiner

THIAZOLYLIDINE UREA AND AMIDE DERIVATIVES AND METHODS OF USE THEREOF

This application claims priority to U.S. Provisional Application Ser. No. 61/015,996, filed Dec. 21, 2007, which is incorporated herein by reference.

TECHNICAL FIELD

The invention relates to novel thiazolylidine urea and amide derivatives that are positive allosteric modulators of neuronal nicotinic receptors, compositions comprising the same, processes for preparing such compounds, and methods for using such compounds and compositions.

DESCRIPTION OF RELATED TECHNOLOGY

Nicotinic acetylcholine receptors (nAChRs) belong to the super family of ligand gated ionic channels (LGIC), and gate the flow of cations, controlled by acetylcholine (ACh). The nAChRs can be divided into nicotinic receptors of the muscular junction (NMJ) and neuronal nAChRs or neuronal nicotinic receptors (NNRs). The NNRs are widely distributed throughout the central nervous system (CNS) and the peripheral nervous system (PNS). The NNRs are understood to play an important role in regulating CNS function and the release of many neurotransmitters, for example, ACh, norepinephrine, dopamine, serotonin, and GABA, among others, resulting in a wide range of physiological effects.

Sixteen subunits of nAChRs have been reported to date, which are identified as $\alpha 2$-$\alpha 10$, $\beta 1$-$\beta 4$, $\gamma$, $\delta$, and $\epsilon$. Of these subunits, nine subunits, $\alpha 2$ through $\alpha 7$ and $\beta 2$ through $\beta 4$, prominently exist in the mammalian brain. Multiple functionally distinct nAChR complexes also exist, for example five $\alpha 7$ subunits can form a receptor as a homomeric functional pentamer or combinations of different subunits can complex together as in case of $\alpha 4\beta 2$ and $\alpha 3\beta 4$ receptors (see for example, Vincler, M., et al., *Exp. Opin. Ther. Targets*, 2007, 11 (7): 891-897; Paterson, D., et al., *Prog. Neurobiol.* 2000, 61: 75-111; Hogg, R. C., et al., *Rev. Physiol., Biochem. Pharmacol.*, 2003, 147: 1-46; Gotti, C., et al., *Prog. Neurobiol.*, 2004, 74: 363-396).

The homomeric $\alpha 7$ receptor is one of the most abundant nicotinic receptors, along with $\alpha 4\beta 2$ receptors, in the human brain, wherein it is heavily expressed in the hippocampus, cortex, thalamic nuclei, ventral tegmental area and substantia nigra (see for example, Broad, L. M., et al., *Drugs of the Future*, 2007, 32(2): 161-170).

The role of $\alpha 7$ NNR in neuronal signaling in the CNS also has been actively investigated (see for example, Couturier, S., et al., *Neuron*, 1990, 5: 847-56). The $\alpha 7$ NNRs have been demonstrated to regulate interneuron excitability, modulate the release of excitatory and inhibitory neurotransmitters, and lead to neuroprotective effects in experimental in vitro models of cellular damage (see for example, Alkondon, M., et al., *Prog. Brain Res.*, 2004, 145: 109-20).

Biophysical studies have shown that $\alpha 7$ subunits, when expressed in heterologous expression systems, activate and desensitize rapidly, and furthermore, exhibit relatively higher calcium permeability compared to other NNR combinations (see for example, Dajas-Bailador, et al., *Trends Pharmacol. Sci.*, 2004, 25: 317-24).

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain and tobacco dependence (see for example, Keller, J. J., et al., *Behav. Brain Res.*, 2005, 162: 143-52; Gundish, D., *Expert Opin. Ther. Patents*, 2005, 15 (9): 1221-1239; De Luca, V., et al., *Acta Psychiatr. Scand.*, 2006, 114: 211-5).

More particularly, the $\alpha 7$ NNRs have been linked to conditions and disorders related to attention deficit disorder, ADHD, AD, mild cognitive impairment (MCI), senile dementia, dementia associated with Lewy bodies, dementia associated with Down's syndrome, AIDS dementia, Pick's disease, as well as cognitive deficits associated with schizophrenia (see for example, Martin, L. F., et al., *Psychopharmacology* (Berl), 2004, 174: 54-64; Romanelli, M. N., et al., *Exp. Opin. Ther. Patents*, 2007, 17 (11): 1365-1377). The $\alpha 7$ NNRs have also been reported to slow disease progression in Alzheimer's disease (D'Andrea, M. R., et al., *Curr. Pharm. Des.*, 2006, 12: 677-84).

Accordingly, modulating the activity of $\alpha 7$ NNRs demonstrates promising potential to prevent or treat a variety of diseases indicated above, such as AD, other dementias, schizophrenia and neurodegeneration, with an underlying pathology that involves cognitive function including, for example, aspects of learning, memory, and attention (see for example, Gotti, C., et al., *Curr. Pharm. Des*, 2006, 12: 407-428).

The NNR ligands have been also implicated in smoking cessation, weight control and as potential analgesics (see for example, Balbani, A. P. S., et al., *Exp. Opin. Ther. Patents*, 2003, 13 (7): 287-297; Gurwitz, D., *Exp. Opin. Invest. Drugs*, 1999, 8(6): 747-760; Vincler, M., *Exp. Opin. Invest. Drugs*, 2005, 14 (10): 1191-1198; Bunnelle, W. H., et al., *Exp. Opin. Ther. Patents*, 2003, 13 (7): 1003-1021; Decker, M. W., et al., *Exp. Opin. Invest. Drugs*, 2001, 10 (10): 1819-1830; Vincler, M., et al., *Exp. Opin. Ther. Targets*, 2007, 11 (7): 891-897).

Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems. Accordingly, there is a need to identify subtype-selective compounds that embrace the beneficial effects of nicotine, or an NNR ligand, while eliminating or decreasing adverse effects.

Examples of reported NNR ligands are $\alpha 7$ NNR agonists, such as PNU-282987 (see for example, Hajos, M., et al., *J. Pharmacol. Exp. Ther*, 2005, 312: 1213-22). Another compound is SSR180711A (Pichat, P., et al., (2004) SSR180711A, Society for Neuroscience Abstract number 583.3).

Another compound, AR-R17779, has been reported to improve performance of rats in social recognition, water maze, or inhibitory avoidance models of cognitive domains (Van Kampen, M., et al., *Psychopharmacology* (Berl) 2004, 172: 375-83). AR-R17779 also reportedly facilitates the induction of hippocampal long term potentiation (LTP) in a proposed cellular model for learning and memory in rats (Hunter, B. E., et al., *Neurosci. Lett.*, 1994, 168: 130-4).

Despite the beneficial effects of NNR ligands, it remains uncertain whether chronic treatment with agonists affecting NNRs may provide suboptimal benefit due to sustained activation and desensitization of the NNR. In contrast to agonists, administering a positive allosteric modulator (PAM) can reinforce endogenous cholinergic transmission without directly stimulating the target receptor (see for example, Albuquerque, E. X., et al., *Alzheimer Dis. Assoc. Disord.* 2001, 15 Suppl 1: S19-25). Nicotinic PAMs could selectively modulate the activity of ACh at α7 NNRs. Accordingly, more recently, α7 NNR-selective PAMs have emerged (see for example, Faghih, R., et al., *Recent Patents on CNS Drug Discovery*, 2007, 2 (2): 99-106).

Consequently, it would be beneficial to target α7 NNR function by enhancing effects of the endogenous neurotransmitter acetylcholine via PAMs that can reinforce the endogenous cholinergic neurotransmission without directly activating α7 NNRs, like agonists. Indeed, PAMs for enhancing channel activity have been proven clinically successful for $GABA_A$ receptors where benzodiazepines, barbiturates, and neurosteroids behave as PAMs acting at distinct sites (see for example, Hevers, W., et al., *Mol. Neurobiol.*, 1998, 18: 35-86).

To date, only a few NNR PAMs are known, such as 5-hydroxyindole (5-HI), ivermectin, galantamine, bovine serum albumin, and SLURP-1, a peptide derived from acetylcholinesterase (AChE). Recently, genistein, a kinase inhibitor was reported to increase α7 responses, and PNU-120596, a urea derivative, was reported to increase the potency and maximal efficacy of ACh as well as improve auditory gating deficits induced by amphetamine in rats. Other NNR PAMs include derivatives of quinuclidine, indole, benzopyrazole, thiazole, and benzoisothiazoles (see for example, Hurst, R. S., et al., *J. Neurosci.*, 2005, 25: 4396-4405; Broad, L. M., et al., *Drugs of the Future*, 2007, 32(2):161-170; U.S. Pat. No. 7,160,876).

However, NNR PAMs presently known generally demonstrate weak activity, have a range of non-specific effects, or can only achieve limited access to the central nervous system where α7 NNRs are abundantly expressed. In addition, known iminothiazoline compounds exhibit herbicidal activity (see for example, U.S. Pat. No. 5,312,798; U.S. Pat. No. 5,244,863; U.S. Pat. No. 6,165,943; WO 01/10853; WO 98/42703; EP 0446802), but not reported to show NNR PAM activity.

Accordingly, it would be beneficial to identify and provide new PAM compounds of NNRs and compositions for treating or preventing conditions associated with α7 NNRs. It would further be particularly beneficial if such compounds can provide improved efficacy of treatment while reducing adverse effects associated with compounds targeting neuronal nicotinic receptors by selectively modulating α7 NNRs.

Consequently, the present invention discloses novel thiazolylidine urea and amide derivatives that are PAMs of NNRs, and compositions, methods of preparation and uses thereof.

SUMMARY OF THE INVENTION

One embodiment relates to compounds of formula (I),

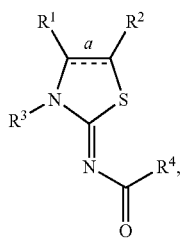

wherein
$R^1$ is hydrogen, methyl, phenyl, pyrazolyl, or hydroxyl;
$R^2$ is hydrogen, alkyl, alkenyl, =$CH_2$, or =$CHR^c$ wherein the alkyl group and the alkenyl group are substituted with 0, 1, 2, or 3 substituents independently selected from the group consisting of alkoxycarbonyl, alkylcarbonyloxy, aryl, aryloxy, arylalkoxy, carboxy, cyano, cycloalkyl, haloalkoxy, heteroaryl, heterocycle, hydroxyl, nitro, and $R^dR^eN$—, wherein a group represented by $R^2$ can be further substituted with 0, 1, or 2 groups selected from halo and alkoxy;
$R^c$ is alkyl or halo;
$R^d$ and $R^e$ are each independently hydrogen, alkyl, alkoxyalkyl, aryl, arylalkyl, cyanoalkyl, heteroaryl, heteroarylalkyl, heterocycle, or heterocyclealkyl;
$R^3$ is optionally substituted aryl, heteroaryl, or -$G^1$-L-$G^2$;
$G^1$ is aryl or heteroaryl;
$G^2$ is aryl, cycloalkyl, heteroaryl, or heterocycle;
L is a bond, O, alkylene, or —O-alkylene-;
$R^4$ is optionally substituted alkyl, cycloalkyl, heteroaryl, heterocycle or —$NR^5R^6$; wherein, $R^5$ and $R^6$ are independently hydrogen, alkyl, (NRiRj)alkyl, alkynyl, aryl, heterocyclealkyl, cycloalkylalkyl, cyanoalkyl, cycloalkyl, alkoxyalkyl, arylalkyl, or heteroarylalkyl; and
a is single or double bond;
provided that when $R^1$ is hydroxyl or when $R^2$ is a radical attached to the thiazole ring through an exocyclic double bond, then a is single bond; and provided that when a is double bond, $R^1$ is hydrogen, $R^2$ is methyl, $R^3$ is phenyl substituted with 3-haloalkyl, 3-halo, 3-haloalkoxy, 2,5-dihalo, 2,3-dihalo, 3,4-dihalo, or 3,5-dihalo, then $R^4$ is heterocycle;
or a pharmaceutically acceptable salt, ester, amide or prodrug thereof.

Another embodiment relates to a method of using compounds of formula (I).

Another embodiment relates to a process for making compounds of formula (I) from an N-1,3-thiazol-2-ylamide of formula (II),

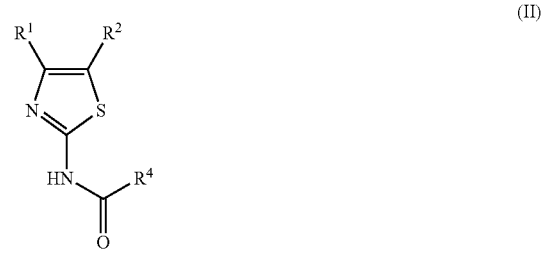

wherein $R^1$ and $R^4$ are as defined above in formula (I) and $R^2$ is hydrogen, alkyl and alkenyl, wherein the alkyl group and the alkenyl group are substituted with 0, 1, 2, or 3 substituents independently selected from the group consisting of alkoxycarbonyl, alkylcarbonyloxy, aryl, aryloxy, arylalkoxy, carboxy, cyano, cycloalkyl, haloalkoxy, heteroaryl, heterocycle, hydroxyl, nitro, and $R^dR^eN$—, wherein a group represented by $R^2$ can be further substituted with 0, 1, or 2 groups selected from halo and alkoxy.

Another embodiment is directed to a method of treating conditions and disorders that are regulated by the NNRs using compounds of formula (I) or therapeutically effective compositions of compounds of formula (I).

Another embodiment is directed to a method of treating a disorder or condition that is modulated by α7 nicotinic acetylcholine receptors in a patient in need of such treatment, comprising administering a therapeutically effective amount of a compound of formula (I).

Another embodiment relates to a method of assessing or diagnosing conditions or disorders related to α7 NNR activity comprising allowing isotope-labeled forms of compounds of formula (I) to interact with cells expressing endogenous α7 NNRs or cells expressing recombinant α7 NNRs and measuring the effects of such isotope-labeled forms of compounds on such cells.

Various aspects also describe the use of NNR ligands, and particularly PAM compounds, to identify other useful target compounds for treating or preventing, or both, diseases or conditions associated with NNR function, in cell-based assays, for example in high-throughput format, using cells or tissues that express native α7 NNR receptors for the purpose of identifying novel α7 NNR agonists or PAMs of α7 NNR.

DETAILED DESCRIPTION OF THE INVENTION

Definition of Terms

Figure 1A:
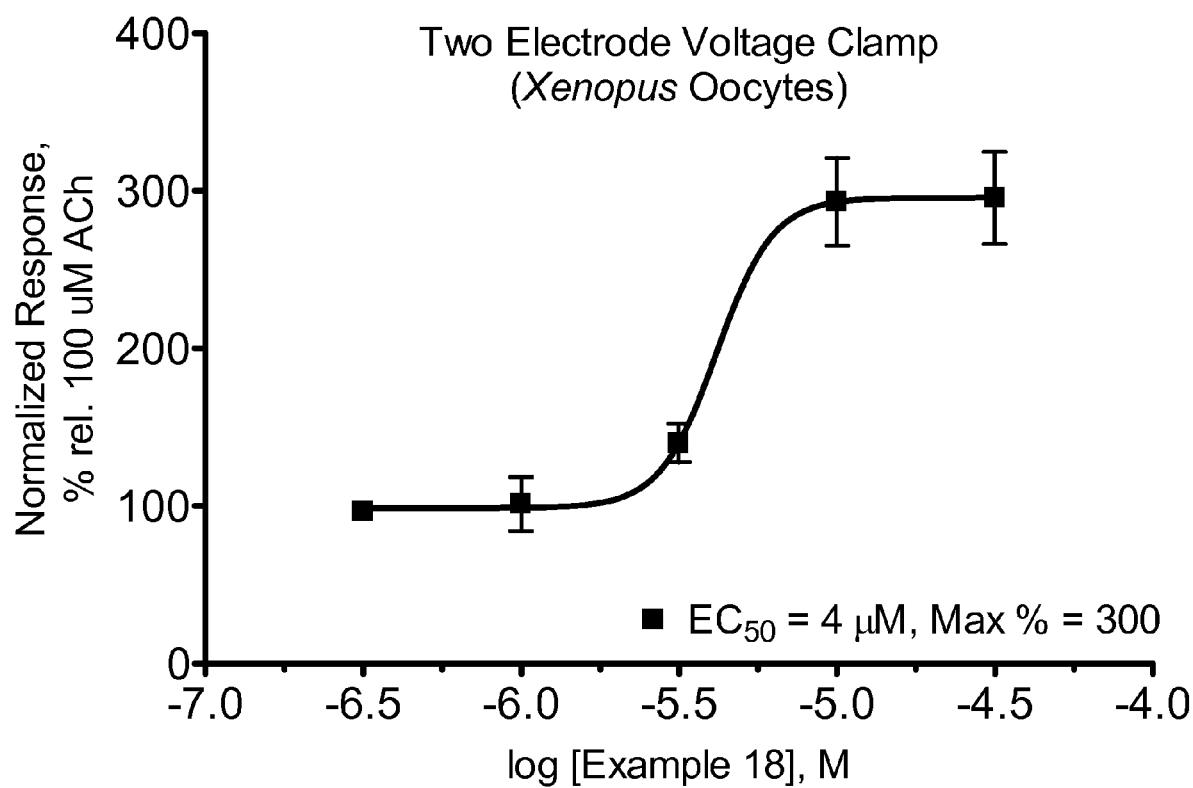
FIG. 1A is a graphical representation of a concentration response curve where responses to a fixed concentration of acetylcholine (ACh) is measured in the presence of increasing concentrations of a PAM (Example 18). The response evoked by ACh alone is considered as 100% and potentiation above this value is plotted on the Y-axis as a function of the concentration of the test modulator (depicted along the X-axis).

Certain terms as used in the specification are intended to refer to the following definitions, as detailed below.

The term "acyl" means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" means an acyl group, as defined herein, appended to the parent molecular moiety through an oxygen atom. Representative examples of acyloxy include, but are not limited to, acetyloxy, propionyloxy, and isobutyryloxy.

The term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxysulfonyl" means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "—O-alkylene-" means a divalent group derived from an oxygen atom joined to a straight or branched chain hydrocarbon of from 1 to 10 carbon atoms. One attachment point of the divalent "—O-alkylene-" group is the oxygen and the other attachment point is a carbon on the straight or branched chain hydrocarbon. Representative examples of alkylene include, but are not limited to, —O—CH$_2$—, —O—CH(CH$_3$)—, —O—C(CH$_3$)$_2$—, —O—CH$_2$CH$_2$—, —O—CH$_2$CH$_2$CH$_2$—, —O—CH$_2$CH$_2$CH$_2$CH$_2$—, and —O—CH$_2$CH(CH$_3$)CH$_2$—.

The term "alkylsulfonyl" means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" means a monocyclic or bicyclic aromatic ring system. Representative examples of aryl include, but are not limited to, phenyl and naphthyl. Bicyclic ring systems are also exemplified by phenyl ring system fused to a cycloalkyl ring. The bicyclic cycloalkyl is connected to the parent molecular moiety through any carbon atom contained within the phenyl ring. Representative examples of bicyclic ring systems include, but are not limited to, 1,2,3,4-tetrahydronaphthalenyl, and indanyl. The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxysulfonyl, alkyl, alkylcarbonyl, alkylsulfonyl, alkynyl, carboxy, cyano, cyanoalkyl, cycloalkyl, formyl, haloalkoxy, haloalkyl, halo, hydroxy, hydroxyalkyl, mercapto, morpholinyl, nitro, thioalkoxy, —$NR^iR^j$, ($NR^iR^j$)alkyl, ($NR^iR^j$)alkoxy, ($NR^iR^j$)carbonyl, ($NR^iR^j$)sulfonyl, —$OCH_2CH=CH_2$, —$OC_6H_5$, and pyridyl wherein $R^i$ and $R^j$ are as defined herein.

The term "arylalkoxy" means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl" means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryl(hydroxyl)alkyl" means an arylalkyl, as defined herein, substituted with 1, 2, or 3 hydroxyl groups on the alkyl portion wherein each hydroxyl group is a substituent on a separate carbon. One hydroxyl group is preferred. Representative examples of aryl(hydroxyl)alkyl include, but are not limited to, 2-hydroxy-1-phenylethyl.

The term "aryloxy" means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "carbonyl" means a —C(O)— group.

The term "carboxy" means a —$CO_2H$ group.

The term "cyano" means a —CN group.

The term "cyanoalkyl" means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkyl" means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptanyl, bicyclo[2.2.1]heptanyl, bicyclo[2.2.2]octanyl, bicyclo[3.2.2]nonanyl, bicyclo[3.3.1]nonanyl, and bicyclo[4.2.1]nonanyl. Bicyclic ring systems are also exemplified by a monocyclic ring system fused to a phenyl or heteroaryl ring. Representative examples of bicyclic ring systems include, but are not limited to, 1,2,3,4-tetrahydronaphthalenyl, indanyl, and 6,7-dihydro-5H-cyclopenta[c]pyridinyl. The bicyclic cycloalkyl is connected to the parent molecular moiety through any carbon atom contained within the unsaturated cycloalkyl ring. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonanyl and tricyclo[3.3.1.1$^{3,7}$]decanyl (adamantanyl).

The cycloalkyl groups of the present invention are optionally substituted with 1, 2, 3, or 4 substituents selected from the group consisting of acyl, acyloxy, alkenyl, alkoxy, alkoxyalkoxy, alkoxyalkyl, alkoxycarbonyl, alkoxysulfonyl, alkyl, alkylsulfonyl, alkynyl, aryl, carboxy, cyano, formyl, haloalkoxy, haloalkyl, halo, hydroxy, hydroxyalkyl, mercapto, nitro, oxo, thioalkoxy, —$NR^iR^j$, ($NR^iR^j$)alkyl, ($NR^iR^j$)alkoxy, ($NR^iR^j$)carbonyl, and ($NR^iR^j$)sulfonyl, wherein $R^i$ and $R^j$ are as defined herein.

The term "cycloalkylalkyl" means a cycloalkyl group appended to the parent molecular moiety through an alkyl group, as defined herein.

The term "formyl" means a —CHO group.

The term "halo" or "halogen" means —Cl, —Br, —I or —F.

The term "haloalkoxy" means at least one halogen, as defined herein, appended to the parent molecular moiety through an alkoxy group, as defined herein. Representative examples of haloalkoxy include, but are not limited to, chloromethoxy, 2-fluoroethoxy, difluoromethoxy, trifluoromethoxy, and pentafluoroethoxy.

The term "haloalkenyl" means alkenyl wherein one or more of the hydrogens thereof are replaced by independently selected F, Cl, Br, or —I.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkynyl" means alkynyl wherein one or more of the hydrogens thereof are replaced by independently selected F, Cl, Br or —I.

The term "heteroaryl" means a monocyclic heteroaryl or a bicyclic heteroaryl. The monocyclic heteroaryl is a 5 or 6 membered ring containing at least one heteroatom independently selected from the group consisting of O, N, and S. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, imidazolium, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl, or a monocyclic heteroaryl fused to a monocyclic heterocycle. The bicyclic heteroaryl is connected to the parent molecular moiety through any carbon atom or any substitutable nitrogen atom contained within the bicyclic heteroaryl. Representative examples of bicyclic heteroaryl include, but are not limited to, benzimidazolyl, benzofuranyl, benzothiazolyl, benzothienyl, benzoxadiazolyl, cinnolinyl, dihydro-1-oxo-1H-indenyl, dihydroquinolinyl, dihydroisoquinolinyl, furopyridinyl, indazolyl, indolyl, isoquinolinyl, naphthyridinyl, pyrido[3,2- b]pyrazinyl, pyrido[2,3-b]pyrazinyl, quinolinyl, quinoxalinyl, tetrahydroquinolinyl, thienopyridinyl, and triazolopyridinyl.

The heteroaryl groups of the invention are substituted with 0, 1, 2, 3 or 4 substituents independently selected from acyl, acyloxy, alkenyl, alkoxy, alkoxyalkoxy, alkoxyalkyl, alkoxycarbonyl, alkoxysulfonyl, alkyl, alkylsulfonyl, alkynyl, carboxy, cyano, cycloalkyl, formyl, haloalkoxy, haloalkyl, halo, hydroxy, hydroxyalkyl, mercapto, morpholinyl, nitro, thioalkoxy, —NR$^i$R$^j$, (NR$^i$R$^j$)alkyl, (NR$^i$R$^j$)alkoxy, (NR$^i$R$^j$)carbonyl, and (NR$^i$R$^j$)sulfonyl, wherein R$^i$ and R$^j$ are as defined herein.

The term "heteroarylalkyl" means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, pyridin-2-ylethyl, pyridin-3-ylethyl, pyridin-4-ylethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroaryl(hydroxyl)alkyl" means a heteroarylalkyl, as defined herein, substituted with 1, 2, or 3 hydroxyl groups on the alkyl portion wherein each hydroxyl group is a substituent on a separate carbon. One hydroxyl group is preferred. Representative examples of heteroaryl(hydroxyl)alkyl include, but are not limited to, 2-hydroxy-1-pyrid-2-ylethyl.

The term "heterocycle" or "heterocyclic" means a monocyclic heterocycle or a bicyclic heterocycle. The monocyclic heterocycle is a 3, 4, 5, 6 or 7 membered ring containing at least one heteroatom independently selected from the group consisting of O, N, and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 2,5-dihydro-1H-pyrrolyl, 2,3-dihydrothiazolyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a cycloalkyl, or a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodithiolyl, 4H-benzo[d][1,3]dioxinyl, bicyclo[2,2,1]diazaheptanyl, 3,6-diazabicyclo[3.2.0]heptanyl, 2,5-diazabicyclo[2.2.1]heptanyl, 2,3-dihydro-1-benzofuranyl, 2,3-dihydro-1-benzothienyl, 2,3-dihydro-1H-indolyl, hexahydropyrrolo[3,4-c]pyrrolyl, indolinyl, octahydropyrrolo[3,4-c]pyrrolyl, octahydro-1H-pyrrolo[3,4-b]pyridinyl, and 1,2,3,4-tetrahydroquinolinyl; provided that 2,3-dihydrobenzo[b][1,4]dioxinyl and benzo[d][1,3]dioxolyl derivatives are excluded.

The heterocycles of this invention are optionally substituted with 1, 2, 3, or 4 substituents independently selected from the group consisting of acyl, acyloxy, alkenyl, alkoxy, alkoxyalkoxy, alkoxyalkyl, alkoxycarbonyl, alkoxysulfonyl, alkyl, alkylcarbonyl, alkylsulfonyl, alkynyl, benzyl, carboxy, cyano, cycloalkyl, formyl, haloalkoxy, haloalkyl, halo, hydroxy, hydroxyalkyl, mercapto, morpholinyl, nitro, phenyl, pyridinyl, pyrimidinyl, thioalkoxy, —NR$^i$R$^j$, (NR$^i$R$^j$)alkyl, (NR$^i$R$^j$)alkoxy, (NR$^i$R$^j$)carbonyl, and (NR$^i$R$^j$)sulfonyl, wherein R$^i$ and R$^j$ are as defined herein.

The term "heterocyclealkyl" means a heterocycle group appended to the parent molecular moiety through an alkyl group, as defined herein.

The term "hydroxy" or "hydroxyl" means an —OH group.

The term "hydroxyalkyl" means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" means a —SH group.

The term "nitro" means a —NO$_2$ group.

The term "—NR$^i$R$^j$" means two groups, R$^i$ and R$^j$, which are appended to the parent molecular moiety through a nitrogen atom. R$^i$ and R$^j$ are each independently hydrogen, alkoxyalkyl, alkoxycarbonyl, alkyl, alkylcarbonyl, or formyl. In addition, R$^i$ and R$^j$ taken together with the nitrogen atom to which they are attached, may form a 4, 5, 6 or 7 membered heterocyclic ring. Representative examples of —NR$^i$R$^j$ include, but are not limited to, amino, methylamino, acetylamino, and acetyl(methyl)amino.

The term "(NR$^i$R$^j$)alkyl" means a —NR$^i$R$^j$ group, as defined herein, appended to the parent molecular moiety through an alkyl group, as defined herein. Representative examples of (NR$^i$R$^j$)alkyl include, but are not limited to, (amino)methyl, (dimethylamino)methyl, and (ethylamino)methyl.

The term "(NR$^i$R$^j$)alkoxy" means a —NR$^i$R$^j$ group, as defined herein, appended to the parent molecular moiety through an alkoxy group, as defined herein. Representative examples of (NR$^i$R$^j$)alkoxy include, but are not limited to, (amino)propoxy, (dimethylamino)butoxy, and (diethylamino)ethoxy.

The term "(NR$^i$R$^j$)carbonyl" means a —NR$^i$R$^j$ group, as defined herein, appended to the parent molecular moiety through a carbonyl group, as defined herein. Representative examples of (NR$^i$R$^j$)carbonyl include, but are not limited to, aminocarbonyl, (methylamino)carbonyl, (dimethylamino)carbonyl, and (ethylmethylamino)carbonyl.

The term "(NR$^i$R$^j$)sulfonyl" means a —NR$^i$R$^j$ group, as defined herein, appended to the parent molecular moiety through a sulfonyl group, as defined herein. Representative examples of (NR$^i$R$^j$)sulfonyl include, but are not limited to, aminosulfonyl, (methylamino)sulfonyl, (dimethylamino)sulfonyl, and (ethylmethylamino)sulfonyl.

The term "oxo" means a =O moiety.

The term "Positive Allosteric Modulator (PAM)" means a compound that enhances activity of an endogenous ligand, such as but not limited to ACh, or an exogenously administered agonist.

The term "pharmaceutically acceptable salt" or "salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid. Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester" or "ester" refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid such as hydrochloric acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" or "amide" refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkylamine or dialkylamine, for example with methylamine, diethylamine, or piperidine. They also can be prepared by reaction of the compound containing a primary or secondary amine group with an acid such as sulfuric acid and an alkylcarboxylic acid such as acetic acid, or with acid and an arylcarboxylic acid such as benzoic acid under dehydrating conditions such as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "pharmaceutically acceptable carrier" or "carrier", as used herein, means a non-toxic, inert solid, semisolid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The term "sulfonyl" means a —$S(O)_2$— group.

The phrase "therapeutically effective amount" of the compound means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The term "thioalkoxy" means an alkyl group, as defined herein, appended to the parent molecular moiety through a sulfur atom. Representative examples of thioalkoxy include, but are no limited to, methylthio, ethylthio, and propylthio.

Although typically it may be recognized that an asterisk is used to indicate that the exact subunit composition of a receptor is uncertain, for example α3β4* indicates a receptor that contains the α3 and β4 proteins in combination with other subunits, the term α7 as used herein is intended to include receptors wherein the exact subunit composition is both certain and uncertain. For example, α7 includes homomeric $(α7)_5$ receptors and α7* receptors, which denote an NNR containing at least one α7 subunit.

Compounds of the Invention

An embodiment relates to compounds of formula (I):

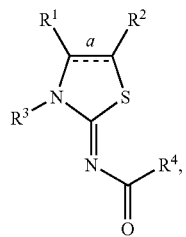

(I)

wherein $R^1$ is hydrogen, methyl, phenyl, pyrazolyl, or hydroxyl;

$R^2$ is hydrogen, alkyl, alkenyl, =$CH_2$, or =$CHR^c$ wherein the alkyl group and the alkenyl group are substituted with 0, 1, 2, or 3 substituents independently selected from the group consisting of alkoxycarbonyl, alkylcarbonyloxy, aryl, aryloxy, arylalkoxy, carboxy, cyano, cycloalkyl, haloalkoxy, heteroaryl, heterocycle, hydroxyl, nitro, and $R^dR^eN$—, wherein a group represented by $R^2$ can be further substituted with 0, 1, or 2 groups selected from halo and alkoxy;

$R^c$ is alkyl or halo;

$R^d$ and $R^e$ are each independently hydrogen, alkyl, alkoxyalkyl, aryl, arylalkyl, cyanoalkyl, heteroaryl, heteroarylalkyl, heterocycle, or heterocyclealkyl;

$R^3$ is optionally substituted aryl, heteroaryl, or -$G^1$-L-$G^2$;

$G^1$ is aryl or heteroaryl;

$G^2$ is aryl, cycloalkyl, heteroaryl, or heterocycle;

L is a bond, O, alkylene, or —O-alkylene-;

$R^4$ is optionally substituted alkyl, cycloalkyl, heteroaryl, heterocycle or —$NR^5R^6$; wherein, $R^5$ and $R^6$ are independently hydrogen, alkyl, ($NR^iR^j$)alkyl, alkynyl, aryl, heterocyclealkyl, cycloalkylalkyl, cyanoalkyl, cycloalkyl, alkoxyalkyl, arylalkyl, or heteroarylalkyl; and a is single or double bond;

provided that when $R^1$ is hydroxyl or when $R^2$ is a radical attached to the thiazole ring through an exocyclic double bond, then a is single bond;

or a pharmaceutically acceptable salt, ester, amide or prodrug thereof.

Another embodiment relates to compounds of formula (I), further provided that when a is double bond, $R^1$ is hydrogen, $R^2$ is methyl, $R^3$ is phenyl substituted with 3-haloalkyl, 3-halo, 3-haloalkoxy, 2,5-dihalo, 2,3-dihalo, 3,4-dihalo, or 3,5-dihalo, then $R^4$ is heterocycle.

Another embodiment is a compound of formula (I), wherein $R^2$ is hydrogen or alkyl.

Another embodiment is a compound of formula (I), wherein $R^2$ is hydrogen or alkyl, wherein the alkyl group is optionally substituted with 1 or 2 alkoxy, alkylcarbonyl, cyano, heteroaryl, hydroxy, or $R^dR^eN$—.

Another embodiment is a compound of formula (I), wherein $R^4$ is alkyl, cycloalkyl, heteroaryl, heterocycle or —$NR^5R^6$.

Another embodiment is a compound of formula (I), wherein $R^2$ is alkyl substituted with hydroxyl, and $R^4$ is heterocycle.

Another embodiment is a compound of formula (I), wherein $R^3$ is aryl or heteroaryl.

Another embodiment is a compound of formula (I), wherein $R^1$ is hydrogen, and $R^2$ is methyl.

Another embodiment is a compound of formula (I), wherein $R^1$ is methyl, and $R^2$ is methyl.

Another embodiment is a compound of formula (I), wherein $R^3$ is -$G^1$-L-$G^2$.

Another embodiment is a compound of formula (I), wherein $R^3$ is -$G^1$-L-$G^2$ and $R^4$ is heterocycle.

Another embodiment is a compound of formula (I), wherein $R^3$ is optionally substituted phenyl, naphthyl, isothiazolyl, thienyl, thiazolyl, benzothienyl, 4H-benzo[d][1,3]dioxinyl, 1,3-benzothiazolyl, pyridinyl, triazolopyridinyl, benzofuranyl, pyridazinyl, pyrimidinyl, pyrazinyl, quinoxalinyl, dihydro-1-oxo-1H-indenyl, biphenyl, thienylphenyl, phenylthienyl, pyrazolylphenyl, pyrimidinylphenyl, pyridinylphenyl, phenylpyrazinyl, pyrazinylphenyl, phenylpyridazinyl, pyridazinylphenyl, pyrazinopyridyl, pyridopyrazinyl, or pyrazolylpyridinyl.

Another embodiment is a compound of formula (I), wherein $R^4$ is methyl, t-butyl or cyclobutyl.

Another embodiment is a compound of formula (I), wherein $R^4$ is —$NR^5R^6$ wherein, $R^5$ and $R^6$ are independently hydrogen, or optionally substituted methyl, ethyl, propyl, butyl, pentyl, propargyl, cyclopropyl, cyclobutyl, cyclopentyl, cyclohexyl, cycloheptyl, adamantyl, cyclopropylmethyl, cyclopentylmethyl, cyanomethyl, cyanoethyl, 1,3-dioxalanylmethyl, benzyl, phenylethyl, pyridylmethyl, pyridylethyl, methoxyethyl, methoxypropyl, dimethylaminoethyl, dimethylaminopropyl, diethylaminoethyl, tetrahydro furylmethyl, phenyl, pyrrolidinylpropyl, pyrrolidinylmethyl, or piperazinylethyl; or heterocycle selected from optionally substituted piperidine, pyrrolidine, indoline, octahydropyrrolopyrrole, octahydropyrrolopyridine, diazabicyclo[2,2,1]heptane, diazabicyclo[3,2,0]heptane, azepane, diazepane, morpholine, thiomorpholine, piperazine, pyridylpiperazine, pyrimidinylpiperazine, dihydropyrrole, azetidine, benzylpiperidine, acetylpiperazine, phenylpiperazine, or imidazole.

Specific embodiments include, but are not limited to, compounds of formula (I), described in the examples 1-516.

Compounds of formula (I) that show α7 NNR PAM activity include, but are not limited to:

N'-[(2Z)-3-(4-methoxyphenyl)-5-methyl-1,3-thiazol-2(3H)-ylidene]-N,N-dimethylurea;
N-[(2Z)-3-[4-(difluoromethoxy)phenyl]-5-methyl-1,3-thiazol-2(3H)-ylidene]pyrrolidine-1-carboxamide;
N-[(2Z)-3-[4-(difluoromethoxy)phenyl]-5-methyl-1,3-thiazol-2(3H)-ylidene]piperidine-1-carboxamide;
N'-[(2Z)-3-[4-(difluoromethoxy)phenyl]-5-methyl-1,3-thiazol-2(3H)-ylidene]-N,N-diethylurea;
N-[(2Z)-5-methyl-3-[4-(trifluoromethoxy)phenyl]-1,3-thiazol-2(3H)-ylidene]pyrrolidine-1-carboxamide;
N,N-diethyl-N'-[(2Z)-5-methyl-3-[4-(trifluoromethoxy)phenyl]-1,3-thiazol-2(3H)-ylidene]urea;
N,N-dimethyl-N'-[(2Z)-5-methyl-3-[4-(trifluoromethoxy)phenyl]-1,3-thiazol-2(3H)-ylidene]urea;
N-[(2Z)-3-(4-chlorophenyl)-5-methyl-1,3-thiazol-2(3H)-ylidene]pyrrolidine-1-carboxamide;
N-[(2Z)-3-(4-chlorophenyl)-5-methyl-1,3-thiazol-2(3H)-ylidene]piperidine-1-carboxamide;
N'-[(2Z)-3-(4-chlorophenyl)-5-methyl-1,3-thiazol-2(3H)-ylidene]-N,N-diethylurea;
N'-[(2Z)-3-(4-chlorophenyl)-5-methyl-1,3-thiazol-2(3H)-ylidene]-N-methyl-N-phenylurea;
N'-[(2Z)-3-(4-chlorophenyl)-5-methyl-1,3-thiazol-2(3H)-ylidene]-N,N-dimethylurea;
N-[(2Z)-3-(4-fluorophenyl)-5-methyl-1,3-thiazol-2(3H)-ylidene]pyrrolidine-1-carboxamide;
N-[(2Z)-3-(4-fluorophenyl)-5-methyl-1,3-thiazol-2(3H)-ylidene]piperidine-1-carboxamide;
N,N-diethyl-N'-[(2Z)-3-(4-fluorophenyl)-5-methyl-1,3-thiazol-2(3H)-ylidene]urea;
N'-[(2Z)-3-(4-fluorophenyl)-5-methyl-1,3-thiazol-2(3H)-ylidene]-N,N-dimethylurea;
N-[(2Z)-3-(4-fluorophenyl)-5-methyl-1,3-thiazol-2(3H)-ylidene]cyclobutanecarboxamide;
N-[(2Z)-5-methyl-3-[4-(trifluoromethyl)phenyl]-1,3-thiazol-2(3H)-ylidene]pyrrolidine-1-carboxamide;
N,N-dimethyl-N'-[(2Z)-5-methyl-3-[4-(trifluoromethyl)phenyl]-1,3-thiazol-2(3H)-ylidene]urea;
2-methyl-N-[(2Z)-5-methyl-3-[4-(trifluoromethyl)phenyl]-1,3-thiazol-2(3H)-ylidene]pyrrolidine-1-carboxamide;
(2R)-2-methyl-N-[(2Z)-5-methyl-3-[4-(trifluoromethyl)phenyl]-1,3-thiazol-2(3H)-ylidene]pyrrolidine-1-carboxamide;
(2S)-2-methyl-N-[(2Z)-5-methyl-3-[4-(trifluoromethyl)phenyl]-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]-2,5-dihydro-1H-pyrrole-1-carboxamide;
N-[(2Z)-5-methyl-3-[4-(trifluoromethyl)phenyl]-1,3-thiazol-2(3H)-ylidene]azetidine-1-carboxamide;
N-[(2Z)-5-methyl-3-(2-naphthyl)-1,3-thiazol-2(3H)-ylidene]pyrrolidine-1-carboxamide;
N-[(2Z)-5-methyl-3-(3-methylisothiazol-5-yl)-1,3-thiazol-2(3H)-ylidene]pyrrolidine-1-carboxamide;
N-[(2Z)-3-(4-bromophenyl)-1,3-thiazol-2(3H)-ylidene]pyrrolidine-1-carboxamide;
N-(3-fluorobenzyl)-N-methyl-N'-[(2Z)-5-methyl-3-(2-naphthyl)-1,3-thiazol-2(3H)-ylidene]urea;
(3R)-N-[(2Z)-3-(5-cyanothien-2-yl)-5-methyl-1,3-thiazol-2(3H)-ylidene]-3-fluoropyrrolidine-1-carboxamide;
N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-[4-(trifluoromethyl)phenyl]-1,3-thiazol-2(3H)-ylidene]pyrrolidine-1-carboxamide;
(3R)-3-fluoro-N-[(2Z)-5-(hydroxymethyl)-3-[5-(trifluoromethyl)thien-2-yl]-1,3-thiazol-2(3H)-ylidene]pyrrolidine-1-carboxamide;
(3R)-N-[(2Z)-3-(5-chlorothien-2-yl)-5-(hydroxymethyl)-1,3-thiazol-2(3H)-ylidene]-3-fluoropyrrolidine-1-carboxamide;
(3R)-N-[(2Z)-3-(1-benzothien-5-yl)-5-(hydroxymethyl)-1,3-thiazol-2(3H)-ylidene]-3-fluoropyrrolidine-1-carboxamide;
(3R)-3-fluoro-N-[(2Z)-5-(hydroxymethyl)-3-(2,2,4,4-tetrafluoro-4H-1,3-benzodioxin-6-yl)-1,3-thiazol-2(3H)-ylidene]pyrrolidine-1-carboxamide;
(3R)-N-[(2Z)-3-(5,6-difluoro-2-naphthyl)-5-(hydroxymethyl)-1,3-thiazol-2(3H)-ylidene]-3-fluoropyrrolidine-1-carboxamide;
N-[(2Z)-5-methyl-3-phenyl-1,3-thiazol-2(3H)-ylidene]pyrrolidine-1-carboxamide;
N-[(2Z)-5-methyl-3-(3-methylphenyl)-1,3-thiazol-2(3H)-ylidene]pyrrolidine-1-carboxamide;
N-[(2Z)-5-methyl-3-(4-methylphenyl)-1,3-thiazol-2(3H)-ylidene]pyrrolidine-1-carboxamide;
N-[(2Z)-3-(3-hydroxyphenyl)-5-methyl-1,3-thiazol-2(3H)-ylidene]pyrrolidine-1-carboxamide;
N-[(2Z)-3-(4-methoxyphenyl)-5-methyl-1,3-thiazol-2(3H)-ylidene]pyrrolidine-1-carboxamide;
N-[(2Z)-3-(3-fluorophenyl)-5-methyl-1,3-thiazol-2(3H)-ylidene]pyrrolidine-1-carboxamide;
N-[(2Z)-3-(3-chlorophenyl)-5-methyl-1,3-thiazol-2(3H)-ylidene]pyrrolidine-1-carboxamide;
N-[(2Z)-3-(3-bromophenyl)-5-methyl-1,3-thiazol-2(3H)-ylidene]pyrrolidine-1-carboxamide;
N-[(2Z)-3-(3-cyanophenyl)-5-methyl-1,3-thiazol-2(3H)-ylidene]pyrrolidine-1-carboxamide;
N-[(2Z)-3-(4-cyanophenyl)-5-methyl-1,3-thiazol-2(3H)-ylidene]pyrrolidine-1-carboxamide;
N-[(2Z)-3-[4-(dimethylamino)phenyl]-5-methyl-1,3-thiazol-2(3H)-ylidene]pyrrolidine-1-carboxamide;
N-[(2Z)-5-methyl-3-[3-(trifluoromethoxy)phenyl]-1,3-thiazol-2(3H)-ylidene]pyrrolidine-1-carboxamide;
N-[(2Z)-5-methyl-3-(4-phenoxyphenyl)-1,3-thiazol-2(3H)-ylidene]pyrrolidine-1-carboxamide;
N-[(2Z)-3-[4-(benzyloxy)phenyl]-5-methyl-1,3-thiazol-2(3H)-ylidene]pyrrolidine-1-carboxamide;
N-[(2Z)-3-(3,4-dimethylphenyl)-5-methyl-1,3-thiazol-2(3H)-ylidene]pyrrolidine-1-carboxamide;
N-[(2Z)-3-(3,5-dimethylphenyl)-5-methyl-1,3-thiazol-2(3H)-ylidene]pyrrolidine-1-carboxamide;
N-[(2Z)-3-(3,4-dichlorophenyl)-5-methyl-1,3-thiazol-2(3H)-ylidene]pyrrolidine-1-carboxamide;
N-[(2Z)-3-(3,5-dichlorophenyl)-5-methyl-1,3-thiazol-2(3H)-ylidene]pyrrolidine-1-carboxamide;
N-[(2Z)-5-methyl-3-[4-(methylthio)phenyl]-1,3-thiazol-2(3H)-ylidene]pyrrolidine-1-carboxamide;
N-[(2Z)-3-(3-methoxyphenyl)-5-methyl-1,3-thiazol-2(3H)-ylidene]pyrrolidine-1-carboxamide;
N-[(2Z)-3-(4-chloro-3-methylphenyl)-5-methyl-1,3-thiazol-2(3H)-ylidene]pyrrolidine-1-carboxamide;
N-[(2Z)-3-(4-benzylphenyl)-5-methyl-1,3-thiazol-2(3H)-ylidene]pyrrolidine-1-carboxamide;
N-[(2Z)-3-(1-benzothien-5-yl)-5-methyl-1,3-thiazol-2(3H)-ylidene]pyrrolidine-1-carboxamide;
N-[(2Z)-5-methyl-3-(5-methylthien-2-yl)-1,3-thiazol-2(3H)-ylidene]pyrrolidine-1-carboxamide;

N-[(2Z)-5-methyl-3-[6-(trifluoromethyl)pyridin-3-yl]-1,3-thiazol-2(3H)-ylidene]pyrrolidine-1-carboxamide;
N-[(2Z)-5-methyl-3-[5-(trifluoromethyl)pyridin-3-yl]-1,3-thiazol-2(3H)-ylidene]pyrrolidine-1-carboxamide;
N-[(2Z)-3-[4-(methylthio)phenyl]-1,3-thiazol-2(3H)-ylidene]pyrrolidine-1-carboxamide;
N-[(2Z)-3-phenyl-1,3-thiazol-2(3H)-ylidene]pyrrolidine-1-carboxamide;
N-[(2Z)-3-(3-chlorophenyl)-1,3-thiazol-2(3H)-ylidene]pyrrolidine-1-carboxamide;
N-[(2Z)-3-[3-(trifluoromethyl)phenyl]-1,3-thiazol-2(3H)-ylidene]pyrrolidine-1-carboxamide;
N-[(2Z)-3-(4-chlorophenyl)-1,3-thiazol-2(3H)-ylidene]pyrrolidine-1-carboxamide;
N-[(2Z)-3-(4-methylphenyl)-1,3-thiazol-2(3H)-ylidene]pyrrolidine-1-carboxamide;
N-[(2Z)-3-(4-chloro-3-methylphenyl)-1,3-thiazol-2(3H)-ylidene]pyrrolidine-1-carboxamide;
N-[(2Z)-3-(3,4-dichlorophenyl)-1,3-thiazol-2(3H)-ylidene]pyrrolidine-1-carboxamide;
N-[(2Z)-3-(3,4-dimethylphenyl)-1,3-thiazol-2(3H)-ylidene]pyrrolidine-1-carboxamide;
N-[(2Z)-3-(4-cyanophenyl)-1,3-thiazol-2(3H)-ylidene]pyrrolidine-1-carboxamide;
N-[(2Z)-3-(3-chloro-4-methylphenyl)-1,3-thiazol-2(3H)-ylidene]pyrrolidine-1-carboxamide;
N-[(2Z)-3-[4-(difluoromethoxy)phenyl]-1,3-thiazol-2(3H)-ylidene]pyrrolidine-1-carboxamide;
N-[(2Z)-3-(3,5-dichlorophenyl)-5-methyl-1,3-thiazol-2(3H)-ylidene]-2,2-dimethylpropanamide;
N-[(2Z)-3-(4-fluorophenyl)-5-methyl-1,3-thiazol-2(3H)-ylidene]-2,2-dimethylpropanamide;
N-[(2Z)-3-(4-chlorophenyl)-5-methyl-1,3-thiazol-2(3H)-ylidene]-2,2-dimethylpropanamide;
N-[(2Z)-3-(3,4-dichlorophenyl)-5-methyl-1,3-thiazol-2(3H)-ylidene]-2,2-dimethylpropanamide;
2,2-dimethyl-N-[(2Z)-5-methyl-3-[4-(trifluoromethyl)phenyl]-1,3-thiazol-2(3H)-ylidene]propanamide;
N-[(2Z)-3-[6-(trifluoromethyl)pyridin-3-yl]-1,3-thiazol-2(3H)-ylidene]pyrrolidine-1-carboxamide;
N-[(2Z)-3-[3-fluoro-4-(trifluoromethyl)phenyl]-1,3-thiazol-2(3H)-ylidene]pyrrolidine-1-carboxamide;
N-[(2Z)-3-(6-fluoro-5-methylpyridin-3-yl)-1,3-thiazol-2(3H)-ylidene]pyrrolidine-1-carboxamide;
2,2-dimethyl-N-[(2Z)-5-methyl-3-(5-methylthien-2-yl)-1,3-thiazol-2(3H)-ylidene]propanamide;
N-[(2Z)-3-(6-fluoropyridin-3-yl)-5-methyl-1,3-thiazol-2(3H)-ylidene]-2,2-dimethylpropanamide;
2,2-dimethyl-N-[(2Z)-5-methyl-3-[6-(trifluoromethyl)pyridin-3-yl]-1,3-thiazol-2(3H)-ylidene]propanamide;
N-[(2Z)-3-[3-fluoro-4-(trifluoromethyl)phenyl]-5-methyl-1,3-thiazol-2(3H)-ylidene]-2,2-dimethylpropanamide;
N-[(2Z)-3-(6-fluoro-5-methylpyridin-3-yl)-5-methyl-1,3-thiazol-2(3H)-ylidene]-2,2-dimethylpropanamide;
N-[(2Z)-3-(2-fluoropyridin-4-yl)-5-methyl-1,3-thiazol-2(3H)-ylidene]-2,2-dimethylpropanamide;
(3R)-N-[(2Z)-3-(3-bromophenyl)-5-methyl-1,3-thiazol-2(3H)-ylidene]-3-fluoropyrrolidine-1-carboxamide;
(3R)-N-[(2Z)-3-(4-cyano-3-methylphenyl)-5-methyl-1,3-thiazol-2(3H)-ylidene]-3-fluoropyrrolidine-1-carboxamide;
(3R)-3-fluoro-N-[(2Z)-5-methyl-3-(3-methylphenyl)-1,3-thiazol-2(3H)-ylidene]pyrrolidine-1-carboxamide;
(3R)-N-[(2Z)-3-(4-bromophenyl)-5-methyl-1,3-thiazol-2(3H)-ylidene]-3-fluoropyrrolidine-1-carboxamide;
(3R)-3-fluoro-N-[(2Z)-5-methyl-3-(4-phenoxyphenyl)-1,3-thiazol-2(3H)-ylidene]pyrrolidine-1-carboxamide;
(3R)-3-fluoro-N-[(2Z)-5-methyl-3-(4-methylphenyl)-1,3-thiazol-2(3H)-ylidene]pyrrolidine-1-carboxamide;
(3R)-N-[(2Z)-3-(4-ethylphenyl)-5-methyl-1,3-thiazol-2(3H)-ylidene]-3-fluoropyrrolidine-1-carboxamide;
(3R)-3-fluoro-N-[(2Z)-3-(3-fluorophenyl)-5-methyl-1,3-thiazol-2(3H)-ylidene]pyrrolidine-1-carboxamide;
(3R)-3-fluoro-N-[(2Z)-3-(4-fluorophenyl)-5-methyl-1,3-thiazol-2(3H)-ylidene]pyrrolidine-1-carboxamide;
(3R)-3-fluoro-N-[(2Z)-5-methyl-3-[4-(trifluoromethyl)phenyl]-1,3-thiazol-2(3H)-ylidene]pyrrolidine-1-carboxamide;
(3R)-N-[(2Z)-3-(4-chlorophenyl)-5-methyl-1,3-thiazol-2(3H)-ylidene]-3-fluoropyrrolidine-1-carboxamide;
(3R)-3-fluoro-N-[(2Z)-3-(4-iodophenyl)-5-methyl-1,3-thiazol-2(3H)-ylidene]pyrrolidine-1-carboxamide;
(3R)-N-[(2Z)-3-(3-cyanophenyl)-5-methyl-1,3-thiazol-2(3H)-ylidene]-3-fluoropyrrolidine-1-carboxamide;
(3R)-3-fluoro-N-[(2Z)-5-methyl-3-(2-naphthyl)-1,3-thiazol-2(3H)-ylidene]pyrrolidine-1-carboxamide;
(3R)-N-[(2Z)-3-(5-bromothien-2-yl)-5-methyl-1,3-thiazol-2(3H)-ylidene]-3-fluoropyrrolidine-1-carboxamide;
(3R)-N-[(2Z)-3-(3,4-dichlorophenyl)-5-methyl-1,3-thiazol-2(3H)-ylidene]-3-fluoropyrrolidine-1-carboxamide;
(3R)-3-fluoro-N-[(2Z)-3-(3-iodophenyl)-5-methyl-1,3-thiazol-2(3H)-ylidene]pyrrolidine-1-carboxamide;
(3R)-N-[(2Z)-3-(3-chloro-4-methylphenyl)-5-methyl-1,3-thiazol-2(3H)-ylidene]-3-fluoropyrrolidine-1-carboxamide;
(3R)-N-[(2Z)-3-(1-benzothien-5-yl)-5-methyl-1,3-thiazol-2(3H)-ylidene]-3-fluoropyrrolidine-1-carboxamide;
N-[(2Z)-3-(2-naphthyl)-1,3-thiazol-2(3H)-ylidene]pyrrolidine-1-carboxamide;
N-[(2Z)-3-(5-chlorothien-2-yl)-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]indoline-1-carboxamide;
N-ethyl-N-methyl-N'-[(2Z)-5-methyl-3-[4-(trifluoromethyl)phenyl]-1,3-thiazol-2(3H)-ylidene]urea;
N-methyl-N'-[(2Z)-5-methyl-3-[4-(trifluoromethyl)phenyl]-1,3-thiazol-2(3H)-ylidene]-N-propylurea;
N-(1,3-dioxolan-2-ylmethyl)-N-methyl-N'-[(2Z)-5-methyl-3-[4-(trifluoromethyl)phenyl]-1,3-thiazol-2(3H)-ylidene]urea;
N-methyl-N-(3-methylbutyl)-N'-[(2Z)-5-methyl-3-[4-(trifluoromethyl)phenyl]-1,3-thiazol-2(3H)-ylidene]urea;
N-methyl-N'-[(2Z)-5-methyl-3-[4-(trifluoromethyl)phenyl]-1,3-thiazol-2(3H)-ylidene]-N-prop-2-ynylurea;
N,N-diethyl-N'-[(2Z)-5-methyl-3-[4-(trifluoromethyl)phenyl]-1,3-thiazol-2(3H)-ylidene]urea;
N-ethyl-N'-[(2Z)-5-methyl-3-[4-(trifluoromethyl)phenyl]-1,3-thiazol-2(3H)-ylidene]-N-propylurea;
N-butyl-N-ethyl-N'-[(2Z)-5-methyl-3-[4-(trifluoromethyl)phenyl]-1,3-thiazol-2(3H)-ylidene]urea;
N,N-dibutyl-N'-[(2Z)-5-methyl-3-[4-(trifluoromethyl)phenyl]-1,3-thiazol-2(3H)-ylidene]urea;
2,5-dimethyl-N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]piperidine-1-carboxamide;
N-(2-methoxyethyl)-N-methyl-N'-[(2Z)-5-methyl-3-[4-(trifluoromethyl)phenyl]-1,3-thiazol-2(3H)-ylidene]urea;
N-benzyl-N-ethyl-N'-[(2Z)-5-methyl-3-[4-(trifluoromethyl)phenyl]-1,3-thiazol-2(3H)-ylidene]urea;
N-benzyl-N-isopropyl-N'-[(2Z)-5-methyl-3-[4-(trifluoromethyl)phenyl]-1,3-thiazol-2(3H)-ylidene]urea;

N-benzyl-N-butyl-N'-[(2Z)-5-methyl-3-[4-(trifluoromethyl)phenyl]-1,3-thiazol-2(3H)-ylidene]urea;
4-benzyl-N-[(2Z)-5-methyl-3-[4-(trifluoromethyl)phenyl]-1,3-thiazol-2(3H)-ylidene]piperidine-1-carboxamide;
N-isopropyl-N'-[(2Z)-5-methyl-3-[4-(trifluoromethyl)phenyl]-1,3-thiazol-2(3H)-ylidene]urea;
N-(sec-butyl)-N'-[(2Z)-5-methyl-3-[4-(trifluoromethyl)phenyl]-1,3-thiazol-2(3H)-ylidene]urea;
N-(1-methylbutyl)-N'-[(2Z)-5-methyl-3-[4-(trifluoromethyl)phenyl]-1,3-thiazol-2(3H)-ylidene]urea;
N-(1,1-dimethylpropyl)-N'-[(2Z)-5-methyl-3-[4-(trifluoromethyl)phenyl]-1,3-thiazol-2(3H)-ylidene]urea;
N-(1-ethylpropyl)-N'-[(2Z)-5-methyl-3-[4-(trifluoromethyl)phenyl]-1,3-thiazol-2(3H)-ylidene]urea;
N-(2-methoxy-1-methylethyl)-N'-[(2Z)-5-methyl-3-[4-(trifluoromethyl)phenyl]-1,3-thiazol-2(3H)-ylidene]urea;
N-cyclopropyl-N'-[(2Z)-5-methyl-3-[4-(trifluoromethyl)phenyl]-1,3-thiazol-2(3H)-ylidene]urea;
N-cyclobutyl-N'-[(2Z)-5-methyl-3-[4-(trifluoromethyl)phenyl]-1,3-thiazol-2(3H)-ylidene]urea;
N-cyclopentyl-N'-[(2Z)-5-methyl-3-[4-(trifluoromethyl)phenyl]-1,3-thiazol-2(3H)-ylidene]urea;
N-[(2Z)-3-(4-chlorophenyl)-4,5-dimethyl-1,3-thiazol-2(3H)-ylidene]pyrrolidine-1-carboxamide;
N-[(2Z)-4,5-dimethyl-3-[4-(trifluoromethyl)phenyl]-1,3-thiazol-2(3H)-ylidene]pyrrolidine-1-carboxamide;
N-[(2Z)-3-(6-chloropyridin-3-yl)-4,5-dimethyl-1,3-thiazol-2(3H)-ylidene]pyrrolidine-1-carboxamide;
N-[(2Z)-3-(6-chloropyridin-3-yl)-5-methyl-1,3-thiazol-2(3H)-ylidene]pyrrolidine-1-carboxamide;
N-[(2Z)-3-(3-methyl-1-benzothien-5-yl)-1,3-thiazol-2(3H)-ylidene]pyrrolidine-1-carboxamide;
N-methyl-N'-[(2Z)-5-methyl-3-[4-(trifluoromethyl)phenyl]-1,3-thiazol-2(3H)-ylidene]-N-pentylurea;
N-[(2'Z)-5-chloro-5'-methyl-2,3'-bi-1,3-thiazol-2'-ylidene]pyrrolidine-1-carboxamide;
N-[(2Z)-3-(4-fluorophenyl)-1,3-thiazol-2(3H)-ylidene]pyrrolidine-1-carboxamide; and
N-[(2Z)-3-(5-methylthien-2-yl)-1,3-thiazol-2(3H)-ylidene]pyrrolidine-1-carboxamide.

Compounds of formula (I) may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. Various stereoisomers and mixtures thereof and are specifically included within the scope of the specification. Stereoisomers include enantiomers and diastereomers, and mixtures of enantiomers or diastereomers. Individual stereoisomers of compounds may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds including geometric isomers of carbon-carbon double bonds and carbon-nitrogen double bonds are included herein. Substituents around a carbon-carbon or a carbon-nitrogen double bond are designated as being of Z or E configuration and substituents around a cycloalkyl or heterocycle are designated as being of cis or trans configuration. All geometric isomeric forms and mixtures thereof of the compounds described herein are encompassed within the scope of the specification.

Amides, Esters and Prodrugs

Prodrugs are pharmacologically inactive derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

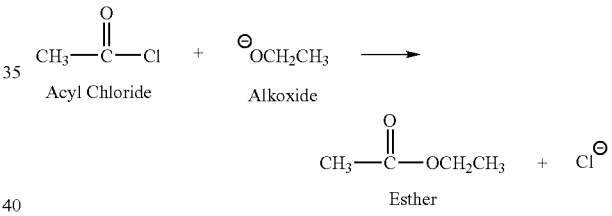

Amides can be prepared from substrates of formula (I) containing either an amino group or a carboxy group in similar fashion. Esters can also react with amines or ammonia to form amides.

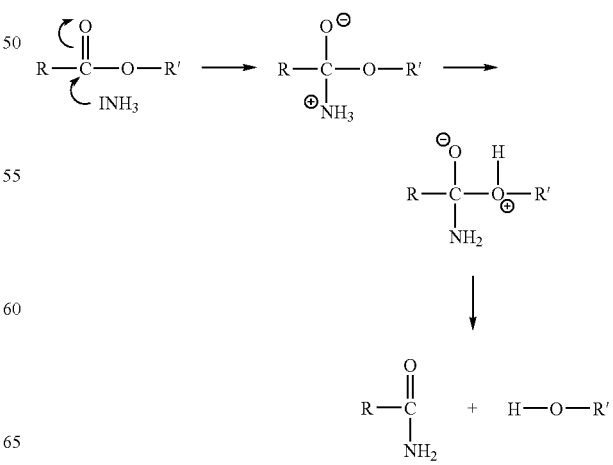

Another way to make amides from compounds of formula (I) is to heat carboxylic acids and amines together.

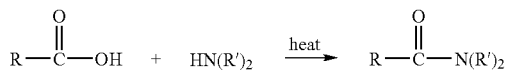

Various embodiments of formula (I) that are substrates for prodrugs, amides and esters include, but not limited to, Examples 35, 35A, 36, 36B, 36C, 37, 38, 39, 40, 41, 42, 42D, 47, 152, 153, 154, 155, 156, 157, 158, 159, 185, 159, 185, 186, 282, 318, 337, and 338. In addition, compounds of formula (I), including but not limited to Examples 164, 165, 218, 219, 221, 222, are examples of amides and esters.

Compositions of the Invention

An embodiment provides pharmaceutical compositions comprising a therapeutically effective amount of a compound of formula (I) or a pharmaceutically acceptable salt, ester, amide or prodrug thereof, in combination with a pharmaceutically acceptable carrier. The compositions comprise compounds of the formula (I) formulated together with one or more non-toxic pharmaceutically acceptable carriers. The pharmaceutical compositions can be formulated for oral administration in solid or liquid form, for parenteral injection or for rectal administration.

The pharmaceutical compositions can be administered to humans and other mammals orally, rectally, parenterally, intracistemally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of formula (I) are mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of formula (I) with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of compounds of various embodiments include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, eardrops, eye ointments, powders and solutions are also contemplated as being within the scope of this specification.

The ointments, pastes, creams and gels may contain, in addition to one or more active compounds of various embodiments, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to one or more compounds of various embodiments, lactose, talc, silicic acid, aluminum hydroxide, calcium silicates and polyamide powder, or mixtures of these substances. Sprays can additionally contain customary propellants such as chlorofluorohydrocarbons.

Compounds and compositions also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of various embodiments, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this specification. Aqueous liquid compositions also are particularly useful.

The compounds and compositions can be used in the form of pharmaceutically acceptable salts, esters, or amides derived from inorganic or organic acids.

Yet another aspect relates to radiolabelled or isotopically labelled pharmaceutical compositions. Radiolabelled or isotopically labelled forms of compounds of formula (I) are provided as compositions and administered in accordance with the method embodiments. The radiolabelled or isotopically labelled forms of compounds of formula (I) may be used as a pharmaceutical agent or may be useful in the discovery of other compounds which are modulators of $\alpha 7$ NNR. In these uses, the compounds of various embodiments possess at least one atom of a deuterium or tritium.

Another embodiment contemplates pharmaceutically active compounds either chemically synthesized or formed by in vivo biotransformation to compounds of formula (I). The compounds, compositions, and methods of various embodiments will be better understood by reference to the following examples and reference examples, which are intended as an illustration of and not a limitation upon the scope of the specification.

Methods of the Invention

Present compounds and compositions are useful for modulating the effects of NNRs, particularly by allosteric modulation. Such compounds can be useful for the treatment and prevention of a number of NNR-mediated diseases or conditions.

$\alpha 7$ NNRs have been shown to play a significant role in enhancing cognitive function, including aspects of learning, memory and attention (Levin, E. D., *J. Neurobiol.*, 2002, 53: 633-640). As such, $\alpha 7$ ligands are suitable for the treatment of cognitive disorders including, for example, attention deficit disorder, attention deficit hyperactivity disorder (ADHD), Alzheimer's disease (AD), mild cognitive impairment (MCI), senile dementia, AIDS dementia, Pick's disease, dementia associated with Lewy bodies, and dementia associated with Down's syndrome, as well as cognitive deficits associated with schizophrenia.

In addition, $\alpha 7$-NNRs have been shown to be involved in the neuroprotective effects of nicotine both in vitro (Jonnala, R. B. et al., *J. Neurosci. Res.*, 2001, 66: 565-572) and in vivo (Shimohama, S., *Brain Res.*, 1998, 779: 359-363). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of $\alpha 7$ NNRs by β-amyloid peptides linked to Alzheimer's disease has been implicated as a key factor in development of the cognitive deficits associated with the disease (Liu, Q.-S., et al., *PNAS*, 2001, 98: 4734-4739). The activation of $\alpha 7$ NNRs has been shown to block this neurotoxicity (Kihara, T., *J. Biol. Chem.*, 2001, 276: 13541-13546). As such, selective ligands that enhance $\alpha 7$ activity can counter the deficits of Alzheimer's and other neurodegenerative diseases.

Schizophrenia is a complex disease that is characterized by abnormalities in perception, cognition, and emotions. Significant evidence implicates the involvement of α7 NNRs in this disease, including a measured deficit of these receptors in post-mortem patients (Leonard, S., *Eur. J. Pharmacol.*, 2000, 393: 237-242). Deficits in sensory processing (gating) are one of the hallmarks of schizophrenia. These deficits can be normalized by nicotinic ligands that operate at the α7 NNR (Adler, L. E., *Schizophrenia Bull.*, 1998, 24: 189-202; Stevens, K. E., *Psychopharmacology*, 1998, 136: 320-327). Thus, α7 NNR ligands demonstrate potential in the treatment of schizophrenia.

Present compounds are useful for treating and preventing a condition or disorder affecting cognition, neurodegeneration, and schizophrenia. Cognitive impairment associated with schizophrenia often limits the ability of patients to function normally; a symptom not adequately treated by commonly available treatments, for example, treatment with an atypical antipsychotic. (Rowley, M., *J. Med. Chem.*, 2001, 44: 477-501). Such cognitive deficit has been linked to dysfunction of the nicotinic cholinergic system, in particular with decreased activity at α7 NNR receptors. (Friedman, J. I., *Biol Psychiatry*, 2002, 51: 349-357). Thus, activators of α7 NNR receptors can provide useful treatment for enhancing cognitive function in schizophrenic patients who are being treated with atypical antipsychotics. Accordingly, the combination of an α7 NNR modulator and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like. Accordingly, it is contemplated that present compounds and compositions also can be administered in combination with an atypical antipsychotic.

One of the measurable abnormalities in schizophrenic patients, is the P50 auditory gating deficit, an indication of impaired information processing and diminished ability to "filter" unimportant or repetitive sensory information. On the basis of clinical observations that these deficits are normalized by nicotine, it has been suggested that the high prevalence of smoking among patients with schizophrenia (>80%) may a form of self medication. Pharmacological studies have shown that nicotine's mechanisms of action is via α7 NNRs. Restoration of P50 gating deficits in humans by α7 selective ligands, agonists and PAMs could lead to discontinuation of continuous smoking. Therefore, NNR ligands that are selective for the α7 subtype can be used in therapy for smoking cessation, with an improved side effect profile compared to nicotine.

A population of α7 NNRs in the spinal cord modulate serotonergic transmission that have been associated with the pain-relieving effects of nicotinic compounds (Cordero-Erausquin, et al., *Proc. Nat. Acad. Sci.*, 2001, 98: 2803-2807). The α7 NNR ligands demonstrate therapeutic potential for the treatment of pain states, including acute pain, post-surgical pain, as well as chronic pain states including inflammatory pain and neuropathic pain. Moreover, α7 NNRs are expressed on the surface of primary macrophages that are involved in the inflammation response, and that activation of the α7 NNR inhibits release of TNF and other cytokines that trigger the inflammation response (Wang, H., *Nature*, 2003, 421: 384-388). TNF-α plays a pathological role in diverse inflammatory diseases including arthritis and psoriasis and endometriosis. Therefore, selective α7 NNR ligands and modulators demonstrate potential for treating conditions involving inflammation and pain.

Accordingly, present compounds are useful for treating, preventing or both treating and preventing pain, particularly in mammals. Administration of present compounds is useful for treating nociceptive and neuropathic forms of pain, for example, chronic pain, post-surgical pain, neuropathic pain, and diabetic neuropathy.

Furthermore, the administration of a therapeutically effective amount of a compound of formula (I) to a mammal provides a method of treating or preventing condition or disorder selected from attention deficit disorder, attention deficit hyperactivity disorder (ADHD), Alzheimer's disease (AD), mild cognitive impairment (MCI), senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, and depression.

Accordingly, an embodiment is directed to a method of treating conditions and disorders that are regulated by the NNRs using therapeutically effective amounts of present compositions or compounds.

Another embodiment relates to a method of using compounds of formula (I), or a pharmaceutically acceptable salt, ester, amide or prodrug thereof. Compositions containing compounds of formula (I) can be administered in accordance with described methods, typically as part of a therapeutic regimen for treatment or prevention of conditions and disorders related to NNR activity, and more particularly allosteric modulation of NNR activity.

Another embodiment is a method of using compounds of formula (I) for treating or preventing conditions and disorders related to NNR modulation in mammals. More particularly, the method is useful for conditions and disorders related to attention deficit disorder, attention deficit hyperactivity disorder (ADHD), Alzheimer's disease (AD), mild cognitive impairment (MCI), schizophrenia, senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, smoking cessation, depression, and various other conditions modulated by α7 NNRs modulators.

Another embodiment is a method of using present compounds for treating or preventing acute pain, post-surgical pain, chronic pain, inflammation, inflammatory pain, neuropathic pain and diabetic neuropathy.

Another embodiment relates to a method of using compounds of formula (I) for treating or preventing conditions and disorders related to NNR modulation in mammals. More particularly, the method is useful for combining a compound of formula (I) with an atypical antipsychotic. Further, another embodiment is a method of administering the compositions containing present compounds in combination with a nicotinic agonist or an atypical antipsychotic.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers.

The total daily dose of a compound administered to a human or lower animal range from about 0.001 mg/kg body weight to about 1 g/kg body weight. In another embodiment, doses can be in the range of from about 0.001 mg/kg body weight to about 100 mg/kg body weight. If desired, the effective daily dose can be divided into multiple doses for purposes of administration. Consequently, single dose compositions may contain such amounts or submultiples thereof to make up the daily dose.

Another embodiment relates to a method of assessing or diagnosing conditions or disorders related to α7 NNR activity comprising allowing isotope-labeled forms of compounds of formula (I) to interact with cells expressing endogenous α7 NNRs or cells expressing recombinant α7 NNRs and measuring the effects of such isotope-labeled forms of compounds on such cells as explained in Determination of Biological Activity section.

Various embodiments also describe the use of NNR ligands, and particularly PAM compounds, to identify other useful target compounds for treating or preventing, or both, diseases or conditions associated with NNR function, in cell-based assays, for example in high-throughput format, using cells or tissues that express native α7 NNRs for the purpose of identifying novel α7 NNR agonists or PAMs of α7 NNRs.

Another embodiment is a method of identifying an α7 NNR agonist comprising allowing a compound of formula (I) to interact with cells or cell lines endogenously expressing α7 NNRs or cells expressing recombinant α7 NNRs in a fluorescent medium and measuring changes in such fluorescence by known protocols or as described in Determination of Biological Activity section.

Processes of Making the Invention

Another embodiment relates to a process for making compounds of formula (I) from an N-1,3-thiazol-2-ylamide of formula (II),

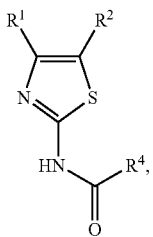

(II)

wherein $R^1$ and $R^4$ are as defined above in formula (I), and $R^2$ is hydrogen, alkyl and alkenyl, wherein the alkyl group and the alkenyl group are substituted with 0, 1, 2, or 3 substituents independently selected from the group consisting of alkoxycarbonyl, alkylcarbonyloxy, aryl, aryloxy, arylalkoxy, carboxy, cyano, cycloalkyl, haloalkoxy, heteroaryl, heterocycle, hydroxyl, nitro, and $R^dR^eN—$, wherein a group represented by $R^2$ can be further substituted with 0, 1, or 2 groups selected from halo and alkoxy.

In another embodiment, the process is for making compounds of formula (I) by coupling an N-1,3-thiazol-2-ylamide of formula (II) with an aryl bromide or iodide, or heteroaryl bromide or iodide using a copper catalyst.

Another embodiment is a process for coupling an N-1,3-thiazol-2-ylamide of formula (II) with an aryl bromide or iodide, or heteroaryl bromide or iodide in the presence of a base. About 1 to about 3 equivalents of an aryl bromide or iodide, or heteroaryl bromide or iodide is used in the process.

In another embodiment of the process for coupling an N-1,3-thiazol-2-ylamide of formula (II), the base is selected from cesium carbonate, potassium carbonate, potassium phosphate, potassium hydroxide, sodium hydride, potassium tert-butoxide, and tetraethylammonium carbonate. The amount of base used can be about 1 equivalent to about 3 equivalents.

In yet another embodiment of the process, an optional additive such as tetrabutylammonium bromide or lithium chloride may be used.

In addition, catalysts and ligands may be used. Catalysts that can be used in the process are copper(I) trifluoromethanesulfonate benzene complex, copper(I) 2-thiophenecarboxylate, copper(I) iodide, copper dust (with a crown ether), copper (I) oxide, copper (I) bromide, copper (I) chloride, copper (I) acetate, copper (II) oxide. The catalysts are used in an amount of about 0.15 equivalents to about 0.50 equivalents.

Optional ligands that can be used in the process are 5-chloro-1,10-phenanthroline, (S)-(−)-1,1'-bi(2-naphthol), ethyl 2-oxocyclohexanecarboxylate, pipecolinic acid, proline, collidine, N,N'-dimethylethylenediamine, N,N,N',N'-tetramethylethylenediamine, trans-cyclohexane-1,2-diamine, trans-N,N'-dimethylcyclohexane-1,2-diamine, 1,10-phenanthroline, 4,7-dimethoxy-1,10-phenanthroline, benzotriazole, N,N-diethylsalicylamide, 1-((1-benzylpyrrolidin-2-yl)methyl)-2-methyl-1H-imidazole, 9-azajulolidine, oxalyl hydrazide, histidine, quinolin-8-ol, 2-aminopyrimidine-4,6-diol, 1-trimethylsilylsulfanyl-2-(dimethylamino)methyl-3-trimethylsilylbenzene, 1,2-dihydroxybenzene, ethylene glycol, phenanthrene-9,10-dione, 2,5-hexanedione, 2,2,6,6-tetramethylheptane-3,5-dione, 2-isobutyrylcyclohexanone, diphenyl pyrrolidine-2-phosphonate, 2-(diphenylphosphinyl)-benzaldoxime, and N,N-dibenzyldinaphtho[2,1-d:1',2'-f][1,3,2]dioxaphosphepin-4-amine.

Solvents used in the process can be selected from but not limited to 1-methyl-2-pyrrolidinone, dimethyl sulfoxide, dimethylformamide, dimethylacetamide, butyronitrile, 1,4-dioxane, xylene, and toluene.

To create a reaction solution of N-1,3-thiazol-2-ylamide of formula (II), liquid ligands such as ethyl 2-oxocyclohexanecarboxylate and liquid aryl bromides or iodides and liquid heteroaryl bromides or iodides are preferentially added with the solvent; or aryl bromides or iodides and heteroaryl bromides or iodides are optionally added with the solvent.

In general, the reaction mixture is maintained at about 20° C. to about 180° C. in the dark for about 6 hours to about 24 hours. The reaction mixture is maintained in a sealed reaction vessel in an inert atmosphere. The sealed reaction vessel may be a septum sealed vessel.

In another embodiment, the process of preparing a compound of formula (I) in a sealed reaction vessel, comprises:
(a) combining the N-1,3-thiazol-2-ylamide of formula (II) with about 1 to about 3 equivalents of an aryl bromide or iodide, or heteroaryl bromide or iodide in the presence of about 1 equivalent to about 3 equivalents of a base selected from cesium carbonate, potassium carbonate, potassium phosphate, potassium hydroxide, sodium hydride, potassium tert-butoxide, and tetraethylammonium carbonate;
(b) adding an optional additive such as tetrabutylammonium bromide or lithium chloride;
(c) adding a catalyst in an amount of about 0.15 equivalents to about 0.50 equivalents, wherein the catalyst is copper(I) trifluoromethanesulfonate benzene complex, copper(I) 2-thiophenecarboxylate, copper(I) iodide, copper dust (with a crown ether), copper (I) oxide, copper (I) bromide, copper (I) chloride, copper (I) acetate, or copper (II) oxide;

(d) adding an optional ligand in an amount of about 0.15 equivalents to about 1.0 equivalents, wherein the optional ligand is 5-chloro-1,10-phenanthroline, (S)-(−)-1,1'-bi(2-naphthol), ethyl 2-oxocyclohexanecarboxylate, pipecolinic acid, proline, collidine, N,N'-dimethylethylenediamine, N,N,N',N'-tetramethylethylenediamine, trans-cyclohexane-1,2-diamine, trans-N,N'-dimethylcyclohexane-1,2-diamine, 1,10-phenanthroline, 4,7-dimethoxy-1,10-phenanthroline, benzotriazole, N,N-diethylsalicylamide, 1-((1-benzylpyrrolidin-2-yl)methyl)-2-methyl-1H-imidazole, 9-azajulolidine, oxalyl hydrazide, histidine, quinolin-8-ol, 2-aminopyrimidine-4,6-diol, 1-trimethylsilylsulfanyl-2-(dimethylamino)methyl-3-trimethylsilylbenzene, 1,2-dihydroxybenzene, ethylene glycol, phenanthrene-9,10-dione, 2,5-hexanedione, 2,2,6,6-tetramethylheptane-3,5-dione, 2-isobutyrylcyclohexanone, diphenyl pyrrolidine-2-phosphonate, 2-(diphenylphosphinyl)-benzaldoxime, or N,N-dibenzyldinaphtho[2,1-d:1',2'-f][1,3,2]dioxaphosphepin-4-amine;

(e) evacuating the vessel and filling with nitrogen several times;

(f) adding a solvent, wherein the solvent is selected from 1-methyl-2-pyrrolidinone, dimethyl sulfoxide, dimethylformamide, dimethylacetamide, butyronitrile, 1,4-dioxane, xylene, and toluene;

(g) creating a reaction solution of about 0.8 M to about 1.5 M of N-1,3-thiazol-2-ylamide of formula (II); wherein liquid ligands such as ethyl 2-oxocyclohexanecarboxylate and liquid aryl bromides or iodides and liquid heteroaryl bromides or iodides are preferentially added with the solvent; or aryl bromides or iodides and heteroaryl bromides or iodides are optionally added with the solvent; and (h) maintaining temperature of the reaction mixture at about 20° C. to about 180° C. in the dark for about 6 hours to about 24 hours.

The above novel processes and other known methods have been used in preparing compounds of formula (I) and are further described in the Examples 1-516, which are intended as an illustration of and not a limitation upon the scope of the inventive processes.

Preparation of Compounds of Formula (I)

The methods described below can entail use of various enantiomers. Where the stereochemistry is shown in the Schemes, it is intended for illustrative purposes only.

The instant compounds can be prepared according to the synthetic methods described in this section, Methods of the Invention and Examples sections. Certain groups described in the Schemes are meant to illustrate certain substituent contained within the scope of the specification and are not intended to limit the scope. Representative procedures are shown in, but are not limited to, Schemes 1-10.

Scheme 1

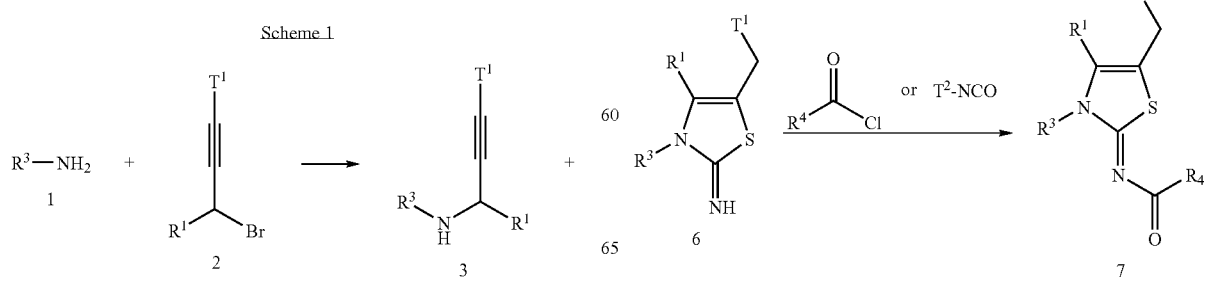

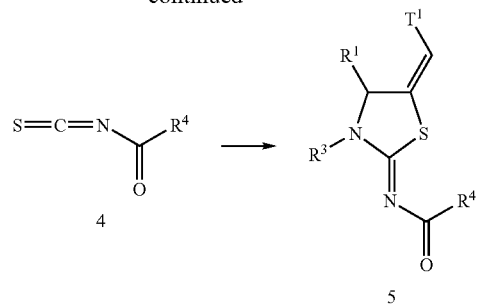

As outlined in Scheme 1, compounds of formula 5 are representative of compounds of formula 5 wherein $T^1$ is hydrogen or alkyl, and $R^1$, $R^3$ and $R^4$ are as defined in formula (I), can be prepared accordingly. Compounds of formula 1 when treated with compounds of formula 2 in a solvent such as toluene at about 70° C. to about 100° C. over 8 to about 24 hours provides compounds of formula 3. Compounds of formula 3 when treated with an acylisothiocyanate of formula 4, wherein $R^4$ is as defined in formula (I) in a solvent such as tetrahydrofuran at about 30° C. to about 65° C. over 2 to about 12 hours furnishes compounds of formula 5, which are representatives of compounds of formula (I).

Scheme 2

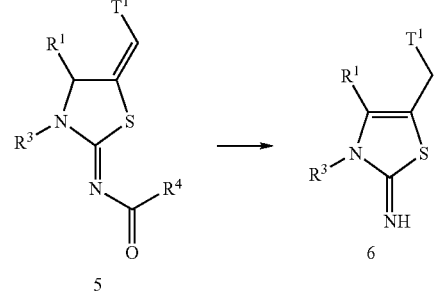

As outlined in Scheme 2, compound of formula 5, wherein $R^1$ and $R^3$ are as defined in formula (I), $T^1$ is hydrogen or alkyl, and $R^4$ is alkyl can be converted to the compound of formula 6 by treatment with an acid such as concentrated hydrochloric acid in a solvent such as methanol at a temperature of about 25° C. to about 65° C. over 12 to about 48 hours furnishes compounds of formula 6.

Scheme 3

As outlined in Scheme 3, compounds of formula 6 when treated with acyl chloride, carbamyl chloride, or isocyanate, wherein $T^2$ is alkyl, cycloalkyl, aryl, or heteroaryl, in a solvent such as acetonitrile at about 50° C. to about 100° C. over 8 to about 24 hours supplies compounds of formula 7 wherein $T^1$ is hydrogen or alkyl, and $R^1$, $R^3$ and $R^4$ are as defined for formula (I).

Scheme 4

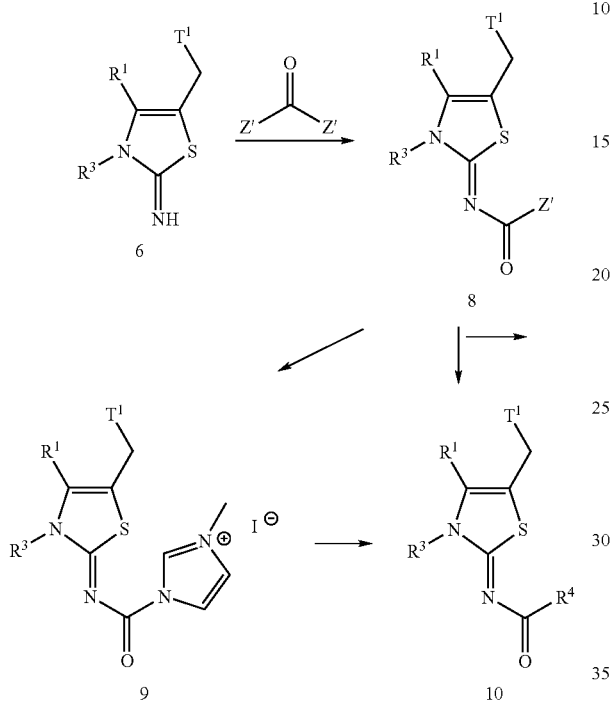

As outlined in Scheme 4, compounds of formula 6 can be treated with compounds of formula Z'C(O)Z', wherein Z' is chloro, imidazolyl, or —O-succinimidyl in a solvent such as acetonitrile for a period of about 1 hour to about 8 hours to provide compounds of formula 8, wherein $T^1$ is hydrogen or alkyl, $R^1$ and $R^3$ are as defined for formula (I), and Z' is chloro, imidazolyl, or —O-succinimidyl. When Z' is imidazolyl, compounds of formula 8 can be treated with methyl iodide, methyl sulfate, or methyl trifluoromethanesulfonate at room temperature in a solvent such as acetonitrile for about 3 days to about 7 days to give compounds of formula 9. Then compounds of formula 9 can be treated with amines or heterocycles such as but not limited to pyrrolidine and 1-(piperazin-1-yl)ethanone in the presence of a base such as diisopropylethylamine in a solvent such as acetonitrile at about 50° C. to about 75° C. over 1 to about 8 hours to give compounds of formula 10. Alternatively, the reaction can be conducted at ambient temperature over 5 minutes to about 24 hours. When Z' is chloro or —O-succinimidyl, compounds of formula 8 can be treated with amines or heterocycles such as but not limited to pyrrolidine to provide compounds of formula 10.

Scheme 5

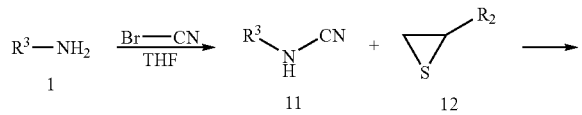

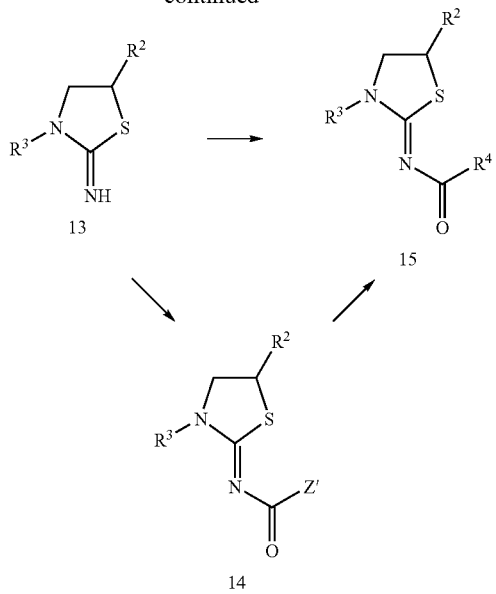

As outlined in Scheme 5, compounds of formula 1, wherein $R^3$ is defined in formula (I), can be treated with cyanogen bromide in tetrahydrofuran to give compounds of formula 11. Cyanamides of formula 11 can be treated with thiiranes of formula 12, wherein $R^2$ is defined in formula (I), in the presence of a base such as potassium carbonate and in a solvent such as 2-butanone at or near the reflux temperature for a period of about 1 hour to about 5 hours to furnish compounds of formula 13. Compounds of formula 13 can be converted to compounds of formula 15 as described in Scheme 3. Compounds of formula 13 can also be converted to compounds of formula 14 and subsequently 15 as described in Scheme 4.

Scheme 6

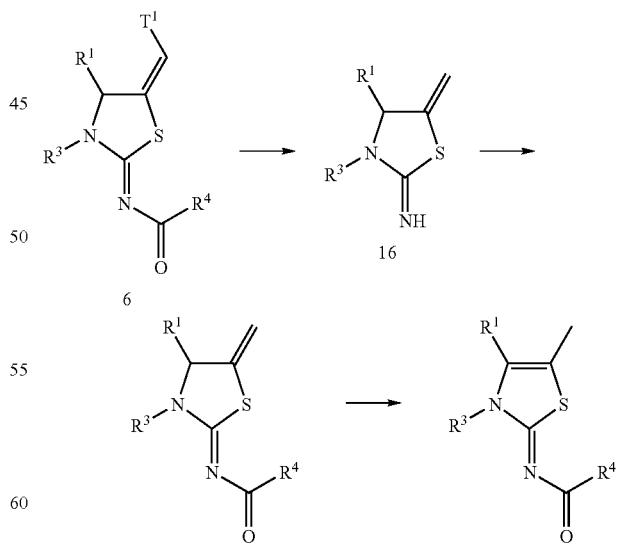

As outlined in Scheme 6, compounds of formula 6, wherein $T^1$ is hydrogen, $R^1$ and $R^3$ are as defined for formula (I), and $R^4$ is methyl, can be treated with sodium perborate in acetic acid to give compounds of formula 16. Compounds of formula 16 can be transformed to compounds of formula 17 first by reacting with phosgene in the presence of diisopropylamine in dichloromethane at about −40 to about −50° C. and then introducing an amine and allowing the reaction mixture to warm to room temperature. Compounds of formula 17, wherein $R^4$ contains a nitrogen attached to the adjacent carbonyl, can be treated with a base such as sodium methoxide in methanol at about 40° C. to about 60° C. from about 4 to about 10 hours to provide compounds of formula 18.

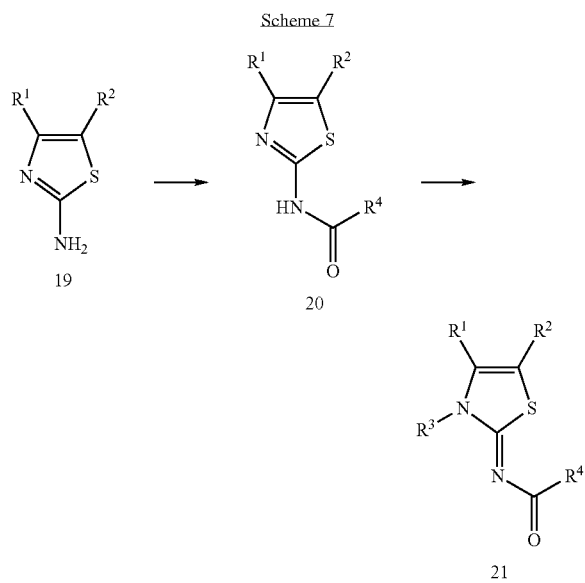

Scheme 7

As outlined in Scheme 7, thiazole-2-amines of formula 19, wherein $R^1$ and $R^2$ are defined for formulas (I) and (II), can be converted to compounds of formula 20. A one-step method for this conversion involves reacting an acyl chloride in the presence of a base such as triethylamine in a solvent like acetonitrile for about 5 minutes to about 60 minutes. A two-step alternative involves first reacting the thiazole-2-amine of formula 19 with carbonyldiimidazole in tetrahydrofuran at about 60° C. for about 4 hours to about 10 hours, or with phosgene in the presence of diisopropylethylamine in dichloromethane at about −60° C. to about −45° C. for about 15 minutes to about 60 minutes, or with N,N′-disuccinimidyl carbonate in the presence of pyridine in acetonitrile at ambient temperature for about 15 minutes to about 60 minutes. Subsequently, the respective leaving groups can be displaced with an amine or heterocycle bearing an NH moiety. For the imidazolyl group, this occurs in tetrahydrofuran at about 60° C. over 4 hours to about 8 hours. For the chloro, this occurs in dichloromethane initially at about −60° C. followed by gradual warming to ambient temperature. For the —O-succinimidyl moiety, this occurs at room temperature with overnight stirring.

Compounds of formula 20, wherein $R^2$ and $R^4$ are described for formula (I), can be converted to compounds of formula 21, wherein $R^3$ is defined for formula (I), in a copper catalyzed coupling reaction with an aryl iodide or bromide, or heteroaryl bromide or iodide. Several reaction conditions accomplish this transformation. One set of conditions include copper(I) trifluoromethanesulfonate benzene complex, 5-chloro-1,10-phenanthroline, and cesium carbonate in 1-methyl-2-pyrrolidinone at about 120° C. for about 10 hours to about 24 hours. Another set of conditions include copper(I) 2-thiophenecarboxylate and cesium carbonate in 1-methyl-2-pyrrolidinone at about 130° C. to about 140° C. for about 10 days to about 24 hours. Yet another set of conditions include copper(I) iodide, ethyl 2-oxocyclohexanecarboxylate and cesium carbonate in dimethyl sulfoxide at about 70° C. for about 2 hours to about 8 hours and then at about 90° C. to about 95° C. for about 15 hours to about 24 hours.

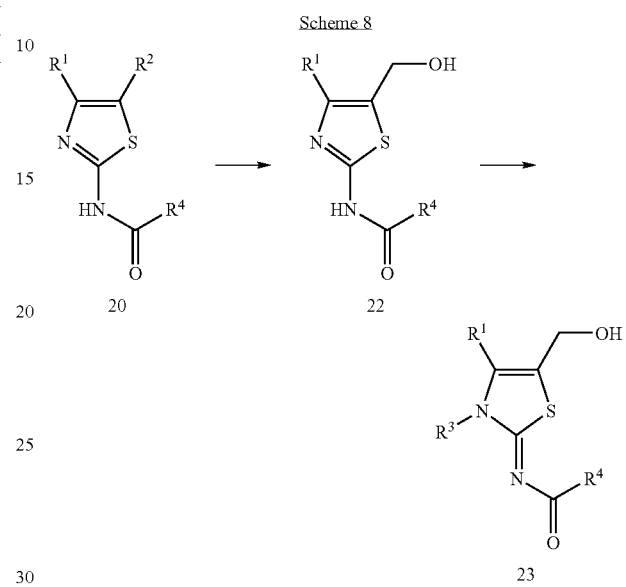

Scheme 8

As outlined in Scheme 8, compounds of formula 20, wherein $R^1$ and $R^4$ are define for formula (I) and $R^2$ is hydrogen, can be transformed to compounds of formula 22 by treatment overnight with 37% formaldehyde in a solvent such as ethanol and in the presence of a base such as potassium phosphate buffer solution at about 40° C. to about 50° C. Compounds of formula 22 can be converted to compounds of formula 23, wherein $R^3$ is defined for formula (I), by reacting compounds of formula 22 with an aryl bromide or iodide or heteroaryl bromide or iodide in the presence of copper(I) iodide, cesium carbonate, and ethyl 2-cyclohexanecarboxylate in dimethyl sulfoxide overnight at about 95° C.

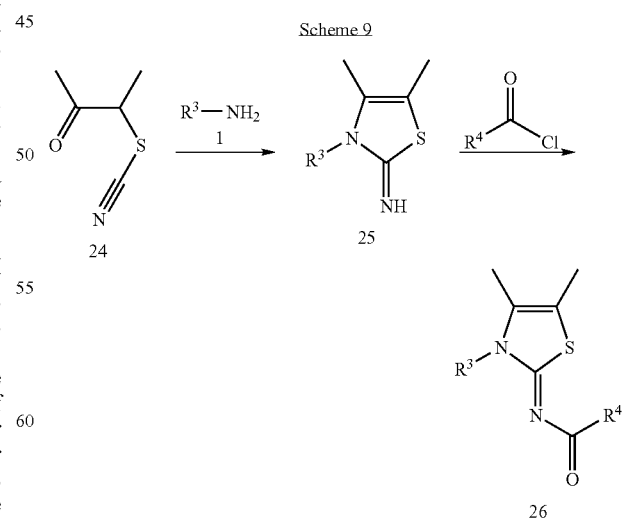

Scheme 9

As outlined in Scheme 9, 3-thiocyano-2-butanone, 24, can be reacted with amines of formula 1, wherein $R^3$ is defined for formula (I), over 3 hours to about 8 hours in refluxing toluene to provide compounds of formula 25. Compounds of formula 25 can be reacted with acyl chlorides or carbamyl chlorides in the presence of a base such as diisopropylethylamine in a solvent such as acetonitrile at about 70° C. to about 80° C. for about 15 hours to about 24 hours to supply compounds of formula 26.

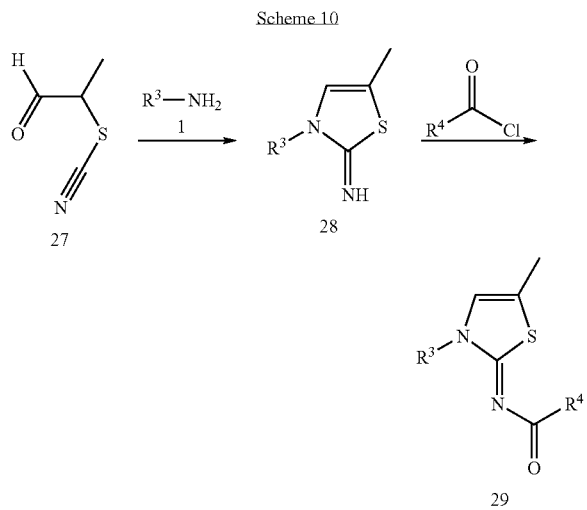

Scheme 10

As outlined in Scheme 10, 2-thiocyanatopropanal, 27, can be reacted in the synthetic sequence described in Scheme 9 to furnish compounds of formula 28 and subsequently compounds of formula 29.

In addition, nitrogen protecting groups can be used for protecting amine groups during the synthesis of compounds of formula (I). Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation and acetyl and trifluoroacetyl protecting groups may be removed by variety of conditions including the use of sodium, potassium or lithium hydroxide in aqueous organic or alcoholic solvents.

The compounds and intermediates thereof may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Some compounds have at least one basic site whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

EXAMPLES

Abbreviations

DMSO for dimethyl sulfoxide, MeOH for methanol, HPLC for high performance liquid chromatography, ERK for extracellular receptor kinase, FBS for fetal bovine serum, HBSS for Hank's Balanced Salt Solution, HEPES for 4-(2-hydroxyethyl)-1-piperazineethanesulfonic acid, PBS for phosphate buffered saline, and SDS for sodium dodecyl sulfate.

General Procedures and Preparation of Intermediates

Preparation of Propargyl Anilines

To a stirred solution of aniline in anhydrous toluene was dropwise added propargyl bromide (0.99 equivalents). The mixture was heated to 80° C. overnight after which it was allowed to cool to ambient temperature and filtered. The filtrate was concentrated under reduced pressure and purified by column chromatography using dichloromethane as eluant to provide the title compound.

Intermediate P1. 4-methoxy-N-prop-2-ynylaniline

The title compound was obtained according to the procedure outlined in the General Procedure for Preparation of Propargyl Anilines using 4-methoxyaniline. MS (DCI) m/z 162 (M+H)$^+$.

Intermediate P2. 4-(difluoromethoxy)-N-prop-2-ynylaniline

The title compound was obtained according to the procedure outlined in the General Procedure for Preparation of Propargyl Anilines using 4-difluoromethoxyaniline. MS (DCI) m/z 198 (M+H)$^+$.

Intermediate P3. N-prop-2-ynyl-4-(trifluoromethoxy)aniline

The title compound was obtained according to the procedure outlined in the General Procedure for Preparation of Propargyl Anilines using 4-(trifluoromethoxy)aniline. MS (DCI) m/z 216 (M+H)$^+$.

Intermediate P4. 4-chloro-N-prop-2-ynylaniline

The title compound was obtained according to the procedure outlined in the General Procedure for Preparation of Propargyl Anilines using 4-chloroaniline. MS (DCI) m/z 166 (M+H)$^+$.

Intermediate P5. 4-fluoro-N-prop-2-ynylaniline

The title compound was obtained according to the procedure outlined in the General Procedure for Preparation of Propargyl Anilines using 4-fluoroaniline. MS (DCI) m/z 150 (M+H)$^+$.

Intermediate P6.
N-prop-2-ynyl-4-(trifluoromethyl)aniline

The title compound was obtained according to the procedure outlined in the General Procedure for Preparation of Propargyl Anilines using 4-(trifluoromethyl)aniline. MS (DCI) m/z 200 (M+H)$^+$.

Preparation of Thiazoline Acetamides

A solution of propargyl aniline and acetyl isothiocyanate (1 equivalent) in dry tetrahydrofuran was stirred at 50° C. for 6 hours. The solvent was removed under reduced pressure and the residue purified by column chromatography using dichloromethane as eluant to provide the title compound.

Intermediate A1. N-[(2Z)-3-(4-methoxyphenyl)-5-methylene-1,3-thiazolidin-2-ylidene]acetamide The title compound was obtained according to the procedure outlined in the General Procedure for Preparation of Thiazoline Acetamides using Intermediate PI. MS (ESI) m/z 263 (M+H)$^+$.

Intermediate A2. N-{(2Z)-3-[4-(difluoromethoxy)phenyl]-5-methylene-1,3-thiazolidin-2-ylidene}acetamide The title compound was obtained according to the procedure outlined in the General Procedure for Preparation of Thiazoline Acetamides using Intermediate P2. MS (ESI) m/z 299 (M+H)$^+$.

Intermediate A3. N-{(2Z)-5-methylene-3-[4-(trifluoromethoxy)phenyl]-1,3-thiazolidin-2-ylidene}acetamide The title compound was obtained according to the procedure outlined in the General Procedure for Preparation of Thiazoline Acetamides using Intermediate P3. MS (ESI) m/z 317 (M+H)$^+$.

Intermediate A4. N-[(2Z)-3-(4-chlorophenyl)-5-methylene-1,3-thiazolidin-2-ylidene]acetamide The title compound was obtained according to the procedure outlined in the General Procedure for Preparation of Thiazoline Acetamides using Intermediate P4. MS (ESI) m/z 267 (M+H)$^+$.

Intermediate A5. N-[(2Z)-3-(4-fluorophenyl)-5-methylene-1,3-thiazolidin-2-ylidene]acetamide The title compound was obtained according to the procedure outlined in the General Procedure for Preparation of Thiazoline Acetamides using Intermediate P5. MS (ESI) m/z 251 (M+H)$^+$.

Intermediate A6. N-{(2Z)-5-methylene-3-[4-(trifluoromethyl)phenyl]-1,3-thiazolidin-2-ylidene}acetamide The title compound was obtained according to the procedure outlined in the General Procedure for Preparation of Thiazoline Acetamides using Intermediate P6. MS (ESI) m/z 301 (M+H)$^+$.

Preparation of Thiazoline Imines

A thiazolidin-2-ylidene acetamide was suspended in methanol and then concentrated aqueous hydrochloric acid (20 equivalents) was added. The resultant mixture was heated at 65° C. for 20 hours. After cooling, the mixture was concentrated under reduced pressure by removing most of the organic phase. The residue was diluted with dichloromethane and washed with a cold aqueous ammonium hydroxide solution (pH 10 after wash). The organic layer was washed with water and brine (250 mL), dried, and concentrated to give the title compound. Crude material will be used without additional purification for the next step.

Intermediate I1. 3-(4-methoxyphenyl)-5-methyl-1,3-thiazol-2(3H)-imine

The title compound was obtained according to the procedure outlined in General Procedure for Preparation of Thiazoline Imines using Intermediate A1. MS (ESI) m/z 221 (M+H).

Intermediate I2. 3-[4-(difluoromethoxy)phenyl]-5-methyl-1,3-thiazol-2(3H)-imine The title compound was obtained according to the procedure outlined in General Procedure for Preparation of Thiazoline Imines using Intermediate A2. MS (ESI) m/z 257 (M+H).

Intermediate I3. 5-methyl-3-[4-(trifluoromethoxy)phenyl]-1,3-thiazol-2(3H)-imine The title compound was obtained according to the procedure outlined in General Procedure for Preparation of Thiazoline Imines using Intermediate A3. MS (ESI) m/z 275 (M+H).

Intermediate I4. 3-(4-chlorophenyl)-5-methyl-1,3-thiazol-2(3H)-imine

The title compound was obtained according to the procedure outlined in General Procedure for Preparation of Thiazoline Imines using Intermediate A4. MS (ESI) m/z 225 (M+H).

Intermediate I5. 3-(4-fluorophenyl)-5-methyl-1,3-thiazol-2(3H)-imine

The title compound was obtained according to the procedure outlined in General Procedure for Preparation of Thiazoline Imines using Intermediate A5. MS (ESI) m/z 209 (M+H).

Intermediate I6. 5-methyl-3-[4-(trifluoromethyl)phenyl]-1,3-thiazol-2(3H)-imine The title compound was obtained according to the procedure outlined in General Procedure for Preparation of Thiazoline Imines using Intermediate A6. MS (ESI) m/z 259 (M+H).

Thiazolylidine Ureas and Amides

A mixture of thiazoline imine, triethylamine (3 equivalents), and a reagent selected from a carbamyl chloride, an acyl chloride or an isocyanate (1.5 equivalents) in acetonitrile was heated to 70° C. for 15 hours followed by concentration under reduced pressure. The residue was extracted with dichloromethane (3×20 mL), the combined organic layers were washed with a saturated aqueous solution of sodium bicarbonate, water and then brine. The organic solution was dried over sodium sulfate, filtered, and concentrated under reduced pressure. The residue was purified by column chromatography using a mixture of dichloromethane-methanol (95:5) as eluant to provide the title compound.

Example 1

N'-[(2Z)-3-(4-methoxyphenyl)-5-methyl-1,3-thiazol-2(3H)-ylidene]-N,N-dimethylurea The title compound was obtained according to the procedure outlined in the General Procedure for Preparation of Thiazoline Ureas and Amides using Intermediate I1 and N,N-dimethyl carbamoyl chloride.

$^1$H NMR (CDCl$_3$) δ ppm 1.70 (3H), 2.95 (6H), 3.75 (3H), 6.60 (1H), 7.10-7.35 (4H); MS (ESI) 292 (M+H)$^+$.

Example 2

N-[(2Z)-3-[4-(difluoromethoxy)phenyl]-5-methyl-1,3-thiazol-2(3H)-ylidene]pyrrolidine-1-carboxamide The title compound was obtained according to the procedure outlined in the General Procedure for Preparation of Thiazoline Ureas and Amides using Intermediate I2 and 1-pyrrolidinecarbonyl chloride.

$^1$H NMR (CDCl$_3$) δ ppm 1.65 (4H), 2.01 (3H), 3.40 (4H), 6.60 (1H), 7.15-7.40 (5H); MS (ESI) 354 (M+H)$^+$.

Example 3

N-[(2Z)-3-[4-(difluoromethoxy)phenyl]-5-methyl-1,3-thiazol-2(3H)-ylidene]piperidine-1-carboxamide The title compound was obtained according to the procedure outlined in the General Procedure for Preparation of Thiazoline Ureas and Amides using Intermediate I2 and 1-piperidinecarbonyl chloride.

$^1$H NMR (CDCl$_3$) δ ppm 1.60 (6H), 2.21 (3H), 3.45 (4H), 6.65 (1H), 7.10-7.45 (5H); MS (ESI) m/z 368 (M+H)$^+$.

Example 4

N'-[(2Z)-3-[4-(difluoromethoxy)phenyl]-5-methyl-1,3-thiazol-2(3H)-ylidene]-N,N-diethylurea The title compound was obtained according to the procedure outlined in the General Procedure for Preparation of Thiazoline Ureas and Amides using Intermediate I2 and N,N-diethyl carbamoyl chloride.

$^1$H NMR (CDCl$_3$) δ ppm 1.25 (6H), 2.21 (3H), 3.45 (4H), 6.55 (1H), 7.05-7.40 (5H); MS (ESI) m/z 356 (M+H)$^+$.

Example 5

N-[(2Z)-5-methyl-3-[4-(trifluoromethoxy)phenyl]-1,3-thiazol-2(3H)-ylidene]pyrrolidine-1-carboxamide The title compound was obtained according to the procedure outlined in the General Procedure for Preparation of Thiazoline Ureas and Amides using Intermediate I3 and 1-pyrrolidinecarbonyl chloride.

$^1$H NMR (CDCl$_3$) δ ppm 1.65 (4H), 2.00 (3H), 3.45 (4H), 6.70 (1H), 7.15-7.40 (4H); MS (ESI) m/z 372 (M+H)$^+$.

Example 6

N,N-diethyl-N'-[(2Z)-5-methyl-3-[4-(trifluoromethoxy)phenyl]-1,3-thiazol-2(3H)-ylidene]urea The title compound was obtained according to the procedure outlined in the General Procedure for Preparation of Thiazoline Ureas and Amides using Intermediate I3 and N,N-diethyl carbamoyl chloride.

$^1$H NMR (CDCl$_3$) δ ppm 1.28 (6H), 1.95 (3H), 3.40 (4H), 6.55 (1H), 7.00-7.40 (4H); MS (ESI) m/z 374 (M+H)$^+$.

Example 7

N,N-dimethyl-N'-[(2Z)-5-methyl-3-[4-(trifluoromethoxy)phenyl]-1,3-thiazol-2(3H)-ylidene]urea The title compound was obtained according to the procedure outlined in the General Procedure for Preparation of Thiazoline Ureas and Amides using Intermediate I3 and N-dimethyl carbamoyl chloride.

$^1$H NMR (CDCl$_3$) δ ppm 1.90 (3H), 2.95 (6H), 6.75 (1H), 7.15-7.35 (4H); MS (ESI) m/z 346 (M+H)$^+$.

Example 8

N-[(2Z)-3-(4-chlorophenyl)-5-methyl-1,3-thiazol-2(3H)-ylidene]pyrrolidine-1-carboxamide The title compound was obtained according to the procedure outlined in the General Procedure for Preparation of Thiazoline Ureas and Amides using Intermediate I4 and 1-pyrrolidinecarbonyl chloride.

$^1$H NMR (CDCl$_3$) δ ppm 1.65 (4H), 2.00 (3H), 3.50 (4H), 6.85 (1H), 7.10-7.45 (4H); MS (ESI) m/z 322 (M+H)$^+$.

Example 9

N-[(2Z)-3-(4-chlorophenyl)-5-methyl-1,3-thiazol-2(3H)-ylidene]piperidine-1-carboxamide The title compound was obtained according to the procedure outlined in the General Procedure for Preparation of Thiazoline Ureas and Amides using Intermediate I4 and 1-piperidinecarbonyl chloride.

$^1$H NMR (CDCl$_3$) δ ppm 1.50 (6H), 2.20 (3H), 3.55 (4H), 6.90 (1H), 7.15-7.50 (4H); MS (ESI) m/z 336 (M+H)$^+$.

Example 10

N'-[(2Z)-3-(4-chlorophenyl)-5-methyl-1,3-thiazol-2(3H)-ylidene]-N,N-diethylurea

The title compound was obtained according to the procedure outlined in the General Procedure for Preparation of Thiazoline Ureas and Amides using Intermediate I4 and N,N-diethyl carbamoyl chloride.

$^1$H NMR (CDCl$_3$) δ ppm 1.25 (6H), 2.05 (3H), 3.45 (4H), 6.95 (1H), 7.00-7.45 (4H); MS (ESI) m/z 324 (M+H)$^+$.

Example 11

N'-[(2Z)-3-(4-chlorophenyl)-5-methyl-1,3-thiazol-2(3H)-ylidene]-N-methyl-N-phenylurea The title compound was obtained according to the procedure outlined in the General Procedure for Preparation of Thiazoline Ureas and Amides using Intermediate I4 and N-methyl(phenyl) carbamoyl chloride.

$^1$H NMR (CDCl$_3$) δ ppm 2.15 (3H), 2.80 (3H), 6.90 (1H), 7.00-7.75 (9H); MS (ESI) m/z 358 (M+H)$^+$.

Example 12

N'-[(2Z)-3-(4-chlorophenyl)-5-methyl-1,3-thiazol-2 (3H)-ylidene]-N,N-dimethylurea The title compound was obtained according to the procedure outlined in the General Procedure for Preparation of Thiazoline Ureas and Amides using Intermediate I4 and N-dimethyl carbamoyl chloride.

$^1$H NMR (CDCl$_3$) δ ppm 2.00 (3H), 3.00 (6H), 6.85 (1H), 7.10-7.45 (4H); MS (ESI) m/z 296 (M+H)$^+$.

Example 13

N-[(2Z)-3-(4-fluorophenyl)-5-methyl-1,3-thiazol-2 (3H)-ylidene]pyrrolidine-1-carboxamide The title compound was obtained according to the procedure outlined in the General Procedure for Preparation of Thiazoline Ureas and Amides using Intermediate I5 and 1-pyrrolidinecarbonyl chloride.

$^1$H NMR (CDCl$_3$) δ ppm 1.65 (4H), 2.05 (3H), 3.55 (4H), 6.95 (1H), 7.30-7.55 (4H); MS (ESI) m/z 306 (M+H)$^+$.

Example 14

N-[(2Z)-3-(4-fluorophenyl)-5-methyl-1,3-thiazol-2 (3H)-ylidene]piperidine-1-carboxamide The title compound was obtained according to the procedure outlined in the General Procedure for Preparation of Thiazoline Ureas and Amides using Intermediate I5 and 1-piperidinecarbonyl chloride.

$^1$H NMR (CDCl$_3$) δ ppm 1.55 (6H), 2.25 (3H), 3.35 (4H), 6.95 (1H), 7.35-7.50 (4H); MS (ESI) m/z 320 (M+H)$^+$.

Example 15

N,N-diethyl-N'-[(2Z)-3-(4-fluorophenyl)-5-methyl-1, 3-thiazol-2(3H)-ylidene]urea The title compound was obtained according to the procedure outlined in the General Procedure for Preparation of Thiazoline Ureas and Amides using Intermediate I5 and N,N-diethyl carbamoyl chloride.

$^1$H NMR (CDCl$_3$) δ ppm 1.20 (6H), 2.00 (3H), 3.55 (4H), 6.90 (1H), 7.20-7.55 (4H); MS (ESI) m/z 308 (M+H)$^+$.

Example 16

N'-[(2Z)-3-(4-fluorophenyl)-5-methyl-1,3-thiazol-2 (3H)-ylidene]-N,N-dimethylurea The title compound was obtained according to the procedure outlined in the General Procedure for Preparation of Thiazoline Ureas and Amides using Intermediate I5 and N,N-dimethyl carbamoyl chloride.

$^1$H NMR (CDCl$_3$) δ ppm 1.95 (3H), 3.20 (6H), 6.95 (1H), 7.20-7.50 (4H); MS (ESI) m/z 280 (M+H)$^+$.

Example 17

N-[(2Z)-3-(4-fluorophenyl)-5-methyl-1,3-thiazol-2 (3H)-ylidene]cyclobutanecarboxamide The title compound was obtained according to the procedure outlined in the General Procedure for Preparation of Thiazoline Ureas and Amides using Intermediate I5 and cyclobutane carbonyl chloride.

$^1$H NMR (CDCl$_3$) δ ppm 1.95 (3H), 2.00-2.30 (6H), 2.85 (1H), 6.95 (1H), 7.25-7.50 (4H); MS (ESI) m/z 291 (M+H)$^+$.

Example 18

N-[(2Z)-5-methyl-3-[4-(trifluoromethyl)phenyl]-1,3-thiazol-2(3H)-ylidene]pyrrolidine-1-carboxamide Example 18A N-[(2Z)-5-methyl-3-[4-(trifluoromethyl)phenyl]-1,3-thiazol-2(3H)-ylidene]-1H-imidazole-1-carboxamide Intermediate I6 (5.43 g, 21.05 mmol) in dry acetonitrile (10 mL) was treated with carbonyldiimidazole (21.05 mmol, 3.75 g). After 3 hours, the reaction was diluted with 200 mL of dichloromethane, and then washed with a saturated solution of sodium bicarbonate (75 mL), water (75 mL) and brine. The organic layer was dried over sodium sulfate and concentrated under reduced pressure to give the title compound used without additional purification in the next step.

MS (ESI) 353 (M+H)$^+$.

Example 18B 3-methyl-1-({[(2Z)-5-methyl-3-[4-(trifluoromethyl) phenyl]-1,3-thiazol-2(3H)-ylidene]amino}carbonyl)-1H-imidazol-3-ium iodide N-[(2Z)-5-methyl-3-[4-(trifluoromethyl)phenyl]-1,3-thiazol-2(3H)-ylidene]-1H-imidazole-1-carboxamide (2.0 g, 5.68 mmol, Example 18A) in acetonitrile (10 mL) was treated with iodomethane (3 mL). The mixture was stirred at room temperature for five days, the solvent was evaporated, and the title product was used directly for the next step.

Example 18C

N-[(2Z)-5-methyl-3-[4-(trifluoromethyl)phenyl]-1,3-thiazol-2(3H)-ylidene]pyrrolidine-1-carboxamide To a solution of 3-methyl-1-({[(2Z)-5-methyl-3-[4-(trifluoromethyl)phenyl]-1,3-thiazol-2(3H)-ylidene] amino}carbonyl)-1H-imidazol-3-ium iodide (0.1 g, 0.2 mmol, Example 18B) and pyrrolidine (1.2 equivalents) in anhydrous acetonitrile (3 mL) was added Hunig's base (33 mg, 1.2 equivalents), and the resultant solution was heated at 60° C. for 3 hours. After cooling to room temperature, the reaction mixture was diluted with dichloromethane (25 mL) and washed with water and brine, dried over sodium sulfate, and concentrated under reduced pressure. The crude residue was chromatographed over silica using dichloromethane to give the title compound.

¹H NMR (CDCl₃) δ ppm 1.60 (4H), 2.00 (3H), 3.50 (4H), 6.85 (1H), 7.20-7.35 (4H); MS (ESI) m/z 356 (M+H)⁺.

Example 19

N,N-dimethyl-N'-[(2Z)-5-methyl-3-[4-(trifluoromethyl)phenyl]-1,3-thiazol-2(3H)-ylidene]urea The title compound was obtained using the procedure described in Example 18 substituting pyrrolidine with dimethylamine.
¹H NMR (CDCl₃) δ ppm 1.90 (3H), 3.35 (6H), 6.90 (1H), 7.25-7.35 (4H); MS (ESI) m/z 330 (M+H)⁺.

Example 20

2-methyl-N-[(2Z)-5-methyl-3-[4-(trifluoromethyl)phenyl]-1,3-thiazol-2(3H)-ylidene]pyrrolidine-1-carboxamide The title compound was obtained using the procedure described in Example 18 substituting pyrrolidine with 2-methylpyrrolidine.
¹H NMR (CDCl₃) δ ppm 1.25 (3H), 1.40-1.60 (4H), 2.00 (3H), 3.35 (2H), 3.45 (1H), 6.95 (1H), 7.20-7.55 (4H); MS (ESI) m/z 370 (M+H)⁺.

Example 21

(2R)-2-methyl-N-[(2Z)-5-methyl-3-[4-(trifluoromethyl)phenyl]-1,3-thiazol-2(3H)-ylidene]pyrrolidine-1-carboxamide The title compound was obtained using the procedure described in Example 18 substituting pyrrolidine with (R)-2-methylpyrrolidine.
¹H NMR (CDCl₃) δ ppm 1.25 (3H), 1.45-1.60 (4H), 2.05 (3H), 3.35 (2H), 3.45 (1H), 6.95 (1H), 7.20-7.55 (4H); MS (ESI) m/z 370 (M+H)⁺.

Example 22

(2S)-2-methyl-N-[(2Z)-5-methyl-3-[4-(trifluoromethyl)phenyl]-1,3-thiazol-2(3H)-ylidene]pyrrolidine-1-carboxamide The title compound was obtained using the procedure described in Example 18 substituting pyrrolidine with (S)-2-methylpyrrolidine.
¹H NMR (CDCl₃) δ ppm 1.25 (3H), 1.40-1.60 (4H), 2.05 (3H), 3.35 (2H), 3.50 (1H), 6.95 (1H), 7.20-7.55 (4H); MS (ESI) m/z 370 (M+H)⁺.

Example 23

N-[(2Z)-5-methyl-3-[4-(trifluoromethyl)phenyl]-1,3-thiazol-2(3H)-ylidene]-2,5-dihydro-1H-pyrrole-1-carboxamide The title compound was obtained using the procedure described in Example 18 substituting pyrrolidine with 2,5-dihydro-1H-pyrrole.
¹H NMR (CDCl₃) δ ppm 2.05 (3H), 3.55 (4H), 5.75 (2H), 6.95 (1H), 7.25-7.50 (4H); MS (ESI) m/z 354 (M+H)⁺.

Example 24

N-[(2Z)-3-(4-chlorophenyl)-1,3-thiazolidin-2-ylidene]pyrrolidine-1-carboxamide

Example 24A (2Z)-3-(4-chlorophenyl)-1,3-thiazolidin-2-imine

N-(4-Chlorophenyl)cyanamide (250 mg, 1.638 mmol), thiirane (98 μL, 1.646 mmol) and potassium carbonate (238 mg, 1.720 mmol) in 2-butanone were heated to reflux. After 2 hours, the reaction was cool down, diluted with 100 mL of dichloromethane, and washed with water (2×75 mL) and brine (75 mL). The organic phase was dried over magnesium sulfate, filtered and concentrated under reduced pressure to give the title compound which was used directly for the next step.
¹H NMR (CDCl₃) δ ppm 3.25 (2H), 4.05 (2H), 7.40 (4H); MS (ESI) m/z 307 (M+H)⁺.

Example 24B

N-[(2Z)-3-(4-chlorophenyl)-1,3-thiazolidin-2-ylidene]pyrrolidine-1-carboxamide

The title compound was obtained according to the procedure outlined in the General Procedure for Preparation of Thiazoline Ureas and Amides using (2Z)-3-(4-chlorophenyl)-1,3-thiazolidin-2-imine (Example 24A) and 1-pyrrolidinecarbonyl chloride.
¹H NMR (CD₃OD) δ ppm 1.90 (4H), 3.50 (6H), 4.05 (2H), 7.40-7.55 (4H); MS (ESI) m/z 310 (M+H)⁺.

Example 25

(3R)-N-[(2Z)-3-(4-chlorophenyl)-1,3-thiazolidin-2-ylidene]-3-fluoropyrrolidine-1-carboxamide Example 25A N-[(2Z)-3-(4-chlorophenyl)-1,3-thiazolidin-2-ylidene]-1H-imidazole-1-carboxamide (2Z)-3-(4-Chlorophenyl)-1,3-thiazolidin-2-imine (233 mg, 1.095 mmol, Example 24A) and carbonyldiimidazole (195 mg, 1.205 mmol) in dry tetrahydrofuran were heated at 65° C. After 14 hours the reaction mixture cooled down, diluted with 75 mL of dichloromethane, and washed successively with sodium bicarbonate (50 mL) water and brine (50 mL), dried over magnesium sulfate and concentrated under reduced pressure to give the title compound.
¹H NMR (CD₃OD) δ ppm 3.40 (2H), 4.25 (2H), 6.95 (1H), 7.40 (1H), 7.50 (4H), 8.05 (1H); MS (ESI) m/z 307 (M+H)⁺.

Example 25B 1-({[(2Z)-3-(4-chlorophenyl)-1,3-thiazolidin-2-ylidene]amino}carbonyl)-3-methyl-1H-imidazol-3-ium iodide N-[(2Z)-3-(4-Chlorophenyl)-1,3-thiazolidin-2-ylidene]-1H-imidazole-1-carboxamide (320 mg, 1.043 mmol, Example 25A) was suspended in dry acetonitrile (5 mL), and then iodomethane (0.325 mL, 5.22 mmol) was added. The mixture stirred at room temperature. After four days, the solvent was evaporated to give the title product.

Example 25C (3R)-N-[(2Z)-3-(4-chlorophenyl)-1,3-thiazolidin-2-ylidene]-3-fluoropyrrolidine-1-carboxamide To a solution of 1-({[(2Z)-3-(4-chlorophenyl)-1,3-thiazolidin-2-ylidene]amino}carbonyl)-3-methyl-1H-imidazol-3-ium iodide (0.22 mmol, Example 25B) and (R)-2-fluoropyrrolidine (1.2 equivalents) in anhydrous acetonitrile (3 mL) was added Hunig's base (35 mg, 1.2 equivalents), and the solution was heated at 60° C. for 3 hours. After cooling to room temperature, the reaction mixture was diluted with dichloromethane (25 mL) and washed with water and brine, dried over sodium sulfate, and concentrated under reduced pressure. The crude residue was chromatographed over silica using dichloromethane to give the title compound.
$^1$H NMR (CD$_3$OD) δ ppm 2.00 (2H), 3.40 (6H), 4.05 (2H), 5.10-5.25 (1H) 7.40-7.55 (4H); MS (ESI) m/z 328 (M+H)$^+$.

Example 26

N'-[(2Z)-3-(4-chlorophenyl)-1,3-thiazolidin-2-ylidene]-N-methyl-N-prop-2-ynylurea 1-({[(2Z)-3-(4-Chlorophenyl)-1,3-thiazolidin-2-ylidene]amino}carbonyl)-3-methyl-1H-imidazol-3-ium iodide (97 mg, 0.216 mmol, Example 25B), N-methylprop-2-yn-1-amine (0.020 mL, 0.238 mmol) and diisopropylethylamine (0.041 mL, 0.238 mmol) were heated in acetonitrile at 65° C. After 1 hour, the mixture was concentrated and the residue was purified by chromatography over silica using dichloromethane:methanol 95:5 as eluant to provide the title compound.
$^1$H NMR (CD$_3$OD) δ ppm 2.90 (3H), 3.20 (3H), 4.05 (2H), 4.15 (2H), 7.40-7.50 (4H); MS (ESI) m/z 308 (M+H)$^+$.

Example 27

N'-[(2Z)-3-(4-chlorophenyl)-1,3-thiazolidin-2-ylidene]-N-(3-fluorobenzyl)-N-methylurea To a solution of 1-({[(2Z)-3-(4-Chlorophenyl)-1,3-thiazolidin-2-ylidene]amino}carbonyl)-3-methyl-1H-imidazol-3-ium iodide (94 mg, 0.209 mmol, Example 25B) in dry acetonitrile (3 mL) were added diisopropylethylamine (0.040 mL, 0.230 mmol) and 1-(3-fluorophenyl)-N-methylmethanamine (0.032 mL, 0.230 mmol). The mixture was heated for 2 hours, and then cooled and concentrated under reduced pressure. The residue was purified by chromatography over silica using dichloromethane:methanol 95:5 as eluant to provide the title compound.
$^1$H NMR (CD$_3$OD) δ ppm 2.85 (3H), 3.25 (2H), 4.05 (2H), 4.55 (2H), 6.80-7.50 (8H); MS (ESI) m/z 378 (M+H)$^+$.

Example 28

N-{(2Z)-5-methylene-3-[4-(trifluoromethyl)phenyl]-1,3-thiazolidin-2-ylidene}azetidine-1-carboxamide

Example 28A 5-methylene-3-[4-(trifluoromethyl)phenyl]-1,3-thiazolidin-2-imine Intermediate A6 (4.955 g, 16.5 mmol) was dissolved into acetic acid (40 mL) and treated with sodium perborate (2.70 g, 33 mmol). More sodium perborate was added after 60 minutes (327 mg) and 80 minutes (327 mg). After another 20 minutes the mixture was concentrated from ethyl acetate three times, and partitioned between 1:1 ethyl acetate/hexanes (80 mL) and concentrated ammonium hydroxide (50 mL). The aqueous phase was separated and extracted with more 1:1 ethyl acetate/hexanes, and the combined organic phases were dried (sodium sulfate), concentrated onto silica, and chromatographed thrice on silica (ethyl acetate/dichloromethane/hexanes).
$^1$H NMR (400 MHz, CD$_2$Cl$_2$) δ ppm 4.78 (2H), 5.14 (1H), 5.31 (1H), 7.2 (1H), 7.63 (2H), 7.78 (2H); MS (ESI) m/z 259 (M+H)$^+$.

Example 28B

N-{(2Z)-5-methylene-3-[4-(trifluoromethyl)phenyl]-1,3-thiazolidin-2-ylidene}azetidine-1-carboxamide Example 28A (0.43 g) was dissolved into dichloromethane (20 mL) and chilled to −45° C. Then 20% phosgene in toluene (0.98 mL) was added over less than five seconds, followed three minutes later with diisopropylethylamine (0.40 mL). The solution was stirred 16 minutes at −45° C., treated with azetidine (0.25 mL), and stirred briefly before being warmed to room temperature. Concentrated aqueous ammonium hydroxide (3 mL) was added, followed by ethyl acetate (3 mL). The aqueous phase was separated and extracted with dichloromethane, and the combined organic phases were dried (sodium sulfate), concentrated, and chromatographed on silica (ethyl acetate/dichloromethane/hexanes). The appropriate fractions were concentrated, dissolved into 3:2 dichloromethane/hexanes, and washed twice with 0.1 M aqueous KH$_2$PO$_4$; each aqueous phase was back-extracted with dichloromethane. The combined organic phases were dried (sodium sulfate) and concentrated to give the title compound.
$^1$H NMR (500 MHz, CD$_2$Cl$_2$) δ ppm 2.20 (2H), 3.99 (4H), 4.72 (2H), 5.26 (1H), 5.32 (1H), 7.65 (2H), 7.76 (2H); MS (ESI) m/z 342 (M+H)$^+$.

Example 29

N-[(2Z)-5-methyl-3-[4-(trifluoromethyl)phenyl]-1,3-thiazol-2(3H)-ylidene]azetidine-1-carboxamide Example 28B (25 mg, 0.07 mmol) was suspended in methanol (0.7 mL), treated with 25% sodium methoxide (3 drops), and heated at 50° C. for 6 hours, then at room temperature over the weekend. The mixture was concentrated, passed through silica (methanol/dichloromethane), and concentrated, and the residue was again mixed in methanol (0.7 mL), treated with 25% sodium methoxide (3 drops), and heated at 50° C. for 2 hours. The mixture was concentrated, passed through silica (methanol/dichloromethane), and concentrated to give the title compound.
$^1$H NMR (400 MHz, CD$_2$Cl$_2$) δ ppm 2.15 (2H), 2.23 (3H), 3.94 (4H), 6.71 (1H), 7.68-7.75 (4H); MS (ESI) m/z 342 (M+H)$^+$.

Example 30

N-[(2Z)-5-methyl-3-(2-naphthyl)-1,3-thiazol-2(3H)-ylidene]pyrrolidine-1-carboxamide

Example 30A

N-(5-methyl-1,3-thiazol-2-yl)pyrrolidine-1-carboxamide

A solution of 5-methylthiazol-2-amine (4.8 g, 42 mmol), N,N-carbonyldiimidazole (9.8 g, 61 mmol), and 4-dimethylaminopyridine (0.1 g, 1.0 mmol) in tetrahydrofuran (90 mL) was heated at 65° C. for 6 hours. Pyrrolidine (5.1 mL, 61 mmol) was then added and heating was continued at 65° C. for 48 hours. The mixture was concentrated, and the residue was diluted with methanol and then triturated with diethyl ether. The solids were collected by filtration, washed with diethyl ether, and recrystallized from ethyl acetate to give the title compound.

$^1$H NMR (300 MHz, CDCl$_3$) δ ppm 1.96 (4H), 2.35 (3H), 3.45 (4H), 6.95 (1H); MS (DCI/NH$_3$) m/z 212 (M+H)$^+$.

Example 30B

N-[(2Z)-5-methyl-3-(2-naphthyl)-1,3-thiazol-2(3H)-ylidene]pyrrolidine-1-carboxamide Example 30A (32 mg, 0.15 mmol), 2-bromonaphthalene (38 mg, 0.18 mmol), copper(I) trifluoromethanesulfonate benzene complex (8 mg, 0.03 mmol in Cu), 5-chlorophenanthroline (13 mg, 0.061 mmol), and cesium carbonate (55 mg, 0.17 mmol) were added to a reaction vial with a septum-containing cap, and flushed with nitrogen three times. Then anhydrous 1-methyl-2-pyrrolidinone (0.15 mL) was added through the septum, the mixture was stirred for 15 minutes at room temperature, and then heated at 120° C. in the dark for 16 hours. Then the mixture was quenched with 2:1 water/concentrated aqueous ammonium hydroxide (0.45 mL), and extracted thrice with 4:1 ethyl acetate/hexanes. The combined organic phases were washed with more aqueous ammonium hydroxide, dried (sodium sulfate), concentrated, and chromatographed on silica (ethyl acetate/dichloromethane/hexanes) to give the title compound.

$^1$H NMR (300 MHz, MeOH-d$_4$) δ ppm 1.7-1.9 (4H), 2.28 (3H), 3.27 (2H), 3.38 (2H), 7.03 (1H), 7.49-7.57 (2H), 7.67 (1H), 7.84-7.98 (4H); MS (ESI) m/z 338 (M+H)$^+$.

Example 31

N-[(2Z)-5-methyl-3-(3-methylisothiazol-5-yl)-1,3-thiazol-2(3H)-ylidene]pyrrolidine-1-carboxamide Example 30A (32 mg, 0.15 mmol), 5-bromo-3-methylisothiazole (32 mg, 0.18 mmol), copper (I) 2-thiophenecarboxylate (5.7 mg, 0.030 mmol), and cesium carbonate (59 mg, 0.18 mmol) were added to a reaction vial with a septum-containing cap, and flushed with nitrogen three times. Then anhydrous 1-methyl-2-pyrrolidinone (0.15 mL) was added through the septum, the mixture was stirred for 15 minutes at room temperature, and then heated at 100° C. in the dark for over 7 hours. Then the mixture was quenched with 2:1 water/concentrated aqueous ammonium hydroxide (0.45 mL), and extracted thrice with 4:1 ethyl acetate/hexanes. The combined organic phases were washed with more aqueous ammonium hydroxide, dried (sodium sulfate), concentrated, and chromatographed on silica (ethyl acetate/dichloromethane/hexanes) to give the title compound.

$^1$H NMR (300 MHz, CDCl$_3$) δ ppm 1.85-2.05 (4H), 2.30 (3H), 2.48 (3H), 3.57 (2H), 3.77 (2H), 6.92 (1H), 7.01 (1H); MS (ESI) m/z 309 (M+H)$^+$.

Example 32

N-[(2Z)-3-(4-bromophenyl)-1,3-thiazol-2(3H)-ylidene]pyrrolidine-1-carboxamide

Example 32A

N-1,3-thiazol-2-ylpyrrolidine-1-carboxamide

Thiazol-2-amine (7.01 g, 10.0 mmol) was dissolved into dichloromethane (700 mL) and cooled to −60° C. The resulting suspension was treated with 20% phosgene in toluene (54 mL, 103 mmol) over 5 minutes and stirred for 10 minutes more before the addition of diisopropylethylamine (24 mL, 138 mmol). After the mixture was stirred for another 20 minutes near −60° C., pyrrolidine (17.5 mL, 210 mmol) was added, and after a few minutes the cold bath was removed. The mixture was warmed to 10° C. over a period of more than an hour, and then was quenched with concentrated aqueous ammonium hydroxide (100 mL) and stirred thoroughly. The aqueous phase was separated and extracted with dichloromethane, and the combined organic phases were washed twice with water; each aqueous phase was back-extracted with dichloromethane. The combined organic phases were concentrated to a slurry and diluted with 2:1 hexanes/ethyl acetate (30 mL). The solids were collected by filtration, rinsed with more 2:1 hexanes/ethyl acetate, slurried and rinsed in 2:1 hexanes/dichloromethane, and dried under vacuum to give the title compound.

$^1$H NMR (300 MHz, d$_6$-DMSO) δ ppm 1.77-1.93 (4H), 3.33-3.45 (4H), 7.01 (1H), 7.33 (1H); MS (ESI) m/z 198 (M+H)$^+$.

Example 32B

N-[(2Z)-3-(4-bromophenyl)-1,3-thiazol-2(3H)-ylidene]pyrrolidine-1-carboxamide

Example 32A (60 mg, 0.30 mmol), 1,4-dibromobenzene (106 mg, 0.45 mmol), copper (I) 2-thiophenecarboxylate (11.5 mg, 0.060 mmol), and cesium carbonate (118 mg, 0.36 mmol) were added to a reaction vial with a septum-containing cap, and flushed with nitrogen three times. Then anhydrous 1-methyl-2-pyrrolidinone (0.30 mL) was added through the septum, the mixture was stirred a while at room temperature, and then heated at 130° C. in the dark for 16 hours. Then the mixture was quenched with concentrated aqueous ammonium hydroxide (0.30 mL), mixed with dilute brine and 4:1 ethyl acetate/hexanes, and passed through diatomaceous earth with a 4:1 ethyl acetate/hexanes rinse. The aqueous phase was separated and back-extracted with 4:1 ethyl acetate/hexanes. The combined organic phases were washed twice with concentrated aqueous ammonium hydroxide, dried (sodium sulfate), concentrated, and chromatographed on silica (1% ethanol/19% ethyl acetate/40% dichloromethane/40% hexanes) to give the title compound.

$^1$H NMR (300 MHz, CDCl$_3$) δ ppm 1.73-1.92 (4H), 3.36 (2H), 3.49 (2H), 6.50 (1H), 6.94 (1H), 7.46 (2H), 7.59 (2H).

Example 33

N-(3-fluorobenzyl)-N-methyl-N'-[(2Z)-5-methyl-3-(2-naphthyl)-1,3-thiazol-2(3H)-ylidene]urea Example 33A N-(3-fluorobenzyl)-N-methyl-N'-(5-methyl-1,3-thiazol-2-yl)urea 5-Methylthiazol-2-amine (571 mg, 5.00 mmol) was dissolved into dichloromethane (30 mL) and cooled to near −45° C. Diphosgene (360 μL, 3.0 mmol) was added rapidly over a second or two, and the mixture was stirred for 5 minutes before diisopropylethylamine (1.74 mL, 10 mmol) was added. The solution was stirred for another 30 minutes, 3-fluorobenzyl-methylamine (1.03 mL, 7.5 mmol) was added, and after another couple of minutes the cold bath was removed. When the reaction solution had warmed to near room temperature, it was quenched with 1 M aqueous potassium phosphate monobasic (15 mL). The aqueous phase was separated and back-extracted with dichloromethane, and the combined organic phases were washed with more 1 M aqueous $KH_2PO_4$ (5 mL). The aqueous phase was separated and back-extracted with dichloromethane. The combined organic phases were dried (sodium sulfate), concentrated, and chromatographed on acidic alumina (ethyl acetate/hexanes) to give the title compound.

$^1$H NMR (300 MHz, $d_6$-DMSO) δ ppm 2.26 (3H), 2.93 (3H), 4.59 (2H), 6.9-7.2 (4H), 7.33-7.44 (1H); MS (ESI) m/z 280 (M+H)$^+$.

Example 33B

N-(3-fluorobenzyl)-N-methyl-N'-[(2Z)-5-methyl-3-(2-naphthyl)-1,3-thiazol-2(3H)-ylidene]urea Example 33A (56 mg, 0.20 mmol), 2-bromonaphthalene (50 mg, 0.24 mmol), copper (I) 2-thiophenecarboxylate (7.7 mg, 0.04 mmol), and cesium carbonate (78 mg, 0.24 mmol) were added to a reaction vial with a septum-containing cap, and flushed with nitrogen three times. Then anhydrous 1-methyl-2-pyrrolidinone (0.20 mL) was added through the septum, the mixture was stirred a while at room temperature, and then heated at 140° C. in the dark for 18 hours. Then the mixture was quenched with concentrated aqueous ammonium hydroxide (0.40 mL), mixed with 4:1 ethyl acetate/hexanes, and passed through diatomaceous earth with a 4:1 ethyl acetate/hexanes rinse. The aqueous phase was separated and back-extracted with 4:1 ethyl acetate/hexanes. The combined organic phases were washed with concentrated aqueous ammonium hydroxide, dried (sodium sulfate), concentrated, and purified by reverse phase HPLC using an acetonitrile/water 10 mM ammonium acetate method to give the title compound.

$^1$H NMR (300 MHz, $d_4$-MeOH) δ ppm 2.33 (3H), 2.8-3.0 (3H), 4.45-4.60 (2H), 6.7-8.1 (12H); MS (ESI) m/z 406 (M+H)$^+$.

Example 34

(3R)-N-[(2Z)-3-(5-cyanothien-2-yl)-5-methyl-1,3-thiazol-2(3H)-ylidene]-3-fluoropyrrolidine-1-carboxamide Example 34A (3R)-3-fluoro-N-(5-methyl-1,3-thiazol-2-yl)pyrrolidine-1-carboxamide 5-Methylthiazol-2-amine (2.28 g, 20.0 mmol) was dissolved into dichloromethane (200 mL) and cooled to near −50° C. 20% Phosgene in toluene (12.6 mL, 24 mmol) was added rapidly over less than 30 seconds and stirred for 10 minutes more at −45° C. before the addition of diisopropylethylamine (17.4 mL, 100 mmol). The mixture was stirred for another 30 minutes near −45° C., (R)-3-fluoropyrrolidine hydrochloride (5.02 g, 40 mmol) was added, and after five minutes the cold bath was removed and the reaction warmed slowly to room temperature. The solution was quenched and stirred thoroughly with concentrated aqueous ammonium hydroxide (25 mL). The aqueous phase was separated and extracted with dichloromethane, and the combined organic phases were washed twice with water; each aqueous phase was back-extracted with dichloromethane. The combined organic phases were concentrated and then slurried in 3:1 hexanes/ethyl acetate. The solids were collected by filtration, rinsed with more 3:1 hexanes/ethyl acetate, and then slurried and rinsed first with 3:1 hexanes/dichloromethane, and then with 1:1 hexanes/dichloromethane to give the title compound.

$^1$H NMR (300 MHz, $d_6$-DMSO) δ ppm 1.9-2.23 (2H), 2.28 (3H), 3.2-3.8 (4H), 5.34 (1H), 6.99 (1H), 10.5 (1H); MS (ESI) m/z 230 (M+H)$^+$.

Example 34B (3R)-N-[(2Z)-3-(5-cyanothien-2-yl)-5-methyl-1,3-thiazol-2(3H)-ylidene]-3-fluoropyrrolidine-1-carboxamide Example 34A (46 mg, 0.20 mmol), copper (I) iodide (7.6 mg, 0.04 mmol), (S)-(−)-1,1'-bi(2-naphthol) (11.5 mg, 0.04 mmol), and cesium carbonate (78 mg, 0.24 mmol) were added to a reaction vial with a septum-containing cap, and flushed with nitrogen three times. Then 5-bromothiophene-2-carbonitrile (27 µL, 0.24 mmol) and anhydrous 1-methyl-2-pyrrolidinone (0.20 mL) were added through the septum, the mixture was stirred a while at room temperature, and then heated in the dark first at 70° C. for 5 hours and then at 90° C. for 15 hours. Then the mixture was quenched with concentrated aqueous ammonium hydroxide (0.40 mL), mixed with 4:1 ethyl acetate/hexanes, and passed through diatomaceous earth with a 4:1 ethyl acetate/hexanes rinse. The aqueous phase was separated and back-extracted with 4:1 ethyl acetate/hexanes. The combined organic phases were washed with concentrated aqueous ammonium hydroxide, dried (sodium sulfate), concentrated, and chromatographed twice on silica (ethyl acetate/dichloromethane) to give the title compound.

$^1$H NMR (300 MHz, $d_4$-MeOH) δ ppm 2.0-2.4 (2H), 2.33 (3H), 3.5-4.2 (4H), 5.2-5.5 (1H), 7.39 (1H), 7.64 (1H), 7.69 (1H); MS (ESI) m/z 337 (M+H)$^+$.

Example 35

N-[(2Z)-5-(hydroxymethyl)-3-(2-naphthyl)-1,3-thiazol-2(3H)-ylidene]pyrrolidine-1-carboxamide Example 35A N-[5-(hydroxymethyl)-1,3-thiazol-2-yl]pyrrolidine-1-carboxamide Example 32A (1.973 g, 10.0 mmol) was suspended into ethanol (25 mL) and treated first with 1.0 M aqueous pH~13 potassium phosphate buffer (2.0 mL) and then with 37% aqueous formaldehyde (3.0 mL, 40 mmol). Then the mixture was heated at 40° C. overnight. More buffer (2.0 mL) was added and heating was continued until the next day. The mixture was treated with 2 M aqueous $H_3PO_4$ (1.5 mL), partially concentrated, and concentrated twice from acetonitrile. The residue was suspended in water (10 mL) and pressed with a glass rod to induce solidification. The solids were collected by filtration, rinsed with water and 3:1 ethyl acetate/hexanes, and dried under vacuum to give the title compound.

MS (ESI) m/z 228 (M+H)$^+$.

Example 35B

N-[(2Z)-5-(hydroxymethyl)-3-(2-naphthyl)-1,3-thiazol-2(3H)-ylidene]pyrrolidine-1-carboxamide Example 35A (46 mg, 0.20 mmol), copper (I) iodide (7.6 mg, 0.04 mmol), 2-bromonaphthalene (50 mg, 0.24 mmol), and cesium carbonate (78 mg, 0.24 mmol) were added to a reaction vial with a septum-containing cap, and flushed with nitrogen three times. Then ethyl 2-oxocyclohexanecarboxylate (12.8 µL, 0.08 mmol) and anhydrous dimethyl sulfoxide (0.20 mL) were added through the septum, the mixture was stirred one hour at room temperature, and then heated in the dark first at 70° C. for 16 hours and then at 90° C. for 5.5 hours. Then the mixture was quenched with concentrated aqueous ammonium hydroxide (0.60 mL), mixed with 4:1 ethyl acetate/hexanes, and passed through diatomaceous earth with both concentrated aqueous ammonium hydroxide and 4:1 ethyl acetate/hexanes rinses. The organic phase was separated, dried (sodium sulfate), concentrated, and chromatographed on silica (ethyl acetate/hexanes) to give the title compound.

$^1$H NMR (300 MHz, d$_4$-MeOH) δ ppm 1.7-1.9 (4H), 3.31 (2H), 3.40 (2H), 4.62 (2H), 7.31 (1H), 7.52-7.60 (2H), 7.72 (1H), 7.89-7.96 (2H), 7.97 (1H), 8.03 (1H); MS (ESI) m/z 354 (M+H)$^+$.

Example 36

(3R)-3-fluoro-N-[(2Z)-5-(hydroxymethyl)-3-(2-naphthyl)-1,3-thiazol-2(3H)-ylidene]pyrrolidine-1-carboxamide Example 36A (3R)-3-fluoro-N-1,3-thiazol-2-ylpyrrolidine-1-carboxamide A solution of 2-aminothiazole (10.02 g, 100 mmol) and pyridine (8.3 mL, 103 mmol) in anhydrous acetonitrile (300 mL) was added to a thick suspension of N,N'-disuccinimidyl carbonate (26.13 g, 102 mmol) in acetonitrile (25 mL) with a small acetonitrile rinse. The mixture was stirred thoroughly for another 20 minutes, and then (R)-3-fluoropyrrolidine hydrochloride (13.06 g, 104 mmol) and diisopropylethylamine (70 mL, 402 mmol) were added and the reaction was stirred at room temperature overnight before being concentrated under vacuum. The residue was dissolved into ethyl acetate (100 mL), and then partitioned with hexanes (20 mL) and 3:1 water/brine (20 mL). The aqueous phase was separated and repeatedly back-extracted with 5:1 ethyl acetate/hexanes. The combined organic phases were washed with brine, and the aqueous phase was back-extracted with more 5:1 solution. The combined organic phases were then concentrated. The solids were dissolved into 6:1 dichloromethane/hexanes, mixed with 4:1 water/brine, and filtered through diatomaceous earth with a 6:1 dichloromethane/hexanes rinse. The filtrate was washed with more dilute brine, and the aqueous phase was separated and back-extracted with more 6:1 solution. This wash with dilute brine was repeated two more times. Then the organic phase was dried (sodium sulfate) and concentrated under vacuum to give the title compound.

$^1$H NMR (300 MHz, d$_6$-DMSO) δ ppm 1.93-2.26 (2H), 3.36-3.81 (4H), 5.36 (1H), 7.03 (1H), 7.35 (1H), 10.7 (1H); MS (ESI) 216 (M+H)$^+$.

Example 36B (3R)-3-fluoro-N-[5-(hydroxymethyl)-1,3-thiazol-2-yl]pyrrolidine-1-carboxamide Example 36A (15.1 g, 70 mmol) was suspended into ethanol (100 mL) and treated first with 1.0 M aqueous pH~13 potassium phosphate buffer (40 mL) and then with 37% aqueous formaldehyde (26.1 mL, 350 mmol). Then the mixture was heated at 45° C. overnight with thorough stirring. Then the mixture was mostly concentrated, and concentrated twice more from acetonitrile. The residue was then partitioned with 4 M aqueous ammonium chloride (10 mL), concentrated aqueous ammonium hydroxide (10 mL), and 4:1 ethyl acetate/acetonitrile (350 mL). The aqueous phase was separated and extracted twice with 4:1 ethyl acetate/acetonitrile. The combined organic phases were washed three times with 1:1 brine/concentrated aqueous ammonium hydroxide (20 mL), and each aqueous phase was back-extracted two or three times with more 4:1 ethyl acetate/acetonitrile. The combined organic phases were dried (sodium sulfate) and concentrated. The pasty residue was diluted with acetonitrile (25 mL), mixed with a spatula to induce solidification, and mixed further with ethyl acetate (10 mL). The solids were collected by filtration, rinsed first with 1:1 acetonitrile/ethyl acetate and then with 1:1 dichloromethane/hexanes, and then dried under vacuum to give the title compound.

$^1$H NMR (300 MHz, d$_6$-DMSO) δ ppm 1.9-2.25 (2H), 3.3-3.8 (4H), 4.52 (2H), 5.26 (1H), 5.35 (1H), 7.15 (1H), 10.7 (1H); MS (ESI) m/z 268 (M+H)$^+$.

Example 36C (3R)-3-fluoro-N-[(2Z)-5-(hydroxymethyl)-3-(2-naphthyl)-1,3-thiazol-2(3H)-ylidene]pyrrolidine-1-carboxamide Example 36B (49 mg, 0.20 mmol), copper (I) iodide (7.6 mg, 0.04 mmol), 2-bromonaphthalene (50 mg, 0.24 mmol), and cesium carbonate (98 mg, 0.30 mmol) were added to a reaction vial with a septum-containing cap, and flushed with nitrogen three times. Then ethyl 2-oxocyclohexanecarboxylate (12.8 µL, 0.08 mmol) and anhydrous dimethyl sulfoxide (0.20 mL) were added through the septum, the mixture was stirred one hour at room temperature, and then heated in the dark first at 70° C. overnight and then at 95° C. for one day. Then the mixture was quenched with concentrated aqueous ammonium hydroxide (0.60 mL), passed through diatomaceous earth with an ethyl acetate rinse, concentrated, and chromatographed on silica (ethyl acetate/hexanes) to give the title compound.

$^1$H NMR (300 MHz, d$_4$-MeOH) δ ppm 1.85-2.3 (2H), 3.3-3.8 (4H), 4.63 (2H), 5.0-5.35 (1H), 7.32 (1H), 7.54-7.60 (2H), 7.72 (1H), 7.90-8.06 (4H); MS (ESI) m/z 372 (M+H)$^+$.

Example 37

(3R)-3-fluoro-N-[(2Z)-5-(hydroxymethyl)-3-[4-(trifluoromethyl)phenyl]-1,3-thiazol-2(3H)-ylidene]pyrrolidine-1-carboxamide Example 36B (49 mg, 0.20 mmol), copper (I) iodide (7.6 mg, 0.04 mmol), and cesium carbonate (98 mg, 0.30 mmol) were added to a reaction vial with a septum-containing cap, and flushed with nitrogen three times. Then 1-iodo-4-(trifluoromethyl)benzene (35 µL, 0.24 mmol), ethyl 2-oxocyclohexanecarboxylate (12.8 µL, 0.08 mmol) and anhydrous dimethyl sulfoxide (0.20 mL) were added through the septum, the mixture was stirred one hour at room temperature, and then heated at 70° C. in the dark overnight. Then the mixture was quenched with concentrated aqueous ammonium hydroxide (0.60 mL), passed through diatomaceous earth with an ethyl acetate rinse, concentrated, and chromatographed on silica (ethyl acetate/hexanes) to give the title compound.

$^1$H NMR (500 MHz, d$_4$-MeOH) δ ppm 1.93-2.26 (2H), 3.37-3.76 (4H), 4.60 (2H), 5.11-5.32 (1H), 7.28 (1H), 7.80-7.86 (4H); MS (ESI) m/z 390 (M+H)$^+$.

Example 38

(3R)-3-fluoro-N-[(2Z)-5-(hydroxymethyl)-3-[5-(trifluoromethyl)thien-2-yl]-1,3-thiazol-2(3H)-ylidene]pyrrolidine-1-carboxamide Example 36B (74 mg, 0.30 mmol), copper (I) iodide (12 mg, 0.06 mmol), and cesium carbonate (147 mg, 0.45 mmol) were added to a reaction vial with a septum-containing cap, and flushed with nitrogen three times. Then 2-bromo-5-(trifluoromethyl)thiophene (48.5 μL, 0.36 mmol), ethyl 2-oxocyclohexanecarboxylate (19.5 L, 0.12 mmol) and anhydrous dimethyl sulfoxide (0.30 mL) were added through the septum, the mixture was stirred 30 minutes at room temperature, and then heated at 95° C. in the dark for 19 hours. Then the mixture was quenched with concentrated aqueous ammonium hydroxide (0.60 mL), passed through diatomaceous earth with an ethyl acetate rinse, concentrated, and purified by reverse phase HPLC using an acetonitrile/water 10 mM ammonium acetate method to give the title compound.
$^1$H NMR (300 MHz, d$_4$-MeOH) δ ppm 2.0-2.4 (2H), 3.5-4.15 (4H), 4.63 (2H), 5.21-5.49 (1H), 7.35-7.38 (1H), 7.45-7.49 (1H), 7.77 (1H); MS (ESI) m/z 396 (M+H)$^+$.

Example 39

(3R)-N-[(2Z)-3-(5-chlorothien-2-yl)-5-(hydroxymethyl)-1,3-thiazol-2(3H)-ylidene]-3-fluoropyrrolidine-1-carboxamide Example 36B (74 mg, 0.30 mmol), copper (I) iodide (12 mg, 0.06 mmol), and cesium carbonate (147 mg, 0.45 mmol) were added to a reaction vial with a septum-containing cap, and flushed with nitrogen three times. Then 2-bromo-5-chlorothiophene (39.5 μL, 0.36 mmol), ethyl 2-oxocyclohexanecarboxylate (19.5 μL, 0.12 mmol) and anhydrous dimethyl sulfoxide (0.30 mL) were added through the septum, the mixture was stirred 30 minutes at room temperature, and then heated at 95° C. in the dark for 19 hours. Then the mixture was quenched with concentrated aqueous ammonium hydroxide (0.60 mL), passed through diatomaceous earth with an ethyl acetate rinse, concentrated, and purified by reverse phase HPLC using an acetonitrile/water 10 mM ammonium acetate method to give the title compound.
$^1$H NMR (300 MHz, d$_4$-MeOH) δ ppm 2.0-2.4 (2H), 3.45-4.1 (4H), 4.61 (2H), 5.20-5.48 (1H), 6.92 (1H), 7.11 (1H), 7.65 (1H); MS (ESI) m/z 362 (M+H)$^+$.

Example 40

(3R)-N-[(2Z)-3-(1-benzothien-5-yl)-5-(hydroxymethyl)-1,3-thiazol-2(3H)-ylidene]-3-fluoropyrrolidine-1-carboxamide Example 36B (74 mg, 0.30 mmol), 5-bromobenzo[b]thiophene (77 mg, 0.36 mmol), copper (I) iodide (12 mg, 0.06 mmol), and cesium carbonate (147 mg, 0.45 mmol) were added to a reaction vial with a septum-containing cap, and flushed with nitrogen three times. Then ethyl 2-oxocyclohexanecarboxylate (19.5 μL, 0.12 mmol) and anhydrous dimethyl sulfoxide (0.30 mL) were added through the septum, the mixture was stirred 30 minutes at room temperature, and then heated at 95° C. in the dark for 19 hours. Then the mixture was quenched with concentrated aqueous ammonium hydroxide (0.60 mL), passed through diatomaceous earth with an ethyl acetate rinse, concentrated, and purified by reverse phase HPLC using an acetonitrile/water 10 mM ammonium acetate method to give the title compound.
$^1$H NMR (300 MHz, d$_4$-MeOH) δ ppm 1.85-2.25 (2H), 3.3-3.8 (4H), 4.61 (2H), 5.0-5.35 (1H), 7.26 (1H), 7.46 (1H), 7.51-7.56 (1H), 7.71 (1H), 7.99-8.06 (2H); MS (ESI) m/z 378 (M+H)$^+$.

Example 41

(3R)-3-fluoro-N-[(2Z)-5-(hydroxymethyl)-3-(2,2,4,4-tetrafluoro-4H-1,3-benzodioxin-6-yl)-1,3-thiazol-2(3H)-ylidene]pyrrolidine-1-carboxamide Example 36B (74 mg, 0.30 mmol), copper (I) iodide (12 mg, 0.06 mmol), and cesium carbonate (147 mg, 0.45 mmol) were added to a reaction vial with a septum-containing cap, and flushed with nitrogen three times. Then 6-bromo-2,2,4,4-tetrafluoro-4H-benzo[d][1,3]dioxine (59 μL, 0.36 mmol), ethyl 2-oxocyclohexanecarboxylate (19.5 μL, 0.12 mmol) and anhydrous dimethyl sulfoxide (0.30 mL) were added through the septum, the mixture was stirred 30 minutes at room temperature, and then heated at 95° C. in the dark for 19 hours. Then the mixture was quenched with concentrated aqueous ammonium hydroxide (0.60 mL), passed through diatomaceous earth with an ethyl acetate rinse, concentrated, and purified by reverse phase HPLC using an acetonitrile/water 10 mM ammonium acetate method to give the title compound.
$^1$H NMR (300 MHz, d$_4$-MeOH) δ ppm 1.9-2.3 (2H), 3.3-3.8 (4H), 4.60 (2H), 5.07-5.38 (1H), 7.31 (1H), 7.47 (1H), 7.92 (1H), 8.20 (1H); MS (ESI) m/z 452 (M+H)$^+$.

Example 42

(3R)-N-[(2Z)-3-(5,6-difluoro-2-naphthyl)-5-(hydroxymethyl)-1,3-thiazol-2(3H)-ylidene]-3-fluoropyrrolidine-1-carboxamide Example 42A 6-bromo-1,1-difluoronaphthalen-2(1H)-one A solution containing 6-bromonaphthalen-2-ol (2 g, 8.97 mmol) in N,N-dimethylformamide (5 mL) was added dropwise to a slurry of Selectfluor™ fluorinating reagent in N,N-dimethylformamide (8 mL) under nitrogen (Examples 42A-42C were similarly described in US2003/0149315.). The temperature of the reaction mixture was maintained around room temperature during addition. The solution was stirred at room temperature for 2 hours. Toluene (40 mL) was added and mixture was stirred for 10 minutes. Then water (30 mL) was added and the mixture was stirred an additional 10 minutes. The organic layer was separated from the aqueous layer and washed with water (2×50 mL). The organic layer was dried over sodium sulfate and concentrated to give the title compound.
$^1$H NMR (CDCl3) δ ppm 6.25 (2H), 7.40 (1H), 7.55 (1H)-7.70 (1H); MS (ESI) m/z 260 (M+H)$^+$.

Example 42B 6-bromo-1,1,2,2-tetrafluoro-1,2-dihydronaphthalene

A solution of 6-bromo-1,1-difluoronaphthalen-2(1H)-one (1.74 g, 6.72 mmol) in dry toluene (6 mL) was heated to 60°

C. under nitrogen. Then Deoxofluor™ ([bis(2-methoxyethyl) amino]sulfur trifluoride (2.478 mL, 13.44 mmol)) was added via syringe. The reaction mixture stirred at 60-65° C. After 3 hours the reaction mixture was cooled down to 0° C. (ice-bath) and quenched by adding methanol dropwise and then subsequently neutralized with sodium hydroxide (4 M). Toluene (25 mL) was added to the mixture and the aqueous layer was separated. The organic layer was washed once with brine (20 mL) and once with water (20 mL) and then dried over sodium sulfate. The product was obtained after evaporation of the solvent. The crude material was added to a silica column (SF40-150) and was eluted with pentane separating 6-bromo-1,2,4-trifluoronaphthalene MS (ESI) m/z 262 (M+H)$^+$ from the desired 6-bromo-1,1,2,2-tetrafluoro-1,2-dihydronaphthalene MS (ESI) m/z 282 (M+H)$^+$.

Example 42C 6-bromo-1,2-difluoronaphthalene

Zinc (341 mg, 5.22 mmol) was added to a stirred mixture of 6-bromo-1,1,2,2-tetrafluoro-1,2-dihydronaphthalene (730 mg, 2.60 mmol) in tetrahydrofuran and concentrated ammonium hydroxide (4 mL) at 0° C. The mixture was allowed to warm slowly to room temperature. After 6 hours the reaction was diluted with 35 mL of dichloromethane and extracted. The organic layer was washed with water (2×30 mL) dried and concentrated. The residue was purified by chromatography on silica gel eluting with pentane:hexane (1:1) to provide the title compound.
$^1$H NMR (CDCl$_3$) δ ppm 7.35 (1H), 7.55 (1H), 7.60 (1H), 7.95 (2H); MS (ESI) 244 (M+H)$^+$.

Example 42D (3R)-N-[(2Z)-3-(5,6-difluoro-2-naphthyl)-5-(hydroxymethyl)-1,3-thiazol-2(3H)-ylidene]-3-fluoro-pyrrolidine-1-carboxamide Example 36B (49 mg, 0.20 mmol), 6-bromo-1,2-difluoronaphthalene (58 mg, 0.24 mmol, Example 42C), copper (I) iodide (7.6 mg, 0.04 mmol), and cesium carbonate (98 mg, 0.30 mmol) were added to a reaction vial with a septum-containing cap, and flushed with nitrogen three times. Then ethyl 2-oxocyclohexanecarboxylate (12.8 µL, 0.08 mmol) and anhydrous dimethyl sulfoxide (0.20 mL) were added through the septum, the mixture was stirred 30 minutes at room temperature, and then heated at 95° C. in the dark overnight. Then the mixture was quenched with concentrated aqueous ammonium hydroxide (0.60 mL), passed through diatomaceous earth with an ethyl acetate rinse, concentrated, and purified by reverse phase HPLC using an acetonitrile/water 10 mM ammonium acetate method to give the title compound.
$^1$H NMR (300 MHz, d$_4$-MeOH) δ ppm 1.8-2.35 (2H), 3.3-3.8 (4H), 4.62 (2H), 5.01-5.36 (1H), 7.34 (1H), 7.54 (1H), 7.82 (1H), 7.91 (1H), 8.13 (1H), 8.20 (1H); MS (ESI) m/z 408 (M+H)$^+$.

Example 43

N-[(2Z)-5-methyl-3-phenyl-1,3-thiazol-2(3H)-ylidene]pyrrolidine-1-carboxamide

To a 4 mL vial equipped with a septum cap and stir bar was added N-(5-methyl-1,3-thiazol-2-yl)pyrrolidine-1-carboxamide (21 mg, 0.1 mmol), copper(I) trifluoromethanesulfonate benzene complex (10 mg, 0.02 mmol), 5-chloro-1,10-phenanthroline (8.5 mg, 0.04 mmol) and cesium carbonate (38.9 mg, 0.12 mmol). The mixture was placed under a nitrogen atmosphere. Iodobenzene (0.12 mmol) in 1-methyl-2-pyrrolidinone (1.0 mL) was added to the mixture. The reaction mixture was heated at 120° C. for overnight. A solution of concentrated ammonium hydroxide/water (1:2, 1 mL) was added and the mixture was filtered and solvent removed under reduced pressure. The residue was purified by reverse phase HPLC (C8, gradient 10-100% acetonitrile/water/0.1% trifluoroacetic acid).
$^1$H NMR (500 MHz, DMSO-d$_6$/D$_2$O) δ ppm 1.76 (t, 4H) 2.20-2.23 (m, 3H) 3.26 (t, 4H) 7.12-7.15 (m, 1H) 7.37-7.42 (m, 1H) 7.48-7.54 (m, 2H) 7.57-7.62 (m, 2H); LCMS (APCI) m/z 288 (M+H)$^+$.

Example 44

N-[(2Z)-5-methyl-3-(3-methylphenyl)-1,3-thiazol-2 (3H)-ylidene]pyrrolidine-1-carboxamide The title compound was prepared using the procedure described in Example 43 substituting 1-iodo-3-methylbenzene for iodobenzene.
$^1$H NMR (500 MHz, DMSO-d$_6$/D$_2$O) δ ppm 1.76 (t, 4H) 2.17-2.25 (m, 3H) 2.33-2.40 (m, 3H) 3.26 (t, 4H) 7.11-7.14 (m, 1H) 7.18-7.23 (m, 1H) 7.37-7.41 (m, 2H) 7.42-7.45 (m, 1H); MS (ESI) m/z 302 (M+H)$^+$.

Example 45

N-[(2Z)-5-methyl-3-(4-methylphenyl)-1,3-thiazol-2 (3H)-ylidene]pyrrolidine-1-carboxamide The title compound was prepared using the procedure described in Example 43 substituting 1-iodo-4-methylbenzene for iodobenzene.
$^1$H NMR (500 MHz, DMSO-d$_6$/D$_2$O) δ ppm 1.76 (t, 4H) 2.18-2.24 (m, 3H) 2.32-2.37 (m, 3H) 3.26 (t, 4H) 7.07-7.11 (m, 1H) 7.31 (d, 2H) 7.47 (d, 2H); MS (ESI) m/z 302 (M+H)$^+$.

Example 46

N-[(2Z)-3-(3-aminophenyl)-5-methyl-1,3-thiazol-2 (3H)-ylidene]pyrrolidine-1-carboxamide The title compound was prepared using the procedure described in Example 43 substituting 3-indoaniline for iodobenzene.
$^1$H NMR (500 MHz, DMSO-d$_6$/D$_2$O) δ ppm 1.77 (t, 4H) 2.20-2.25 (m, 3H) 3.28 (t, 4H) 7.02-7.08 (m, 1H) 7.10-7.17 (m, 1H) 7.22-7.30 (m, 1H) 7.33-7.39 (m, 1H) 7.42-7.49 (m, 1H); MS (ESI) m/z 303 (M+H)$^+$.

Example 47

N-[(2Z)-3-(3-hydroxyphenyl)-5-methyl-1,3-thiazol-2 (3H)-ylidene]pyrrolidine-1-carboxamide The title compound was prepared using the procedure described in Example 43 substituting 3-iodophenol for iodobenzene.
$^1$H NMR (500 MHz, DMSO-d$_6$/D$_2$O) δ ppm 1.77 (t, 4H) 2.16-2.24 (m, 3H) 3.27 (t, 4H) 6.76-6.81 (m, 1H) 6.96-7.01 (m, 1H) 7.03-7.06 (m, 1H) 7.07-7.10 (m, 1H) 7.25-7.34 (m, 1H); MS (ESI) m/z 304 (M+H)$^+$, 302 (M−H)$^−$.

Example 48

N-[(2Z)-3-(4-methoxyphenyl)-5-methyl-1,3-thiazol-2(3H)-ylidene]pyrrolidine-1-carboxamide The title compound was prepared using the procedure described in Example 43 substituting 1-iodo-4-methoxybenzene for iodobenzene.

$^1$H NMR (500 MHz, DMSO-$d_6$/$D_2O$) δ ppm 1.68-1.82 (m, 4H) 2.17-2.25 (m, 3H) 3.18-3.32 (m, 4H) 3.78-3.83 (m, 3H) 6.99-7.09 (m, 3H) 7.46-7.52 (m, 2H); MS (ESI) m/z 318 (M+H)$^+$.

Example 49

N-[(2Z)-3-(3-fluorophenyl)-5-methyl-1,3-thiazol-2(3H)-ylidene]pyrrolidine-1-carboxamide The title compound was prepared using the procedure described in Example 43 substituting 1-fluoro-3-iodobenzene for iodobenzene.

$^1$H NMR (500 MHz, DMSO-$d_6$/$D_2O$) δ ppm 1.77 (t, 4H) 2.17-2.25 (m, 3H) 3.29 (t, 4H) 7.17-7.21 (m, 1H) 7.21-7.27 (m, 1H) 7.45-7.50 (m, 1H) 7.52-7.58 (m, 1H) 7.58-7.63 (m, 1H); MS (ESI) m/z 306 (M+H)$^+$.

Example 50

N-[(2Z)-3-(3-chlorophenyl)-5-methyl-1,3-thiazol-2(3H)-ylidene]pyrrolidine-1-carboxamide The title compound was prepared using the procedure described in Example 43 substituting 1-chloro-3-iodobenzene for iodobenzene.

$^1$H NMR (500 MHz, DMSO-$d_6$/$D_2O$) δ ppm 1.78 (t, 4H) 2.18-2.25 (m, 3H) 3.28 (t, 4H) 7.18-7.21 (m, 1H) 7.43-7.48 (m, 1H) 7.51-7.56 (m, 1H) 7.56-7.61 (m, 1H) 7.80-7.83 (m, 1H); MS (ESI) m/z 322 (M+H)$^+$.

Example 51

N-[(2Z)-3-(2-bromophenyl)-5-methyl-1,3-thiazol-2(3H)-ylidene]pyrrolidine-1-carboxamide The title compound was prepared using the procedure described in Example 43 substituting 1-bromo-2-iodobenzene for iodobenzene.

$^1$H NMR (500 MHz, DMSO-$d_6$/$D_2O$) δ ppm 1.59-1.81 (m, 4H) 2.17-2.25 (m, 3H) 2.92-3.34 (m, 4H) 6.91-6.96 (m, 1H) 7.38-7.50 (m, 2H) 7.51-7.58 (m, 1H) 7.79-7.85 (m, 1H); MS (ESI) m/z 368 (M+H)$^+$.

Example 52

N-[(2Z)-3-(3-bromophenyl)-5-methyl-1,3-thiazol-2(3H)-ylidene]pyrrolidine-1-carboxamide The title compound was prepared using the procedure described in Example 43 substituting 1-bromo-3-iodobenzene for iodobenzene.

$^1$H NMR (500 MHz, DMSO-$d_6$/$D_2O$) δ ppm 1.73-1.85 (m, 4H) 2.17-2.26 (m, 3H) 3.23-3.35 (m, 4H) 7.16-7.22 (m, 1H) 7.43-7.51 (m, 1H) 7.54-7.64 (m, 2H) 7.92-7.99 (m, 1H); MS (ESI) m/z 368 (M+H)$^+$.

Example 53

N-[(2Z)-3-(3-cyanophenyl)-5-methyl-1,3-thiazol-2(3H)-ylidene]pyrrolidine-1-carboxamide The title compound was prepared using the procedure described in Example 43 substituting 3-iodobenzonitrile for iodobenzene.

$^1$H NMR (500 MHz, DMSO-$d_6$/$D_2O$) δ ppm 1.73-1.83 (m, 4H) 2.20-2.25 (m, 3H) 3.23-3.32 (m, 4H) 7.22-7.26 (m, 1H) 7.67-7.74 (m, 1H) 7.82-7.86 (m, 1H) 7.97-8.02 (m, 1H) 8.15-8.19 (m, 1H); MS (ESI) m/z 313 (M+H)$^+$.

Example 54

N-[(2Z)-3-(4-cyanophenyl)-5-methyl-1,3-thiazol-2(3H)-ylidene]pyrrolidine-1-carboxamide The title compound was prepared using the procedure described in Example 43 substituting 4-iodobenzonitrile for iodobenzene.

$^1$H NMR (500 MHz, DMSO-$d_6$/$D_2O$) δ ppm 1.71-1.84 (m, 4H) 2.20-2.25 (m, 3H) 3.30 (t, 4H) 7.21-7.26 (m, 1H) 7.90 (d, 2H) 7.97 (d, 2H); MS (ESI) m/z 313 (M+H)$^+$.

Example 55

N-[(2Z)-3-[4-(dimethylamino)phenyl]-5-methyl-1,3-thiazol-2(3H)-ylidene]pyrrolidine-1-carboxamide The title compound was prepared using the procedure described in Example 43 substituting 4-bromo-N,N-dimethylaniline for iodobenzene.

$^1$H NMR (500 MHz, DMSO-$d_6$/$D_2O$) δ ppm 1.72-1.81 (m, 4H) 2.18-2.22 (m, 3H) 2.94-2.99 (m, 6H) 3.22-3.29 (m, 4H) 6.87 (d, 2H) 7.02-7.06 (m, 1H) 7.40 (d, 2H); MS (ESI) m/z 331 (M+H)$^+$.

Example 56

N-[(2Z)-5-methyl-3-[3-(trifluoromethyl)phenyl]-1,3-thiazol-2(3H)-ylidene]pyrrolidine-1-carboxamide The title compound was prepared using the procedure described in Example 43 substituting 1-iodo-3-(trifluoromethyl)benzene for iodobenzene.

$^1$H NMR (500 MHz, DMSO-$d_6$/$D_2O$) δ ppm 1.70-1.84 (m, 4H) 2.18-2.27 (m, 3H) 3.22-3.34 (m, 4H) 7.25-7.30 (m, 1H) 7.72-7.78 (m, 2H) 7.85-7.91 (m, 1H) 8.16-8.20 (m, 1H); MS (ESI) m/z 356 (M+H)$^+$.

Example 57

N-[(2Z)-5-methyl-3-[3-(trifluoromethoxy)phenyl]-1,3-thiazol-2(3H)-ylidene]pyrrolidine-1-carboxamide The title compound was prepared using the procedure described in Example 43 substituting 1-iodo-3-(trifluoromethoxy)benzene for iodobenzene.

¹H NMR (500 MHz, DMSO-d₆/D₂O) δ ppm 1.70-1.83 (m, 4H) 2.19-2.24 (m, 3H) 3.22-3.32 (m, 4H) 7.17-7.23 (m, 1H) 7.37-7.43 (m, 1H) 7.60-7.68 (m, 2H) 7.76-7.81 (m, 1H); MS (ESI) m/z 372 (M+H)⁺.

Example 58

N-[(2Z)-5-methyl-3-(4-phenoxyphenyl)-1,3-thiazol-2(3H)-ylidene]pyrrolidine-1-carboxamide The title compound was prepared using the procedure described in Example 43 substituting 1-iodo-4-phenoxybenzene for iodobenzene.
¹H NMR (500 MHz, DMSO-d₆/D₂O) δ ppm 1.72-1.82 (m, 4H) 2.20-2.24 (m, 3H) 3.23-3.32 (m, 4H) 7.04-7.24 (m, 4H) 7.40-7.48 (m, 1H) 7.57-7.68 (m, 5H); MS (ESI) m/z 380 (M+H)⁺.

Example 59

N-[(2Z)-3-[4-(benzyloxy)phenyl]-5-methyl-1,3-thiazol-2(3H)-ylidene]pyrrolidine-1-carboxamide The title compound was prepared using the procedure described in Example 43 substituting 1-(benzyloxy)-4-iodobenzene for iodobenzene.
¹H NMR (500 MHz, DMSO-d₆/D₂O) δ ppm 1.72-1.81 (m, 4H) 2.17-2.23 (m, 3H) 3.20-3.29 (m, 4H) 5.12-5.16 (m, 2H) 7.06-7.09 (m, 1H) 7.09-7.15 (m, 2H) 7.32-7.38 (m, 1H) 7.38-7.45 (m, 2H) 7.45-7.52 (m, 4H); MS (ESI) m/z 394 (M+H)⁺.

Example 60

N-[(2Z)-3-(3,4-dimethylphenyl)-5-methyl-1,3-thiazol-2(3H)-ylidene]pyrrolidine-1-carboxamide The title compound was prepared using the procedure described in Example 43 substituting 4-iodo-1,2-dimethylbenzene for iodobenzene.
¹H NMR (500 MHz, DMSO-d₆/D₂O) δ ppm 1.70-1.82 (m, 4H) 2.19-2.23 (m, 3H) 2.24-2.29 (m, 6H) 3.22-3.32 (m, 4H) 7.07-7.10 (m, 1H) 7.23-7.27 (m, 1H) 7.29-7.33 (m, 1H) 7.36-7.39 (m, 1H); MS (ESI) m/z 316 (M+H)⁺.

Example 61

N-[(2Z)-3-(3,5-dimethylphenyl)-5-methyl-1,3-thiazol-2(3H)-ylidene]pyrrolidine-1-carboxamide The title compound was prepared using the procedure described in Example 43 substituting 1-iodo-3,5-dimethylbenzene for iodobenzene.
¹H NMR (500 MHz, DMSO-d₆/D₂O) δ ppm 1.77 (t, 4H) 2.18-2.23 (m, 3H) 2.28-2.35 (m, 6H) 3.27 (t, 4H) 7.01-7.04 (m, 1H) 7.09-7.13 (m, 1H) 7.21-7.25 (m, 2H); MS (ESI) m/z 316 (M+H)⁺.

Example 62

N-[(2Z)-5-methyl-3-pyridin-2-yl-1,3-thiazol-2(3H)-ylidene]pyrrolidine-1-carboxamide The title compound was prepared using the procedure described in Example 43 substituting 2-iodopyridine for iodobenzene.
¹H NMR (500 MHz, DMSO-d₆/D₂O) δ ppm 1.77-1.88 (m, 4H) 2.18-2.26 (m, 3H) 3.27-3.49 (m, 4H) 7.37-7.42 (m, 1H) 7.57-7.59 (m, 1H) 7.97-8.04 (m, 1H) 8.41 (d, 1H) 8.50-8.55 (m, 1H); MS (ESI) m/z 289 (M+H)⁺.

Example 63

Example 63 has been removed and is not part of this document.

Example 64

N-[(2Z)-3-(3,4-dichlorophenyl)-5-methyl-1,3-thiazol-2(3H)-ylidene]pyrrolidine-1-carboxamide The title compound was prepared using the procedure described in Example 43 substituting 1,2-dichloro-4-iodobenzene for iodobenzene.
¹H NMR (500 MHz, DMSO-d₆/D₂O) δ ppm 1.73-1.83 (m, 4H) 2.18-2.24 (m, 3H) 3.25-3.34 (m, 4H) 7.20-7.23 (m, 1H) 7.65 (dd, 1H) 7.76 (d, 1H) 8.04 (d, 1H); MS (ESI) m/z 356 (M+H)⁺.

Example 65

N-[(2Z)-3-(3,5-dichlorophenyl)-5-methyl-1,3-thiazol-2(3H)-ylidene]pyrrolidine-1-carboxamide The title compound was prepared using the procedure described in Example 43 substituting 1,3-dichloro-5-iodobenzene for iodobenzene.
¹H NMR (500 MHz, DMSO-d₆/D₂O) δ ppm 1.74-1.85 (m, 4H) 2.18-2.24 (m, 3H) 3.25-3.36 (m, 4H) 7.23-7.27 (m, 1H) 7.59-7.65 (m, 1H) 7.80-7.84 (m, 2H); MS (ESI) m/z 356 (M+H)⁺.

Example 66

N-[(2Z)-5-methyl-3-[4-(methylthio)phenyl]-1,3-thiazol-2(3H)-ylidene]pyrrolidine-1-carboxamide To a 4 mL vial equipped with a septum cap and stir bar was added N-(5-methyl-1,3-thiazol-2-yl)pyrrolidine-1-carboxamide (50 mg, 0.24 mmol), copper(I) trifluoromethanesulfonate benzene complex (23.8 mg, 0.05 mmol), 5-chloro-1,10-phenanthroline (20.3 mg, 0.09 mmol) and cesium carbonate (84.8 mg, 0.26 mmol). The mixture was placed under a nitrogen atmosphere. (4-Bromophenyl)(methyl)sulfane (0.28 mmol) in 1-methyl-2-pyrrolidinone (1.0 mL) was added to the mixture. The reaction mixture was heated at 120° C. for overnight. A solution of concentrated ammonium hydroxide/water (1:2, 1 mL) was added and the mixture was filtered and solvent removed under reduced pressure. The residue was purified by reverse phase HPLC (C8, gradient 10-100% acetonitrile/water/0.1% trifluoroacetic acid).
¹H NMR (500 MHz, DMSO-d₆/D₂O) δ ppm 1.71-1.81 (m, 4H) 2.18-2.24 (m, 3H) 2.47-2.52 (m, 3H) 3.22-3.31 (m, 4H) 7.09-7.13 (m, 1H) 7.36 (d, 2H) 7.55 (d, 2H); MS (ESI) m/z 334 (M+H)⁺.

Example 67

N-[(2Z)-3-(3-methoxyphenyl)-5-methyl-1,3-thiazol-2(3H)-ylidene]pyrrolidine-1-carboxamide The title compound was prepared using the procedure described in Example 66 substituting 1-iodo-3-methoxybenzene for (4-bromophenyl)(methyl)sulfane.

¹H NMR (500 MHz, DMSO-d₆/D₂O) δ ppm 1.70-1.83 (m, 4H) 2.18-2.25 (m, 3H) 3.22-3.35 (m, 4H) 3.78-3.83 (m, 3H) 6.95 (d, 1H) 7.11-7.19 (m, 2H) 7.20-7.26 (m, 1H) 7.37-7.46 (m, 1H); MS (ESI) m/z 318 (M+H)⁺.

Example 68

N-[(2Z)-3-(4-chloro-3-methylphenyl)-5-methyl-1,3-thiazol-2(3H)-ylidene]pyrrolidine-1-carboxamide The title compound was prepared using the procedure described in Example 66 substituting 4-bromo-1-chloro-2-methylbenzene for (4-bromophenyl)(methyl)sulfane.
¹H NMR (500 MHz, DMSO-d₆/D₂O) δ ppm 1.70-1.84 (m, 4H) 2.16-2.24 (m, 3H) 2.34-2.41 (m, 3H) 3.22-3.33 (m, 4H) 7.12-7.16 (m, 1H) 7.46-7.56 (m, 2H) 7.60-7.64 (m, 1H); MS (ESI) m/z 336 (M+H)⁺.

Example 69

N-[(2Z)-3-(4-benzylphenyl)-5-methyl-1,3-thiazol-2(3H)-ylidene]pyrrolidine-1-carboxamide In a 4 mL vial charged with a stir bar, N-(5-methyl-1,3-thiazol-2-yl)pyrrolidine-1-carboxamide (58 mg, 0.27 mmol) was added, followed by copper(I) trifluoromethanesulfonate benzene complex (27 mg, 0.05 mmol), 5-chloro-1,10-phenanthroline (23 mg, 0.11 mmol) and cesium carbonate (97 mg, 0.3 mmol). A loose cap with septum was placed on the vial, and the vial was placed under vacuum in a vacuum oven for 30 minutes. The solid mixture was purged with nitrogen gas a couple of times. Then, 1-benzyl-4-bromobenzene (74 mg, 0.3 mmol) dissolved in 1-methyl-2-pyrrolidinone (1.0 mL) was added to the mixture. The vial was capped and placed on a heater/stirrer and heated to 120° C. overnight. Then 1 mL of a solution of concentrated ammonium hydroxide/water (1:2) was added. The reaction was filtered and concentrated to dryness. The residue was purified by reverse phase HPLC (C8, gradient 10-100% acetonitrile/water/0.1% trifluoroacetic acid).
¹H NMR (500 MHz, DMSO-d₆/D₂O) δ ppm 1.66-1.86 (m, 4H) 2.16-2.22 (m, 3H) 3.19-3.31 (m, 4H) 3.96-4.02 (m, 2H) 7.07-7.12 (m, 1H) 7.17-7.24 (m, 1H) 7.25-7.38 (m, 6H) 7.49-7.54 (m, 2H); MS (ESI) m/z 378 (M+H)⁺.

Example 70

N-[(2Z)-3-(1-benzothien-5-yl)-5-methyl-1,3-thiazol-2(3H)-ylidene]pyrrolidine-1-carboxamide The title compound was prepared using the procedure described in Example 69 substituting 5-bromobenzo[b]thiophene for 1-benzyl-4-bromobenzene.
¹H NMR (500 MHz, DMSO-d₆/D₂O) δ ppm 1.63-1.82 (m, 4H) 2.18-2.28 (m, 3H) 3.02-3.39 (m, 4H) 7.18-7.21 (m, 1H) 7.53 (d, 1H) 7.59 (dd, 1H) 7.85 (d, 1H) 8.06-8.13 (m, 2H); MS (ESI) m/z 344 (M+H)⁺.

Example 71

N-[(2Z)-5-methyl-3-(5-methylthien-2-yl)-1,3-thiazol-2(3H)-ylidene]pyrrolidine-1-carboxamide The title compound was prepared using the procedure described in Example 69 substituting 2-bromo-5-methylthiophene for 1-benzyl-4-bromobenzene.
¹H NMR (500 MHz, DMSO-d₆/D₂O) δ ppm 1.79-1.93 (m, 4H) 2.21-2.24 (m, 3H) 2.41-2.44 (m, 3H) 3.34 (t, 2H) 3.58 (t, 2H) 6.71 (dd, 1H) 7.12 (d, 1H) 7.48-7.56 (m, 1H); MS (ESI) m/z 308 (M+H)⁺.

Example 72

N-[(2Z)-5-methyl-3-(2-methyl-1,3-benzothiazol-5-yl)-1,3-thiazol-2(3H)-ylidene]pyrrolidine-1-carboxamide The title compound was prepared using the procedure described in Example 69 substituting 5-bromo-2-methylbenzo[d]thiazole for 1-benzyl-4-bromobenzene.
¹H NMR (500 MHz, DMSO-d₆/D₂O) δ ppm 1.67-1.81 (m, 4H) 2.20-2.27 (m, 3H) 2.81-2.85 (m, 3H) 3.18-3.33 (m, 4H) 7.20-7.24 (m, 1H) 7.63 (dd, 1H) 8.08-8.16 (m, 2H); MS (ESI) m/z 359 (M+H)⁺.

Example 73

N-[(2Z)-5-methyl-3-[6-(trifluoromethyl)pyridin-3-yl]-1,3-thiazol-2(3H)-ylidene]pyrrolidine-1-carboxamide The title compound was prepared using the procedure described in Example 69 substituting 5-bromo-2-(trifluoromethyl)pyridine for 1-benzyl-4-bromobenzene.
¹H NMR (500 MHz, DMSO-d₆/D₂O) δ ppm 1.74-1.82 (m, 4H) 2.22-2.25 (m, 3H) 3.25-3.34 (m, 4H) 7.32-7.35 (m, 1H) 8.08 (d, 1H) 8.42 (dd, 1H) 9.07-9.13 (m, 1H); MS (ESI) m/z 357 (M+H)⁺.

Example 74

N-[(2Z)-5-methyl-3-[5-(trifluoromethyl)pyridin-3-yl]-1,3-thiazol-2(3H)-ylidene]pyrrolidine-1-carboxamide The title compound was prepared using the procedure described in Example 69 substituting 3-bromo-5-(trifluoromethyl)pyridine for 1-benzyl-4-bromobenzene.
¹H NMR (500 MHz, DMSO-d₆/D₂O) δ ppm 1.72-1.83 (m, 4H) 2.21-2.25 (m, 3H) 3.21-3.36 (m, 4H) 7.37-7.41 (m, 1H) 8.67-8.70 (m, 1H) 8.94-8.96 (m, 1H) 9.12-9.14 (m, 1H); MS (ESI) m/z 357 (M+H)⁺.

Example 75

N-[(2Z)-3-[4-(methylthio)phenyl]-1,3-thiazol-2(3H)-ylidene]pyrrolidine-1-carboxamide In a 4 mL vial charged with a stir bar, N-1,3-thiazol-2-ylpyrrolidine-1-carboxamide (53 mg, 0.27 mmol, Example 32A) was added, followed by copper(I) trifluoromethanesulfonate benzene complex (27 mg, 0.05 mmol), 5-chloro-1,10-phenanthroline (23 mg, 0.11 mmol) and cesium carbonate (97 mg, 0.3 mmol). A loose cap with a septum was placed on the vial, and then the vial was placed under vacuum in a vacuum oven for 30 minutes. The mixture was purged with nitrogen gas a couple of times. Then (4-bromophenyl)(methyl)sulfane (61 mg, 0.3 mmol) dissolved in 1-methyl-2-pyrrolidinone (1.0 mL) was added to the solid mixture. The vial was capped and placed on a heater/stirrer and heated to 120° C. overnight. Then a 1 mL solution of concentrated ammonium hydroxide/water (1:2) was added. The reaction was filtered and concentrated to dryness. The residue was purified by reverse phase HPLC (C8, gradient 10-100% acetonitrile/water/0.1% trifluoroacetic acid).

$^1$H NMR (500 MHz, DMSO-$d_6$/$D_2O$) δ ppm 1.72-1.81 (m, 4H) 2.51-2.52 (m, 3H) 3.18-3.32 (m, 4H) 6.81 (d, 1H) 7.34-7.42 (m, 3H) 7.52-7.60 (m, 2H); MS (ESI) m/z 320 (M+H)$^+$.

Example 76

N-[(2Z)-3-phenyl-1,3-thiazol-2(3H)-ylidene]pyrrolidine-1-carboxamide

The title compound was prepared using the procedure described in Example 75 substituting iodobenzene for (4-bromophenyl)(methyl)sulfane.

$^1$H NMR (500 MHz, DMSO-$d_6$/$D_2O$) δ ppm 1.66-1.81 (m, 4H) 3.16-3.33 (m, 4H) 6.82 (d, 1H) 7.36-7.44 (m, 2H) 7.49-7.56 (m, 2H) 7.58-7.64 (m, 2H); MS (ESI) m/z 274 (M+H)$^+$.

Example 77

N-[(2Z)-3-(3-chlorophenyl)-1,3-thiazol-2(3H)-ylidene]pyrrolidine-1-carboxamide

The title compound was prepared using the procedure described in Example 75 substituting 1-chloro-3-iodobenzene for (4-bromophenyl)(methyl)sulfane.

$^1$H NMR (500 MHz, DMSO-$d_6$/$D_2O$) δ ppm 1.72-1.84 (m, 4H) 3.23-3.33 (m, 4H) 6.83 (d, 1H) 7.40-7.50 (m, 2H) 7.52-7.63 (m, 2H) 7.77-7.86 (m, 1H); MS (ESI) m/z 308 (M+H)$^+$.

Example 78

N-[(2Z)-3-[3-(trifluoromethyl)phenyl]-1,3-thiazol-2(3H)-ylidene]pyrrolidine-1-carboxamide The title compound was prepared using the procedure described in Example 75 substituting 1-iodo-3-(trifluoromethyl)benzene for (4-bromophenyl)(methyl)sulfane.

$^1$H NMR (500 MHz, DMSO-$d_6$/$D_2O$) δ ppm 1.69-1.87 (m, 4H) 3.19-3.37 (m, 4H) 6.86 (d, 1H) 7.53 (d, 1H) 7.75-7.80 (m, 2H) 7.86-7.93 (m, 1H) 8.16-8.21 (m, 1H); MS (ESI) m/z 342 (M+H)$^+$.

Example 79

N-[(2Z)-3-(4-chlorophenyl)-1,3-thiazol-2(3H)-ylidene]pyrrolidine-1-carboxamide

The title compound was prepared using the procedure described in Example 75 substituting 1-chloro-4-iodobenzene for (4-bromophenyl)(methyl)sulfane.

1H NMR (500 MHz, DMSO-$d_6$/$D_2O$) δ ppm 1.66-1.84 (m, 4H) 3.17-3.34 (m, 4H) 6.83 (d, 1H) 7.41 (d, 1H) 7.55-7.70 (m, 4H); MS (ESI) 308 (M+H)$^+$.

Example 80

N-[(2Z)-3-(4-methylphenyl)-1,3-thiazol-2(3H)-ylidene]pyrrolidine-1-carboxamide

The title compound was prepared using the procedure described in Example 75 substituting 1-iodo-4-methylbenzene for (4-bromophenyl)(methyl)sulfane.

$^1$H NMR (500 MHz, DMSO-$d_6$/$D_2O$) δ ppm 1.69-1.82 (m, 4H) 2.34-2.38 (m, 3H) 3.19-3.32 (m, 4H) 6.81 (d, 1H) 7.27-7.39 (m, 3H) 7.44-7.57 (m, 2H); MS (ESI) m/z 288 (M+H)$^+$.

Example 81

N-[(2Z)-3-(4-chloro-3-methylphenyl)-1,3-thiazol-2(3H)-ylidene]pyrrolidine-1-carboxamide The title compound was prepared using the procedure described in Example 75 substituting 4-bromo-1-chloro-2-methylbenzene for (4-bromophenyl)(methyl)sulfane.

$^1$H NMR (500 MHz, DMSO-$d_6$/$D_2O$) δ ppm 1.71-1.82 (m, 4H) 2.36-2.39 (m, 3H) 3.21-3.31 (m, 4H) 6.83 (d, 1H) 7.40 (d, 1H) 7.46-7.58 (m, 2H) 7.60-7.66 (m, 1H); MS (ESI) m/z 322 (M+H)$^+$.

Example 82

N-[(2Z)-3-(3,4-dichlorophenyl)-1,3-thiazol-2(3H)-ylidene]pyrrolidine-1-carboxamide The title compound was prepared using the procedure described in Example 75 substituting 1,2-dichloro-4-iodobenzene for (4-bromophenyl)(methyl)sulfane.

$^1$H NMR (500 MHz, DMSO-$d_6$/$D_2O$) δ ppm 1.75-1.82 (m, 4H) 3.27-3.33 (m, 4H) 6.85 (d, 1H) 7.47 (d, 1H) 7.66 (dd, 1H) 7.76-7.79 (m, 1H) 8.03-8.07 (m, 1H); MS (ESI) m/z 342 (M+H)$^+$.

Example 83

N-[(2Z)-3-(3,4-dimethylphenyl)-1,3-thiazol-2(3H)-ylidene]pyrrolidine-1-carboxamide The title compound was prepared using the procedure described in Example 75 substituting 4-iodo-1,2-dimethylbenzene for (4-bromophenyl)(methyl)sulfane.

$^1$H NMR (500 MHz, DMSO-$d_6$/$D_2O$) δ ppm 1.74-1.80 (m, 4H) 2.24-2.29 (m, 6H) 3.21-3.29 (m, 4H) 6.80 (d, 1H) 7.24-7.41 (m, 4H); MS (ESI) m/z 302 (M+H)$^+$.

Example 84

N-[(2Z)-3-(4-cyanophenyl)-1,3-thiazol-2(3H)-ylidene]pyrrolidine-1-carboxamide

The title compound was prepared using the procedure described in Example 75 substituting 4-iodobenzonitrile for (4-bromophenyl)(methyl)sulfane.

$^1$H NMR (500 MHz, DMSO-$d_6$/$D_2O$) δ ppm 1.72-1.85 (m, 4H) 3.21-3.35 (m, 4H) 6.87 (d, 1H) 7.49 (d, 1H) 7.86-7.94 (m, 2H) 7.95-8.02 (m, 2H); MS (ESI) m/z 299 (M+H)$^+$.

Example 85

N-[(2Z)-3-(3-chloro-4-methylphenyl)-1,3-thiazol-2(3H)-ylidene]pyrrolidine-1-carboxamide The title compound was prepared using the procedure described in Example 75 substituting 4-bromo-2-chloro-1-methylbenzene for (4-bromophenyl)(methyl)sulfane.

$^1$H NMR (500 MHz, DMSO-$d_6$/$D_2O$) δ ppm 1.75-1.81 (m, 4H) 2.36-2.40 (m, 3H) 3.23-3.32 (m, 4H) 6.82 (d, 1H) 7.41 (d, 1H) 7.47-7.51 (m, 2H) 7.77-7.81 (m, 1H); MS (ESI) m/z 322 (M+H)$^+$.

Example 86

N-[(2Z)-3-[4-(difluoromethoxy)phenyl]-1,3-thiazol-2(3H)-ylidene]pyrrolidine-1-carboxamide

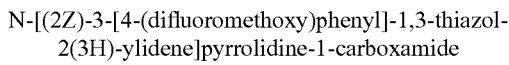

The title compound was prepared using the procedure described in Example 75 substituting 1-bromo-4-(difluoromethoxy)benzene for (4-bromophenyl)(methyl)sulfane.

$^1$H NMR (500 MHz, DMSO-d$_6$/D$_2$O) δ ppm 1.71-1.80 (m, 4H) 3.20-3.37 (m, 4H) 6.84 (d, 1H) 7.24-7.28 (m, 1H) 7.29-7.35 (m, 2H) 7.37-7.42 (m, 1H) 7.62-7.73 (m, 2H); MS (ESI) m/z 340 (M+H)$^+$.

Example 87

N-[(2Z)-3-(3,5-dichlorophenyl)-5-methyl-1,3-thiazol-2(3H)-ylidene]-2,2-dimethylpropanamide

Example 87A 2,2-dimethyl-N-(5-methyl-1,3-thiazol-2-yl)propanamide

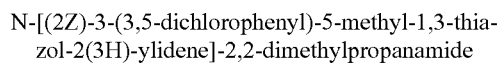

5-Methylthiazol-2-amine (5.71 g, 50.0 mmol) and pivaloyl chloride (6.78 mL, 55.0 mmol) were mixed in anhydrous acetonitrile (80 mL) and treated with triethylamine (14.0 mL, 100 mmol) resulting in an exotherm. After 15 minutes, the warm suspension was cooled for 5 minutes with a water bath. The solids were collected by filtration and rinsed with more acetonitrile. The filtrate was partially concentrated and the solids which precipitated were also collected by filtration and rinsed with acetonitrile. The two crops were combined and rinsed with water, and when solids precipitated from the filtrate they were collected by filtration and added to the previously collected material. The crude product was washed with 1:1 dichloromethane/hexanes and dried under vacuum to give the title compound.

1H NMR (300 MHz, d$_6$-DMSO) δ ppm 1.22 (9H), 2.33 (3H), 7.13 (1H), 11.51 (1H); MS (DCI) m/z 199 (M+H)$^+$.

Example 87B

N-[(2Z)-3-(3,5-dichlorophenyl)-5-methyl-1,3-thiazol-2(3H)-ylidene]-2,2-dimethylpropanamide

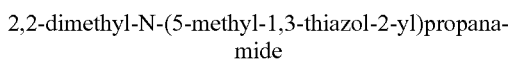

In a 4 mL vial charged with a stir bar, 2,2-dimethyl-N-(5-methyl-1,3-thiazol-2-yl)propanamide (71 mg, 0.35 mmol) was added, followed by copper(I) trifluoromethanesulfonate benzene complex (35 mg, 0.07 mmol), 5-chloro-1,10-phenanthroline (30 mg, 0.14 mmol) and cesium carbonate (126 mg, 0.39 mmol). A loose cap with septum was placed on the vial and the vial was placed under vacuum in a vacuum oven for 30 minutes. The solid mixture was purged with nitrogen gas a couple of times. Then 1,3-dichloro-5-iodobenzene (115 mg, 0.42 mmol) dissolved in 1-methyl-2-pyrrolidinone (1.0 mL) was added to the solid mixture. The vial was capped and placed on a heater/stirrer and heated to 120° C. overnight. Then a 1 mL solution of concentrated ammonium hydroxide/water (1:2) was added. The reaction was filtered and concentrated to dryness. The residue was purified by reverse phase HPLC (C8, gradient 10-100% acetonitrile/water/0.1% trifluoroacetic acid).

$^1$H NMR (500 MHz, DMSO-d$_6$/D$_2$O) δ ppm 1.08-1.12 (m, 9H) 2.25-2.31 (m, 3H) 7.41-7.47 (m, 1H) 7.68 (t, 1H) 7.81-7.85 (m, 2H); MS (ESI) m/z 343 (M+H)$^+$.

Example 88

N-[(2Z)-3-(4-fluorophenyl)-5-methyl-1,3-thiazol-2(3H)-ylidene]-2,2-dimethylpropanamide

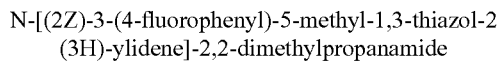

The title compound was prepared using the procedure described in Example 87B substituting 1-fluoro-4-iodobenzene for 1,3-dichloro-5-iodobenzene.

$^1$H NMR (500 MHz, DMSO-d$_6$/D$_2$O) δ ppm 1.05-1.11 (m, 9H) 2.23-2.31 (m, 3H) 7.28-7.43 (m, 3H) 7.61-7.71 (m, 2H); MS (ESI) m/z 293 (M+H)$^+$.

Example 89

N-[(2Z)-3-(4-chlorophenyl)-5-methyl-1,3-thiazol-2(3H)-ylidene]-2,2-dimethylpropanamide

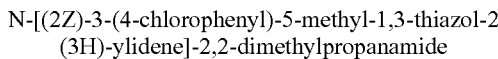

The title compound was prepared using the procedure described in Example 87B substituting 1-chloro-4-iodobenzene for 1,3-dichloro-5-iodobenzene.

$^1$H NMR (500 MHz, DMSO-d$_6$/D$_2$O) δ ppm 1.03-1.14 (s, 9H) 2.26-2.31 (m, 3H) 7.38-7.42 (m, 1H) 7.59-7.71 (m, 4H); MS (ESI) m/z 309 (M+H)$^+$.

Example 90

N-[(2Z)-3-(3,4-dichlorophenyl)-5-methyl-1,3-thiazol-2(3H)-ylidene]-2,2-dimethylpropanamide

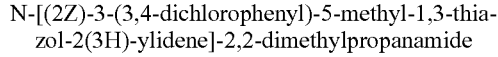

The title compound was prepared using the procedure described in Example 87B substituting 1,2-dichloro-4-iodobenzene for 1,3-dichloro-5-iodobenzene.

$^1$H NMR (500 MHz, DMSO-d$_6$/D$_2$O) δ ppm 1.07-1.11 (m, 9H) 2.25-2.30 (m, 3H) 7.36-7.43 (m, 1H) 7.64 (dd, 1H) 7.79 (d, 1H) 8.04-8.08 (m, 1H); MS (ESI) m/z 343 (M+H)$^+$.

Example 91

2,2-dimethyl-N-[(2Z)-5-methyl-3-[4-(trifluoromethyl)phenyl]-1,3-thiazol-2(3H)-ylidene]propanamide

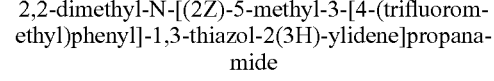

The title compound was prepared using the procedure described in Example 87B substituting 1-iodo-4-(trifluoromethyl)benzene for 1,3-dichloro-5-iodobenzene.

$^1$H NMR (500 MHz, DMSO-d$_6$/D$_2$O) δ ppm 1.07-1.10 (m, 9H) 2.25-2.33 (m, 3H) 7.40-7.45 (m, 1H) 7.91 (q, 4H); MS (ESI) m/z 343 (M+H)$^+$.

Example 92

N-[(2Z)-3-[6-(trifluoromethyl)pyridin-3-yl]-1,3-thiazol-2(3H)-ylidene]pyrrolidine-1-carboxamide

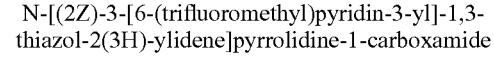

In a 4 mL vial charged with a stir bar, N-1,3-thiazol-2-ylpyrrolidine-1-carboxamide (46 mg, 0.23 mmol, Example 32A) was added, followed by copper(I) trifluoromethanesulfonate benzene complex (30 mg, 0.05 mmol), 5-chloro-1,10-phenanthroline (23 mg, 0.09 mmol) and cesium carbonate (100 mg, 0.3 mmol). A loose cap with septum was placed on the vial and the vial was placed under vacuum in a vacuum oven for 30 minutes. The solid mixture was purged with nitrogen gas a couple of times. Then 5-bromo-2-(trifluoromethyl)pyridine (68 mg, 0.3 mmol) dissolved in 1-methyl-2-pyrrolidinone (1.0 mL) was added to the solid mixture. The vial was capped and placed on a heater/stirrer and heated to 120° C. overnight. Then a 1 mL solution of concentrated ammonium hydroxide/water (1:2) was added. The reaction was filtered and concentrated to dryness. The residue was purified by reverse phase HPLC (C18, gradient 10-95% acetonitrile/water/0.1% trifluoroacetic acid) to provide the title compound.

$^1$H NMR (500 MHz, DMSO-$d_6$/$D_2$O) δ ppm 1.71-1.84 (m, 4H) 3.28-3.37 (m, 4H) 6.93 (d, 1H) 7.59 (d, 1H) 8.09 (d, 1H) 8.45 (dd, 1H) 9.09-9.14 (m, 1H); MS (ESI) m/z 343 (M+H)$^+$.

Example 93

N-[(2Z)-3-[3-fluoro-4-(trifluoromethyl)phenyl]-1,3-thiazol-2(3H)-ylidene]pyrrolidine-1-carboxamide The title compound was prepared using the procedure described in Example 92 substituting 4-bromo-2-fluoro-1-(trifluoromethyl)benzene for 5-bromo-2-(trifluoromethyl)pyridine.

$^1$H NMR (500 MHz, DMSO-$d_6$/$D_2$O) δ ppm 1.75-1.85 (m, 4H) 3.26-3.37 (m, 4H) 6.89 (d, 1H) 7.53 (d, 1H) 7.74-7.83 (m, 1H) 7.90-8.06 (m, 2H); MS (ESI) m/z 360 (M+H)$^+$.

Example 94

N-[(2Z)-3-(6-fluoro-5-methylpyridin-3-yl)-1,3-thiazol-2(3H)-ylidene]pyrrolidine-1-carboxamide The title compound was prepared using the procedure described in Example 92 substituting 5-bromo-2-fluoro-3-methylpyridine for 5-bromo-2-(trifluoromethyl)pyridine.

$^1$H NMR (500 MHz, DMSO-$d_6$/$D_2$O) δ ppm 1.69-1.87 (m, 4H) 2.24-2.34 (m, 3H) 3.20-3.36 (m, 4H) 6.87 (d, 1H) 7.46 (d, 1H) 8.17 (dd, 1H) 8.32-8.37 (m, 1H); MS (ESI) m/z 307 (M+H)$^+$.

Example 95

2,2-dimethyl-N-[(2Z)-5-methyl-3-(5-methylthien-2-yl)-1,3-thiazol-2(3H)-ylidene]propanamide In a 4 mL vial charged with a stir bar, 2,2-dimethyl-N-(5-methyl-1,3-thiazol-2-yl)propanamide (62 mg, 0.3 mmol, Example 87A) was added, followed by copper(I) trifluoromethanesulfonate benzene complex (31 mg, 0.06 mmol), 5-chloro-1,10-phenanthroline (26 mg, 0.12 mmol) and cesium carbonate (107 mg, 0.33 mmol). A loose cap with septum was placed on the vial and then the vial was placed under vacuum in a vacuum oven for 30 minutes. The mixture was purged with nitrogen gas a couple of times. Then 2-bromo-5-methylthiophene (58 mg, 0.33 mmol) dissolved in 1-methyl-2-pyrrolidinone (1.0 mL) was added to the solid mixture. The vial was capped and placed on a heater/stirrer and heated to 120° C. overnight. Then 1 mL of a solution of concentrated ammonium hydroxide/water (1:2) was added. The reaction was filtered and concentrated to dryness. The residue was purified by reverse phase HPLC (C8, gradient 10-100% acetonitrile/water/0.1% trifluoroacetic acid) to provide the title compound.

$^1$H NMR (500 MHz, DMSO-$d_6$/$D_2$O) δ ppm 1.23-1.27 (m, 9H) 2.28-2.31 (m, 3H) 2.43-2.46 (m, 3H) 6.70-6.76 (m, 1H) 7.22 (d, 1H) 7.68-7.75 (m, 1H); MS (ESI) m/z 295 (M+H)$^+$.

Example 96

N-[(2Z)-3-(6-fluoropyridin-3-yl)-5-methyl-1,3-thiazol-2(3H)-ylidene]-2,2-dimethylpropanamide The title compound was prepared using the procedure described in Example 95 substituting 2-fluoro-5-iodopyridine for 2-bromo-5-methylthiophene.

$^1$H NMR (500 MHz, DMSO-$d_6$/$D_2$O) δ ppm 1.04-1.11 (m, 9H) 2.26-2.32 (m, 3H) 7.30-7.52 (m, 2H) 8.26-8.32 (m, 1H) 8.50-8.54 (m, 1H); MS (ESI) m/z 294 (M+H)$^+$.

Example 97

2,2-dimethyl-N-[(2Z)-5-methyl-3-[6-(trifluoromethyl)pyridin-3-yl]-1,3-thiazol-2(3H)-ylidene]propanamide The title compound was prepared using the procedure described in Example 95 substituting 5-bromo-2-(trifluoromethyl)pyridine for 2-bromo-5-methylthiophene.

$^1$H NMR (500 MHz, DMSO-$d_6$/$D_2$O) δ ppm 1.09-1.11 (m, 9H) 2.30-2.33 (m, 3H) 7.48-7.54 (m, 1H) 8.14 (d, 1H) 8.41 (dd, 1H) 9.09-9.13 (m, 1H); MS (ESI) m/z 344 (M+H)$^+$.

Example 98

N-[(2Z)-3-[3-fluoro-4-(trifluoromethyl)phenyl]-5-methyl-1,3-thiazol-2(3H)-ylidene]-2,2-dimethylpropanamide The title compound was prepared using the procedure described in Example 95 substituting 4-bromo-2-fluoro-1-(trifluoromethyl)benzene for 2-bromo-5-methylthiophene.

$^1$H NMR (500 MHz, DMSO-$d_6$/$D_2$O) δ ppm 1.09-1.13 (m, 9H) 2.27-2.31 (m, 3H) 7.41-7.50 (m, 1H) 7.73-7.77 (m, 1H) 7.94-8.02 (m, 2H); MS (ESI) m/z 361 (M+H)$^+$.

Example 99

N-[(2Z)-3-(6-fluoro-5-methylpyridin-3-yl)-5-methyl-1,3-thiazol-2(3H)-ylidene]-2,2-dimethylpropanamide The title compound was prepared using the procedure described in Example 95 substituting 5-bromo-2-fluoro-3-methylpyridine for 2-bromo-5-methylthiophene.

$^1$H NMR (500 MHz, DMSO-$d_6$/$D_2$O) δ ppm 1.06-1.10 (m, 9H) 2.27-2.30 (m, 3H) 2.30-2.34 (m, 3H) 7.35-7.44 (m, 1H) 8.15 (dd, 1H) 8.30-8.39 (m, 1H); MS (ESI) m/z 308 (M+H)$^+$.

Example 100

2,2-dimethyl-N-[(2Z)-5-methyl-3-[6-(1H-pyrazol-1-yl)pyridin-2-yl]-1,3-thiazol-2(3H)-ylidene]propanamide The title compound was prepared using the procedure described in Example 95 substituting 2-bromo-6-(1H-pyrazol-1-yl)pyridine for 2-bromo-5-methylthiophene.

$^1$H NMR (500 MHz, DMSO-$d_6$/$D_2$O) δ ppm 1.16-1.21 (m, 9H) 2.30-2.34 (m, 3H) 6.61-6.66 (m, 1H) 7.86-7.92 (m, 2H) 7.96-7.98 (m, 1H) 8.21 (t, 1H) 8.45 (d, 1H) 8.74-8.77 (m, 1H); MS (ESI) m/z 342 (M+H)$^+$.

Example 101

N-[(2Z)-3-(2-fluoropyridin-4-yl)-5-methyl-1,3-thiazol-2(3H)-ylidene]-2,2-dimethylpropanamide The title compound was prepared using the procedure described in Example 95 substituting 4-bromo-2-fluoropyridine for 2-bromo-5-methylthiophene.

$^1$H NMR (500 MHz, DMSO-$d_6$/$D_2$O) δ ppm 1.06-1.19 (m, 9H) 2.28-2.30 (m, 3H) 7.52-7.55 (m, 1H) 7.71-7.74 (m, 1H) 7.77-7.82 (m, 1H) 8.42 (d, 1H); MS (ESI) m/z 294 (M+H)$^+$.

Example 102

(3R)-N-[(2Z)-3-(3-bromophenyl)-5-methyl-1,3-thiazol-2(3H)-ylidene]-3-fluoropyrrolidine-1-carboxamide In a 4 mL vial charged with a stir bar, (3R)-3-fluoro-N-(5-methyl-1,3-thiazol-2-yl)pyrrolidine-1-carboxamide (40 mg, 0.17 mmol, Example 34A) was added, followed by copper(I) trifluoromethanesulfonate benzene complex (17 mg, 0.03 mmol), 5-chloro-1,10-phenanthroline (15 mg, 0.07 mmol) and cesium carbonate (61 mg, 0.19 mmol). A loose cap with septum was placed on the vial and then the vial was placed under vacuum in a vacuum oven for 30 minutes. The mixture was purged with nitrogen gas a couple of times. 1,3-Dibromobenzene (47 mg, 0.2 mmol) dissolved in 1-methyl-2-pyrrolidinone (1.0 mL) was added to the mixture. The vial was capped and placed on a heater/stirrer and heated to 120° C. overnight. Then 1 mL of a solution of concentrated ammonium hydroxide/water (1:2) was added. The reaction was filtered and concentrated to dryness. The residue was purified by reverse phase HPLC (C8, gradient 10-100% acetonitrile/water/0.1% trifluoroacetic acid) to provide the title compound.

$^1$H NMR (500 MHz, DMSO-$d_6$/$D_2O$) δ ppm 1.92-2.16 (m, 2H) 2.20-2.25 (m, 3H) 3.24-3.67 (m, 4H) 5.28 (dd, 1H) 7.17-7.27 (m, 1H) 7.43-7.52 (m, 1H) 7.57-7.67 (m, 2H) 7.90-7.98 (m, 1H); MS (ESI) m/z 384 (M+H)$^+$.

Example 103

(3R)-N-[(2Z)-3-(4-cyano-3-methylphenyl)-5-methyl-1,3-thiazol-2(3H)-ylidene]-3-fluoropyrrolidine-1-carboxamide The title compound was prepared using the procedure described in Example 102 substituting 4-bromo-2-methylbenzonitrile for 1,3-dibromobenzene.

$^1$H NMR (500 MHz, DMSO-$d_6$/$D_2O$) δ ppm 1.91-2.19 (m, 2H) 2.18-2.28 (m, 3H) 3.26-3.66 (m, 4H) 5.26 (dd, 1H) 7.19-7.28 (m, 1H) 7.68-7.75 (m, 1H) 7.76-7.84 (m, 1H) 7.86-7.97 (m, 1H); MS (ESI) m/z 345 (M+H)$^+$.

Example 104

(3R)-3-fluoro-N-[(2Z)-5-methyl-3-(3-methylphenyl)-1,3-thiazol-2(3H)-ylidene]pyrrolidine-1-carboxamide The title compound was prepared using the procedure described in Example 102 substituting 1-bromo-3-methylbenzene for 1,3-dibromobenzene.

$^1$H NMR (500 MHz, DMSO-$d_6$/$D_2O$) δ ppm 1.94-2.16 (m, 2H) 2.20-2.24 (m, 3H) 2.35-2.38 (m, 3H) 3.18-3.66 (m, 4H) 5.11-5.39 (m, 1H) 7.12-7.17 (m, 1H) 7.19-7.26 (m, 1H) 7.34-7.45 (m, 3H); MS (ESI) m/z 320 (M+H)$^+$.

Example 105

(3R)-N-[(2Z)-3-(4-bromophenyl)-5-methyl-1,3-thiazol-2(3H)-ylidene]-3-fluoropyrrolidine-1-carboxamide The title compound was prepared using the procedure described in Example 102 substituting 1,4-dibromobenzene for 1,3-dibromobenzene.

$^1$H NMR (500 MHz, DMSO-$d_6$/$D_2O$) δ ppm 1.91-2.16 (m, 2H) 2.18-2.28 (m, 3H) 2.95-3.67 (m, 4H) 5.07-5.43 (m, 1H) 7.12-7.21 (m, 1H) 7.54-7.66 (m, 2H) 7.66-7.74 (m, 2H); MS (ESI) m/z 384 (M+H)$^+$.

Example 106

(3R)-3-fluoro-N-[(2Z)-5-methyl-3-(4-phenoxyphenyl)-1,3-thiazol-2(3H)-ylidene]pyrrolidine-1-carboxamide The title compound was prepared using the procedure described in Example 102 substituting 1-bromo-4-phenoxybenzene for 1,3-dibromobenzene.

$^1$H NMR (500 MHz, DMSO-$d_6$/$D_2O$) δ ppm 1.88-2.17 (m, 2H) 2.18-2.26 (m, 3H) 3.22-3.65 (m, 4H) 5.09-5.41 (m, 1H) 7.06-7.18 (m, 5H) 7.19-7.26 (m, 1H) 7.42-7.49 (m, 2H) 7.56-7.65 (m, 2H); MS (ESI) m/z 398 (M+H)$^+$.

Example 107

(3R)-3-fluoro-N-[(2Z)-5-methyl-3-(4-methylphenyl)-1,3-thiazol-2(3H)-ylidene]pyrrolidine-1-carboxamide The title compound was prepared using the procedure described in Example 102 substituting 1-bromo-4-methylbenzene for 1,3-dibromobenzene.

$^1$H NMR (500 MHz, DMSO-$d_6$/$D_2O$) δ ppm 1.88-2.16 (m, 2H) 2.19-2.25 (m, 3H) 2.34-2.39 (m, 3H) 3.06-3.65 (m, 4H) 5.17-5.36 (m, 1H) 7.10-7.16 (m, 1H) 7.29-7.35 (m, 2H) 7.43-7.50 (m, 2H); MS (ESI) m/z 320 (M+H)$^+$.

Example 108

(3R)-N-[(2Z)-3-(4-ethylphenyl)-5-methyl-1,3-thiazol-2(3H)-ylidene]-3-fluoropyrrolidine-1-carboxamide The title compound was prepared using the procedure described in Example 102 substituting 1-bromo-4-ethylbenzene for 1,3-dibromobenzene.

$^1$H NMR (500 MHz, DMSO-$d_6$/$D_2O$) δ ppm 1.22 (t, 3H) 1.88-2.14 (m, 2H) 2.20-2.26 (m, 3H) 2.67 (q, 2H) 3.24-3.66 (m, 4H) 5.12-5.37 (m, 1H) 7.09-7.15 (m, 1H) 7.30-7.41 (m, 2H) 7.43-7.56 (m, 2H); MS (ESI) m/z 334 (M+H)$^+$.

Example 109

(3R)-3-fluoro-N-[(2Z)-3-(3-fluorophenyl)-5-methyl-1,3-thiazol-2(3H)-ylidene]pyrrolidine-1-carboxamide The title compound was prepared using the procedure described in Example 102 substituting 1-bromo-3-fluorobenzene for 1,3-dibromobenzene.

$^1$H NMR (500 MHz, DMSO-$d_6$/$D_2O$) δ ppm 1.92-2.15 (m, 2H) 2.21-2.25 (m, 3H) 3.24-3.67 (m, 4H) 5.12-5.40 (m, 1H) 7.17-7.35 (m, 2H) 7.42-7.67 (m, 3H); MS (ESI) m/z 324 (M+H)$^+$.

Example 110

(3R)-3-fluoro-N-[(2Z)-3-(4-fluorophenyl)-5-methyl-1,3-thiazol-2(3H)-ylidene]pyrrolidine-1-carboxamide The title compound was prepared using the procedure described in Example 102 substituting 1-bromo-4-fluorobenzene for 1,3-dibromobenzene.

¹H NMR (500 MHz, DMSO-d₆/D₂O) δ ppm 1.89-2.14 (m, 2H) 2.16-2.31 (m, 3H) 3.15-3.64 (m, 4H) 5.06-5.39 (m, 1H) 7.10-7.19 (m, 1H) 7.28-7.41 (m, 2H) 7.57-7.73 (m, 2H); MS (ESI) m/z 324 (M+H)⁺.

Example 111

(3R)-3-fluoro-N-[(2Z)-5-methyl-3-[3-(trifluoromethyl)phenyl]-1,3-thiazol-2(3H)-ylidene]pyrrolidine-1-carboxamide The title compound was prepared using the procedure described in Example 102 substituting 1-bromo-3-(trifluoromethyl)benzene for 1,3-dibromobenzene.
¹H NMR (500 MHz, DMSO-d₆/D₂O) δ ppm 1.92-2.17 (m, 2H) 2.21-2.29 (m, 3H) 3.25-3.67 (m, 4H) 5.16-5.39 (m, 1H) 7.27-7.36 (m, 1H) 7.71-7.79 (m, 2H) 7.85-7.94 (m, 1H) 8.10-8.19 (m, 1H); MS (ESI) m/z 374 (M+H)⁺.

Example 112

(3R)-3-fluoro-N-[(2Z)-5-methyl-3-[4-(trifluoromethyl)phenyl]-1,3-thiazol-2(3H)-ylidene]pyrrolidine-1-carboxamide The title compound was prepared using the procedure described in Example 102 substituting 1-bromo-4-(trifluoromethyl)benzene for 1,3-dibromobenzene.
¹H NMR (500 MHz, DMSO-d₆/D₂O) δ ppm 1.90-2.16 (m, 2H) 2.20-2.29 (m, 3H) 3.28-3.65 (m, 4H) 5.09-5.41 (m, 1H) 7.20-7.28 (m, 1H) 7.81-8.00 (m, 4H); MS (ESI) m/z 374 (M+H)⁺.

Example 113

(3R)-N-[(2Z)-3-(4-chlorophenyl)-5-methyl-1,3-thiazol-2(3H)-ylidene]-3-fluoropyrrolidine-1-carboxamide The title compound was prepared using the procedure described in Example 102 substituting 1-bromo-4-chlorobenzene for 1,3-dibromobenzene.
¹H NMR (500 MHz, DMSO-d₆/D₂O) δ ppm 1.91-2.17 (m, 2H) 2.20-2.25 (m, 3H) 3.22-3.67 (m, 4H) 5.13-5.41 (m, 1H) 7.13-7.21 (m, 1H) 7.49-7.70 (m, 4H); MS (ESI) m/z 340 (M+H)⁺.

Example 114

(3R)-3-fluoro-N-[(2Z)-3-(4-iodophenyl)-5-methyl-1,3-thiazol-2(3H)-ylidene]pyrrolidine-1-carboxamide The title compound was prepared using the procedure described in Example 102 substituting 1,4-diiodobenzene for 1,3-dibromobenzene.
¹H NMR (500 MHz, DMSO-d₆/D₂O) δ ppm 1.91-2.16 (m, 2H) 2.19-2.27 (m, 3H) 3.24-3.62 (m, 4H) 5.04-5.41 (m, 1H) 7.11-7.24 (m, 1H) 7.38-7.50 (m, 2H) 7.80-7.91 (m, 2H); MS (ESI) m/z 432 (M+H)⁺.

Example 115

(3R)-N-[(2Z)-3-(3-cyanophenyl)-5-methyl-1,3-thiazol-2(3H)-ylidene]-3-fluoropyrrolidine-1-carboxamide The title compound was prepared using the procedure described in Example 102 substituting 3-bromobenzonitrile for 1,3-dibromobenzene.
¹H NMR (500 MHz, DMSO-d₆/D₂O) δ ppm 1.86-2.14 (m, 2H) 2.14-2.26 (m, 3H) 3.19-3.67 (m, 4H) 5.12-5.45 (m, 1H) 7.23-7.36 (m, 1H) 7.69-7.75 (m, 1H) 7.80-7.90 (m, 1H) 7.96-8.03 (m, 1H) 8.10-8.20 (m, 1H); MS (ESI) m/z 331 (M+H)⁺.

Example 116

(3R)-3-fluoro-N-[(2Z)-5-methyl-3-(2-naphthyl)-1,3-thiazol-2(3H)-ylidene]pyrrolidine-1-carboxamide The title compound was prepared using the procedure described in Example 102 substituting 2-bromonaphthalene for 1,3-dibromobenzene.
¹H NMR (500 MHz, DMSO-d₆/D₂O) δ ppm 1.85-2.15 (m, 2H) 2.24-2.29 (m, 3H) 3.21-3.69 (m, 4H) 5.07-5.40 (m, 1H) 7.26-7.30 (m, 1H) 7.52-7.65 (m, 2H) 7.75-7.83 (m, 1H) 7.96-8.02 (m, 2H) 8.05 (d, 1H) 8.12 (d, 1H); MS (ESI) m/z 356 (M+H)⁺.

Example 117

(3R)-N-[(2Z)-3-(5-bromothien-2-yl)-5-methyl-1,3-thiazol-2(3H)-ylidene]-3-fluoropyrrolidine-1-carboxamide The title compound was prepared using the procedure described in Example 102 substituting 2,5-dibromothiophene for 1,3-dibromobenzene.
¹H NMR (500 MHz, DMSO-d₆/D₂O) δ ppm 2.06-2.23 (m, 2H) 2.23-2.29 (m, 3H) 3.38-3.70 (m, 2H) 3.77-3.98 (m, 2H) 5.28-5.53 (m, 1H) 7.15-7.20 (m, 1H) 7.21-7.27 (m, 1H) 7.65-7.74 (m, 1H); MS (ESI) m/z 391 (M+H)⁺.

Example 118

Example 118 has been removed and is not part of this document.

Example 119

(3R)-N-[(2Z)-3-(3,4-dichlorophenyl)-5-methyl-1,3-thiazol-2(3H)-ylidene]-3-fluoropyrrolidine-1-carboxamide The title compound was prepared using the procedure described in Example 102 substituting 4-bromo-1,2-dichlorobenzene for 1,3-dibromobenzene.
¹H NMR (500 MHz, DMSO-d₆/D₂O) δ ppm 1.90-2.17 (m, 2H) 2.20-2.26 (m, 3H) 3.26-3.68 (m, 4H) 5.19-5.38 (m, 1H) 7.19-7.25 (m, 1H) 7.63-7.70 (m, 1H) 7.77 (dd, 1H) 8.02 (dd, 1H); MS (ESI) m/z 374 (M+H)⁺.

Example 120

(3R)-3-fluoro-N-[(2Z)-3-(3-iodophenyl)-5-methyl-1,3-thiazol-2(3H)-ylidene]pyrrolidine-1-carboxamide The title compound was prepared using the procedure described in Example 102 substituting 1,3-diiodobenzene for 1,3-dibromobenzene.
¹H NMR (500 MHz, DMSO-d₆/D₂O) δ ppm 1.93-2.16 (m, 2H) 2.19-2.26 (m, 3H) 3.28-3.66 (m, 4H) 5.15-5.45 (m, 1H)

7.16-7.24 (m, 1H) 7.29-7.37 (m, 1H) 7.54-7.66 (m, 1H) 7.76 (d, 1H) 8.10 (d, 1H); MS (ESI) m/z 432 (M+H)$^+$.

Example 121

(3R)-N-[(2Z)-3-(3-chloro-4-methylphenyl)-5-methyl-1,3-thiazol-2(3H)-ylidene]-3-fluoropyrrolidine-1-carboxamide The title compound was prepared using the procedure described in Example 102 substituting 4-bromo-2-chloro-1-methylbenzene for 1,3-dibromobenzene.
$^1$H NMR (500 MHz, DMSO-d$_6$/D$_2$O) δ ppm 1.94-2.17 (m, 2H) 2.20-2.26 (m, 3H) 2.35-2.41 (m, 3H) 3.25-3.68 (m, 4H) 5.18-5.40 (m, 1H) 7.15-7.23 (m, 1H) 7.45-7.53 (m, 2H) 7.72-7.80 (m, 1H); MS (ESI) m/z 354 (M+H)$^+$.

Example 122

(3R)-N-[(2Z)-3-(1-benzothien-5-yl)-5-methyl-1,3-thiazol-2(3H)-ylidene]-3-fluoropyrrolidine-1-carboxamide The title compound was prepared using the procedure described in Example 102 substituting 5-bromobenzo[b]thiophene for 1,3-dibromobenzene.
$^1$H NMR (500 MHz, DMSO-d$_6$/D$_2$O)) δ ppm 1.82-2.16 (m, 2H) 2.17-2.29 (m, 3H) 3.19-3.64 (m, 4H) 5.12-5.36 (m, 1H) 7.20-7.24 (m, 1H) 7.51-7.57 (m, 1H) 7.57-7.64 (m, 1H) 7.84-7.89 (m, 1H) 8.05-8.15 (m, 2H); MS (ESI) m/z 362 (M+H)$^+$.

Example 123

N-[(2Z)-3-(5-bromothien-2-yl)-1,3-thiazol-2(3H)-ylidene]pyrrolidine-1-carboxamide In a 4 mL vial charged with a stir bar, N-1,3-thiazol-2-ylpyrrolidine-1-carboxamide (69 mg, 0.35 mmol, Example 32A) was added, followed by copper(I) trifluoromethanesulfonate benzene complex (35 mg, 0.07 mmol), 5-chloro-1,10-phenanthroline (30 mg, 0.14 mmol) and cesium carbonate (125 mg, 0.39 mmol). A loose cap with a septum was placed on the vial and then the vial was placed under vacuum in a vacuum oven for 30 minutes. The solid mixture was purged with nitrogen gas a couple of times. 2,5-Dibromothiophene (102 mg, 0.42 mmol) dissolved in 1-methyl-2-pyrrolidinone (1.0 mL) was added to the mixture. The vial was capped and placed on a heater/stirrer and heated to 120° C. overnight. Then 1 mL of a solution of concentrated ammonium hydroxide/water (1:2) was added. The reaction was filtered and concentrated to dryness. The residue was purified by reverse phase HPLC (C8, gradient 10-100% acetonitrile/water/0.1% trifluoroacetic acid) to provide the title compound.
$^1$H NMR (500 MHz, DMSO-d$_6$/D$_2$O) δ ppm 1.80-1.99 (m, 4H) 3.36 (t, 2H) 3.61 (t, 2H) 7.02 (d, 1H) 7.19 (d, 1H) 7.31 (d, 1H) 7.93 (d, 1H); MS (ESI) m/z 358 (M+H)$^+$.

Example 124

N-[(2Z)-3-(2-naphthyl)-1,3-thiazol-2(3H)-ylidene]pyrrolidine-1-carboxamide

The title compound was prepared using the procedure described in Example 123 substituting 2-bromonaphthalene for 2,5-dibromothiophene.
$^1$H NMR (500 MHz, DMSO-d$_6$/D$_2$O) δ ppm 1.67-1.83 (m, 4H) 3.16-3.37 (m, 4H) 6.88 (d, 1H) 7.53 (d, 1H) 7.58-7.65 (m, 2H) 7.77-7.83 (m, 1H) 7.97-8.04 (m, 2H) 8.06 (d, 1H) 8.08-8.17 (m, 1H); MS (ESI) m/z 324 (M+H)$^+$.

Example 125

N-[(2Z)-3-(5-chlorothien-2-yl)-1,3-thiazol-2(3H)-ylidene]pyrrolidine-1-carboxamide The title compound was prepared using the procedure described in Example 123 substituting 2-bromo-5-chlorothiophene for 2,5-dibromothiophene.
$^1$H NMR (500 MHz, DMSO-d$_6$/D$_2$O) δ ppm 1.82-1.98 (m, 4H) 3.36 (t, 2H) 3.61 (t, 2H) 7.01 (d, 1H) 7.10 (d, 1H) 7.33 (d, 1H) 7.93 (d, 1H); MS (ESI) m/z 314 (M+H)$^+$.

Example 126

N-[(2Z)-5-methyl-3-[4-(trifluoromethyl)phenyl]-1,3-thiazol-2(3H)-ylidene]indoline-1-carboxamide In a 20 mL vial, a solution of 3-methyl-1-({[(2Z)-5-methyl-3-[4-(trifluoromethyl)phenyl]-1,3-thiazol-2(3H)-ylidene]amino}carbonyl)-1H-imidazol-3-ium iodide (62 mg, 0.13 mmol, Example 18B) dissolved in acetonitrile (0.6 mL) was added followed by the addition of diisopropylethylamine (28 µL, 0.16 mmol) dissolved in acetonitrile (0.6 mL). Then, to the solution was added indoline (17 mg, 0.14 mmol) dissolved in acetonitrile (0.7 mL). The vial was capped and shaken overnight at room temperature. The reaction was concentrated to dryness. The residue was purified by reverse phase HPLC (C18, gradient 10-95% acetonitrile/water/0.1% trifluoroacetic acid) to provide the title compound.
$^1$H NMR (500 MHz, DMSO-d$_6$/D$_2$O) δ ppm 2.26-2.30 (m, 3H) 2.99 (t, 2H) 3.95 (t, 2H) 6.72-6.97 (m, 2H) 7.04-7.26 (m, 2H) 7.57-7.74 (m, 1H) 7.81-7.93 (m, 4H); MS (ESI) m/z 404 (M+H)$^+$.

Example 127

N-ethyl-N-methyl-N'-[(2Z)-5-methyl-3-[4-(trifluoromethyl)phenyl]-1,3-thiazol-2(3H)-ylidene]urea In a 20 mL vial, a solution of 3-methyl-1-({[(2Z)-5-methyl-3-[4-(trifluoromethyl)phenyl]-1,3-thiazol-2(3H)-ylidene]amino}carbonyl)-1H-imidazol-3-ium iodide (50 mg, 0.10 mmol, Example 18B) dissolved in acetonitrile (0.6 mL) was added followed by the addition of diisopropylethylamine (28 µL, 0.13 mmol) dissolved in acetonitrile (0.6 mL). Then, to the solution was added N-methylethanamine hydrochloride (11 mg, 0.11 mmol) dissolved in acetonitrile (0.5 mL). The vial was capped and shaken overnight at room temperature. The reaction was concentrated to dryness. The residue was purified by reverse phase HPLC (C18, gradient 10-95% acetonitrile/water/0.1% trifluoroacetic acid) to provide the title compound.
$^1$H NMR (500 MHz, DMSO-d$_6$/D$_2$O) δ ppm 0.98 (t, 3H) 2.20-2.24 (m, 3H) 2.81-2.88 (m, 3H) 3.32-3.38 (m, 2H) 7.09-7.18 (m, 1H) 7.81-7.90 (m, 4H); MS (ESI) m/z 344 (M+H)$^+$.

Example 128

N-methyl-N'-[(2Z)-5-methyl-3-[4-(trifluoromethyl)phenyl]-1,3-thiazol-2(3H)-ylidene]-N-propylurea In a 20 mL vial a solution of 3-methyl-1-({[(2Z)-5-methyl-3-[4-(trifluoromethyl)phenyl]-1,3-thiazol-2(3H)-ylidene]

amino}carbonyl)-1H-imidazol-3-ium iodide (50 mg, 0.10 mmol, Example 18B) dissolved in acetonitrile (0.6 mL) was added followed by the addition of diisopropylethylamine (28 µL, 0.13 mmol) dissolved in acetonitrile (0.6 mL). Then, to the solution was added N-methylpropan-1-amine (8 mg, 0.11 mmol) dissolved in acetonitrile (0.5 mL). The vial was capped and shaken overnight at room temperature. The reaction was concentrated to dryness. The residue was purified by reverse phase HPLC (C18, gradient 10-95% acetonitrile/water/0.1% trifluoroacetic acid) to provide the title compound.
$^1$H NMR (500 MHz, DMSO-d$_6$/D$_2$O) δ ppm 0.60-0.90 (m, 3H) 1.31-1.58 (m, 2H) 2.20-2.24 (m, 3H) 2.78-2.91 (m, 3H) 3.16-3.26 (m, 2H) 7.04-7.19 (m, 1H) 7.72-7.92 (m, 4H); MS (ESI) m/z 358 (M+H)$^+$.

Example 129

N-(1,3-dioxolan-2-ylmethyl)-N-methyl-N'-[(2Z)-5-methyl-3-[4-(trifluoromethyl)phenyl]-1,3-thiazol-2(3H)-ylidene]urea The title compound was prepared using the procedure described in Example 128 substituting 1-(1,3-dioxolan-2-yl)-N-methylmethanamine for N-methylpropan-1-amine.
$^1$H NMR (500 MHz, DMSO-d$_6$/D$_2$O) δ ppm 2.18-2.28 (m, 3H) 2.90-2.95 (m, 3H) 3.37-3.43 (m, 2H) 3.67-3.89 (m, 4H) 4.80-4.99 (m, 1H) 7.09-7.18 (m, 1H) 7.79-7.88 (m, 4H); MS (ESI) m/z 402 (M+H)$^+$.

Example 130

N-methyl-N-(3-methylbutyl)-N'-[(2Z)-5-methyl-3-[4-(trifluoromethyl)phenyl]-1,3-thiazol-2(3H)-ylidene]urea The title compound was prepared using the procedure described in Example 128 substituting N,3-dimethylbutan-1-amine for N-methylpropan-1-amine.
$^1$H NMR (500 MHz, DMSO-d$_6$/D$_2$O) δ ppm 0.58-0.89 (m, 6H) 1.05-1.45 (m, 3H) 2.20-2.23 (m, 3H) 2.77-2.90 (m, 3H) 3.24-3.28 (m, 2H) 6.96-7.23 (m, 1H) 7.70-7.93 (m, 4H); MS (ESI) m/z 386 (M+H)$^+$.

Example 131

N-methyl-N'-[(2Z)-5-methyl-3-[4-(trifluoromethyl)phenyl]-1,3-thiazol-2(3H)-ylidene]-N-prop-2-ynylurea The title compound was prepared using the procedure described in Example 128 substituting N-methylprop-2-yn-1-amine for N-methylpropan-1-amine.
$^1$H NMR (500 MHz, DMSO-d$_6$/D$_2$O) δ ppm 2.21-2.27 (m, 3H) 2.86-2.89 (m, 1H) 2.89-2.92 (m, 3H) 4.10-4.16 (m, 2H) 7.13-7.19 (m, 1H) 7.83-7.89 (m, 4H); MS (ESI) m/z 354 (M+H)$^+$.

Example 132

N,N-diethyl-N'-[(2Z)-5-methyl-3-[4-(trifluoromethyl)phenyl]-1,3-thiazol-2(3H)-ylidene]urea The title compound was prepared using the procedure described in Example 128 substituting diethylamine hydrochloride for N-methylpropan-1-amine.
$^1$H NMR (500 MHz, DMSO-d$_6$/D$_2$O) δ ppm 0.91-1.11 (m, 6H) 2.17-2.31 (m, 3H) 3.22-3.28 (m, 4H) 7.08-7.12 (m, 1H) 7.76-7.90 (m, 4H); MS (ESI) m/z 358 (M+H)$^+$.

Example 133

N-ethyl-N'-[(2Z)-5-methyl-3-[4-(trifluoromethyl)phenyl]-1,3-thiazol-2(3H)-ylidene]-N-propylurea The title compound was prepared using the procedure described in Example 128 substituting N-ethylpropan-1-amine for N-methylpropan-1-amine.
$^1$H NMR (500 MHz, DMSO-d$_6$/D$_2$O) δ ppm 0.59-0.84 (m, 3H) 0.91-1.04 (m, 3H) 1.27-1.50 (m, 2H) 2.19-2.26 (m, 3H) 3.09-3.27 (m, 4H) 7.06-7.17 (m, 1H) 7.76-7.84 (m, 4H); MS (ESI) m/z 372 (M+H)$^+$.

Example 134

N-butyl-N-ethyl-N'-[(2Z)-5-methyl-3-[4-(trifluoromethyl)phenyl]-1,3-thiazol-2(3H)-ylidene]urea The title compound was prepared using the procedure described in Example 128 substituting N-ethylbutan-1-amine for N-methylpropan-1-amine.
$^1$H NMR (500 MHz, DMSO-d$_6$/D$_2$O) δ ppm 0.54-1.56 (m, 10H) 2.16-2.26 (m, 3H) 3.15-3.28 (m, 4H) 7.02-7.15 (m, 1H) 7.75-7.95 (m, 4H); MS (ESI) m/z 386 (M+H)$^+$.

Example 135

N,N-dibutyl-N'-[(2Z)-5-methyl-3-[4-(trifluoromethyl)phenyl]-1,3-thiazol-2(3H)-ylidene]urea The title compound was prepared using the procedure described in Example 128 substituting dibutylamine for N-methylpropan-1-amine.
$^1$H NMR (500 MHz, DMSO-d$_6$/D$_2$O) δ ppm 0.32-1.73 (m, 14H) 2.11-2.31 (m, 3H) 3.08-3.26 (m, 4H) 6.70-7.25 (m, 1H) 7.61-7.98 (m, 4H); MS (ESI) m/z 414 (M+H)$^+$.

Example 136

2,5-dimethyl-N-[(2Z)-5-methyl-3-[4-(trifluoromethyl)phenyl]-1,3-thiazol-2(3H)-ylidene]pyrrolidine-1-carboxamide The title compound was prepared using the procedure described in Example 128 substituting 2,5-dimethylpyrrolidine for N-methylpropan-1-amine.
$^1$H NMR (500 MHz, DMSO-d$_6$/D$_2$O) δ ppm 0.87-1.21 (m, 6H) 1.39-1.58 (m, 2H) 1.79-2.12 (m, 2H) 2.16-2.29 (m, 3H) 3.71-4.11 (m, 2H) 6.98-7.19 (m, 1H) 7.62-7.92 (m, 4H); MS (ESI) m/z 384 (M+H)$^+$.

Example 137

2-methyl-N-[(2Z)-5-methyl-3-[4-(trifluoromethyl)phenyl]-1,3-thiazol-2(3H)-ylidene]piperidine-1-carboxamide The title compound was prepared using the procedure described in Example 128 substituting 2-methylpiperidine for N-methylpropan-1-amine.
$^1$H NMR (500 MHz, DMSO-d$_6$/D$_2$O) δ ppm 0.99-1.11 (m, 3H) 1.12-1.66 (m, 6H) 2.16-2.25 (m, 3H) 267-287 (m, 1H)

3299-4217 (m, 1H) 4344-4.63 (m, 1H) 7.05-7.16 (m, 1H) 7.73-7.92 (m, 4H); MS (ESI) m/z 384 (M+H)+.

Example 138

N-(2-methoxyethyl)-N-methyl-N'-[(2Z)-5-methyl-3-[4-(trifluoromethyl)phenyl]-1,3-thiazol-2(3H)-ylidene]urea The title compound was prepared using the procedure described in Example 128 substituting 2-methoxy-N-methylethanamine for N-methylpropan-1-amine.

$^1$H NMR (500 MHz, DMSO-d$_6$/D$_2$O) δ ppm 2.18-2.28 (m, 3H) 2.87-2.92 (m, 3H) 3.06-3.23 (m, 3H) 3.34-3.49 (m, 4H) 7.08-7.14 (m, 1H) 7.76-7.89 (m, 4H); MS (ESI) m/z 374 (M+H)+.

Example 139

N-benzyl-N-ethyl-N'-[(2Z)-5-methyl-3-[4-(trifluoromethyl)phenyl]-1,3-thiazol-2(3H)-ylidene]urea In a 20 mL vial, a solution of 3-methyl-1-({[(2Z)-5-methyl-3-[4-(trifluoromethyl)phenyl]-1,3-thiazol-2(3H)-ylidene]amino}carbonyl)-1H-imidazol-3-ium iodide (45 mg, 0.09 mmol, Example 18B) dissolved in acetonitrile (0.6 mL) was added followed by the addition of diisopropylamine (21 μL, 0.12 mmol) dissolved in acetonitrile (0.6 mL). Then to the solution was added N-benzylethanamine (14 mg, 0.1 mmol) dissolved in acetonitrile (0.5 mL). The vial was capped and shaken overnight at room temperature. The reaction was concentrated to dryness. The residue was purified by reverse phase HPLC (C18, gradient 10-95% acetonitrile/water/0.1% trifluoroacetic acid) to provide the title compound.

$^1$H NMR (500 MHz, DMSO-d$_6$/D$_2$O) δ ppm 1.00 (t, 3H) 2.19-2.24 (m, 3H) 3.22-3.36 (m, 2H) 4.45-4.51 (m, 2H) 7.02-7.36 (m, 6H) 7.66-7.78 (m, 4H); MS (ESI) m/z 420 (M+H)+.

Example 140

N-benzyl-N-isopropyl-N'-[(2Z)-5-methyl-3-[4-(trifluoromethyl)phenyl]-1,3-thiazol-2(3H)-ylidene]urea The title compound was prepared using the procedure described in Example 139 substituting N-benzylpropan-2-amine for N-benzylethanamine.

$^1$H NMR (500 MHz, DMSO-d$_6$/D$_2$O) δ ppm 0.93-1.14 (m, 6H) 2.09-2.29 (m, 3H) 4.34-4.51 (m, 3H) 7.00-7.36 (m, 6H) 7.54-7.76 (m, 4H); MS (ESI) m/z 434 (M+H).

Example 141

N-benzyl-N-butyl-N'-[(2Z)-5-methyl-3-[4-(trifluoromethyl)phenyl]-1,3-thiazol-2(3H)-ylidene]urea The title compound was prepared using the procedure described in Example 139 substituting N-benzylbutan-1-amine for N-benzylethanamine.

$^1$H NMR (500 MHz, DMSO-d$_6$/D$_2$O) δ ppm 0.55-0.88 (m, 3H) 0.95-1.25 (m, 2H) 1.23-1.55 (m, 2H) 2.12-2.31 (m, 3H) 3.16-3.32 (m, 2H) 4.43-4.55 (m, 2H) 6.81-7.35 (m, 5H) 7.58-7.83 (m, 5H); MS (ESI) m/z 448 (M+H)+.

Example 142

4-benzyl-N-[(2Z)-5-methyl-3-[4-(trifluoromethyl)phenyl]-1,3-thiazol-2(3H)-ylidene]piperidine-1-carboxamide The title compound was prepared using the procedure described in Example 139 substituting 4-benzylpiperidine for N-benzylethanamine.

$^1$H NMR (500 MHz, DMSO-d$_6$/D$_2$O) δ ppm 0.89-1.13 (m, 2H) 1.40-1.84 (m, 2H) 2.16-2.27 (m, 3H) 2.60-2.82 (m, 2H) 3.01-3.08 (m, 2H) 3.16-3.27 (m, 1H) 3.99-4.33 (m, 2H) 6.93-7.37 (m, 6H) 7.66-7.89 (m, 4H); MS (ESI) m/z 460 (M+H).

Example 143

N-isopropyl-N'-[(2Z)-5-methyl-3-[4-(trifluoromethyl)phenyl]-1,3-thiazol-2(3H)-ylidene]urea In a 20 mL vial a solution of 3-methyl-1-({[(2Z)-5-methyl-3-[4-(trifluoromethyl)phenyl]-1,3-thiazol-2(3H)-ylidene]amino}carbonyl)-1H-imidazol-3-ium iodide (45 mg, 0.1 mmol, Example 18B) dissolved in acetonitrile (0.6 mL) was added followed by the addition of diisopropylethylamine (22 μL, 0.13 mmol) dissolved in acetonitrile (0.6 mL). Then to the solution was added propan-2-amine (6 mg, 0.11 mmol) dissolved in acetonitrile (0.5 mL). The vial was capped and shaken overnight at room temperature. The reaction was concentrated to dryness. The residue was purified by reverse phase HPLC (C18, gradient 10-95% acetonitrile/water/0.1% trifluoroacetic acid) to provide the title compound.

$^1$H NMR (500 MHz, DMSO-d$_6$/D$_2$O) δ ppm 1.00-1.16 (m, 6H) 2.16-2.24 (m, 3H) 3.66-3.85 (m, 1H) 6.91-7.09 (m, 1H) 7.78-7.87 (m, 4H); MS (ESI) m/z 344 (M+H)+, 342 (M−H)−.

Example 144

N-(sec-butyl)-N'-[(2Z)-5-methyl-3-[4-(trifluoromethyl)phenyl]-1,3-thiazol-2(3H)-ylidene]urea The title compound was prepared using the procedure described in Example 143 substituting butan-2-amine for propan-2-amine.

$^1$H NMR (500 MHz, DMSO-d$_6$/D$_2$O) δ ppm 0.81 (t, 3H) 0.98-1.09 (m, 3H) 1.22-1.50 (m, 2H) 2.09-2.29 (m, 3H) 3.33-3.72 (m, 1H) 6.86-7.10 (m, 1H) 7.62-8.05 (m, 4H); MS (ESI) m/z 358 (M+H)+, 356 (M−H)−.

Example 145

N-(1-methylbutyl)-N'-[(2Z)-5-methyl-3-[4-(trifluoromethyl)phenyl]-1,3-thiazol-2(3H)-ylidene]urea The title compound was prepared using the procedure described in Example 143 substituting pentan-2-amine for propan-2-amine.

$^1$H NMR (500 MHz, DMSO-d$_6$/D$_2$O) δ ppm 0.75-0.90 (m, 3H) 0.97-1.11 (m, 3H) 1.10-1.50 (m, 4H) 2.19-2.26 (m, 3H) 3.55-3.73 (m, 1H) 6.96-7.07 (m, 1H) 7.70-7.90 (m, 4H); MS (ESI) m/z 372 (M+H)+, 370 (M−H)−.

Example 146

N-(1,1-dimethylpropyl)-N'-[(2Z)-5-methyl-3-[4-(trifluoromethyl)phenyl]-1,3-thiazol-2(3H)-ylidene]urea The title compound was prepared using the procedure described in Example 143 substituting 2-methylbutan-2-amine for propan-2-amine.

¹H NMR (500 MHz, DMSO-d₆/D₂O) δ ppm 0.77 (t, 3H) 1.15-1.24 (m, 6H) 1.64 (q, 2H) 2.13-2.24 (m, 3H) 6.90-7.08 (m, 1H) 7.77-7.84 (m, 4H); MS (ESI) m/z 372 (M+H)⁺, 370 (M−H)⁻.

Example 147

N-(1-ethylpropyl)-N'-[(2Z)-5-methyl-3-[4-(trifluoromethyl)phenyl]-1,3-thiazol-2(3H)-ylidene]urea The title compound was prepared using the procedure described in Example 143 substituting pentan-3-amine for propan-2-amine.
¹H NMR (500 MHz, DMSO-d₆/D₂O) δ ppm 0.81 (t, 6H) 1.30-1.52 (m, 4H) 2.15-2.26 (m, 3H) 3.29-3.54 (m, 1H) 6.98-7.10 (m, 1H) 7.72-7.91 (m, 4H); MS (ESI) m/z 372 (M+H)⁺, 370 (M−H)⁻.

Example 148

N-(2-methoxy-1-methylethyl)-N'-[(2Z)-5-methyl-3-[4-(trifluoromethyl)phenyl]-1,3-thiazol-2(3H)-ylidene]urea The title compound was prepared using the procedure described in Example 143 substituting 1-methoxypropan-2-amine for propan-2-amine.
¹H NMR (500 MHz, DMSO-d₆/D₂O) δ ppm 0.97-1.14 (m, 3H) 2.18-2.26 (m, 3H) 3.17-3.22 (m, 1H) 3.22-3.25 (m, 3H) 3.27-3.36 (m, 1H) 3.70-3.94 (m, 1H) 6.93-7.08 (m, 1H) 7.68-7.92 (m, 4H); MS (ESI) m/z 374 (M+H)⁺.

Example 149

N-cyclopropyl-N'-[(2Z)-5-methyl-3-[4-(trifluoromethyl)phenyl]-1,3-thiazol-2(3H)-ylidene]urea The title compound was prepared using the procedure described in Example 143 substituting cyclopropanamine for propan-2-amine.
¹H NMR (500 MHz, DMSO-d₆/D₂O) δ ppm 0.31-0.66 (m, 4H) 2.18-2.25 (m, 3H) 2.54-2.66 (m, 1H) 6.91-7.12 (m, 1H) 7.71-7.88 (m, 4H); MS (ESI) m/z 342 (M+H)⁺, 340 (M−H)⁻.

Example 150

N-cyclobutyl-N'-[(2Z)-5-methyl-3-[4-(trifluoromethyl)phenyl]-1,3-thiazol-2(3H)-ylidene]urea The title compound was prepared using the procedure described in Example 143 substituting cyclobutanamine for propan-2-amine.
¹H NMR (500 MHz, DMSO-d₆/D₂O) δ ppm 1.48-1.69 (m, 2H) 1.79-1.97 (m, 2H) 2.06-2.19 (m, 2H) 2.19-2.25 (m, 3H) 3.91-4.20 (m, 1H) 6.91-7.09 (m, 1H) 7.42-7.89 (m, 4H); MS (ESI) m/z 356 (M+H)⁺, 354 (M−H)⁻.

Example 151

N-cyclopentyl-N'-[(2Z)-5-methyl-3-[4-(trifluoromethyl)phenyl]-1,3-thiazol-2(3H)-ylidene]urea The title compound was prepared using the procedure described in Example 143 substituting cyclopentanamine for propan-2-amine.

¹H NMR (500 MHz, DMSO-d₆/D₂O) δ ppm 1.28-1.92 (m, 8H) 2.15-2.25 (m, 3H) 3.81-4.00 (m, 1H) 6.86-7.11 (m, 1H) 7.66-7.97 (m, 4H); MS (ESI) m/z 370 (M+H)⁺, 368 (M−H)⁻.

Example 152

(3R)-N-[(2Z)-3-(3,5-dichlorophenyl)-5-(hydroxymethyl)-1,3-thiazol-2(3H)-ylidene]-3-fluoropyrrolidine-1-carboxamide In a 4 mL vial charged with a stir bar, (3R)-3-fluoro-N-[5-(hydroxymethyl)-1,3-thiazol-2-yl]pyrrolidine-1-carboxamide (43 mg, 0.18 mmol, Example 36B) was added followed by copper iodide (8 mg, 0.04 mmol) and cesium carbonate (88 mg, 0.27 mmol). A loose cap with septum was placed on the vial and then the vial was placed under vacuum for 30 minutes. The solid mixture was purged with nitrogen gas a couple of times. Then ethyl 2-cyclohexanecarboxylate (12 mg, 0.07 mmol) dissolved in dry dimethyl sulfoxide (0.4 mL) was added to the mixture followed by 1,3-dichloro-5-iodobenzene (60 mg, 0.22 mmol) dissolved in dry dimethyl sulfoxide (0.7 mL). The vial was capped and the resulting mixture was shaken at room temperature for 1 hour followed by shaking at 95° C. overnight. Then 1 mL of concentrated ammonium hydroxide solution was added. The reaction was filtered and concentrated to dryness. The residue was purified by reverse phase HPLC (C18, gradient 10-95% acetonitrile/water/0.1% trifluoroacetic acid) to provide the title compound.
¹H NMR (500 MHz, DMSO-d₆/D₂O) δ ppm 1.91-2.17 (m, 2H) 3.32-3.74 (m, 4H) 4.44-4.53 (m, 2H) 5.10-5.39 (m, 1H) 7.26-7.27 (m, 1H) 7.52 (t, 1H) 7.72-7.75 (m, 2H); MS (ESI) m/z 390 (M+H)⁺.

Example 153

(3R)-N-[(2Z)-3-(3-chlorophenyl)-5-(hydroxymethyl)-1,3-thiazol-2(3H)-ylidene]-3-fluoropyrrolidine-1-carboxamide The title compound was prepared using the procedure described in Example 152 substituting 1-chloro-3-iodobenzene for 1,3-dichloro-5-iodobenzene.
¹H NMR (500 MHz, DMSO-d₆/D₂O) δ ppm 1.93-2.18 (m, 2H) 3.31-3.70 (m, 4H) 4.45-4.52 (m, 2H) 5.10-5.38 (m, 1H) 7.19-7.22 (m, 1H) 7.40-7.46 (m, 1H) 7.51-7.55 (m, 2H) 7.69-7.77 (m, 1H); MS (ESI) m/z 356 (M+H)⁺.

Example 154

(3R)-N-[(2Z)-3-(3,4-dimethylphenyl)-5-(hydroxymethyl)-1,3-thiazol-2(3H)-ylidene]-3-fluoropyrrolidine-1-carboxamide The title compound was prepared using the procedure described in Example 152 substituting 4-iodo-1,2-dimethylbenzene for 1,3-dichloro-5-iodobenzene.
¹H NMR (500 MHz, DMSO-d₆/D₂O) δ ppm 1.92-2.16 (m, 2H) 2.27-2.29 (m, 6H) 3.28-3.61 (m, 4H) 4.43-4.49 (m, 2H) 5.10-5.35 (m, 1H) 7.09-7.12 (m, 1H) 7.22-7.28 (m, 2H) 7.30-7.37 (m, 1H); MS (ESI) m/z 350 (M+H)⁺.

Example 155

(3R)-N-[(2Z)-3-(3,5-dimethylphenyl)-5-(hydroxymethyl)-1,3-thiazol-2(3H)-ylidene]-3-fluoropyrrolidine-1-carboxamide The title compound was prepared using the procedure described in Example 152 substituting 1-iodo-3,5-dimethylbenzene for 1,3-dichloro-5-iodobenzene.

¹H NMR (500 MHz, DMSO-d₆/D₂O) δ ppm 2.00-2.14 (m, 2 H) 2.31-2.34 (m, 6H) 3.32-3.66 (m, 4 H) 4.41-4.52 (m, 2 H) 5.06-5.38 (m, 1 H) 7.01-7.04 (m, 1 H) 7.12-7.14 (m, 1H) 7.18-7.21 (m, 2 H); MS (ESI) m/z 350 (M+H)⁺.

Example 156

(3R)-N-[(2Z)-3-(4-chloro-3-methylphenyl)-5-(hydroxymethyl)-1,3-thiazol-2(3H)-ylidene]-3-fluoropyrrolidine-1-carboxamide The title compound was prepared using the procedure described in Example 152 substituting 1-chloro-4-iodo-2-methylbenzene for 1,3-dichloro-5-iodobenzene.
¹H NMR (500 MHz, DMSO-d₆/D₂O) δ ppm 1.91-2.15 (m, 2H) 2.37-2.41 (m, 3H) 3.32-3.67 (m, 4H) 4.41-4.54 (m, 2H) 5.11-5.37 (m, 1H) 7.15-7.18 (m, 1H) 7.40-7.53 (m, 2H) 7.55-7.59 (m, 1H); MS (ESI) m/z 370 (M+H)⁺.

Example 157

(3R)-3-fluoro-N-[(2Z)-5-(hydroxymethyl)-3-[4-(trifluoromethoxy)phenyl]-1,3-thiazol-2(3H)-ylidene]pyrrolidine-1-carboxamide The title compound was prepared using the procedure described in Example 152 substituting 1-iodo-4-(trifluoromethoxy)benzene for 1,3-dichloro-5-iodobenzene.
¹H NMR (500 MHz, DMSO-d₆/D₂O) δ ppm 1.90-2.16 (m, 2 H) 3.31-3.64 (m, 4H) 4.47-4.50 (m, 2 H) 5.12-5.35 (m, 1 H) 7.18-7.21 (m, 1 H) 7.38-7.49 (m, 2 H) 7.67-7.76 (m, 2 H); MS (ESI) m/z 406 (M+H)⁺.

Example 158

(3R)-N-[(2Z)-3-(3,4-dichlorophenyl)-5-(hydroxymethyl)-1,3-thiazol-2(3H)-ylidene]-3-fluoropyrrolidine-1-carboxamide The title compound was prepared using the procedure described in Example 152 substituting 1,2-dichloro-4-iodobenzene for 1,3-dichloro-5-iodobenzene.
¹H NMR (500 MHz, DMSO-d₆/D₂O) δ ppm 1.94-2.16 (m, 2 H) 3.33-3.69 (m, 4H) 4.45-4.51 (m, 2 H) 5.12-5.38 (m, 1 H) 7.20-7.24 (m, 1 H) 7.56-7.75 (m, 2 H) 7.92-7.97 (m, 1 H); MS (ESI) m/z 390 (M+H)⁺.

Example 159

(3R)-3-fluoro-N-[(2Z)-3-[3-fluoro-4-(trifluoromethyl)phenyl]-5-(hydroxymethyl)-1,3-thiazol-2(3H)-ylidene]pyrrolidine-1-carboxamide The title compound was prepared using the procedure described in Example 152 substituting 4-bromo-2-fluoro-1-(trifluoromethyl)benzene for 1,3-dichloro-5-iodobenzene.
¹H NMR (500 MHz, DMSO-d₆/D₂O) δ ppm 1.97-2.18 (m, 2 H) 3.40-3.70 (m, 4H) 4.47-4.51 (m, 2 H) 5.09-5.40 (m, 1 H) 7.26-7.33 (m, 1 H) 7.68-7.92 (m, 3 H); MS (ESI) m/z 408 (M+H)⁺.

Example 160

N-[(2Z)-3-(4-chlorophenyl)-4,5-dimethyl-1,3-thiazol-2(3H)-ylidene]pyrrolidine-1-carboxamide Example 160A 3-(4-chlorophenyl)-4,5-dimethyl-1,3-thiazol-2(3H)-imine hydrochloride A flask fitted with a Dean-Stark trap was charged with 3-thiocyano-2-butanone (258 mg, 2.0 mmol; prepared according to Gregory, J. T.; Mathes, R. A. *J. Am. Chem. Soc.* 1952, 1719) and 4-chloroaniline hydrochloride (326 mg, 2.0 mmol) in anhydrous toluene (20 mL). The resulting suspension became clear upon initial heating to reflux, then a precipitate formed. After 4 hours, the mixture was cooled. The title compound was collected by filtration and washed with toluene and ice-cold acetone.
¹H NMR (300 MHz, DMSO-d₆) δ ppm 1.79 (d, J=0.7 Hz, 3 H) 2.25 (d, J=0.7 Hz, 3H) 7.59-7.66 (m, 2 H) 7.71-7.79 (m, 2 H) 9.35 (br s, 1 H); MS (DCI/NH₃) m/z 239 (M+H)⁺.

Example 160B

N-[(2Z)-3-(4-chlorophenyl)-4,5-dimethyl-1,3-thiazol-2(3H)-ylidene]pyrrolidine-1-carboxamide To a suspension of 3-(4-chlorophenyl)-4,5-dimethyl-1,3-thiazol-2(3H)-imine hydrochloride (90 mg, 0.33 mmol, Example 160A) in acetonitrile (2.0 mL) containing diisopropylethylamine (102 mg, 0.79 mmol) was added 1-pyrrolidinecarbonyl chloride (53 mg, 39 mmol). The mixture was heated at 75° C. for 18 hours, then concentrated. The residue was dissolved in dichloromethane (10 mL). The organic layer was washed with dilute aqueous ammonium chloride (5 mL) and water (2×5 mL) and the dichloromethane was removed under reduced pressure. The residue was purified on a Waters Symmetry C₈ 30×100 mm column (flow rate 40 mL/min, 5-95% gradient of acetonitrile in 0.1% aqueous trifluoroacetic acid) to afford the title product.
¹H NMR (300 MHz, DMSO-d₆) δ ppm 1.63-1.73 (m, 2 H) 1.65-1.75 (m, 2 H) 1.82 (s, 3 H) 2.15 (s, 3 H) 3.02 (t, J=6.4 Hz, 2 H) 3.21 (t, J=6.4 Hz, 2 H) 7.36-7.43 (m, 2 H) 7.54-7.62 (m, 2 H); MS (DCI/NH₃) m/z 336 (M+H)⁺.

Example 161

N-[(2Z)-4,5-dimethyl-3-[4-(trifluoromethyl)phenyl]-1,3-thiazol-2(3H)-ylidene]pyrrolidine-1-carboxamide Example 161A 4,5-dimethyl-3-[4-(trifluoromethyl)phenyl]-1,3-thiazol-2(3H)-imine hydrochloride The title compound was prepared from 4-trifluoromethylphenylaniline hydrochloride and 3-thiocyano-2-butanone as described for Example 160A.
¹H NMR (300 MHz, DMSO-d₆) δ ppm 1.79 (d, J=1.0 Hz, 3 H) 2.26 (d, J=1.0 Hz, 3H) 7.85 (m, 2 H) 8.07 (m, 2 H) 9.40 (br s, 1 H); MS (DCI/NH₃) m/z 273 (M+H)⁺.

Example 161B

N-[(2Z)-4,5-dimethyl-3-[4-(trifluoromethyl)phenyl]-1,3-thiazol-2(3H)-ylidene]pyrrolidine-1-carboxamide The title compound was prepared from 4,5-dimethyl-3-[4-(trifluoromethyl)phenyl]-1,3-thiazol-2(3H)-imine hydrochloride (90 mg, 0.33 mmol) according to the procedure described for Example 160B.
¹H NMR (300 MHz, DMSO-D6) δ ppm 1.60-1.75 (m, 4 H) 1.84 (d, J=1.0 Hz, 3H) 2.16 (d, J=1.0 Hz, 3 H) 3.00 (t, J=6.4 Hz, 2 H) 3.22 (t, J=6.4 Hz, 2 H) 7.63 (m, 2 H) 7.90 (m, 2 H); MS (DCI/NH₃) m/z 370 (M+H)⁺

Example 162

N-[(2Z)-3-(6-chloropyridin-3-yl)-4,5-dimethyl-1,3-thiazol-2(3H)-ylidene]pyrrolidine-1-carboxamide

Example 162A 3-(6-chloropyridin-3-yl)-4,5-dimethyl-1,3-thiazol-2(3H)-imine hydrochloride The title compound was prepared from 5-amino-2-chloropyridine hydrochloride and 3-thiocyano-2-butanone as described for Example 160A.

$^1$H NMR (300 MHz, DMSO-$d_6$) δ ppm 1.81 (br s, 3 H) 2.26 (br s, 3 H) 7.88 (d, J=8.5 Hz, 1 H) 8.18 (dd, J=8.5, 2.7 Hz, 1 H) 8.69 (d, J=2.7 Hz, 1 H) 9.57 (br s, 1 H); MS (DCI/NH$_3$) m/z 240 (M+H)$^+$.

Example 162B

N-[(2Z)-3-(6-chloropyridin-3-yl)-4,5-dimethyl-1,3-thiazol-2(3H)-ylidene]pyrrolidine-1-carboxamide The title compound was prepared from 3-(6-chloropyridin-3-yl)-4,5-dimethyl-1,3-thiazol-2(3H)-imine hydrochloride (90 mg, 0.38 mmol) according to the procedure described for Example 160B.

$^1$H NMR (300 MHz, DMSO-$d_6$) δ ppm 1.63-1.77 (m, 4 H) 1.87 (d, J=1.0 Hz, 3 H) 2.16 (d, J=1.0 Hz, 3 H) 3.03 (t, J=6.3 Hz, 2 H) 3.22 (t, J=6.1 Hz, 2 H) 7.71 (dd, J=8.5, 0.7 Hz, 1 H) 7.99 (dd, J=8.5, 2.7 Hz, 1 H) 8.49 (dd, J=2.7, 0.7 Hz, 1 H); MS (DCI/NH$_3$) m/z 337 (M+H)$^+$.

Example 163

N-[(2Z)-3-(6-chloropyridin-3-yl)-5-methyl-1,3-thiazol-2(3H)-ylidene]pyrrolidine-1-carboxamide

Example 163A 3-(6-chloropyridin-3-yl)-5-methyl-1,3-thiazol-2(3H)-imine hydrochloride The title compound was prepared from 5-amino-2-chloropyridine hydrochloride and 2-thiocyanatopropanal as described for Example 160A. The title compound was used without additional purification.

MS (DCI/NH$_3$) m/z 226 (M+H)$^+$.

Example 163B

N-[(2Z)-3-(6-chloropyridin-3-yl)-5-methyl-1,3-thiazol-2(3H)-ylidene]pyrrolidine-1-carboxamide The title compound was prepared from 3-(6-chloropyridin-3-yl)-5-methyl-1,3-thiazol-2(3H)-imine hydrochloride (90 mg, 0.40 mmol) according to the procedure described for Example 160B.

$^1$H NMR (300 MHz, MeOH-$d_4$) δ ppm 1.83-1.90 (m, 4 H) 2.28 (d, J=1.4 Hz, 3 H) 3.33-3.43 (m, 4 H) 7.06 (q, J=1.4 Hz, 1 H) 7.58 (d, J=8.5 Hz, 1 H) 8.10 (dd, J=8.5, 2.7 Hz, 1 H) 8.67 (d, J=2.7 Hz, 1 H); MS (DCI/NH$_3$) m/z 323 (M+H)$^+$.

Example 164

4-acetyl-N-[(2Z)-5-methyl-3-[4-(trifluoromethyl)phenyl]-1,3-thiazol-2(3H)-ylidene]piperazine-1-carboxamide In a 20 mL vial were combined a solution of 3-methyl-1-({[(2Z)-5-methyl-3-[4-(trifluoromethyl)phenyl]-1,3-thiazol-2(3H)-ylidene]amino}carbonyl)-1H-imidazol-3-ium iodide (45 mg, 0.09 mmol, Example 18B) dissolved in acetonitrile (0.6 mL) and diisopropylethylamine (21 µL, 0.12 mmol) dissolved in acetonitrile (0.6 mL). Then, to the solution was added 1-(piperazin-1-yl)ethanone (13 mg, 0.1 mmol) dissolved in acetonitrile (0.5 mL). The vial was capped and shaken overnight at room temperature. The reaction was checked by LC/MS and concentrated to dryness. The residue was dissolved in 1:1 DMSO/MeOH and purified by reverse phase HPLC (C18, gradient 10-95% acetonitrile/water/0.1% trifluoroacetic acid) to supply the title compound.

$^1$H NMR (500 MHz, DMSO-$d_6$/D$_2$O) δ ppm 1.98-2.01 (m, 3 H) 2.22-2.26 (m, 3H) 3.33-3.55 (m, 8 H) 7.01-7.17 (m, 1 H) 7.78-7.89 (m, 4 H); MS (ESI) m/z 413 (M+H)$^+$.

Example 165

{(2Z)-2-(acetylimino)-3-[4-(trifluoromethyl)phenyl]-2,3-dihydro-1,3-thiazol-5-yl}methyl acetate N-{(2Z)-5-Methylene-3-[4-(trifluoromethyl)phenyl]-1,3-thiazolidin-2-ylidene}acetamide (4.51 g, 15.0 mmol, Intermediate A6) was dissolved into acetic acid (60 mL) and treated with 1 M iodine monochloride in dichloromethane (30 mL) over three minutes. After about 15 minutes more iodine monochloride solution (0.8 mL) was added, and after another ten minutes the solution was partially concentrated, and then concentrated twice from toluene. The residue was triturated with 20% ethyl acetate/toluene and the allyl chloride was collected by filtration. The filtrate was concentrated and redissolved into acetic acid (20 mL), treated with potassium acetate (2.95 g, 30 mmol), stirred 6 hours at room temperature, and concentrated thrice from ethyl acetate. The residue was mixed with a little ethyl acetate and filtered through basic alumina with a 2% methanol/ethyl acetate rinse. The filtrate was concentrated and chromatographed on silica (ethyl acetate/dichloromethane/hexanes) to give the title compound.

$^1$H NMR (500 MHz, CD$_2$Cl$_2$) δ ppm 2.08 (3H), 2.17 (3H), 5.10 (2H), 7.16 (1H), 7.69 (2H), 7.80 (2H); MS (ESI) m/z 359 (M+H)$^+$.

The following examples were prepared using but not limited to the chemistry methodologies described in the previous examples:

Example 166

N-[(2Z)-3-(3-methyl-1-benzothien-5-yl)-1,3-thiazol-2(3H)-ylidene]pyrrolidine-1-carboxamide;

Example 167

N-methyl-N'-[(2Z)-5-methyl-3-[4-(trifluoromethyl)phenyl]-1,3-thiazol-2(3H)-ylidene]-N-pentylurea;

Example 168

N-[(2'Z)-5-chloro-5'-methyl-2,3'-bi-1,3-thiazol-2'-ylidene]
pyrrolidine-1-carboxamide;

Example 169

N-[(2Z)-3-(4-fluorophenyl)-1,3-thiazol-2(3H)-ylidene]pyrrolidine-1-carboxamide;

Example 170

N-[(2Z)-3-(5-methylthien-2-yl)-1,3-thiazol-2(3H)-ylidene]
pyrrolidine-1-carboxamide;

Example 171

(3R)-N-[(2Z)-3-(2-chloro-1-benzothien-5-yl)-5-methyl-1,3-thiazol-2(3H)-ylidene]-3-fluoropyrrolidine-1-carboxamide;

Example 172

(3R)-3-fluoro-N-[(2Z)-5-methyl-3-[1,2,4]triazolo[1,5-a]pyridin-6-yl-1,3-thiazol-2(3H)-ylidene]pyrrolidine-1-carboxamide;

Example 173

N-[(2Z)-3-(2,3-dichlorophenyl)-5-methyl-1,3-thiazol-2(3H)-ylidene]-2,2-dimethylpropanamide;

Example 174

N-[(2Z)-3-[2,4-bis(trifluoromethyl)phenyl]-5-methyl-1,3-thiazol-2(3H)-ylidene]-2,2-dimethylpropanamide;

Example 175

N-[(2Z)-3-[4-(difluoromethoxy)phenyl]-5-methyl-1,3-thiazol-2(3H)-ylidene]-2,2-dimethylpropanamide;

Example 176

N-[(2Z)-3-(5-pyridin-2-ylthien-2-yl)-1,3-thiazol-2(3H)-ylidene]pyrrolidine-1-carboxamide;

Example 177

N-[(2Z)-3-(1-benzofuran-2-yl)-1,3-thiazol-2(3H)-ylidene]
pyrrolidine-1-carboxamide;

Example 178

N-[(2Z)-3-(5-methyl-1-benzothien-2-yl)-1,3-thiazol-2(3H)-ylidene]pyrrolidine-1-carboxamide;

Example 179

N-[(2Z)-3-thien-2-yl-1,3-thiazol-2(3H)-ylidene]pyrrolidine-1-carboxamide;

Example 180

N-[(2Z)-3-(2,2'-bithien-5-yl)-1,3-thiazol-2(3H)-ylidene]
pyrrolidine-1-carboxamide;

Example 181

N-[(2Z)-3-(5-cyanothien-2-yl)-1,3-thiazol-2(3H)-ylidene]
pyrrolidine-1-carboxamide;

Example 182

N-[(2Z)-3-(4-chlorophenyl)-1,3-thiazolidin-2-ylidene]-1H-imidazole-1-carboxamide;

Example 183

(3R)-N-[(2Z)-3-[5-(aminocarbonyl)thien-2-yl]-5-methyl-1,3-thiazol-2(3H)-ylidene]-3-fluoropyrrolidine-1-carboxamide;

Example 184

N'-[(2Z)-3-(5-chlorothien-2-yl)-5-methyl-1,3-thiazol-2(3H)-ylidene]-N-(3-fluorobenzyl)-N-methylurea;

Example 185

(3R)-N-[(2Z)-3-(4-cyanophenyl)-5-(hydroxymethyl)-1,3-thiazol-2(3H)-ylidene]-3-fluoropyrrolidine-1-carboxamide;

Example 186

(3R)-3-fluoro-N-[(2Z)-5-(hydroxymethyl)-3-(5,6,8-trifluoro-2-naphthyl)-1,3-thiazol-2(3H)-ylidene]pyrrolidine-1-carboxamide;

Example 187

N-[(2Z)-3-(4-methoxyphenyl)-5-methylene-1,3-thiazolidin-2-ylidene]acetamide;

Example 188

N-[(2Z)-3-(4-methoxyphenyl)-5-methyl-1,3-thiazol-2(3H)-ylidene]acetamide;

Example 189

N-{(2Z)-3-[4-(difluoromethoxy)phenyl]-5-methylene-1,3-thiazolidin-2-ylidene}acetamide;

Example 190

N-[(2Z)-3-[4-(difluoromethoxy)phenyl]-5-methyl-1,3-thiazol-2(3H)-ylidene]acetamide;

Example 191

N'-[(2Z)-3-[4-(difluoromethoxy)phenyl]-5-methyl-1,3-thiazol-2(3H)-ylidene]-N,N-diisopropylurea;

Example 192

N'-[(2Z)-3-[4-(difluoromethoxy)phenyl]-5-methyl-1,3-thiazol-2(3H)-ylidene]-N-methyl-N-phenylurea;

Example 193

N'-[(2Z)-3-[4-(difluoromethoxy)phenyl]-5-methyl-1,3-thiazol-2(3H)-ylidene]-N,N-dimethylurea;

Example 194

N-{(2Z)-5-methylene-3-[4-(trifluoromethoxy)phenyl]-1,3-thiazolidin-2-ylidene}acetamide;

Example 195

N-[(2Z)-5-methyl-3-[4-(trifluoromethoxy)phenyl]-1,3-thiazol-2(3H)-ylidene]acetamide;

Example 196

N-[(2Z)-5-methyl-3-[4-(trifluoromethoxy)phenyl]-1,3-thiazol-2(3H)-ylidene]piperidine-1-carboxamide;

Example 197

N,N-diisopropyl-N'-[(2Z)-5-methyl-3-[4-(trifluoromethoxy)phenyl]-1,3-thiazol-2(3H)-ylidene]urea;

Example 198

N-methyl-N'-[(2Z)-5-methyl-3-[4-(trifluoromethoxy)phenyl]-1,3-thiazol-2(3H)-ylidene]-N-phenylurea;

Example 199

N-[(2Z)-3-(4-chlorophenyl)-5-methylene-1,3-thiazolidin-2-ylidene]acetamide;

Example 200

N-[(2Z)-3-(4-chlorophenyl)-5-methyl-1,3-thiazol-2(3H)-ylidene]acetamide;

Example 201

N'-[(2Z)-3-(4-chlorophenyl)-5-methyl-1,3-thiazol-2(3H)-ylidene]-N,N-diisopropylurea;

Example 202

N-[(2Z)-3-(6,7-dicyano-2-naphthyl)-5-methyl-1,3-thiazol-2(3H)-ylidene]-2,2-dimethylpropanamide;

Example 203

N-[(2Z)-3-(4-benzylphenyl)-5-methyl-1,3-thiazol-2(3H)-ylidene]-2,2-dimethylpropanamide;

Example 204

N'-[(2Z)-3-(4-fluorophenyl)-5-methyl-1,3-thiazol-2(3H)-ylidene]-N,N-diisopropylurea;

Example 205

N-[(2Z)-3-[4-(cyanomethyl)phenyl]-5-methyl-1,3-thiazol-2(3H)-ylidene]pyrrolidine-1-carboxamide;

Example 206

N-[(2Z)-3-[4-(cyanomethyl)phenyl]-5-methyl-1,3-thiazol-2(3H)-ylidene]piperidine-1-carboxamide;

Example 207

N'-[(2Z)-3-[4-(cyanomethyl)phenyl]-5-methyl-1,3-thiazol-2(3H)-ylidene]-N,N-diethylurea;

Example 208

N'-[(2Z)-3-[4-(cyanomethyl)phenyl]-5-methyl-1,3-thiazol-2(3H)-ylidene]-N,N-dimethylurea;

Example 209

N-[(2Z)-5-methyl-3-[4-(trifluoromethyl)phenyl]-1,3-thiazol-2(3H)-ylidene]piperidine-1-carboxamide;

Example 210

N-[(2Z)-3-[4-(cyanomethyl)phenyl]-5-methyl-1,3-thiazol-2(3H)-ylidene]-2,2-dimethylpropanamide;

Example 211

N-[(2Z)-3-(2,6-dimethylpyrimidin-4-yl)-5-methyl-1,3-thiazol-2(3H)-ylidene]-2,2-dimethylpropanamide;

Example 212

N-[(2Z)-5-methyl-3-[4-(trifluoromethyl)phenyl]-1,3-thiazol-2(3H)-ylidene]-1H-imidazole-1-carboxamide;

Example 213 tert-butyl(2R,3S)-2-methyl-1-({[(2Z)-5-methyl-3-[4-(trifluoromethyl)phenyl]-1,3-thiazol-2(3H)-ylidene]amino}carbonyl)pyrrolidin-3-ylcarbamate;

Example 214

2-isopropyl-N-[(2Z)-5-methyl-3-[4-(trifluoromethyl)phenyl]-1,3-thiazol-2(3H)-ylidene]pyrrolidine-1-carboxamide;

Example 215

2-isobutyl-N-[(2Z)-5-methyl-3-[4-(trifluoromethyl)phenyl]-1,3-thiazol-2(3H)-ylidene]pyrrolidine-1-carboxamide;

Example 216

(3R)-3-(dimethylamino)-N-[(2Z)-5-methyl-3-[4-(trifluoromethyl)phenyl]-1,3-thiazol-2(3H)-ylidene]pyrrolidine-1-carboxamide;

Example 217 tert-butyl (3S)-1-({[(2Z)-5-methyl-3-[4-(trifluoromethyl)phenyl]-1,3-thiazol-2(3H)-ylidene]amino}carbonyl)pyrrolidin-3-ylcarbamate;

Example 218 tert-butyl 5-({[(2Z)-5-methyl-3-[4-(trifluoromethyl)phenyl]-1,3-thiazol-2(3H)-ylidene]amino}carbonyl)hexahydropyrrolo[3,4-c]pyrrole-2(1H)-carboxylate;

Example 219 tert-butyl (1S,5R)-3-({[(2Z)-5-methyl-3-[4-(trifluoromethyl)phenyl]-1,3-thiazol-2(3H)-ylidene]amino}carbonyl)-3,6-diazabicyclo[3.2.0]heptane-6-carboxylate;

Example 220 tert-butyl (3R)-3-methyl-1-({[(2Z)-5-methyl-3-[4-(trifluoromethyl)phenyl]-1,3-thiazol-2(3H)-ylidene]amino}carbonyl)pyrrolidin-3-ylcarbamate;

Example 221 tert-butyl 6-({[(2Z)-5-methyl-3-[4-(trifluoromethyl)phenyl]-1,3-thiazol-2(3H)-ylidene]amino}carbonyl)octahydro-1H-pyrrolo[3,4-b]pyridine-1-carboxylate;

Example 222 tert-butyl (1S,4S)-5-({[(2Z)-5-methyl-3-[4-(trifluoromethyl)phenyl]-1,3-thiazol-2(3H)-ylidene]amino}carbonyl)-2,5-diazabicyclo[2.2.1]heptane-2-carboxylate;

Example 223

(3S)-3-amino-N-[(2Z)-5-methyl-3-[4-(trifluoromethyl)phenyl]-1,3-thiazol-2(3H)-ylidene]pyrrolidine-1-carboxamide;

Example 224

(2R,3S)-3-amino-2-methyl-N-[(2Z)-5-methyl-3-[4-(trifluoromethyl)phenyl]-1,3-thiazol-2(3H)-ylidene]pyrrolidine-1-carboxamide;

Example 225

N-[(2Z)-5-methyl-3-[4-(trifluoromethyl)phenyl]-1,3-thiazol-2(3H)-ylidene]hexahydropyrrolo[3,4-c]pyrrole-2(1H)-carboxamide;

Example 226

(3R)-3-amino-3-methyl-N-[(2Z)-5-methyl-3-[4-(trifluoromethyl)phenyl]-1,3-thiazol-2(3H)-ylidene]pyrrolidine-1-carboxamide;

Example 227

(1R,5R)-N-[(2Z)-5-methyl-3-[4-(trifluoromethyl)phenyl]-1,3-thiazol-2(3H)-ylidene]-3,6-diazabicyclo[3.2.0]heptane-3-carboxamide;

Example 228

(4aS,7aS)-N-[(2Z)-5-methyl-3-[4-(trifluoromethyl)phenyl]-1,3-thiazol-2(3H)-ylidene]octahydro-6H-pyrrolo[3,4-b]pyridine-6-carboxamide;

Example 229

(1S,4S)-N-[(2Z)-5-methyl-3-[4-(trifluoromethyl)phenyl]-1,3-thiazol-2(3H)-ylidene]-2,5-diazabicyclo[2.2.1]heptane-2-carboxamide;

Example 230

N'-[(2Z)-3-(4-chlorophenyl)-4,5-dimethyl-1,3-thiazol-2(3H)-ylidene]-N,N-dimethylurea;

Example 231

N'-[(2Z)-4,5-dimethyl-3-[4-(trifluoromethyl)phenyl]-1,3-thiazol-2(3H)-ylidene]-N,N-dimethylurea;

Example 232

N'-[(2Z)-3-(3-ethoxyphenyl)-4,5-dimethyl-1,3-thiazol-2(3H)-ylidene]-N,N-dimethylurea;

Example 233

N-[(2Z)-3-(3-ethoxyphenyl)-4,5-dimethyl-1,3-thiazol-2(3H)-ylidene]pyrrolidine-1-carboxamide;

Example 234

N'-[(2Z)-3-(4-chlorophenyl)-4-phenyl-1,3-thiazol-2(3H)-ylidene]-N,N-dimethylurea;

Example 235

N-isopropyl-N-methyl-N'-[(2Z)-5-methyl-3-[4-(trifluoromethyl)phenyl]-1,3-thiazol-2(3H)-ylidene]urea;

Example 236

N-butyl-N-methyl-N'-[(2Z)-5-methyl-3-[4-(trifluoromethyl)phenyl]-1,3-thiazol-2(3H)-ylidene]urea;

Example 237

N-isobutyl-N-methyl-N'-[(2Z)-5-methyl-3-[4-(trifluoromethyl)phenyl]-1,3-thiazol-2(3H)-ylidene]urea;

Example 238

N-cyclohexyl-N-methyl-N'-[(2Z)-5-methyl-3-[4-(trifluoromethyl)phenyl]-1,3-thiazol-2(3H)-ylidene]urea;

Example 239

N-ethyl-N-isopropyl-N'-[(2Z)-5-methyl-3-[4-(trifluoromethyl)phenyl]-1,3-thiazol-2(3H)-ylidene]urea;

Example 240

N-cyclohexyl-N-ethyl-N'-[(2Z)-5-methyl-3-[4-(trifluoromethyl)phenyl]-1,3-thiazol-2(3H)-ylidene]urea;

Example 241

N'-[(2Z)-5-methyl-3-[4-(trifluoromethyl)phenyl]-1,3-thiazol-2(3H)-ylidene]-N,N-dipropylurea;

Example 242

N-isopropyl-N'-[(2Z)-5-methyl-3-[4-(trifluoromethyl)phenyl]-1,3-thiazol-2(3H)-ylidene]-N-propylurea;

Example 243

N-butyl-N'-[(2Z)-5-methyl-3-[4-(trifluoromethyl)phenyl]-1,3-thiazol-2(3H)-ylidene]-N-propylurea;

Example 244

N-(sec-butyl)-N'-[(2Z)-5-methyl-3-[4-(trifluoromethyl)phenyl]-1,3-thiazol-2(3H)-ylidene]-N-propylurea;

Example 245

N-(cyclopropylmethyl)-N'-[(2Z)-5-methyl-3-[4-(trifluoromethyl)phenyl]-1,3-thiazol-2(3H)-ylidene]-N-propylurea;

Example 246

N-(cyanomethyl)-N-methyl-N'-[(2Z)-5-methyl-3-[4-(trifluoromethyl)phenyl]-1,3-thiazol-2(3H)-ylidene]urea;

Example 247

N-(2-cyanoethyl)-N-cyclopropyl-N'-[(2Z)-5-methyl-3-[4-(trifluoromethyl)phenyl]-1,3-thiazol-2(3H)-ylidene]urea;

Example 248

N,N-diisobutyl-N'-[(2Z)-5-methyl-3-[4-(trifluoromethyl)phenyl]-1,3-thiazol-2(3H)-ylidene]urea;

Example 249

3-methyl-N-[(2Z)-5-methyl-3-[4-(trifluoromethyl)phenyl]-1,3-thiazol-2(3H)-ylidene]piperidine-1-carboxamide;

Example 250

4-methyl-N-[(2Z)-5-methyl-3-[4-(trifluoromethyl)phenyl]-1,3-thiazol-2(3H)-ylidene]piperidine-1-carboxamide;

Example 251

2-ethyl-N-[(2Z)-5-methyl-3-[4-(trifluoromethyl)phenyl]-1,3-thiazol-2(3H)-ylidene]piperidine-1-carboxamide;

Example 252

N-[(2Z)-5-methyl-3-[4-(trifluoromethyl)phenyl]-1,3-thiazol-2(3H)-ylidene]-4-propylpiperidine-1-carboxamide;

Example 253

N-[(2Z)-5-methyl-3-[4-(trifluoromethyl)phenyl]-1,3-thiazol-2(3H)-ylidene]azepane-1-carboxamide;

Example 254

N,N-bis(2-ethoxyethyl)-N'-[(2Z)-5-methyl-3-[4-(trifluoromethyl)phenyl]-1,3-thiazol-2(3H)-ylidene]urea;

Example 255

N-ethyl-N-(2-methoxyethyl)-N'-[(2Z)-5-methyl-3-[4-(trifluoromethyl)phenyl]-1,3-thiazol-2(3H)-ylidene]urea;

Example 256

N-(2-methoxyethyl)-N'-[(2Z)-5-methyl-3-[4-(trifluoromethyl)phenyl]-1,3-thiazol-2(3H)-ylidene]-N-propylurea;

Example 257

N-isopropyl-N-(2-methoxyethyl)-N'-[(2Z)-5-methyl-3-[4-(trifluoromethyl)phenyl]-1,3-thiazol-2(3H)-ylidene]urea;

Example 258

N,N-bis(2-methoxyethyl)-N'-[(2Z)-5-methyl-3-[4-(trifluoromethyl)phenyl]-1,3-thiazol-2(3H)-ylidene]urea;

Example 259

N-[(2Z)-5-methyl-3-[4-(trifluoromethyl)phenyl]-1,3-thiazol-2(3H)-ylidene]morpholine-4-carboxamide;

Example 260

N-[(2Z)-5-methyl-3-[4-(trifluoromethyl)phenyl]-1,3-thiazol-2(3H)-ylidene]thiomorpholine-4-carboxamide;

Example 261

N-(2-cyanoethyl)-N-methyl-N'-[(2Z)-5-methyl-3-[4-(trifluoromethyl)phenyl]-1,3-thiazol-2(3H)-ylidene]urea;

Example 262

N-benzyl-N'-[(2Z)-5-methyl-3-[4-(trifluoromethyl)phenyl]-1,3-thiazol-2(3H)-ylidene]urea;

Example 263

N-(3-chlorobenzyl)-N'-[(2Z)-5-methyl-3-[4-(trifluoromethyl)phenyl]-1,3-thiazol-2(3H)-ylidene]urea;

Example 264

N-(3,5-dichlorobenzyl)-N'-[(2Z)-5-methyl-3-[4-(trifluoromethyl)phenyl]-1,3-thiazol-2(3H)-ylidene]urea;

Example 265

N-[(2Z)-5-methyl-3-[4-(trifluoromethyl)phenyl]-1,3-thiazol-2(3H)-ylidene]-N'-(2-phenylethyl)urea;

Example 266

N-[(2Z)-5-methyl-3-[4-(trifluoromethyl)phenyl]-1,3-thiazol-2(3H)-ylidene]-N'-(2-pyridin-2-ylethyl)urea;

Example 267

N-[(2Z)-5-methyl-3-[4-(trifluoromethyl)phenyl]-1,3-thiazol-2(3H)-ylidene]-N'-(2-pyridin-3-ylethyl)urea;

Example 268

N-[(2Z)-5-methyl-3-[4-(trifluoromethyl)phenyl]-1,3-thiazol-2(3H)-ylidene]-N'-(2-pyridin-4-ylethyl)urea;

Example 269

N-[(2Z)-5-methyl-3-[4-(trifluoromethyl)phenyl]-1,3-thiazol-2(3H)-ylidene]-N'-(pyridin-3-ylmethyl)urea;

Example 270

N-[2-(dimethylamino)ethyl]-N'-[(2Z)-5-methyl-3-[4-(trifluoromethyl)phenyl]-1,3-thiazol-2(3H)-ylidene]urea;

Example 271

N-[3-(dimethylamino)propyl]-N'-[(2Z)-5-methyl-3-[4-(trifluoromethyl)phenyl]-1,3-thiazol-2(3H)-ylidene]urea;

Example 272

N-[(2Z)-5-methyl-3-[4-(trifluoromethyl)phenyl]-1,3-thiazol-2(3H)-ylidene]-N'-(2-pyrrolidin-1-ylethyl)urea;

Example 273

N-[(2Z)-5-methyl-3-[4-(trifluoromethyl)phenyl]-1,3-thiazol-2(3H)-ylidene]-N'-(3-pyrrolidin-1-ylpropyl)urea;

Example 274

N-[2-(4-methylpiperazin-1-yl)ethyl]-N'-[(2Z)-5-methyl-3-[4-(trifluoromethyl)phenyl]-1,3-thiazol-2(3H)-ylidene]urea;

Example 275

N-[2-(dimethylamino)ethyl]-N-methyl-N'-[(2Z)-5-methyl-3-[4-(trifluoromethyl)phenyl]-1,3-thiazol-2(3H)-ylidene]urea;

Example 276

N-[3-(dimethylamino)propyl]-N-methyl-N'-[(2Z)-5-methyl-3-[4-(trifluoromethyl)phenyl]-1,3-thiazol-2(3H)-ylidene]urea;

Example 277

N-[2-(dimethylamino)ethyl]-N-ethyl-N'-[(2Z)-5-methyl-3-[4-(trifluoromethyl)phenyl]-1,3-thiazol-2(3H)-ylidene]urea;

Example 278

N-[2-(diethylamino)ethyl]-N-methyl-N'-[(2Z)-5-methyl-3-[4-(trifluoromethyl)phenyl]-1,3-thiazol-2(3H)-ylidene]urea;

Example 279

N,N-dibenzyl-N'-[(2Z)-5-methyl-3-[4-(trifluoromethyl)phenyl]-1,3-thiazol-2(3H)-ylidene]urea;

Example 280

N-methyl-N'-[(2Z)-5-methyl-3-[4-(trifluoromethyl)phenyl]-1,3-thiazol-2(3H)-ylidene]-N-(2-phenylethyl)urea;

Example 281

N-methyl-N'-[(2Z)-5-methyl-3-[4-(trifluoromethyl)phenyl]-1,3-thiazol-2(3H)-ylidene]-N-(2-pyridin-2-ylethyl)urea;

Example 282

4-hydroxy-N-[(2Z)-5-methyl-3-[4-(trifluoromethyl)phenyl]-1,3-thiazol-2(3H)-ylidene]piperidine-1-carboxamide;

Example 283

2,6-dimethyl-N-[(2Z)-5-methyl-3-[4-(trifluoromethyl)phenyl]-1,3-thiazol-2(3H)-ylidene]morpholine-4-carboxamide;

Example 284

4-methyl-N-[(2Z)-5-methyl-3-[4-(trifluoromethyl)phenyl]-1,3-thiazol-2(3H)-ylidene]piperazine-1-carboxamide;

Example 285

4-ethyl-N-[(2Z)-5-methyl-3-[4-(trifluoromethyl)phenyl]-1,3-thiazol-2(3H)-ylidene]piperazine-1-carboxamide;

Example 286

N-[(2Z)-5-methyl-3-[4-(trifluoromethyl)phenyl]-1,3-thiazol-2(3H)-ylidene]-4-phenylpiperazine-1-carboxamide;

Example 287

N-[(2Z)-5-methyl-3-[4-(trifluoromethyl)phenyl]-1,3-thiazol-2(3H)-ylidene]-4-pyridin-2-ylpiperazine-1-carboxamide;

Example 288

4-methyl-N-[(2Z)-5-methyl-3-[4-(trifluoromethyl)phenyl]-1,3-thiazol-2(3H)-ylidene]-1,4-diazepane-1-carboxamide;

Example 289

N-[(2Z)-5-methyl-3-[4-(trifluoromethyl)phenyl]-1,3-thiazol-2(3H)-ylidene]-4-pyrimidin-2-ylpiperazine-1-carboxamide;

Example 290

N-isobutyl-N'-[(2Z)-5-methyl-3-[4-(trifluoromethyl)phenyl]-1,3-thiazol-2(3H)-ylidene]urea;

Example 291

N-[(2Z)-5-methyl-3-[4-(trifluoromethyl)phenyl]-1,3-thiazol-2(3H)-ylidene]-N'-pentylurea;

Example 292

N-(3-methylbutyl)-N'-[(2Z)-5-methyl-3-[4-(trifluoromethyl)phenyl]-1,3-thiazol-2(3H)-ylidene]urea;

Example 293

N-[(2Z)-5-methyl-3-[4-(trifluoromethyl)phenyl]-1,3-thiazol-2(3H)-ylidene]-N'-neopentylurea;

Example 294

N-(2-methoxyethyl)-N'-[(2Z)-5-methyl-3-[4-(trifluoromethyl)phenyl]-1,3-thiazol-2(3H)-ylidene]urea;

Example 295

N-[(2Z)-5-methyl-3-[4-(trifluoromethyl)phenyl]-1,3-thiazol-2(3H)-ylidene]-N'-[(2S)-tetrahydrofuran-2-ylmethyl]urea;

Example 296

N-[(2Z)-5-methyl-3-[4-(trifluoromethyl)phenyl]-1,3-thiazol-2(3H)-ylidene]-N'-[(2R)-tetrahydrofuran-2-ylmethyl]urea;

Example 297

N-[(2Z)-5-methyl-3-[4-(trifluoromethyl)phenyl]-1,3-thiazol-2(3H)-ylidene]-N'-(tetrahydrofuran-3-ylmethyl)urea;

Example 298

N-[(2Z)-5-methyl-3-[4-(trifluoromethyl)phenyl]-1,3-thiazol-2(3H)-ylidene]-N'-prop-2-ynylurea;

Example 299

N-(cyclopropylmethyl)-N'-[(2Z)-5-methyl-3-[4-(trifluoromethyl)phenyl]-1,3-thiazol-2(3H)-ylidene]urea;

Example 300

N-(cyclopentylmethyl)-N'-[(2Z)-5-methyl-3-[4-(trifluoromethyl)phenyl]-1,3-thiazol-2(3H)-ylidene]urea;

Example 301

N-cyclohexyl-N'-[(2Z)-5-methyl-3-[4-(trifluoromethyl)phenyl]-1,3-thiazol-2(3H)-ylidene]urea;

Example 302

N-cycloheptyl-N'-[(2Z)-5-methyl-3-[4-(trifluoromethyl)phenyl]-1,3-thiazol-2(3H)-ylidene]urea;

Example 303

N-1-adamantyl-N'-[(2Z)-5-methyl-3-[4-(trifluoromethyl)phenyl]-1,3-thiazol-2(3H)-ylidene]urea;

Example 304

N-[(2Z)-5-methyl-3-[4-(trifluoromethyl)phenyl]-1,3-thiazol-2(3H)-ylidene]-N'-phenylurea;

Example 305

N-(2-methylphenyl)-N'-[(2Z)-5-methyl-3-[4-(trifluoromethyl)phenyl]-1,3-thiazol-2(3H)-ylidene]urea;

Example 306

N-(3-methylphenyl)-N'-[(2Z)-5-methyl-3-[4-(trifluoromethyl)phenyl]-1,3-thiazol-2(3H)-ylidene]urea;

Example 307

N-(4-methylphenyl)-N'-[(2Z)-5-methyl-3-[4-(trifluoromethyl)phenyl]-1,3-thiazol-2(3H)-ylidene]urea;

Example 308

N-(3-methoxyphenyl)-N'-[(2Z)-5-methyl-3-[4-(trifluoromethyl)phenyl]-1,3-thiazol-2(3H)-ylidene]urea;

Example 309

N-(3-fluorophenyl)-N'-[(2Z)-5-methyl-3-[4-(trifluoromethyl)phenyl]-1,3-thiazol-2(3H)-ylidene]urea;

Example 310

N-(3-chlorophenyl)-N'-[(2Z)-5-methyl-3-[4-(trifluoromethyl)phenyl]-1,3-thiazol-2(3H)-ylidene]urea;

Example 311

N-(3-bromophenyl)-N'-[(2Z)-5-methyl-3-[4-(trifluoromethyl)phenyl]-1,3-thiazol-2(3H)-ylidene]urea;

Example 312

N-[(2Z)-5-methyl-3-[4-(trifluoromethyl)phenyl]-1,3-thiazol-2(3H)-ylidene]-N'-[3-(trifluoromethyl)phenyl]urea;

Example 313

N-(3,5-dichlorophenyl)-N'-[(2Z)-5-methyl-3-[4-(trifluoromethyl)phenyl]-1,3-thiazol-2(3H)-ylidene]urea;

Example 314

N-methyl-N-(4-methylphenyl)-N'-[(2Z)-5-methyl-3-[4-(trifluoromethyl)phenyl]-1,3-thiazol-2(3H)-ylidene]urea;

Example 315

N-{(2Z)-5-methyl-3-[4-(trifluoromethyl)phenyl]-1,3-thiazolidin-2-ylidene}acetamide;

Example 316

N-[(2Z)-4,5-dimethyl-3-(6-morpholin-4-ylpyridin-3-yl)-1,3-thiazol-2(3H)-ylidene]pyrrolidine-1-carboxamide;

Example 317

N-{(2Z)-5-methylene-3-[4-(trifluoromethyl)phenyl]-1,3-thiazolidin-2-ylidene}pyrrolidine-1-carboxamide;

Example 318

N-{(2Z)-4-hydroxy-5-methylene-3-[4-(trifluoromethyl)phenyl]-1,3-thiazolidin-2-ylidene}pyrrolidine-1-carboxamide;

Example 319

N-{(2Z)-5-methylene-4-(1H-pyrazol-1-yl)-3-[4-(trifluoromethyl)phenyl]-1,3-thiazolidin-2-ylidene}acetamide;

Example 320

N-[(2Z)-5-(1H-pyrazol-1-ylmethyl)-3-[4-(trifluoromethyl)phenyl]-1,3-thiazol-2(3H)-ylidene]acetamide;

Example 321

N-{(2Z,5Z)-5-(iodomethylene)-3-[4-(trifluoromethyl)phenyl]-1,3-thiazolidin-2-ylidene}acetamide;

Example 322

N-[(2Z)-5-(cyanomethyl)-3-[4-(trifluoromethyl)phenyl]-1,3-thiazol-2(3H)-ylidene]acetamide;

Example 323

N-[(2Z)-5-[(ethylamino)methyl]-3-[4-(trifluoromethyl)phenyl]-1,3-thiazol-2(3H)-ylidene]acetamide;

Example 324

N-[(2Z)-5-[(propylamino)methyl]-3-[4-(trifluoromethyl)phenyl]-1,3-thiazol-2(3H)-ylidene]acetamide;

Example 325

N-[(2Z)-5-[(butylamino)methyl]-3-[4-(trifluoromethyl)phenyl]-1,3-thiazol-2(3H)-ylidene]acetamide;

Example 326

N-[(2Z)-5-[(tert-butylamino)methyl]-3-[4-(trifluoromethyl)phenyl]-1,3-thiazol-2(3H)-ylidene]acetamide;

Example 327

N-[(2Z)-5-{[(cyanomethyl)amino]methyl}-3-[4-(trifluoromethyl)phenyl]-1,3-thiazol-2(3H)-ylidene]acetamide;

Example 328

N-[(2Z)-5-[(dimethylamino)methyl]-3-[4-(trifluoromethyl)phenyl]-1,3-thiazol-2(3H)-ylidene]acetamide;

Example 329

N-[(2Z)-5-{[butyl(methyl)amino]methyl}-3-[4-(trifluoromethyl)phenyl]-1,3-thiazol-2(3H)-ylidene]acetamide;

Example 330

N-[(2Z)-5-{[(1,3-dioxolan-2-ylmethyl)(methyl)amino]methyl}-3-[4-(trifluoromethyl)phenyl]-1,3-thiazol-2(3H)-ylidene]acetamide;

Example 331

N-[(2Z)-5-[(diethylamino)methyl]-3-[4-(trifluoromethyl)phenyl]-1,3-thiazol-2(3H)-ylidene]acetamide;

Example 332

N-[(2Z)-5-(azetidin-1-ylmethyl)-3-[4-(trifluoromethyl)phenyl]-1,3-thiazol-2(3H)-ylidene]acetamide;

Example 333

N-[(2Z)-5-{[bis(2-methoxyethyl)amino]methyl}-3-[4-(trifluoromethyl)phenyl]-1,3-thiazol-2(3H)-ylidene]acetamide;

Example 334

N-[(2Z)-5-{[(1-phenylethyl)amino]methyl}-3-[4-(trifluoromethyl)phenyl]-1,3-thiazol-2(3H)-ylidene]acetamide;

Example 335

N-[(2Z)-5-methyl-3-(2-methylphenyl)-1,3-thiazol-2(3H)-ylidene]pyrrolidine-1-carboxamide;

Example 336

N-[(2Z)-3-(2-aminophenyl)-5-methyl-1,3-thiazol-2(3H)-ylidene]pyrrolidine-1-carboxamide;

Example 337

N-[(2Z)-3-(2-hydroxyphenyl)-5-methyl-1,3-thiazol-2(3H)-ylidene]pyrrolidine-1-carboxamide;

Example 338

N-[(2Z)-3-(4-hydroxyphenyl)-5-methyl-1,3-thiazol-2(3H)-ylidene]pyrrolidine-1-carboxamide;

Example 339

N-[(2Z)-3-(2-methoxyphenyl)-5-methyl-1,3-thiazol-2(3H)-ylidene]pyrrolidine-1-carboxamide;

Example 340

N-[(2Z)-3-(2-fluorophenyl)-5-methyl-1,3-thiazol-2(3H)-ylidene]pyrrolidine-1-carboxamide;

Example 341

N-[(2Z)-3-(2-chlorophenyl)-5-methyl-1,3-thiazol-2(3H)-ylidene]pyrrolidine-1-carboxamide;

Example 342

N-[(2Z)-3-[3-(dimethylamino)phenyl]-5-methyl-1,3-thiazol-2(3H)-ylidene]pyrrolidine-1-carboxamide;

Example 343

N-[(2Z)-3-(2,3-dimethylphenyl)-5-methyl-1,3-thiazol-2(3H)-ylidene]pyrrolidine-1-carboxamide;

Example 344

N-[(2Z)-3-(2,4-dimethylphenyl)-5-methyl-1,3-thiazol-2(3H)-ylidene]pyrrolidine-1-carboxamide;

Example 345

N-[(2Z)-3-(2,5-dimethylphenyl)-5-methyl-1,3-thiazol-2(3H)-ylidene]pyrrolidine-1-carboxamide;

Example 346

N-[(2Z)-3-(2,4-dimethoxyphenyl)-5-methyl-1,3-thiazol-2(3H)-ylidene]pyrrolidine-1-carboxamide;

Example 347

N-[(2Z)-3-(2,5-dimethoxyphenyl)-5-methyl-1,3-thiazol-2(3H)-ylidene]pyrrolidine-1-carboxamide;

Example 348

N-[(2Z)-3-(3,4-dimethoxyphenyl)-5-methyl-1,3-thiazol-2(3H)-ylidene]pyrrolidine-1-carboxamide;

Example 349

N-[(2Z)-5-methyl-3-(3,4,5-trimethoxyphenyl)-1,3-thiazol-2(3H)-ylidene]pyrrolidine-1-carboxamide;

Example 350

N-[(2Z)-3-(2,3-dichlorophenyl)-5-methyl-1,3-thiazol-2(3H)-ylidene]pyrrolidine-1-carboxamide;

Example 351

N-[(2Z)-3-(2,4-dichlorophenyl)-5-methyl-1,3-thiazol-2(3H)-ylidene]pyrrolidine-1-carboxamide;

Example 352

N-[(2Z)-3-(2,5-dichlorophenyl)-5-methyl-1,3-thiazol-2(3H)-ylidene]pyrrolidine-1-carboxamide;

Example 353

N-[(2Z)-3-(4-aminophenyl)-5-methyl-1,3-thiazol-2(3H)-ylidene]pyrrolidine-1-carboxamide;

Example 354

N-[(2Z)-5-methyl-3-(3-propionylphenyl)-1,3-thiazol-2(3H)-ylidene]pyrrolidine-1-carboxamide;

Example 355

N-[(2Z)-3-(4-tert-butylphenyl)-5-methyl-1,3-thiazol-2(3H)-ylidene]pyrrolidine-1-carboxamide;

Example 356

N-[(2Z)-3-(4-ethylphenyl)-5-methyl-1,3-thiazol-2(3H)-ylidene]pyrrolidine-1-carboxamide;

Example 357

N-[(2Z)-5-methyl-3-(4-propylphenyl)-1,3-thiazol-2(3H)-ylidene]pyrrolidine-1-carboxamide;

Example 358

N-[(2Z)-5-methyl-3-pyridin-3-yl-1,3-thiazol-2(3H)-ylidene]pyrrolidine-1-carboxamide;

Example 359

N-[(2Z)-3-(4-butylphenyl)-5-methyl-1,3-thiazol-2(3H)-ylidene]pyrrolidine-1-carboxamide;

Example 360

N-[(2Z)-5-methyl-3-[3-(methylthio)phenyl]-1,3-thiazol-2(3H)-ylidene]pyrrolidine-1-carboxamide;

Example 361

N-[(2Z)-5-methyl-3-[2,3,5,6-tetrafluoro-4-(trifluoromethyl)phenyl]-1,3-thiazol-2(3H)-ylidene]pyrrolidine-1-carboxamide;

Example 362

N-[(2Z)-3-(3-isopropoxyphenyl)-5-methyl-1,3-thiazol-2(3H)-ylidene]pyrrolidine-1-carboxamide;

Example 363

N-[(2Z)-3-[2,4-bis(trifluoromethyl)phenyl]-5-methyl-1,3-thiazol-2(3H)-ylidene]pyrrolidine-1-carboxamide;

Example 364

N-[(2Z)-3-(4-chloro-3-methoxyphenyl)-5-methyl-1,3-thiazol-2(3H)-ylidene]pyrrolidine-1-carboxamide;

Example 365

N-[(2Z)-5-methyl-3-(1-oxo-2,3-dihydro-1H-inden-5-yl)-1,3-thiazol-2(3H)-ylidene]pyrrolidine-1-carboxamide;

Example 366

N-[(2Z)-3-(4-methoxy-3-methylphenyl)-5-methyl-1,3-thiazol-2(3H)-ylidene]pyrrolidine-1-carboxamide;

Example 367

N-[(2Z)-3-(4-cyclohexylphenyl)-5-methyl-1,3-thiazol-2(3H)-ylidene]pyrrolidine-1-carboxamide;

Example 368

N-[(2Z)-5-methyl-3-(5-phenylthien-2-yl)-1,3-thiazol-2(3H)-ylidene]pyrrolidine-1-carboxamide;

Example 369

N-[(2Z)-5-methyl-3-(1-naphthyl)-1,3-thiazol-2(3H)-ylidene]pyrrolidine-1-carboxamide;

Example 370

N-[(2Z)-5-methyl-3-(6-methylpyridazin-3-yl)-1,3-thiazol-2(3H)-ylidene]pyrrolidine-1-carboxamide;

Example 371

N-[(2Z)-5-methyl-3-(6-methylpyrazin-2-yl)-1,3-thiazol-2 (3H)-ylidene]pyrrolidine-1-carboxamide;

Example 372

N-[(2Z)-5-methyl-3-pyrazin-2-yl-1,3-thiazol-2(3H)-ylidene]pyrrolidine-1-carboxamide;

Example 373

N-[(2Z)-5-methyl-3-quinoxalin-2-yl-1,3-thiazol-2(3H)-ylidene]pyrrolidine-1-carboxamide;

Example 374

N-[(2Z)-5-methyl-3-[5-(trifluoromethyl)pyridin-2-yl]-1,3-thiazol-2(3H)-ylidene]pyrrolidine-1-carboxamide;

Example 375

N-[(2Z)-5-methyl-3-[6-(trifluoromethyl)pyridin-2-yl]-1,3-thiazol-2(3H)-ylidene]pyrrolidine-1-carboxamide;

Example 376

N-[(2Z)-5-methyl-3-[4-(trifluoromethyl)pyridin-2-yl]-1,3-thiazol-2(3H)-ylidene]pyrrolidine-1-carboxamide;

Example 377

N-[(2Z)-3-(4'-fluoro-1,1'-biphenyl-4-yl)-5-methyl-1,3-thiazol-2(3H)-ylidene]pyrrolidine-1-carboxamide;

Example 378

N-[(2Z)-3-(4-acetylphenyl)-1,3-thiazol-2(3H)-ylidene]pyrrolidine-1-carboxamide;

Example 379

N-[(2Z)-3-(4-propionylphenyl)-1,3-thiazol-2(3H)-ylidene]pyrrolidine-1-carboxamide;

Example 380

N-[(2Z)-3-(4-tert-butylphenyl)-1,3-thiazol-2(3H)-ylidene]pyrrolidine-1-carboxamide;

Example 381

N-[(2Z)-3-(4-ethylphenyl)-1,3-thiazol-2(3H)-ylidene]pyrrolidine-1-carboxamide;

Example 382

N-[(2Z)-3-(2,4-dichlorophenyl)-1,3-thiazol-2(3H)-ylidene]pyrrolidine-1-carboxamide;

Example 383

N-[(2Z)-3-(2-methoxyphenyl)-1,3-thiazol-2(3H)-ylidene]pyrrolidine-1-carboxamide;

Example 384

N-[(2Z)-3-(2-methylphenyl)-1,3-thiazol-2(3H)-ylidene]pyrrolidine-1-carboxamide;

Example 385

N-[(2Z)-3-(3,5-dichlorophenyl)-1,3-thiazol-2(3H)-ylidene]pyrrolidine-1-carboxamide;

Example 386

N-[(2Z)-3-(3-methoxyphenyl)-1,3-thiazol-2(3H)-ylidene]pyrrolidine-1-carboxamide;

Example 387

N-[(2Z)-3-(3-methylphenyl)-1,3-thiazol-2(3H)-ylidene]pyrrolidine-1-carboxamide;

Example 388

N-[(2Z)-3-(4-methoxyphenyl)-1,3-thiazol-2(3H)-ylidene]pyrrolidine-1-carboxamide;

Example 389

N-[(2Z)-3-(4-propylphenyl)-1,3-thiazol-2(3H)-ylidene]pyrrolidine-1-carboxamide;

Example 390

N-[(2Z)-3-(2,4-dimethylphenyl)-1,3-thiazol-2(3H)-ylidene]pyrrolidine-1-carboxamide;

Example 391

N-[(2Z)-3-pyridin-3-yl-1,3-thiazol-2(3H)-ylidene]pyrrolidine-1-carboxamide;

Example 392

N-[(2Z)-3-(4-butylphenyl)-1,3-thiazol-2(3H)-ylidene]pyrrolidine-1-carboxamide;

Example 393

N-[(2Z)-3-[3-(methylthio)phenyl]-1,3-thiazol-2(3H)-ylidene]pyrrolidine-1-carboxamide;

Example 394

N-[(2Z)-3-(2,3-dichlorophenyl)-1,3-thiazol-2(3H)-ylidene]pyrrolidine-1-carboxamide;

Example 395

N-[(2Z)-3-(2-chlorophenyl)-1,3-thiazol-2(3H)-ylidene]pyrrolidine-1-carboxamide;

Example 396

N-[(2Z)-3-[2,3,5,6-tetrafluoro-4-(trifluoromethyl)phenyl]-1,3-thiazol-2(3H)-ylidene]pyrrolidine-1-carboxamide;

Example 397

N-[(2Z)-3-(3,5-dimethylphenyl)-1,3-thiazol-2(3H)-ylidene]
pyrrolidine-1-carboxamide;

Example 398

N-[(2Z)-3-(3-isopropoxyphenyl)-1,3-thiazol-2(3H)-ylidene]
pyrrolidine-1-carboxamide;

Example 399

N-[(2Z)-3-[2,4-bis(trifluoromethyl)phenyl]-1,3-thiazol-2
(3H)-ylidene]pyrrolidine-1-carboxamide;

Example 400

N-[(2Z)-3-(3-cyanophenyl)-1,3-thiazol-2(3H)-ylidene]pyrrolidine-1-carboxamide;

Example 401

N-[(2Z)-3-(1-oxo-2,3-dihydro-1H-inden-5-yl)-1,3-thiazol-2
(3H)-ylidene]pyrrolidine-1-carboxamide;

Example 402

N-[(2Z)-3-(4-methoxy-3-methylphenyl)-1,3-thiazol-2(3H)-
ylidene]pyrrolidine-1-carboxamide;

Example 403

N-[(2Z)-3-[4-(dimethylamino)phenyl]-5-methyl-1,3-thiazol-2(3H)-ylidene]-2,2-dimethylpropanamide;

Example 404

2,2-dimethyl-N-[(2Z)-5-methyl-3-[4-(methylthio)phenyl]-
1,3-thiazol-2(3H)-ylidene]propanamide;

Example 405

N-[(2Z)-3-(4-acetylphenyl)-5-methyl-1,3-thiazol-2(3H)-
ylidene]-2,2-dimethylpropanamide;

Example 406

N-[(2Z)-3-(4-tert-butylphenyl)-5-methyl-1,3-thiazol-2(3H)-
ylidene]-2,2-dimethylpropanamide;

Example 407

N-[(2Z)-3-(4-ethylphenyl)-5-methyl-1,3-thiazol-2(3H)-
ylidene]-2,2-dimethylpropanamide;

Example 408

2,2-dimethyl-N-[(2Z)-5-methyl-3-(2-methylphenyl)-1,3-
thiazol-2(3H)-ylidene]propanamide;

Example 409

N-[(2Z)-3-[3-(dimethylamino)phenyl]-5-methyl-1,3-thiazol-2(3H)-ylidene]-2,2-dimethylpropanamide;

Example 410

2,2-dimethyl-N-[(2Z)-5-methyl-3-phenyl-1,3-thiazol-2
(3H)-ylidene]propanamide;

Example 411

N-[(2Z)-3-(2-methoxyphenyl)-5-methyl-1,3-thiazol-2(3H)-
ylidene]-2,2-dimethylpropanamide;

Example 412

N-[(2Z)-3-(3-methoxyphenyl)-5-methyl-1,3-thiazol-2(3H)-
ylidene]-2,2-dimethylpropanamide;

Example 413

2,2-dimethyl-N-[(2Z)-5-methyl-3-(3-methylphenyl)-1,3-
thiazol-2(3H)-ylidene]propanamide;

Example 414

N-[(2Z)-3-(4-methoxyphenyl)-5-methyl-1,3-thiazol-2(3H)-
ylidene]-2,2-dimethylpropanamide;

Example 415

2,2-dimethyl-N-[(2Z)-5-methyl-3-(4-methylphenyl)-1,3-
thiazol-2(3H)-ylidene]propanamide;

Example 416

2,2-dimethyl-N-[(2Z)-5-methyl-3-(2-naphthyl)-1,3-thiazol-
2(3H)-ylidene]propanamide;

Example 417

N-[(2Z)-3-(6-methoxy-2-naphthyl)-5-methyl-1,3-thiazol-2
(3H)-ylidene]-2,2-dimethylpropanamide;

Example 418

N-[(2Z)-3-(2,4-dimethylphenyl)-5-methyl-1,3-thiazol-2
(3H)-ylidene]-2,2-dimethylpropanamide;

Example 419

N-[(2Z)-3-(4-chloro-3-methylphenyl)-5-methyl-1,3-thiazol-
2(3H)-ylidene]-2,2-dimethylpropanamide;

Example 420

N-[(2Z)-3-(4-butylphenyl)-5-methyl-1,3-thiazol-2(3H)-
ylidene]-2,2-dimethylpropanamide;

Example 421

N-[(2Z)-3-(3,4-dimethylphenyl)-5-methyl-1,3-thiazol-2
(3H)-ylidene]-2,2-dimethylpropanamide;

Example 422

2,2-dimethyl-N-[(2Z)-5-methyl-3-[3-(methylthio)phenyl]-
1,3-thiazol-2(3H)-ylidene]propanamide;

Example 423

N-[(2Z)-3-(3-chloro-4-methylphenyl)-5-methyl-1,3-thiazol-2(3H)-ylidene]-2,2-dimethylpropanamide;

Example 424

N-[(2Z)-3-(3,5-dimethylphenyl)-5-methyl-1,3-thiazol-2(3H)-ylidene]-2,2-dimethylpropanamide;

Example 425

N-[(2Z)-3-(3-isopropoxyphenyl)-5-methyl-1,3-thiazol-2(3H)-ylidene]-2,2-dimethylpropanamide;

Example 426

N-[(2Z)-3-(4-chloro-3-methoxyphenyl)-5-methyl-1,3-thiazol-2(3H)-ylidene]-2,2-dimethylpropanamide;

Example 427

N-[(2Z)-3-(4-methoxy-3-methylphenyl)-5-methyl-1,3-thiazol-2(3H)-ylidene]-2,2-dimethylpropanamide;

Example 428

N-[(2Z)-3-(2-chlorophenyl)-5-methyl-1,3-thiazol-2(3H)-ylidene]-2,2-dimethylpropanamide;

Example 429

2,2-dimethyl-N-[(2Z)-5-methyl-3-[2,3,5,6-tetrafluoro-4-(trifluoromethyl)phenyl]-1,3-thiazol-2(3H)-ylidene]propanamide;

Example 430

2,2-dimethyl-N-[(2Z)-5-methyl-3-pyridin-3-yl-1,3-thiazol-2(3H)-ylidene]propanamide;

Example 431

N-[(2Z)-3-(4-cyanophenyl)-5-methyl-1,3-thiazol-2(3H)-ylidene]-2,2-dimethylpropanamide;

Example 432

N-[(2Z)-3-(3-cyanophenyl)-5-methyl-1,3-thiazol-2(3H)-ylidene]-2,2-dimethylpropanamide;

Example 433

N-[(2Z)-3-(2'-methyl-1,1'-biphenyl-4-yl)-1,3-thiazol-2(3H)-ylidene]pyrrolidine-1-carboxamide;

Example 434

N-[(2Z)-3-(3'-methyl-1,1'-biphenyl-4-yl)-1,3-thiazol-2(3H)-ylidene]pyrrolidine-1-carboxamide;

Example 435

N-[(2Z)-3-(4'-methyl-1,1'-biphenyl-4-yl)-1,3-thiazol-2(3H)-ylidene]pyrrolidine-1-carboxamide;

Example 436

N-[(2Z)-3-(3'-chloro-1,1'-biphenyl-4-yl)-1,3-thiazol-2(3H)-ylidene]pyrrolidine-1-carboxamide;

Example 437

N-[(2Z)-3-(4'-chloro-1,1'-biphenyl-4-yl)-1,3-thiazol-2(3H)-ylidene]pyrrolidine-1-carboxamide;

Example 438

N-[(2Z)-3-(4'-methoxy-1,1'-biphenyl-4-yl)-1,3-thiazol-2(3H)-ylidene]pyrrolidine-1-carboxamide;

Example 439

N-[(2Z)-3-[3'-(trifluoromethyl)-1,1'-biphenyl-4-yl]-1,3-thiazol-2(3H)-ylidene]pyrrolidine-1-carboxamide;

Example 440

N-[(2Z)-3-(4-thien-3-ylphenyl)-1,3-thiazol-2(3H)-ylidene]pyrrolidine-1-carboxamide;

Example 441

N-[(2Z)-3-[4'-(trifluoromethyl)-1,1'-biphenyl-4-yl]-1,3-thiazol-2(3H)-ylidene]pyrrolidine-1-carboxamide;

Example 442

N-[(2Z)-3-(3'-ethoxy-1,1'-biphenyl-4-yl)-1,3-thiazol-2(3H)-ylidene]pyrrolidine-1-carboxamide;

Example 443

N-[(2Z)-3-(3'-methoxy-1,1'-biphenyl-4-yl)-1,3-thiazol-2(3H)-ylidene]pyrrolidine-1-carboxamide;

Example 444

N-[(2Z)-3-(3',5'-dichloro-1,1'-biphenyl-4-yl)-1,3-thiazol-2(3H)-ylidene]pyrrolidine-1-carboxamide;

Example 445

N-[(2Z)-3-(2'-chloro-1,1'-biphenyl-4-yl)-1,3-thiazol-2(3H)-ylidene]pyrrolidine-1-carboxamide;

Example 446

N-[(2Z)-3-(2'-methoxy-1,1'-biphenyl-4-yl)-1,3-thiazol-2(3H)-ylidene]pyrrolidine-1-carboxamide;

Example 447

N-[(2Z)-3-(2'-acetyl-1,1'-biphenyl-4-yl)-1,3-thiazol-2(3H)-ylidene]pyrrolidine-1-carboxamide;

Example 448

N-[(2Z)-3-(3'-acetyl-1,1'-biphenyl-4-yl)-1,3-thiazol-2(3H)-ylidene]pyrrolidine-1-carboxamide;

Example 449

N-[(2Z)-3-(4'-acetyl-1,1'-biphenyl-4-yl)-1,3-thiazol-2(3H)-ylidene]pyrrolidine-1-carboxamide;

Example 450

N-[(2Z)-3-(3',4'-dichloro-1,1'-biphenyl-4-yl)-1,3-thiazol-2(3H)-ylidene]pyrrolidine-1-carboxamide;

Example 451

N-[(2Z)-3-(4-pyridin-3-ylphenyl)-1,3-thiazol-2(3H)-ylidene]pyrrolidine-1-carboxamide;

Example 452

N-[(2Z)-3-(2',5'-dichloro-1,1'-biphenyl-4-yl)-1,3-thiazol-2(3H)-ylidene]pyrrolidine-1-carboxamide;

Example 453

N-[(2Z)-3-(3'-cyano-1,1'-biphenyl-4-yl)-1,3-thiazol-2(3H)-ylidene]pyrrolidine-1-carboxamide;

Example 454

N-[(2Z)-3-(2',3'-dichloro-1,1'-biphenyl-4-yl)-1,3-thiazol-2(3H)-ylidene]pyrrolidine-1-carboxamide;

Example 455

N-[(2Z)-3-(2',4'-dichloro-1,1'-biphenyl-4-yl)-1,3-thiazol-2(3H)-ylidene]pyrrolidine-1-carboxamide;

Example 456

N-[(2Z)-3-(4'-cyano-1,1'-biphenyl-4-yl)-1,3-thiazol-2(3H)-ylidene]pyrrolidine-1-carboxamide;

Example 457

N-[(2Z)-3-[4-(1-methyl-1H-pyrazol-4-yl)phenyl]-1,3-thiazol-2(3H)-ylidene]pyrrolidine-1-carboxamide;

Example 458

N-[(2Z)-3-[4-(6-methoxypyridin-3-yl)phenyl]-1,3-thiazol-2(3H)-ylidene]pyrrolidine-1-carboxamide;

Example 459

N-[(2Z)-3-(1,1'-biphenyl-4-yl)-1,3-thiazol-2(3H)-ylidene]pyrrolidine-1-carboxamide;

Example 460

N-[(2Z)-3-[4-(2-methoxypyrimidin-5-yl)phenyl]-1,3-thiazol-2(3H)-ylidene]pyrrolidine-1-carboxamide;

Example 461

N-[(2Z)-3-[4'-(cyanomethyl)-1,1'-biphenyl-4-yl]-1,3-thiazol-2(3H)-ylidene]pyrrolidine-1-carboxamide;

Example 462

N-[(2Z)-3-quinoxalin-6-yl-1,3-thiazol-2(3H)-ylidene]pyrrolidine-1-carboxamide;

Example 463

N-[(2Z)-3-(1-benzothien-5-yl)-1,3-thiazol-2(3H)-ylidene]pyrrolidine-1-carboxamide;

Example 464

N-[(2Z)-3-pyrazin-2-yl-1,3-thiazol-2(3H)-ylidene]pyrrolidine-1-carboxamide;

Example 465

N-[(2Z)-3-quinoxalin-2-yl-1,3-thiazol-2(3H)-ylidene]pyrrolidine-1-carboxamide;

Example 466

N-[(2Z)-3-[2-(methylthio)pyrimidin-4-yl]-1,3-thiazol-2(3H)-ylidene]pyrrolidine-1-carboxamide;

Example 467

N-[(2Z)-3-(6-phenylpyridazin-3-yl)-1,3-thiazol-2(3H)-ylidene]pyrrolidine-1-carboxamide;

Example 468

N-[(2Z)-3-(6-methylpyridin-2-yl)-1,3-thiazol-2(3H)-ylidene]pyrrolidine-1-carboxamide;

Example 469

N-[(2Z)-3-(1-benzothien-3-yl)-1,3-thiazol-2(3H)-ylidene]pyrrolidine-1-carboxamide;

Example 470

N-[(2Z)-3-(4'-fluoro-1,1'-biphenyl-4-yl)-1,3-thiazol-2(3H)-ylidene]pyrrolidine-1-carboxamide;

Example 471

N-[(2Z)-3-(5-fluoropyridin-2-yl)-1,3-thiazol-2(3H)-ylidene]pyrrolidine-1-carboxamide;

Example 472

N-[(2Z)-3-(6-fluoropyridin-3-yl)-1,3-thiazol-2(3H)-ylidene]pyrrolidine-1-carboxamide;

Example 473

N-[(2Z)-3-[5-(trifluoromethyl)pyridin-3-yl]-1,3-thiazol-2(3H)-ylidene]pyrrolidine-1-carboxamide;

Example 474

N-[(2Z)-3-[5-(trifluoromethyl)pyridin-2-yl]-1,3-thiazol-2(3H)-ylidene]pyrrolidine-1-carboxamide;

Example 475

N-[(2Z)-3-[4-(trifluoromethyl)pyridin-2-yl]-1,3-thiazol-2 (3H)-ylidene]pyrrolidine-1-carboxamide;

Example 476

N-[(2Z)-3-[6-(trifluoromethyl)pyridin-2-yl]-1,3-thiazol-2 (3H)-ylidene]pyrrolidine-1-carboxamide;

Example 477

N-[(2Z)-3-(6-ethoxy-2-naphthyl)-1,3-thiazol-2(3H)-ylidene]pyrrolidine-1-carboxamide;

Example 478

N-[(2Z)-3-pyrido[2,3-b]pyrazin-7-yl-1,3-thiazol-2(3H)-ylidene]pyrrolidine-1-carboxamide;

Example 479

N-[(2Z)-3-(4-cyclohexylphenyl)-1,3-thiazol-2(3H)-ylidene]pyrrolidine-1-carboxamide;

Example 480

N-[(2Z)-3-(5-chloropyridin-2-yl)-1,3-thiazol-2(3H)-ylidene]pyrrolidine-1-carboxamide;

Example 481

N-[(2Z)-3-[2-cyano-4-(trifluoromethyl)phenyl]-1,3-thiazol-2(3H)-ylidene]pyrrolidine-1-carboxamide;

Example 482

N-[(2Z)-3-(5-phenylthien-2-yl)-1,3-thiazol-2(3H)-ylidene]pyrrolidine-1-carboxamide;

Example 483

N-[(2Z)-3-[6-(1H-pyrazol-1-yl)pyridin-2-yl]-1,3-thiazol-2 (3H)-ylidene]pyrrolidine-1-carboxamide;

Example 484

N-[(2Z)-3-(6-methylpyrazin-2-yl)-1,3-thiazol-2(3H)-ylidene]pyrrolidine-1-carboxamide;

Example 485

N-[(2Z)-3-(2-methylpyrimidin-4-yl)-1,3-thiazol-2(3H)-ylidene]pyrrolidine-1-carboxamide;

Example 486

N-[(2Z)-3-(2,6-dimethylpyrimidin-4-yl)-1,3-thiazol-2(3H)-ylidene]pyrrolidine-1-carboxamide;

Example 487

N-[(2Z)-3-(2-fluoropyridin-4-yl)-1,3-thiazol-2(3H)-ylidene]pyrrolidine-1-carboxamide;

Example 488

N-[(2Z)-3-(2-methyl-1,3-benzothiazol-5-yl)-1,3-thiazol-2 (3H)-ylidene]pyrrolidine-1-carboxamide;

Example 489

(3R)-3-fluoro-N-[(2Z)-3-(4-isopropylphenyl)-5-methyl-1,3-thiazol-2(3H)-ylidene]pyrrolidine-1-carboxamide;

Example 490

(3R)-N-[(2Z)-3-(3,4-dimethylphenyl)-5-methyl-1,3-thiazol-2(3H)-ylidene]-3-fluoropyrrolidine-1-carboxamide;

Example 491

(3R)-3-fluoro-N-[(2Z)-3-(4-methoxyphenyl)-5-methyl-1,3-thiazol-2(3H)-ylidene]pyrrolidine-1-carboxamide;

Example 492

(3R)-3-fluoro-N-[(2Z)-3-(4'-fluoro-1,1'-biphenyl-4-yl)-5-methyl-1,3-thiazol-2(3H)-ylidene]pyrrolidine-1-carboxamide;

Example 493

2,2-dimethyl-N-[(2Z)-5-methyl-3-quinoxalin-6-yl-1,3-thiazol-2(3H)-ylidene]propanamide;

Example 494

N-[(2Z)-3-(1-benzothien-5-yl)-5-methyl-1,3-thiazol-2(3H)-ylidene]-2,2-dimethylpropanamide;

Example 495

2,2-dimethyl-N-[(2Z)-5-methyl-3-pyrazin-2-yl-1,3-thiazol-2(3H)-ylidene]propanamide;

Example 496

2,2-dimethyl-N-[(2Z)-5-methyl-3-quinoxalin-2-yl-1,3-thiazol-2(3H)-ylidene]propanamide;

Example 497

2,2-dimethyl-N-[(2Z)-5-methyl-3-[2-(methylthio)pyrimidin-4-yl]-1,3-thiazol-2(3H)-ylidene]propanamide;

Example 498

2,2-dimethyl-N-[(2Z)-5-methyl-3-(6-phenylpyridazin-3-yl)-1,3-thiazol-2(3H)-ylidene]propanamide;

Example 499

2,2-dimethyl-N-[(2Z)-5-methyl-3-(6-methylpyridin-2-yl)-1,3-thiazol-2(3H)-ylidene]propanamide;

Example 500

N-[(2Z)-3-(1-benzothien-3-yl)-5-methyl-1,3-thiazol-2(3H)-ylidene]-2,2-dimethylpropanamide;

Example 501

N-[(2Z)-3-(4'-fluoro-1,1'-biphenyl-4-yl)-5-methyl-1,3-thiazol-2(3H)-ylidene]-2,2-dimethylpropanamide;

Example 502

N-[(2Z)-3-(5-fluoropyridin-2-yl)-5-methyl-1,3-thiazol-2(3H)-ylidene]-2,2-dimethylpropanamide;

Example 503

N-[(2Z)-3-(6-chloroquinoxalin-2-yl)-5-methyl-1,3-thiazol-2(3H)-ylidene]-2,2-dimethylpropanamide;

Example 504

2,2-dimethyl-N-[(2Z)-5-methyl-3-[5-(trifluoromethyl)pyridin-3-yl]-1,3-thiazol-2(3H)-ylidene]propanamide;

Example 505

2,2-dimethyl-N-[(2Z)-5-methyl-3-[5-(trifluoromethyl)pyridin-2-yl]-1,3-thiazol-2(3H)-ylidene]propanamide;

Example 506

2,2-dimethyl-N-[(2Z)-5-methyl-3-[4-(trifluoromethyl)pyridin-2-yl]-1,3-thiazol-2(3H)-ylidene]propanamide;

Example 507

2,2-dimethyl-N-[(2Z)-5-methyl-3-[6-(trifluoromethyl)pyridin-2-yl]-1,3-thiazol-2(3H)-ylidene]propanamide;

Example 508

2,2-dimethyl-N-[(2Z)-5-methyl-3-(6-methylpyridazin-3-yl)-1,3-thiazol-2(3H)-ylidene]propanamide;

Example 509

2,2-dimethyl-N-[(2Z)-5-methyl-3-pyrido[2,3-b]pyrazin-7-yl-1,3-thiazol-2(3H)-ylidene]propanamide;

Example 510

N-[(2Z)-3-(4-cyclohexylphenyl)-5-methyl-1,3-thiazol-2(3H)-ylidene]-2,2-dimethylpropanamide;

Example 511

N-[(2Z)-3-(5-chloropyridin-2-yl)-5-methyl-1,3-thiazol-2(3H)-ylidene]-2,2-dimethylpropanamide;

Example 512

N-[(2Z)-3-[2-cyano-4-(trifluoromethyl)phenyl]-5-methyl-1,3-thiazol-2(3H)-ylidene]-2,2-dimethylpropanamide;

Example 513

2,2-dimethyl-N-[(2Z)-5-methyl-3-[2-(trifluoromethyl)pyrimidin-4-yl]-1,3-thiazol-2(3H)-ylidene]propanamide;

Example 514

2,2-dimethyl-N-[(2Z)-5-methyl-3-(5-phenylthien-2-yl)-1,3-thiazol-2(3H)-ylidene]propanamide;

Example 515

2,2-dimethyl-N-[(2Z)-5-methyl-3-(6-methylpyrazin-2-yl)-1,3-thiazol-2(3H)-ylidene]propanamide; and

Example 516

2,2-dimethyl-N-[(2Z)-5-methyl-3-(2-methylpyrimidin-4-yl)-1,3-thiazol-2(3H)-ylidene]propanamide.

DETERMINATION OF BIOLOGICAL ACTIVITY

To determine the effectiveness of compounds of formula (I), as allosteric modulators, the instant compounds were evaluated according to various functional assays. These include (i) Xenopus oocytes injected with α7 NNR RNA or DNA and evaluation of compound effects on current responses evoked by acetylcholine or another agonist (ii) IMR-32 cells endogenous expressing α7 NNRs and measuring $Ca^{2+}$ flux or membrane potential changes utilizing the fluorescence-imaging plate reader (FLIPR)-based assays and (iii) measurement of phospho-ERK activity using western blot assays. These assays allow for evaluation of allosteric modulators using Xenopus oocytes, cells or cell lines expressing endogenous or recombinant α7 NNRs.

(i) Two-Electrode Voltage-Clamp in Xenopus laevis Oocytes.

X. laevis oocytes were prepared for electrophysiological experiments as described in the literature (see for example, Briggs, C. A., Mckenna, D. G., and Piattina-kaplan, M., Human α7 nicotinic acetylcholine receptor responses to novel ligands, Neuropharmacology, 1995, 34: 583-590; Briggs, C. A., and Mckenna, D. G., Activation and inhibition of the human α7 nicotinic acetylcholine receptor by agonists, Neuropharmacology, 1998, 37: 1095-1102). In brief, three to four lobes from ovaries of female adult X. laevis frogs were removed and defolliculated after treatment with collagenase type 1A (2 mg/ml; Sigma) prepared in low-$Ca^{2+}$ Barth's solution (90 mM NaCl, 1.0 mM KCl, 0.66 mM $NaNO_3$, 2.4 mM $NaHCO_3$, 10 mM HEPES, 2.5 mM sodium pyruvate, 0.82 mM $MgCl_2$, and 0.5% (v/v) penicillin-streptomycin solution, pH=7.55, Sigma) for about 1.5 hours to about 2 hours at about 18° C. under constant agitation to obtain isolated oocytes. The oocytes were injected with about 4 ng to about 6 ng of human α7 NNR cRNA, kept at about 18° C. in a humidified incubator in modified Barth's solution (90 mM NaCl, 1.0 mM KCl, 0.66 mM $NaNO_3$, 2.4 mM $NaHCO_3$, 10 mM HEPES, 2.5 mM sodium pyruvate, 0.74 mM $CaCl_2$, 0.82 mM $MgCl_2$, and 0.5% (v/v) penicillin-streptomycin solution, pH 7.55) and used about 2 to 7 days after injection. Responses were measured by two-electrode voltage clamp using parallel oocyte electrophysiology test station (Abbott, Abbott Park, Ill.) (see for example, Trumbull, J. D., Maslana, E. S., McKenna, D. G., Nemcek, T. A., Niforatos, W., Pan, J. Y., Parihar, A. S., Shieh, C. C., Wilkins, J. A., Briggs, C. A., and Bertrand, D., High throughput electrophysiology using a fully automated, multiplexed recording system, Receptors Channels, 2003, 9: 19-28). During recordings, the oocytes were bathed in $Ba^{2+}$—$OR^2$ solution (90 mM NaCl, 2.5 mM KCl, 2.5 mM $BaCl_2$, 1.0 mM $MgCl_2$, 5.0 mM HEPES, and 0.0005 mM atropine, pH 7.4) to prevent activation of $Ca^{2+}$-dependent currents and held at −60 mV at room temperature (about 20° C.). Test compounds were given for 60 seconds before agonist application and subsequently in the presence of 0.1 mM ACh. The data were expressed as percentage potentiation over the response to 0.1 mM ACh alone. FIG. 1A shows the concentration response relationship for Example 18 in potentiating 0.1 mM ACh-evoked α7 currents in oocytes. In this graph, the $EC_{50}$ value is 4 μM and the degree of potentiation is 300%.

(ii) High-Throughput Calcium Flux Assays Using Cells Expressing Endogenous α7 NNRs Since allosteric modulators affect the kinetics of channel function and thus affect calcium dynamics, it is demonstrated that novel modulators can be identified when assays are conducted in the presence of a selective agonist, and conversely, novel agonists can be identified when screened or tested in the presence an allosteric modulator. As such, PAMs and nicotinic acetylcholine receptor agonists can be identified by using IMR-32 cells that endogenously express various nicotinic receptors including α7 NNRs. It is contemplated that such assay can be utilized with a number of cell lines conventionally not amenable to α7 nicotinic compound screening. Accordingly, allosteric modulator compounds described herein can be identified using fluorescence-based throughput functional assay using cell lines such as IMR-32 neuroblastoma or primary dissociated neurons. Although cell types such as IMR-32 neuroblastoma and neurons are known to contain several nicotinic receptor subunits, α7 selective agonists in the present assay selectively stimulate calcium responses only in the presence of PAMs. Any suitable selective α7 agonist can be used. Selective α7 agonists from a range of structural types may be used such as those described in the literature including PNU-282987, SSR180711A and AR-R17779 and others described in earlier patent applications, such as 2-methyl-5-(6-phenyl-pyridazin-3-yl)-octahydro-pyrrolo[3,4-c]pyrrole (see for example, US 20050065178), 5-[6-(5-methyl-hexahydro-pyrrolo[3,4-c]pyrrol-2-yl)-pyridazin-3-yl]-1H-indole (see for example, US 20050065178), 3-[6-(1H-indol-5-yl)-pyradazin-3-yloxy]-1-aza-bicyclo[2.2.2]octane (see for example, US 2005/0137204 and US 2005/0245531), and 4-(5-phenyl-[1,3,4]oxadiazol-2-yl)-1,4-diaza-bicyclo[3.2.2]nonane (see for example, WO 2004/029053).

IMR-32 neuroblastoma cells (ATCC) were grown to confluency in 162 cm² tissue culture flasks in minimum essential media supplemented with 10% FBS and 1 mM sodium pyruvate, 0.1 mM non-essential amino acids and 1% antibiotic-antimycotic. The cells were then dissociated using cell dissociation buffer and 40 μl of 3.5×10⁵ cells/ml cell suspension was plated (about 15,000 cells/well) into black plates with clear bottom and maintained for 48 hours in a tissue culture incubator at 37° C. under an atmosphere of 5% $CO_2$: 95% air. Other clonal cell lines or dissociated primary cortical neurons that express endogenous α7 nicotinic receptors may also be used in this assay. Calcium flux was measured using calcium-3 assay kit (Molecular Devices, Sunnyvale, Calif.) or fluo-4. A stock solution of the dye was prepared by dissolving each vial supplied by the vendor in Hank's balanced salt solution buffer (HBSS) containing 20 mM HEPES. The stock solution was diluted 1:20 using the same buffer before use. After removing the growth media, the cells were loaded with 45 μl of the dye and incubated at room temperature for three hours. Fluorescence measurements were read simultaneously from all the wells by a Fluorometric Imaging Plate Reader (FLIPR) at an excitation wavelength of 480 nm and an emission wavelength of 520 nm. Baseline fluorescence was measured for the first 10 seconds at which 5× concentrations of modulator/test compounds were added to the cell plate and incubated for three minutes. The fluorescence intensity was captured every second for the first 1 minute followed by every 5 seconds for an additional 2 minutes. This procedure was followed by 20 μl of 4× concentration of agonist and readings were taken for a period of three minutes as described above. Data was normalized to maximal responses and plotted as a function of concentration. The concentration dependence of changes fluorescence responses was fitted by nonlinear regression analysis (GraphPad Prism, San Diego, Calif.) to obtain $EC_{50}$ values. Neither agonist alone nor modulator alone evoked responses. However, in the presence of an allosteric modulator, the agonist elicited concentration dependent increase in calcium response and likewise in presence of an α7 selective agonist, modulator responses were revealed. The α7 selective antagonist, methyllycaconitine (MLA), abolishes response demonstrating that the effects are mediated via the α7 receptor.

Figure 1B:
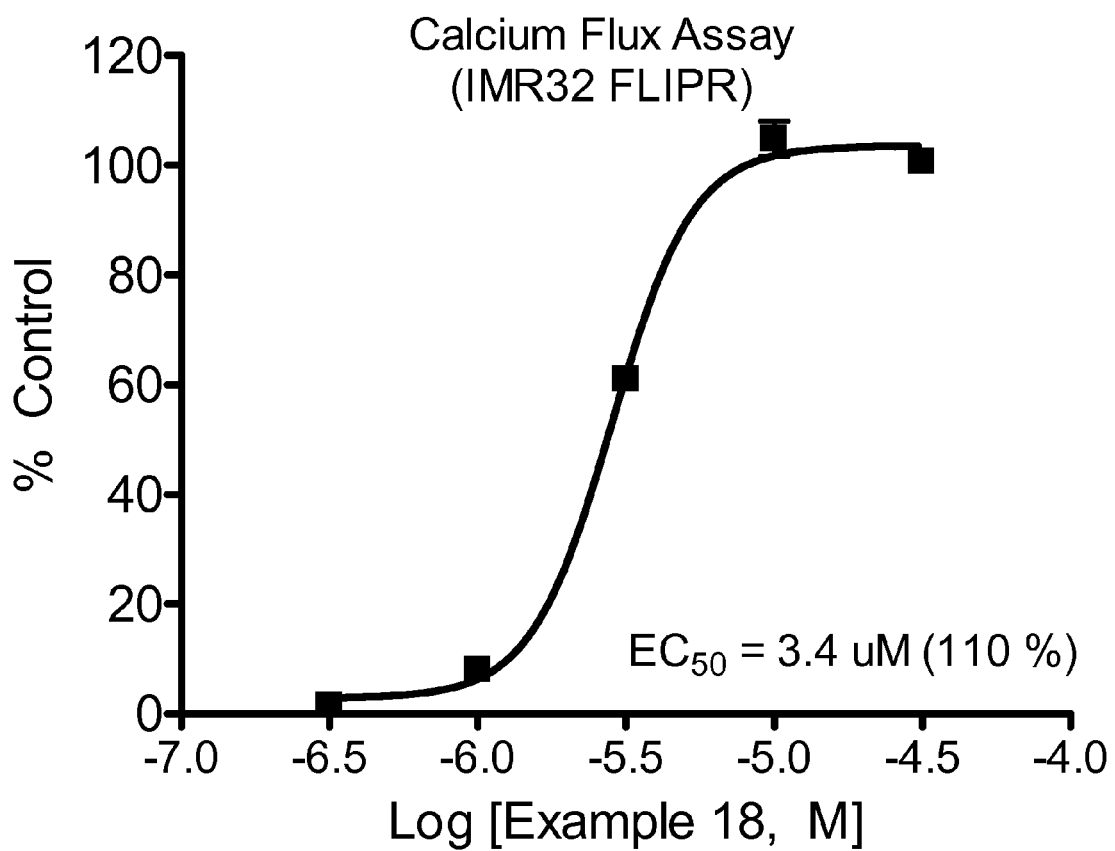
FIG. 1B is a graphical representation of a concentration response curve wherein fluorescence responses are measured as a function of the log of the concentration of the modulator. The data were obtained by assaying effects of a PAM (Example 18) in presence of a fixed concentration of an α7 NNR agonist in cells natively expressing α7 NNRs such as IMR-32. The Y-axis shows the normalized change in fluorescence and the X-axis represents increasing concentrations of the allosteric modulator.

PAMs were identified by measuring fluorescence changes to intracellular calcium in a fluorometric plate reader in the presence of selective α7 NNR agonists using cells natively expressing α7 NNRs. A compound with PAM activity (Example 18) evoked calcium fluorescence response in IMR-32 neuroblastoma cell line, a cell line that expresses endogenous α7 NNRs when assay is conducted in presence of an α7 NNR agonist. The agonist alone or modulator alone did not evoke a calcium response. However, when the agonist and the modulator were co-applied together, calcium responses were triggered. In the example above, 4-(5-phenyl-[1,3,4]oxadiazol-2-yl)-1,4-diaza-bicyclo[3.2.2]nonane (see for example, WO 2004/029053) was used as an agonist at 10 μM in presence of varying concentrations of example 18). In FIG. 1B, the Y-axis is the normalized change in fluorescence and the X-axis represents increasing concentrations of the modulator. In this example, the EC50 value is 3.4 μM, and maximal effects (110% in this example) were realized. The $EC_{50}$ value of PAM compounds as determined in this assay typically can range from 10 nM to 30 μM. Other α7 agonists including 2-methyl-5-(6-phenyl-pyridazin-3-yl)-octahydro-pyrrolo[3,4-c]pyrrole (published in US 20050065178), 5-[6-(5-methyl-hexahydro-pyrrolo[3,4-c]pyrrol-2-yl)-pyridazin-3-yl]-1H-indole (published in US 20050065178), various quinuclidine derivatives (see for example, US 2005/0137204 and US 2005/0245531) and PNU-282987 (see for example, Hajós, M., Hurst, R. S., Hoffmann, W. E., Krause, M., Wall, T. M., Higdon, N. R. and Groppi, V. E., The Selective α7 Nicotinic Acetylcholine Receptor Agonist PNU-282987 [N-[(3R)-1-Azabicyclo[2.2.2]oct-3-yl]-4-chlorobenzamide Hydrochloride] Enhances GABAergic Synaptic Activity in Brain Slices and Restores Auditory Gating Deficits in Anesthetized Rats, *J Pharmacol. Exp Ther.*, 2005, 312: 1213-22) also are suitable for the assay. Likewise, primary neurons and other clonal cell lines that natively express α7 NNRs may also be utilized. Other fluorescence measurements such as those monitoring changes in membrane potential also are suitable for the assay.

(iii) High-Throughput ERK Phosphorylation Assays Using Cells Expressing Endogenous α7 NNRs Rat pheochromocytoma (PC-12) cells (ATCC, Manassas, Va.) were cultured and maintained in F-12K media supplemented with 15% horse serum, 2.5% fetal calf serum, and 2 mM L-glutamine in poly-D lysine coated dishes at 37° C. and 5% $CO_2$. Cells were plated in black-walled clear bottom 96-well Biocoat™ plates coated with poly-D-lysine (BD Biosciences, Bedford, Mass.) and grown for 2-3 days. Afterward, the culture media is replaced with serum-free media to starve cells overnight. On the day of the assay, cell media was removed and cells (60-80% confluent) were treated with agonist and/or modulator in Dulbecco's phosphate buffer saline (D-PBS) (with $Ca^{2+}$, $Mg^{2+}$, and 1 mg/ml D-glucose), as indicated in the result section.

PC-12 cells are treated for 10 minutes at 37° C. with test PAM compounds and then challenged with a selective α7 agonist for 5 minutes at 37° C. in a final volume of 100 μl/well, unless otherwise indicated. After treatment, media was discarded and adherent cells were immediately fixed in the presence of 150 μl/well of 3.7% formaldehyde/phosphate-buffered saline for 30-60 minutes at room temperature. Cells were then washed (4 times/5 minutes) and permeabilized with 2001/well of 0.1% Triton X-100/PBS. Permeabilized cells were blocked using the Odyssey blocking buffer (100 μl/well) and plates were rocked overnight at 4° C. Both anti-total ERK (rabbit) and anti-phospho ERK (mouse) antibodies were diluted to 1/1000 and 1/500, respectively, in Odyssey blocking buffer and added together at 50 μl/well for 2-3 hours at room temperature. Polyclonal rabbit anti-ERK1/2 and monoclonal mouse anti-phospho-ERK 1/2 were purchased from Sigma-Aldrich (St. Louis, Mo.). The plates were washed 4 times with 0.1% Tween 20/PBS (200 ul/well), and incubated with secondary antibodies (1/1000 dilution) in blocking buffer supplemented with 0.2% Tween for 1 hour. Alexa Fluor 680-labeled goat anti-rabbit antibodies were added to recognize total ERK labeling (red color) and IRDye800-labeled donkey anti-mouse antibodies were added to recognize phospho-ERK labeling (green color). Alexa Fluor 680-labeled goat-anti-rabbit antibodies were obtained from Molecular Probes (Eugene, Oreg.). IRDye 800CW-labeled donkey-anti-mouse antibodies were purchased from Rockland (Gilbertsville, Pa.). The plates were washed 4 times with 0.2% Tween and 0.01% SDS/PBS and scanned using the Odyssey infrared scanner. Well intensities were quantitated and phospho-ERK signals were normalized to total ERK signals by the Odyssey software. Data analysis was performed using GraphPad Prism (GraphPad Software, San Diego, Calif.).

Figure 1C:
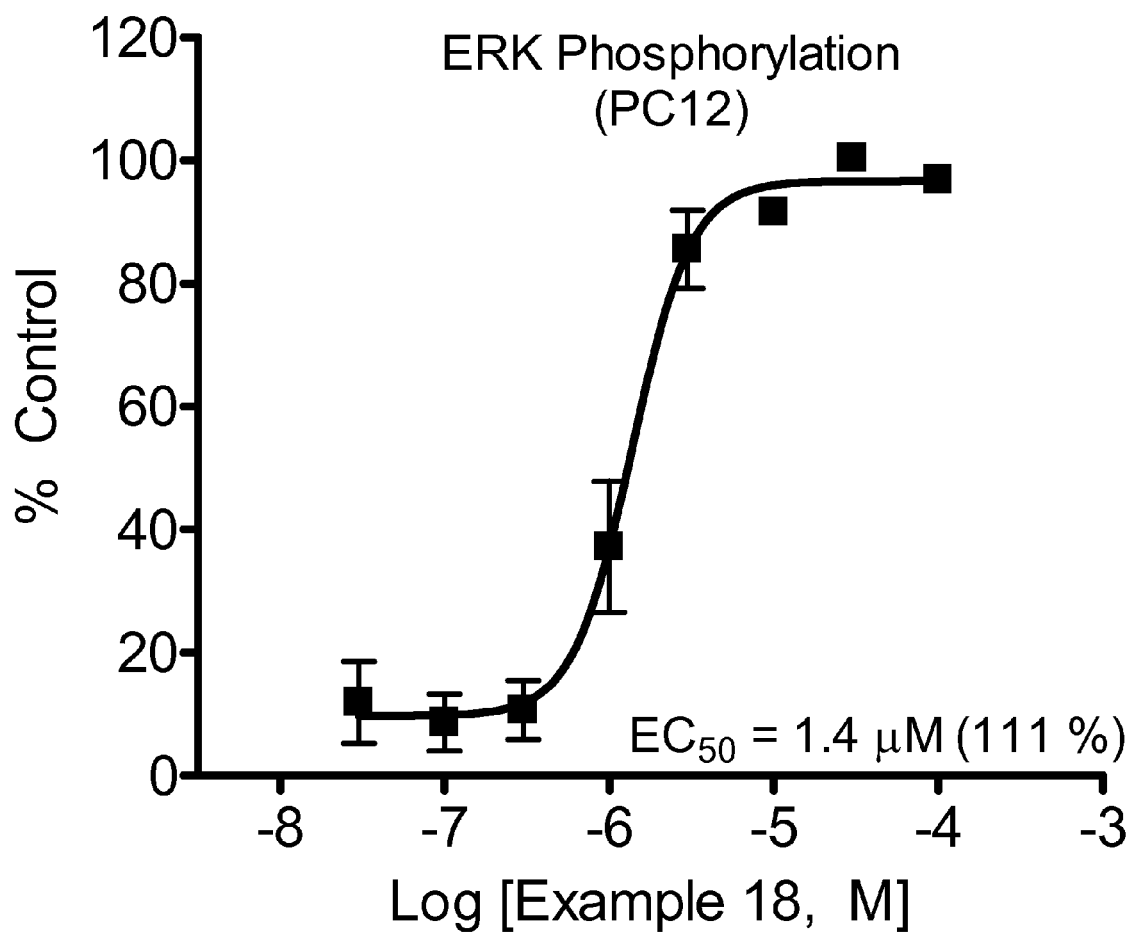
FIG. 1C is a graphical representation of phosphorylation of extracellular receptor kinase (ERK) represented as a function of the log of the concentration of a PAM. The data were obtained by assaying a compound, Example 18, in the presence of a fixed concentration of a selective α7 NNR agonist in cells natively expressing α7 NNRs, for example PC-12 cells. The Y-axis is the normalized change in phospho-ERK1/2 to total ERK ratio and the X-axis represents increasing concentrations of the modulator.

PAMs can be identified by measuring changes in the phosphorylation of ERK (extracellular receptor kinase) by in-cell western analysis. FIG. 1C represents a concentration-response relationship where the Y-axis is the normalized change in phospho-ERK1/2 to total ERK ratio and the X-axis represents increasing concentrations of the allosteric modulator. Compounds with allosteric modulator activity, such as Example 18, evoke concentration-dependent increases in ERK phosphorylation. To obtain data for FIG. 1C, the α7 NNR agonist PNU-282987 (see for example, Hajos et al. *J Pharmacol. Exp Ther.* 2005; 312: 1213-22) was used as the α7 selective agonist. The EC$_{50}$ value of Example 18 is 1.4 μM and a maximal efficacy of 111% was realized (compared to a reference modulator PNU-120596). Typical EC$_{50}$ values in this assay range from about 10 nM to about 30 μM. Other α7 nicotinic receptor agonists including 2-methyl-5-(6-phenyl-pyridazin-3-yl)-octahydro-pyrrolo[3,4-c]pyrrole, 5-[6-(5-methyl-hexahydro-pyrrolo[3,4-c]pyrrol-2-yl)-pyridazin-3-yl]-1H-indole (published in US 20050065178), various quinuclidine derivatives (see for example, US 2005/0137204 and US 2005/0245531) and 4-(5-Phenyl-[1,3,4]oxadiazol-2-yl)-1,4-diaza-bicyclo[3.2.2]nonane and related analogs (see for example, WO 2004/029053) also are suitable for the assay.

The instant compounds are PAMs of α7 NNR that can enhance the effects of naturally occurring neurotransmitter, acetylcholine or exogenous administered agonist. Although not being limited by theory, PAMs generally amplify agonist (acetylcholine) responses by (i) attenuating receptor desensitization so that the receptor remains open for longer duration and/or (ii) by directly amplifying the efficacy of ACh by enhancing maximal receptor activation. In either case, such compounds typically boost endogenous transmission of acetylcholine, and can do so in a temporally and spatially restricted manner since these effects will be localized to regions where the α7 receptors are expressed. Allosteric modulator compounds can modulate function of α7 NNRs by enhancing ion channel function as measured by calcium responses or ERK phosphorylation described herein, or other approaches such as current or membrane potential studies. Preferred compounds are those that behave as PAMs in these assays between a concentration range of about 0.1 nM to about 30 μM. Allosteric modulation of the α7 receptor can trigger key signaling processes that are important to effects on memory, cytoprotection, gene transcription and disease modification. Therefore, the administration of a therapeutically effective amount of a compound of formula (I) to a mammal provides a method of selectively modulating the effects of α7 NNRs.

It is understood that the foregoing detailed description and examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A pharmaceutical compostition comprising a therapeutically effective amount of a compound of formula (I):

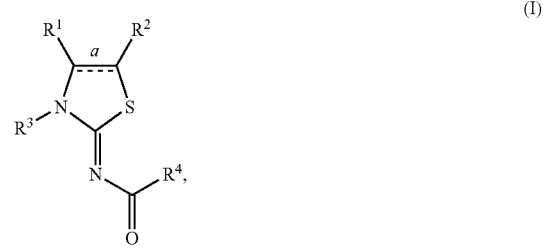

(I)

wherein
$R^1$ is hydrogen, methyl, phenyl, pyrazolyl, or hydroxyl;
$R^2$ is hydrogen, alkyl, alkenyl, =CH$_2$, or =CHR$^c$ wherein the alkyl group and the alkenyl group are substituted with 0, 1, 2, or 3 substituents independently selected from the group consisting of alkoxycarbonyl, alkylcarbonyloxy, aryl, aryloxy, arylalkoxy, carboxy, cyano, cycloalkyl, haloalkoxy, heteroaryl, heterocycle, hydroxyl, nitro, and R$^d$R$^e$N—, wherein a group represented by R$^2$ can be further substituted with 0, 1, or 2 groups selected from halo and alkoxy;
$R^c$ is alkyl or halo;
$R^d$ and $R^e$ are each independently hydrogen, alkyl, alkoxyalkyl, aryl, arylalkyl, cyanoalkyl, heteroaryl, heteroarylalkyl, heterocycle, or heterocyclealkyl;
$R^3$ is optionally substituted phenyl or naphthyl;
$R^4$ is optionally substituted heterocycle; and
a is single or double bond;
provided that when $R^1$ is hydroxyl or when $R^2$ is a radical attached to the thiazole ring through an exocyclic double bond, then a is single bond; and
provided that when a is double bond, $R^1$ is hydrogen, $R^2$ is methyl, $R^3$ is phenyl substituted with 3-haloalkyl, 3-halo, 3-haloalkoxy, 2,5-dihalo, 2,3-dihalo, 3,4-dihalo, or 3,5-dihalo, then $R^4$ is heterocycle;
or a pharmaceutically acceptable salt, thereof, in combination with a pharmaceutically acceptable carrier.

2. The pharmaceutical compostition of claim 1, wherein $R^1$ is hydrogen or methyl.

3. The pharmaceutical composition of claim 1, wherein $R^2$ is hydrogen or alkyl, wherein the alkyl group is optionally substituted with 1 or 2 alkoxy, alkylcarbonyl, cyano, heteroaryl, hydroxy, or $R^d R^e N$—.

4. A pharmaceutical compostion of claim 1, wherein the compound of formula (I) is selected from the group consisting of:
- N-[(2Z)-3-[4-(difluoromethoxy)phenyl]-5-methyl-1,3-thiazol-2(3H)-ylidene]pyrrolidine-1-carboxamide;
- N-[(2Z)-3-[4-(difluoromethoxy)phenyl]-5-methyl-1,3-thiazol-2(3H)-ylidene]piperidine-1-carboxamide;
- N-[(2Z)-5-methyl-3-[4-(trifluoromethoxy)phenyl]-1,3-thiazol-2(3H)-ylidene]pyrrolidine-1-carboxamide;
- N-[(2Z)-3-(4-chlorophenyl)-5-methyl-1,3-thiazol-2(3H)-ylidene]pyrrolidine-1-carboxamide;
- N-[(2Z)-3-(4-chlorophenyl)-5-methyl-1,3-thiazol-2(3H)-ylidene]piperidine-1-carboxamide;
- N-[(2Z)-3-(4-fluorophenyl)-5-methyl-1,3-thiazol-2(3H)-ylidene]pyrrolidine-1-carboxamide;
- N-[(2Z)-3-(4-fluorophenyl)-5-methyl-1,3-thiazol-2(3H)-ylidene]piperidine-1-carboxamide;
- N-[(2Z)-5-methyl-3-[4-(trifluoromethyl)phenyl]-1,3-thiazol-2(3H)-ylidene]pyrrolidine-1-carboxamide;
- 2-methyl-N-[(2Z)-5-methyl-3-[4-(trifluoromethyl)phenyl]-1,3-thiazol-2(3H)-ylidene]pyrrolidine-1-carboxamide;
- (2R)-2-methyl-N-[(2Z)-5-methyl-3-[4-(trifluoromethyl)phenyl]-1,3-thiazol-2(3H)-ylidene]pyrrolidine-1-carboxamide;
- (2S)-2-methyl-N-[(2Z)-5-methyl-3-[4-(trifluoromethyl)phenyl]-1,3-thiazol-2(3H)-ylidene]pyrrolidine-1-carboxamide;
- N-[(2Z)-3-(4-chlorophenyl)-1,3-thiazolidin-2-ylidene]pyrrolidine-1-carboxamide;
- (3R)-N-[(2Z)-3-(4-chlorophenyl)-1,3-thiazolidin-2-ylidene]-3-fluoropyrrolidine-1-carboxamide;
- N-{(2Z)-5-methylene-3-[4-(trifluoromethyl)phenyl]-1,3-thiazolidin-2-ylidene}azetidinel-1-carboxamide;
- N-[(2Z)-5-methyl-3-[4-(trifluoromethyl)phenyl]-1,3-thiazol-2(3H)-ylidene]azetidinel-1-carboxamide;
- N-[(2Z)-5-methyl-3-(2-naphthyl)-1,3-thiazol-2(3H)-ylidene]pyrrolidine-1-carboxamide;
- N-[(2Z)-3-(4-bromophenyl)-1,3-thiazol-2(3H)-ylidene]pyrrolidine-1-carboxamide;
- N-[(2Z)-5-(hydroxymethyl)-3-(2-naphthyl)-1,3-thiazol-2(3H)-ylidene]pyrrolidine-1-carboxamide;
- (3R)-3-fluoro-N-[(2Z)-5-(hydroxymethyl)-3-(2-naphthyl)-1,3-thiazol-2(3H)-ylidene]pyrrolidine-1-carboxamide;
- (3R)-3-fluoro-N-[(2Z)-5-(hydroxymethyl)-3-[4-(trifluoromethyl)phenyl]-1,3-thiazol-2(3H)-ylidene]pyrrolidine-1-carboxamide;
- (3R)-N-[(2Z)-3-(5,6-difluoro-2-naphthyl)-5-(hydroxymethyl)-1,3-thiazol-2(3H)-ylidene]-3-fluoropyrrolidine-1-carboxamide;
- N-[(2Z)-5-methyl-3-phenyl-1,3-thiazol-2(3H)-ylidene]pyrrolidine-1-carboxamide;
- N-[(2Z)-5-methyl-3-(3-methylphenyl)-1,3-thiazol-2(3H)-ylidene]pyrrolidine-1-carboxamide;
- N-[(2Z)-5-methyl-3-(4-methylphenyl)-1,3-thiazol-2(3H)-ylidene]pyrrolidine-1-carboxamide;
- N-[(2Z)-3-(3-aminophenyl)-5-methyl-1,3-thiazol-2(3H)-ylidene]pyrrolidine-1-carboxamide;
- N-[(2Z)-3-(3-hydroxyphenyl)-5-methyl-1,3-thiazol-2(3H)-ylidene]pyrrolidine-1-carboxamide;
- N-[(2Z)-3-(4-methoxyphenyl)-5-methyl-1,3-thiazol-2(3H)-ylidene]pyrrolidine-1-carboxamide;
- N-[(2Z)-3-(3-fluorophenyl)-5-methyl-1,3-thiazol-2(3H)-ylidene]pyrrolidine-1-carboxamide;
- N-[(2Z)-3-(3-chlorophenyl)-5-methyl-1,3-thiazol-2(3H)-ylidene]pyrrolidine-1-carboxamide;
- N-[(2Z)-3-(2-bromophenyl)-5-methyl-1,3-thiazol-2(3H)-ylidene]pyrrolidine-1-carboxamide;
- N-[(2Z)-3-(3-bromophenyl)-5-methyl-1,3-thiazol-2(3H)-ylidene]pyrrolidine-1-carboxamide;
- N-[(2Z)-3-(3-cyanophenyl)-5-methyl-1,3-thiazol-2(3H)-ylidene]pyrrolidine-1-carboxamide;
- N-[(2Z)-3-(4-cyanophenyl)-5-methyl-1,3-thiazol-2(3H)-ylidene]pyrrolidine-1-carboxamide;
- N-[(2Z)-3-[4-(dimethylamino)phenyl]-5-methyl-1,3-thiazol-2(3H)-ylidene]pyrrolidine-1-carboxamide;
- N-[(2Z)-5-methyl-3-[3-(trifluoromethyl)phenyl]-1,3-thiazol-2(3H)-ylidene]pyrrolidine-1-carboxamide;
- N-[(2Z)-5-methyl-3-[3-(trifluoromethoxy)phenyl]-1,3-thiazol-2(3H)-ylidene]pyrrolidine-1-carboxamide;
- N-[(2Z)-5-methyl-3-(4-phenoxyphenyl)-1,3-thiazol-2(3H)-ylidene]pyrrolidine-1-carboxamide;
- N-[(2Z)-3-[4-(benzyloxy)phenyl]-5-methyl-1,3-thiazol-2(3H)-ylidene]pyrrolidine-1-carboxamide;
- N-[(2Z)-3-(3,4-dimethylphenyl)-5-methyl-1,3-thiazol-2(3H)-ylidene]pyrrolidine-1-carboxamide;
- N-[(2Z)-3-(3,5-dimethylphenyl)-5-methyl-1,3-thiazol-2(3H)-ylidene]pyrrolidine-1-carboxamide;
- N-[(2Z)-3-(3,4-dichlorophenyl)-5-methyl-1,3-thiazol-2(3H)-ylidene]pyrrolidine-1-carboxamide;
- N-[(2Z)-3-(3,5-dichlorophenyl)-5-methyl-1,3-thiazol-2(3H)-ylidene]pyrrolidine-1-carboxamide;
- N-[(2Z)-5-methyl-3-[4-(methylthio)phenyl]-1,3-thiazol-2(3H)-ylidene]pyrrolidine-1-carboxamide;
- N-[(2Z)-3-(3-methoxyphenyl)-5-methyl-1,3-thiazol-2(3H)-ylidene]pyrrolidine-1-carboxamide;
- N-[(2Z)-3-(4-chloro-3-methylphenyl)-5-methyl-1,3-thiazol-2(3H)-ylidene]pyrrolidine-1-carboxamide;
- N-[(2Z)-3-(4-benzylphenyl)-5-methyl-1,3-thiazol-2(3H)-ylidene]pyrrolidine-1-carboxamide;
- N-[(2Z)-3-(1-benzothien-5-yl)-5-methyl-1,3-thiazol-2(3H)-ylidene]pyrrolidine-1-carboxamide;
- N-[(2Z)-3-[4-(methylthio)phenyl]-1,3-thiazol-2(3H)-ylidene]pyrrolidine-1-carboxamide;
- N-[(2Z)-3-phenyl-1,3-thiazol-2(3H)-ylidene]pyrrolidine-1-carboxamide;
- N-[(2Z)-3-(3-chlorophenyl)-1,3-thiazol-2(3H)-ylidene]pyrrolidine-1-carboxamide;
- N-[(2Z)-3-[3-(trifluoromethyl)phenyl]-1,3-thiazol-2(3H)-ylidene]pyrrolidine-1-carboxamide;
- N-[(2Z)-3-(4-chlorophenyl)-1,3-thiazol-2(3H)-ylidene]pyrrolidine-1-carboxamide;
- N-[(2Z)-3-(4-methylphenyl)-1,3-thiazol-2(3H)-ylidene]pyrrolidine-1-carboxamide;
- N-[(2Z)-3-(4-chloro-3-methylphenyl)-1,3-thiazol-2(3H)-ylidene]pyrrolidine-1-carboxamide;
- N-[(2Z)-3-(3,4-dichlorophenyl)-1,3-thiazol-2(3H)-ylidene]pyrrolidine-1-carboxamide;
- N-[(2Z)-3-(3,4-dimethylphenyl)-1,3-thiazol-2(3H)-ylidene]pyrrolidine-1-carboxamide;
- N-[(2Z)-3-(4-cyanophenyl)-1,3-thiazol-2(3H)-ylidene]pyrrolidine-1-carboxamide;

N-[(2Z)-3-(3-chloro-4-methylphenyl)-1,3-thiazol-2(3H)-ylidene]pyrrolidine-1-carboxamide;
N-[(2Z)-3-[4-(difluoromethoxy)phenyl]-1,3-thiazol-2(3H)-ylidene]pyrrolidine-1-carboxamide;
N-[(2Z)-3-[3-fluoro-4-(trifluoromethyl)phenyl]-1,3-thiazol-2(3H)-ylidene]pyrrolidine-1-carboxamide;
(3R)-N-[(2Z)-3-(3-bromophenyl)-5-methyl-1,3-thiazol-2(3H)-ylidene]-3-fluoropyrrolidine-1-carboxamide;
(3R)-N-[(2Z)-3-(4-cyano-3-methylphenyl)-5-methyl-1,3-thiazol-2(3H)-ylidene]-3-fluoropyrrolidine-1-carboxamide;
(3R)-3-fluoro-N-[(2Z)-5-methyl-3-(3-methylphenyl)-1,3-thiazol-2(3H)-ylidene]pyrrolidine-1-carboxamide;
(3R)-N-[(2Z)-3-(4-bromophenyl)-5-methyl-1,3-thiazol-2(3H)-ylidene]-3-fluoropyrrolidine-1-carboxamide;
(3R)-3-fluoro-N-[(2Z)-5-methyl-3-(4-phenoxyphenyl)-1,3-thiazol-2(3H)-ylidene]pyrrolidine-1-carboxamide;
(3R)-3-fluoro-N-[(2Z)-5-methyl-3-(4-methylphenyl)-1,3-thiazol-2(3H)-ylidene]pyrrolidine-1-carboxamide;
(3R)-N-[(2Z)-3-(4-ethylphenyl)-5-methyl-1,3-thiazol-2(3H)-ylidene]-3-fluoropyrrolidine-1-carboxamide;
(3R)-3-fluoro-N-[(2Z)-3-(3-fluorophenyl)-5-methyl-1,3-thiazol-2(3H)-ylidene]pyrrolidine-1-carboxamide;
(3R)-3-fluoro-N-[(2Z)-3-(4-fluorophenyl)-5-methyl-1,3-thiazol-2(3H)-ylidene]pyrrolidine-1-carboxamide;
(3R)-3-fluoro-N-[(2Z)-5-methyl-3-[3-(trifluoromethyl)phenyl]-1,3-thiazol-2(3H)-ylidene]pyrrolidine-1-carboxamide;
(3R)-3-fluoro-N-[(2Z)-5-methyl-3-[4-(trifluoromethyl)phenyl]-1,3-thiazol-2(3H)-ylidene]pyrrolidine-1-carboxamide;
(3R)-N-[(2Z)-3-(4-chlorophenyl)-5-methyl-1,3-thiazol-2(3H)-ylidene]-3-fluoropyrrolidine-1-carboxamide;
(3R)-3-fluoro-N-[(2Z)-3-(4-iodophenyl)-5-methyl-1,3-thiazol-2(3H)-ylidene]pyrrolidine-1-carboxamide;
(3R)-N-[(2Z)-3-(3-cyanophenyl)-5-methyl-1,3-thiazol-2(3H)-ylidene]-3-fluoropyrrolidine-1-carboxamide;
(3R)-3-fluoro-N-[(2Z)-5-methyl-3-(2-naphthyl)-1,3-thiazol-2(3H)-ylidene]pyrrolidine-1-carboxamide;
(3R)-N-[(2Z)-3-(3,4-dichlorophenyl)-5-methyl-1,3-thiazol-2(3H)-ylidene]-3-fluoropyrrolidine-1-carboxamide;
(3R)-3-fluoro-N-[(2Z)-3-(3-iodophenyl)-5-methyl-1,3-thiazol-2(3H)-ylidene]pyrrolidine-1-carboxamide;
(3R)-N-[(2Z)-3-(3-chloro-4-methylphenyl)-5-methyl-1,3-thiazol-2(3H)-ylidene]-3-fluoropyrrolidine-1-carboxamide;
N-[(2Z)-3-(2-naphthyl)-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]indoline-1-carboxamide;
2,5-dimethyl-N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]piperidine-1-carboxamide;
4-benzyl-N-[(2Z)-5-methyl-3-[4-(trifluoromethyl)phenyl]-1,3-thiazol-2(3H)-ylidene]piperidine-1-carboxamide;
(3R)-N-[(2Z)-3-(3,5-dichlorophenyl)-5-(hydroxymethyl)-1,3-thiazol-2(3H)-ylidene]-3-fluoropyrrolidine-1-carboxamide;
(3R)-N-[(2Z)-3-(3-chlorophenyl)-5-(hydroxymethyl)-1,3-thiazol-2(3H)-ylidene]-3-fluoropyrrolidine-1-carboxamide;
(3R)-N-[(2Z)-3-(3,4-dimethylphenyl)-5-(hydroxymethyl)-1,3-thiazol-2(3H)-ylidene]-3-fluoropyrrolidine-1-carboxamide;
(3R)-N-[(2Z)-3-(3,5-dimethylphenyl)-5-(hydroxymethyl)-1,3-thiazol-2(3H)-ylidene]-3-fluoropyrrolidine-1-carboxamide;
(3R)-N-[(2Z)-3-(4-chloro-3-methylphenyl)-5-(hydroxymethyl)-1,3-thiazol-2(3H)-ylidene]-3-fluoropyrrolidine-1-carboxamide;
(3R)-3-fluoro-N-[(2Z)-5-(hydroxymethyl)-3-[4-(trifluoromethoxy)phenyl]-1,3-thiazol-2(3H)-ylidene]pyrrolidine-1-carboxamide;
(3R)-N-[(2Z)-3-(3,4-dichlorophenyl)-5-(hydroxymethyl)-1,3-thiazol-2(3H)-ylidene]-3-fluoropyrrolidine-1-carboxamide;
(3R)-3-fluoro-N-[(2Z)-3-[3-fluoro-4-(trifluoromethyl)phenyl]-5-(hydroxymethyl)-1,3-thiazol-2(3H)-ylidene]pyrrolidine-1-carboxamide;
N-[(2Z)-3-(4-chlorophenyl)-4,5-dimethyl-1,3-thiazol-2(3H)-ylidene]pyrrolidine-1-carboxamide;
N-[(2Z)-4,5-dimethyl-3-[4-(trifluoromethyl)phenyl]-1,3-thiazol-2(3H)-ylidene]pyrrolidine-1-carboxamide;
4-acetyl-N-[(2Z)-5-methyl-3-[4-(trifluoromethyl)phenyl]-1,3-thiazol-2(3H)-ylidene]piperazine-1-carboxamide;
N-[(2Z)-3-(4-fluorophenyl)-1,3-thiazol-2(3H)-ylidene]pyrrolidine-1-carboxamide;
(3R)-N-[(2Z)-3-(4-cyanophenyl)-5-(hydroxymethyl)-1,3-thiazol-2(3H)-ylidene]-3-fluoropyrrolidine-1-carboxamide;
(3R)-3-fluoro-N-[(2Z)-5-(hydroxymethyl)-3-(5,6,8-trifluoro-2-naphthyl)-1,3-thiazol-2(3H)-ylidene]pyrrolidine-1-carboxamide;
N-[(2Z)-5-methyl-3-[4-(trifluoromethoxy)phenyl]-1,3-thiazol-2(3H)-ylidene]piperidine-1-carboxamide;
N-[(2Z)-3-[4-(cyanomethyl)phenyl]-5-methyl-1,3-thiazol-2(3H)-ylidene]pyrrolidine-1-carboxamide;
N-[(2Z)-3-[4-(cyanomethyl)phenyl]-5-methyl-1,3-thiazol-2(3H)-ylidene]piperidine-1-carboxamide;
N-[(2Z)-5-methyl-3-[4-(trifluoromethyl)phenyl]-1,3-thiazol-2(3H)-ylidene]piperidine-1-carboxamide;
tert-butyl (2R,3S)-2-methyl-1-({[(2Z)-5-methyl-3-[4-(trifluoromethyl)phenyl]-1,3-thiazol-2(3H)-ylidene]amino}carbonyl)pyrrolidin-3-ylcarbamate;
2-isopropyl-N-[(2Z)-5-methyl-3-[4-(trifluoromethyl)phenyl]-1,3-thiazol-2(3H)-ylidene]pyrrolidine-1-carboxamide;
2-isobutyl-N-[(2Z)-5-methyl-3-[4-(trifluoromethyl)phenyl]-1,3-thiazol-2(3H)-ylidene]pyrrolidine-1-carboxamide;
(3R)-3-(dimethylamino)-N-[(2Z)-5-methyl-3-[4-(trifluoromethyl)phenyl]-1,3-thiazol-2(3H)-ylidene]pyrrolidine-1-carboxamide;
tert-butyl (3S)-1-({[(2Z)-5-methyl-3-[4-(trifluoromethyl)phenyl]-1,3-thiazol-2(3H)-ylidene]amino}carbonyl)pyrrolidin-3-ylcarbamate;
tert-butyl 5-({[(2Z)-5-methyl-3-[4-(trifluoromethyl)phenyl]-1,3-thiazol-2(3H)-ylidene]amino}carbonyl)hexahydropyrrolo[3,4-c]pyrrole-2(1H)-carboxylate;
tert-butyl (1S,5R)-3-({[(2Z)-5-methyl-3-[4-(trifluoromethyl)phenyl]-1,3-thiazol-2(3H)-ylidene]amino}carbonyl)-3,6-diazabicyclo[3.2.0]heptane-6-carboxylate;
tert-butyl (3R)-3-methyl-1-({[(2Z)-5-methyl-3-[4-(trifluoromethyl)phenyl]-1,3-thiazol-2(3H)-ylidene]amino}carbonyl)pyrrolidin-3-ylcarbamate;

tert-butyl 6-({[(2Z)-5-methyl-3-[4-(trifluoromethyl)phenyl]-1,3-thiazol-2(3H)-ylidene]amino}carbonyl)octahydro-1H-pyrrolo[3,4-b]pyridine-1-carboxylate;

tert-butyl (1S,4S)-5-({[(2Z)-5-methyl-3-[4-(trifluoromethyl)phenyl]-1,3-thiazol-2(3H)-ylidene] amino}carbonyl)-2,5-diazabicyclo[2.2.1]heptane-2-carboxylate;

(3S)-3-amino-N-[(2Z)-5-methyl-3-[4-(trifluoromethyl)phenyl]-1,3-thiazol-2(3H)-ylidene]pyrrolidine-1-carboxamide;

(2R,3S)-3-amino-2-methyl-N-[(2Z)-5-methyl-3-[4-(trifluoromethyl)phenyl]-1,3-thiazol-2(3H)-ylidene]pyrrolidine-1-carboxamide;

N-[(2Z)-5-methyl-3-[4-(trifluoromethyl)phenyl]-1,3-thiazol-2(3H)-ylidene]hexahydropyrrolo[3,4-c]pyrrole-2(1H)-carboxamide;

(3R)-3-amino-3-methyl-N-[(2Z)-5-methyl-3-[4-(trifluoromethyl)phenyl]-1,3-thiazol-2(3H)-ylidene]pyrrolidine-1-carboxamide;

(1R,5R)-N-[(2Z)-5-methyl-3-[4-(trifluoromethyl)phenyl]-1,3-thiazol-2(3H)-ylidene]-3,6-diazabicyclo[3.2.0]heptane-3-carboxamide;

(4aS,7aS)-N-[(2Z)-5-methyl-3-[4-(trifluoromethyl)phenyl]-1,3-thiazol-2(3H)-ylidene]octahydro-6H-pyrrolo[3,4-b]pyridine-6-carboxamide;

(1S,4S)-N-[(2Z)-5-methyl-3-[4-(trifluoromethyl)phenyl]-1,3-thiazol-2(3H)-ylidene]-2,5-diazabicyclo[2.2.1]heptane-2-carboxamide;

N-[(2Z)-3-(3-ethoxyphenyl)-4,5-dimethyl-1,3-thiazol-2(3H)-ylidene]pyrrolidine-1-carboxamide;

3-methyl-N-[(2Z)-5-methyl-3-[4-(trifluoromethyl)phenyl]-1,3-thiazol-2(3H)-ylidene]piperidine-1-carboxamide;

4-methyl-N-[(2Z)-5-methyl-3-[4-(trifluoromethyl)phenyl]-1,3-thiazol-2(3H)-ylidene]piperidine-1-carboxamide;

2-ethyl-N-[(2Z)-5-methyl-3-[4-(trifluoromethyl)phenyl]-1,3-thiazol-2(3H)-ylidene]piperidine-1-carboxamide;

N-[(2Z)-5-methyl-3-[4-(trifluoromethyl)phenyl]-1,3-thiazol-2(3H)-ylidene]-4-propylpiperidine-1-carboxamide;

N-[(2Z)-5-methyl-3-[4-(trifluoromethyl)phenyl]-1,3-thiazol-2(3H)-ylidene]azepane-1-carboxamide;

N-[(2Z)-5-methyl-3-[4-(trifluoromethyl)phenyl]-1,3-thiazol-2(3H)-ylidene]morpholine-4-carboxamide;

N-[(2Z)-5-methyl-3-[4-(trifluoromethyl)phenyl]-1,3-thiazol-2(3H)-ylidene]thiomorpholine-4-carboxamide;

4-hydroxy-N-[(2Z)-5-methyl-3-[4-(trifluoromethyl)phenyl]-1,3-thiazol-2(3H)-ylidene]piperidine-1-carboxamide;

2,6-dimethyl-N-[(2Z)-5-methyl-3-[4-(trifluoromethyl)phenyl]-1,3-thiazol-2(3H)-ylidene]morpholine-4-carboxamide;

4-methyl-N-[(2Z)-5-methyl-3-[4-(trifluoromethyl)phenyl]-1,3-thiazol-2(3H)-ylidene]piperazine-1-carboxamide;

4-ethyl-N-[(2Z)-5-methyl-3-[4-(trifluoromethyl)phenyl]-1,3-thiazol-2(3H)-ylidene]piperazine-1-carboxamide;

N-[(2Z)-5-methyl-3-[4-(trifluoromethyl)phenyl]-1,3-thiazol-2(3H)-ylidene]-4-phenylpiperazine-1-carboxamide;

N-[(2Z)-5-methyl-3-[4-(trifluoromethyl)phenyl]-1,3-thiazol-2(3H)-ylidene]-4-pyridin-2-ylpiperazine-1-carboxamide;

4-methyl-N-[(2Z)-5-methyl-3-[4-(trifluoromethyl)phenyl]-1,3-thiazol-2(3H)-ylidene]-1,4-diazepane-1-carboxamide;

N-[(2Z)-5-methyl-3-[4-(trifluoromethyl)phenyl]-1,3-thiazol-2(3H)-ylidene]-4-pyrimidin-2-ylpiperazine-1-carboxamide;

N-{(2Z)-5-methylene-3-[4-(trifluoromethyl)phenyl]-1,3-thiazolidin-2-ylidene}pyrrolidine-1-carboxamide;

N-{(2Z)-4-hydroxy-5-methylene-3-[4-(trifluoromethyl)phenyl]-1,3-thiazolidin-2-ylidene}pyrrolidine-1-carboxamide;

N-[(2Z)-5-methyl-3-(2-methylphenyl)-1,3-thiazol-2(3H)-ylidene]pyrrolidine-1-carboxamide;

N-[(2Z)-3-(2-aminophenyl)-5-methyl-1,3-thiazol-2(3H)-ylidene]pyrrolidine-1-carboxamide;

N-[(2Z)-3-(2-hydroxyphenyl)-5-methyl-1,3-thiazol-2(3H)-ylidene]pyrrolidine-1-carboxamide;

N-[(2Z)-3-(4-hydroxyphenyl)-5-methyl-1,3-thiazol-2(3H)-ylidene]pyrrolidine-1-carboxamide;

N-[(2Z)-3-(2-methoxyphenyl)-5-methyl-1,3-thiazol-2(3H)-ylidene]pyrrolidine-1-carboxamide;

N-[(2Z)-3-(2-fluorophenyl)-5-methyl-1,3-thiazol-2(3H)-ylidene]pyrrolidine-1-carboxamide;

N-[(2Z)-3-(2-chlorophenyl)-5-methyl-1,3-thiazol-2(3H)-ylidene]pyrrolidine-1-carboxamide;

N-[(2Z)-3-[3-(dimethylamino)phenyl]-5-methyl-1,3-thiazol-2(3H)-ylidene]pyrrolidine-1-carboxamide;

N-[(2Z)-3-(2,3-dimethylphenyl)-5-methyl-1,3-thiazol-2(3H)-ylidene]pyrrolidine-1-carboxamide;

N-[(2Z)-3-(2,4-dimethylphenyl)-5-methyl-1,3-thiazol-2(3H)-ylidene]pyrrolidine-1-carboxamide;

N-[(2Z)-3-(2,5-dimethylphenyl)-5-methyl-1,3-thiazol-2(3H)-ylidene]pyrrolidine-1-carboxamide;

N-[(2Z)-3-(2,4-dimethoxyphenyl)-5-methyl-1,3-thiazol-2(3H)-ylidene]pyrrolidine-1-carboxamide;

N-[(2Z)-3-(2,5-dimethoxyphenyl)-5-methyl-1,3-thiazol-2(3H)-ylidene]pyrrolidine-1-carboxamide;

N-[(2Z)-3-(3,4-dimethoxyphenyl)-5-methyl-1,3-thiazol-2(3H)-ylidene]pyrrolidine-1-carboxamide;

N-[(2Z)-5-methyl-3-(3,4,5-trimethoxyphenyl)-1,3-thiazol-2(3H)-ylidene]pyrrolidine-1-carboxamide;

N-[(2Z)-3-(2,3-dichlorophenyl)-5-methyl-1,3-thiazol-2(3H)-ylidene]pyrrolidine-1-carboxamide;

N-[(2Z)-3-(2,4-dichlorophenyl)-5-methyl-1,3-thiazol-2(3H)-ylidene]pyrrolidine-1-carboxamide;

N-[(2Z)-3-(2,5-dichlorophenyl)-5-methyl-1,3-thiazol-2(3H)-ylidene]pyrrolidine-1-carboxamide;

N-[(2Z)-3-(4-aminophenyl)-5-methyl-1,3-thiazol-2(3H)-ylidene]pyrrolidine-1-carboxamide;

N-[(2Z)-5-methyl-3-(3-propionylphenyl)-1,3-thiazol-2(3H)-ylidene]pyrrolidine-1-carboxamide;

N-[(2Z)-3-(4-tert-butylphenyl)-5-methyl-1,3-thiazol-2(3H)-ylidene]pyrrolidine-1-carboxamide;

N-[(2Z)-3-(4-ethylphenyl)-5-methyl-1,3-thiazol-2(3H)-ylidene]pyrrolidine-1-carboxamide;

N-[(2Z)-5-methyl-3-(4-propylphenyl)-1,3-thiazol-2(3H)-ylidene]pyrrolidine-1-carboxamide;

N-[(2Z)-3-(4-butylphenyl)-5-methyl-1,3-thiazol-2(3H)-ylidene]pyrrolidine-1-carboxamide;

N-[(2Z)-5-methyl-3-[3-(methylthio)phenyl]-1,3-thiazol-2(3H)-ylidene]pyrrolidine-1-carboxamide;

N-[(2Z)-5-methyl-3-[2,3,5,6-tetrafluoro-4-(trifluoromethyl)phenyl]-1,3-thiazol-2(3H)-ylidene]pyrrolidine-1-carboxamide;

N-[(2Z)-3-(3-isopropoxyphenyl)-5-methyl-1,3-thiazol-2(3H)-ylidene]pyrrolidine-1-carboxamide;

N-[(2Z)-3-[2,4-bis(trifluoromethyl)phenyl]-5-methyl-1,3-thiazol-2(3H)-ylidene]pyrrolidine-1-carboxamide;

N-[(2Z)-3-(4-chloro-3-methoxyphenyl)-5-methyl-1,3-thiazol-2(3H)-ylidene]pyrrolidine-1-carboxamide;

N-[(2Z)-3-(4-methoxy-3-methylphenyl)-5-methyl-1,3-thiazol-2(3H)-ylidene]pyrrolidine-1-carboxamide;
N-[(2Z)-3-(4-cyclohexylphenyl)-5-methyl-1,3-thiazol-2(3H)-ylidene]pyrrolidine-1-carboxamide;
N-[(2Z)-5-methyl-3-(1-naphthyl)-1,3-thiazol-2(3H)-ylidene]pyrrolidine-1-carboxamide;
N-[(2Z)-3-(4'-fluoro-1,1'-biphenyl-4-yl)-5-methyl-1,3-thiazol-2(3H)-ylidene]pyrrolidine-1-carboxamide;
N-[(2Z)-3-(4-acetylphenyl)-1,3-thiazol-2(3H)-ylidene]pyrrolidine-1-carboxamide;
N-[(2Z)-3-(4-propionylphenyl)-1,3-thiazol-2(3H)-ylidene]pyrrolidine-1-carboxamide;
N-[(2Z)-3-(4-tert-butylphenyl)-1,3-thiazol-2(3H)-ylidene]pyrrolidine-1-carboxamide;
N-[(2Z)-3-(4-ethylphenyl)-1,3-thiazol-2(3H)-ylidene]pyrrolidine-1-carboxamide;
N-[(2Z)-3-(2,4-dichlorophenyl)-1,3-thiazol-2(3H)-ylidene]pyrrolidine-1-carboxamide;
N-[(2Z)-3-(2-methoxyphenyl)-1,3-thiazol-2(3H)-ylidene]pyrrolidine-1-carboxamide;
N-[(2Z)-3-(2-methylphenyl)-1,3-thiazol-2(3H)-ylidene]pyrrolidine-1-carboxamide;
N-[(2Z)-3-(3,5-dichlorophenyl)-1,3-thiazol-2(3H)-ylidene]pyrrolidine-1-carboxamide;
N-[(2Z)-3-(3-methoxyphenyl)-1,3-thiazol-2(3H)-ylidene]pyrrolidine-1-carboxamide;
N-[(2Z)-3-(3-methylphenyl)-1,3-thiazol-2(3H)-ylidene]pyrrolidine-1-carboxamide;
N-[(2Z)-3-(4-methoxyphenyl)-1,3-thiazol-2(3H)-ylidene]pyrrolidine-1-carboxamide;
N-[(2Z)-3-(4-propylphenyl)-1,3-thiazol-2(3H)-ylidene]pyrrolidine-1-carboxamide;
N-[(2Z)-3-(2,4-dimethylphenyl)-1,3-thiazol-2(3H)-ylidene]pyrrolidine-1-carboxamide;
N-[(2Z)-3-pyridin-3-yl-1,3-thiazol-2(3H)-ylidene]pyrrolidine-1-carboxamide;
N-[(2Z)-3-(4-butylphenyl)-1,3-thiazol-2(3H)-ylidene]pyrrolidine-1-carboxamide;
N-[(2Z)-3-[3-(methylthio)phenyl]-1,3-thiazol-2(3H)-ylidene]pyrrolidine-1-carboxamide;
N-[(2Z)-3-(2,3-dichlorophenyl)-1,3-thiazol-2(3H)-ylidene]pyrrolidine-1-carboxamide;
N-[(2Z)-3-(2-chlorophenyl)-1,3-thiazol-2(3H)-ylidene]pyrrolidine-1-carboxamide;
N-[(2Z)-3-[2,3,5,6-tetrafluoro-4-(trifluoromethyl)phenyl]-1,3-thiazol-2(3H)-ylidene]pyrrolidine-1-carboxamide;
N-[(2Z)-3-(3,5-dimethylphenyl)-1,3-thiazol-2(3H)-ylidene]pyrrolidine-1-carboxamide;
N-[(2Z)-3-(3-isopropoxyphenyl)-1,3-thiazol-2(3H)-ylidene]pyrrolidine-1-carboxamide;
N-[(2Z)-3-[2,4-bis(trifluoromethyl)phenyl]-1,3-thiazol-2(3H)-ylidene]pyrrolidine-1-carboxamide;
N-[(2Z)-3-(3-cyanophenyl)-1,3-thiazol-2(3H)-ylidene]pyrrolidine-1-carboxamide;
N-[(2Z)-3-(4-methoxy-3-methylphenyl)-1,3-thiazol-2(3H)-ylidene]pyrrolidine-1-carboxamide;
N-[(2Z)-3-(2'-methyl-1,1'-biphenyl-4-yl)-1,3-thiazol-2(3H)-ylidene]pyrrolidine-1-carboxamide;
N-[(2Z)-3-(3'-methyl-1,1'-biphenyl-4-yl)-1,3-thiazol-2(3H)-ylidene]pyrrolidine-1-carboxamide;
N-[(2Z)-3-(4'-methyl-1,1'-biphenyl-4-yl)-1,3-thiazol-2(3H)-ylidene]pyrrolidine-1-carboxamide;
N-[(2Z)-3-(3'-chloro-1,1'-biphenyl-4-yl)-1,3-thiazol-2(3H)-ylidene]pyrrolidine-1-carboxamide;
N-[(2Z)-3-(4'-chloro-1,1'-biphenyl-4-yl)-1,3-thiazol-2(3H)-ylidene]pyrrolidine-1-carboxamide;
N-[(2Z)-3-(4'-methoxy-1,1'-biphenyl-4-yl)-1,3-thiazol-2(3H)-ylidene]pyrrolidine-1-carboxamide;
N-[(2Z)-3-[3'-(trifluoromethyl)-1,1'-biphenyl-4-yl]-1,3-thiazol-2(3H)-ylidene]pyrrolidine-1-carboxamide;
N-[(2Z)-3-(4-thien-3-ylphenyl)-1,3-thiazol-2(3H)-ylidene]pyrrolidine-1-carboxamide;
N-[(2Z)-3-[4'-(trifluoromethyl)-1,1'-biphenyl-4-yl]-1,3-thiazol-2(3H)-ylidene]pyrrolidine-1-carboxamide;
N-[(2Z)-3-(3'-ethoxy-1,1'-biphenyl-4-yl)-1,3-thiazol-2(3H)-ylidene]pyrrolidine-1-carboxamide;
N-[(2Z)-3-(3'-methoxy-1,1'-biphenyl-4-yl)-1,3-thiazol-2(3H)-ylidene]pyrrolidine-1-carboxamide;
N-[(2Z)-3-(3',5'-dichloro-1,1'-biphenyl-4-yl)-1,3-thiazol-2(3H)-ylidene]pyrrolidine-1-carboxamide;
N-[(2Z)-3-(2'-chloro-1,1'-biphenyl-4-yl)-1,3-thiazol-2(3H)-ylidene]pyrrolidine-1-carboxamide;
N-[(2Z)-3-(2'-methoxy-1,1'-biphenyl-4-yl)-1,3-thiazol-2(3H)-ylidene]pyrrolidine-1-carboxamide;
N-[(2Z)-3-(2'-acetyl-1,1'-biphenyl-4-yl)-1,3-thiazol-2(3H)-ylidene]pyrrolidine-1-carboxamide;
N-[(2Z)-3-(3'-acetyl-1,1'-biphenyl-4-yl)-1,3-thiazol-2(3H)-ylidene]pyrrolidine-1-carboxamide;
N-[(2Z)-3-(4'-acetyl-1,1'-biphenyl-4-yl)-1,3-thiazol-2(3H)-ylidene]pyrrolidine-1-carboxamide;
N-[(2Z)-3-(3',4'-dichloro-1,1'-biphenyl-4-yl)-1,3-thiazol-2(3H)-ylidene]pyrrolidine-1-carboxamide;
N-[(2Z)-3-(4-pyridin-3-ylphenyl)-1,3-thiazol-2(3H)-ylidene]pyrrolidine-1-carboxamide;
N-[(2Z)-3-(2',5'-dichloro-1,1'-biphenyl-4-yl)-1,3-thiazol-2(3H)-ylidene]pyrrolidine-1-carboxamide;
N-[(2Z)-3-(3'-cyano-1,1'-biphenyl-4-yl)-1,3-thiazol-2(3H)-ylidene]pyrrolidine-1-carboxamide;
N-[(2Z)-3-(2',3'-dichloro-1,1'-biphenyl-4-yl)-1,3-thiazol-2(3H)-ylidene]pyrrolidine-1-carboxamide;
N-[(2Z)-3-(2',4'-dichloro-1,1'-biphenyl-4-yl)-1,3-thiazol-2(3H)-ylidene]pyrrolidine-1-carboxamide;
N-[(2Z)-3-(4'-cyano-1,1'-biphenyl-4-yl)-1,3-thiazol-2(3H)-ylidene]pyrrolidine-1-carboxamide;
N-[(2Z)-3-[4-(1-methyl-1H-pyrazol-4-yl)phenyl]-1,3-thiazol-2(3H)-ylidene]pyrrolidine-1-carboxamide;
N-[(2Z)-3-[4-(6-methoxypyridin-3-yl)phenyl]-1,3-thiazol-2(3H)-ylidene]pyrrolidine-1-carboxamide;
N-[(2Z)-3-(1,1'-biphenyl-4-yl)-1,3-thiazol-2(3H)-ylidene]pyrrolidine-1-carboxamide;
N-[(2Z)-3-[4-(2-methoxypyrimidin-5-yl)phenyl]-1,3-thiazol-2(3H)-ylidene]pyrrolidine-1-carboxamide;
N-[(2Z)-3-[4'-(cyanomethyl)-1,1'-biphenyl-4-yl]-1,3-thiazol-2(3H)-ylidene]pyrrolidine-1-carboxamide;
N-[(2Z)-3-(6-ethoxy-2-naphthyl)-1,3-thiazol-2(3H)-ylidene]pyrrolidine-1-carboxamide;
N-[(2Z)-3-(4-cyclohexylphenyl)-1,3-thiazol-2(3H)-ylidene]pyrrolidine-1-carboxamide;
N-[(2Z)-3-[2-cyano-4-(trifluoromethyl)phenyl]-1,3-thiazol-2(3H)-ylidene]pyrrolidine-1-carboxamide;
(3R)-3-fluoro-N-[(2Z)-3-(4-isopropylphenyl)-5-methyl-1,3-thiazol-2(3H)-ylidene]pyrrolidine-1-carboxamide;
(3R)-N-[(2Z)-3-(3,4-dimethylphenyl)-5-methyl-1,3-thiazol-2(3H)-ylidene]-3-fluoropyrrolidine-1-carboxamide;
(3R)-3-fluoro-N-[(2Z)-3-(4-methoxyphenyl)-5-methyl-1,3-thiazol-2(3H)-ylidene]pyrrolidine-1-carboxamide; and
(3R)-3-fluoro-N-[(2Z)-3-(4'-fluoro-1,1'-biphenyl-4-yl)-5-methyl-1,3-thiazol-2(3H)-ylidene]pyrrolidine-1-carboxamide;
and a pharmaceutically acceptable salt thereof.

5. A pharmaceutical composition of claim 1, wherein the compound of formula (I) selected from the group consisting of:

N-[(2Z)-3-[4-(difluoromethoxy)phenyl]-5-methyl-1,3-thiazol-2(3H)-ylidene]pyrrolidine-1-carboxamide;
N-[(2Z)-3-[4-(difluoromethoxy)phenyl]-5-methyl-1,3-thiazol-2(3H)-ylidene]piperidine-1-carboxamide;
N'-[(2Z)-3-[4-(difluoromethoxy)phenyl]-5-methyl-1,3-thiazol-2(3H)-ylidene]-N,N-diethylurea;
N-[(2Z)-5-methyl-3-[4-(trifluoromethoxy)phenyl]-1,3-thiazol-2(3H)-ylidene]pyrrolidine-1-carboxamide;
N-[(2Z)-3-(4-chlorophenyl)-5-methyl-1,3-thiazol-2(3H)-ylidene]pyrrolidine-1-carboxamide;
N-[(2Z)-3-(4-chlorophenyl)-5-methyl-1,3-thiazol-2(3H)-ylidene]piperidine-1-carboxamide;
N-[(2Z)-3-(4-fluorophenyl)-5-methyl-1,3-thiazol-2(3H)-ylidene]pyrrolidine-1-carboxamide;
N-[(2Z)-3-(4-fluorophenyl)-5-methyl-1,3-thiazol-2(3H)-ylidene]piperidine-1-carboxamide;
N-[(2Z)-3-(4-fluorophenyl)-5-methyl-1,3-thiazol-2(3H)-ylidene]cyclobutanecarboxamide;
N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]pyrrolidine-1-carboxamide;
(2R)-2-methyl-N-[(2Z)-5-methyl-3-[4-(trifluoromethyl)phenyl]-1,3-thiazol-2(3H)-ylidene]pyrrolidine-1-carboxamide;
(2S)-2-methyl-N-[(2Z)-5-methyl-3-[4-(trifluoromethyl)phenyl]-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]azetidinel-1-carboxamide;
N-[(2Z)-5-methyl-3-(2-naphthyl)-1,3-thiazol-2(3H)-ylidene]pyrrolidine-1-carboxamide;
N-[(2Z)-3-(4-bromophenyl)-1,3-thiazol-2(3H)-ylidene]pyrrolidine-1-carboxamide;
N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-[4-(trifluoromethyl)phenyl]-1,3-thiazol-2(3H)-ylidene]pyrrolidine-1-carboxamide;
(3R)-N-[(2Z)-3-(5,6-difluoro-2-naphthyl)-5-(hydroxymethyl)-1,3-thiazol-2(3H)-ylidene]-3-fluoropyrrolidine-1-carboxamide;
N-[(2Z)-5-methyl-3-phenyl-1,3-thiazol-2(3H)-ylidene]pyrrolidine-1-carboxamide;
N-[(2Z)-5-methyl-3-(3-methylphenyl)-1,3-thiazol-2(3H)-ylidene]pyrrolidine-1-carboxamide;
N-[(2Z)-5-methyl-3-(4-methylphenyl)-1,3-thiazol-2(3H)-ylidene]pyrrolidine-1-carboxamide;
N-[(2Z)-3-(3-hydroxyphenyl)-5-methyl-1,3-thiazol-2(3H)-ylidene]pyrrolidine-1-carboxamide;
N-[(2Z)-3-(4-methoxyphenyl)-5-methyl-1,3-thiazol-2(3H)-ylidene]pyrrolidine-1-carboxamide;
N-[(2Z)-3-(3-fluorophenyl)-5-methyl-1,3-thiazol-2(3H)-ylidene]pyrrolidine-1-carboxamide;
N-[(2Z)-3-(3-chlorophenyl)-5-methyl-1,3-thiazol-2(3H)-ylidene]pyrrolidine-1-carboxamide;
N-[(2Z)-3-(3-bromophenyl)-5-methyl-1,3-thiazol-2(3H)-ylidene]pyrrolidine-1-carboxamide;
N-[(2Z)-3-(3-cyanophenyl)-5-methyl-1,3-thiazol-2(3H)-ylidene]pyrrolidine-1-carboxamide;
N-[(2Z)-3-(4-cyanophenyl)-5-methyl-1,3-thiazol-2(3H)-ylidene]pyrrolidine-1-carboxamide;
N-[(2Z)-3-[4-(dimethylamino)phenyl]-5-methyl-1,3-thiazol-2(3H)-ylidene]pyrrolidine-1-carboxamide;
N-[(2Z)-5-methyl-3-[3-(trifluoromethoxy)phenyl]-1,3-thiazol-2(3H)-ylidene]pyrrolidine-1-carboxamide;
N-[(2Z)-5-methyl-3-(4-phenoxyphenyl)-1,3-thiazol-2(3H)-ylidene]pyrrolidine-1-carboxamide;
N-[(2Z)-3-[4-(benzyloxy)phenyl]-5-methyl-1,3-thiazol-2(3H)-ylidene]pyrrolidine-1-carboxamide;
N-[(2Z)-3-(3,4-dimethylphenyl)-5-methyl-1,3-thiazol-2(3H)-ylidene]pyrrolidine-1-carboxamide;
N-[(2Z)-3-(3,5-dimethylphenyl)-5-methyl-1,3-thiazol-2(3H)-ylidene]pyrrolidine-1-carboxamide;
N-[(2Z)-3-(3,4-dichlorophenyl)-5-methyl-1,3-thiazol-2(3H)-ylidene]pyrrolidine-1-carboxamide;
N-[(2Z)-3-(3,5-dichlorophenyl)-5-methyl-1,3-thiazol-2(3H)-ylidene]pyrrolidine-1-carboxamide;
N-[(2Z)-5-methyl-3-[4-(methylthio)phenyl]-1,3-thiazol-2(3H)-ylidene]pyrrolidine-1-carboxamide;
N-[(2Z)-3-(3-methoxyphenyl)-5-methyl-1,3-thiazol-2(3H)-ylidene]pyrrolidine-1-carboxamide;
N-[(2Z)-3-(4-chloro-3-methylphenyl)-5-methyl-1,3-thiazol-2(3H)-ylidene]pyrrolidine-1-carboxamide;
N-[(2Z)-3-(4-benzylphenyl)-5-methyl-1,3-thiazol-2(3H)-ylidene]pyrrolidine-1-carboxamide;
N-[(2Z)-3-[4-(methylthio)phenyl]-1,3-thiazol-2(3H)-ylidene]pyrrolidine-1-carboxamide;
N-[(2Z)-3-phenyl-1,3-thiazol-2(3H)-ylidene]pyrrolidine-1-carboxamide;
N-[(2Z)-3-(3-chlorophenyl)-1,3-thiazol-2(3H)-ylidene]pyrrolidine-1-carboxamide;
N-[(2Z)-3-[3-(trifluoromethyl)phenyl]-1,3-thiazol-2(3H)-ylidene]pyrrolidine-1-carboxamide;
N-[(2Z)-3-(4-chlorophenyl)-1,3-thiazol-2(3H)-ylidene]pyrrolidine-1-carboxamide;
N-[(2Z)-3-(4-methylphenyl)-1,3-thiazol-2(3H)-ylidene]pyrrolidine-1-carboxamide;
N-[(2Z)-3-(4-chloro-3-methylphenyl)-1,3-thiazol-2(3H)-ylidene]pyrrolidine-1-carboxamide;
N-[(2Z)-3-(3,4-dichlorophenyl)-1,3-thiazol-2(3H)-ylidene]pyrrolidine-1-carboxamide;
N-[(2Z)-3-(3,4-dimethylphenyl)-1,3-thiazol-2(3H)-ylidene]pyrrolidine-1-carboxamide;
N-[(2Z)-3-(4-cyanophenyl)-1,3-thiazol-2(3H)-ylidene]pyrrolidine-1-carboxamide;
N-[(2Z)-3-(3-chloro-4-methylphenyl)-1,3-thiazol-2(3H)-ylidene]pyrrolidine-1-carboxamide;
N-[(2Z)-3-[4-(difluoromethoxy)phenyl]-1,3-thiazol-2(3H)-ylidene]pyrrolidine-1-carboxamide;
N-[(2Z)-3-[3-fluoro-4-(trifluoromethyl)phenyl]-1,3-thiazol-2(3H)-ylidene]pyrrolidine-1-carboxamide;
(3R)-N-[(2Z)-3-(3-bromophenyl)-5-methyl-1,3-thiazol-2(3H)-ylidene]-3-fluoropyrrolidine-1-carboxamide;
(3R)-N-[(2Z)-3-(4-cyano-3-methylphenyl)-5-methyl-1,3-thiazol-2(3H)-ylidene]-3-fluoropyrrolidine-1-carboxamide;
(3R)-3-fluoro-N-[(2Z)-5-methyl-3-(3-methylphenyl)-1,3-thiazol-2(3H)-ylidene]pyrrolidine-1-carboxamide;
(3R)-N-[(2Z)-3-(4-bromophenyl)-5-methyl-1,3-thiazol-2(3H)-ylidene]-3-fluoropyrrolidine-1-carboxamide;
(3R)-3-fluoro-N-[(2Z)-5-methyl-3-(4-phenoxyphenyl)-1,3-thiazol-2(3H)-ylidene]pyrrolidine-1-carboxamide;
(3R)-3-fluoro-N-[(2Z)-5-methyl-3-(4-methylphenyl)-1,3-thiazol-2(3H)-ylidene]pyrrolidine-1-carboxamide;
(3R)-N-[(2Z)-3-(4-ethylphenyl)-5-methyl-1,3-thiazol-2(3H)-ylidene]-3-fluoropyrrolidine-1-carboxamide;

(3R)-3-fluoro-N-[(2Z)-3-(3-fluorophenyl)-5-methyl-1,3-thiazol-2(3H)-ylidene]pyrrolidine-1-carboxamide;
(3R)-3-fluoro-N-[(2Z)-3-(4-fluorophenyl)-5-methyl-1,3-thiazol-2(3H)-ylidene]pyrrolidine-1-carboxamide;
(3R)-3-fluoro-N-[(2Z)-5-methyl-3-[4-(trifluoromethyl)phenyl]-1,3-thiazol-2(3H)-ylidene]pyrrolidine-1-carboxamide;
(3R)-N-[(2Z)-3-(4-chlorophenyl)-5-methyl-1,3-thiazol-2(3H)-ylidene]-3-fluoropyrrolidine-1-carboxamide;
(3R)-3-fluoro-N-[(2Z)-3-(4-iodophenyl)-5-methyl-1,3-thiazol-2(3H)-ylidene]pyrrolidine-1-carboxamide;
(3R)-N-[(2Z)-3-(3-cyanophenyl)-5-methyl-1,3-thiazol-2(3H)-ylidene]-3-fluoropyrrolidine-1-carboxamide;
(3R)-3-fluoro-N-[(2Z)-5-methyl-3-(2-naphthyl)-1,3-thiazol-2(3H)-ylidene]pyrrolidine-1-carboxamide;
(3R)-N-[(2Z)-3-(3,4-dichlorophenyl)-5-methyl-1,3-thiazol-2(3H)-ylidene]-3-fluoropyrrolidine-1-carboxamide;
(3R)-3-fluoro-N-[(2Z)-3-(3-iodophenyl)-5-methyl-1,3-thiazol-2(3H)-ylidene]pyrrolidine-1-carboxamide;
(3R)-N-[(2Z)-3-(3-chloro-4-methylphenyl)-5-methyl-1,3-thiazol-2(3H)-ylidene]-3-fluoropyrrolidine-1-carboxamide;
N-[(2Z)-3-(2-naphthyl)-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]indoline-1-carboxamide;
2,5-dimethyl-N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]piperidine-1-carboxamide;
4-benzyl-N-[(2Z)-5-methyl-3-[4-(trifluoromethyl)phenyl]-1,3-thiazol-2(3H)-ylidene]piperidine-1-carboxamide;
N-[(2Z)-3-(4-chlorophenyl)-4,5-dimethyl-1,3-thiazol-2(3H)-ylidene]pyrrolidine-1-carboxamide;
N-[(2Z)-4,5-dimethyl-3-[4-(trifluoromethyl)phenyl]-1,3-thiazol-2(3H)-ylidene]pyrrolidine-1-carboxamide;
and a pharmaceutically acceptable salt thereof.
6. A compound selected from the group consisting of:
N-[(2Z)-3-[4-(difluoromethoxy)phenyl]-5-methyl-1,3-thiazol-2(3H)-ylidene]pyrrolidine-1-carboxamide;
N-[(2Z)-3-[4-(difluoromethoxy)phenyl]-5-methyl-1,3-thiazol-2(3H)-ylidene]piperidine-1-carboxamide;
N-[(2Z)-5-methyl-3-[4-(trifluoromethoxy)phenyl]-1,3-thiazol-2(3H)-ylidene]pyrrolidine-1-carboxamide;
N-[(2Z)-3-(4-chlorophenyl)-5-methyl-1,3-thiazol-2(3H)-ylidene]pyrrolidine-1-carboxamide;
N-[(2Z)-3-(4-chlorophenyl)-5-methyl-1,3-thiazol-2(3H)-ylidene]piperidine-1-carboxamide;
N-[(2Z)-3-(4-fluorophenyl)-5-methyl-1,3-thiazol-2(3H)-ylidene]pyrrolidine-1-carboxamide;
N-[(2Z)-3-(4-fluorophenyl)-5-methyl-1,3-thiazol-2(3H)-ylidene]piperidine-1-carboxamide;
N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]pyrrolidine-1-carboxamide;
(2R)-2-methyl-N-[(2Z)-5-methyl-3-[4-(trifluoromethyl)phenyl]-1,3-thiazol-2(3H)-ylidene]pyrrolidine-1-carboxamide;
(2S)-2-methyl-N-[(2Z)-5-methyl-3-[4-(trifluoromethyl)phenyl]-1,3-thiazol-2(3H)-ylidene]pyrrolidine-1-carboxamide;
N-[(2Z)-3-(4-chlorophenyl)-1,3-thiazolidin-2-ylidene]pyrrolidine-1-carboxamide;
(3R)-N-[(2Z)-3-(4-chlorophenyl)-1,3-thiazolidin-2-ylidene]-3-fluoropyrrolidine-1-carboxamide;
N-{(2Z)-5-methylene-3-[4-(trifluoromethyl)phenyl]1,3-thiazolidin-2-ylidene}azetidine-1-carboxamide;
N-[(2Z)-5-methyl-3-[4-(trifluoromethyl)phenyl]-1,3-thiazol-2(3H)-ylidene]azetidine-1-carboxamide;
N-[(2Z)-5-methyl-3-(2-naphthyl)-1,3-thiazol-2(3H)-ylidene]pyrrolidine-1-carboxamide;
N-[(2Z)-3-(4-bromophenyl)-1,3-thiazol-2(3H)-ylidene]pyrrolidine-1-carboxamide;
N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-[4-(trifluoromethyl)phenyl]-1,3-thiazol-2(3H)-ylidene]pyrrolidine-1-carboxamide;
(3R)-N-[(2Z)-3-(5,6-difluoro-2-naphthyl)-5-(hydroxymethyl)-1,3-thiazol-2(3H)-ylidene]-3-fluoropyrrolidine-1-carboxamide;
N-[(2Z)-5-methyl-3-phenyl-1,3-thiazol-2(3H)-ylidene]pyrrolidine-1-carboxamide;
N-[(2Z)-5-methyl-3-(3-methylphenyl)-1,3-thiazol-2(3H)-ylidene]pyrrolidine-1-carboxamide;
N-[(2Z)-5-methyl-3-(4-methylphenyl)-1,3-thiazol-2(3H)-ylidene]pyrrolidine-1-carboxamide;
N-[(2Z)-3-(3-aminophenyl)-5-methyl-1,3-thiazol-2(3H)-ylidene]pyrrolidine-1-carboxamide;
N-[(2Z)-3-(3-hydroxyphenyl)-5-methyl-1,3-thiazol-2(3H)-ylidene]pyrrolidine-1-carboxamide;
N-[(2Z)-3-(4-methoxyphenyl)-5-methyl-1,3-thiazol-2(3H)-ylidene]pyrrolidine-1-carboxamide;
N-[(2Z)-3-(3-fluorophenyl)-5-methyl-1,3-thiazol-2(3H)-ylidene]pyrrolidine-1-carboxamide;
N-[(2Z)-3-(3-chlorophenyl)-5-methyl-1,3-thiazol-2(3H)-ylidene]pyrrolidine-1-carboxamide;
N-[(2Z)-3-(2-bromophenyl)-5-methyl-1,3-thiazol-2(3H)-ylidene]pyrrolidine-1-carboxamide;
N-[(2Z)-3-(3-bromophenyl)-5-methyl-1,3-thiazol-2(3H)-ylidene]pyrrolidine-1-carboxamide;
N-[(2Z)-3-(3-cyanophenyl)-5-methyl-1,3-thiazol-2(3H)-ylidene]pyrrolidine-1-carboxamide;
N-[(2Z)-3-(4-cyanophenyl)-5-methyl-1,3-thiazol-2(3H)-ylidene]pyrrolidine-1-carboxamide;
N-[(2Z)-3-[4-(dimethylamino)phenyl]-5-methyl-1,3-thiazol-2(3H)-ylidene]pyrrolidine-1-carboxamide;
N-[(2Z)-5-methyl-3-[3-(trifluoromethyl)phenyl]-1,3-thiazol-2(3H)-ylidene]pyrrolidine-1-carboxamide;
N-[(2Z)-5-methyl-3-[3-(trifluoromethoxy)phenyl]-1,3-thiazol-2(3H)-ylidene]pyrrolidine-1-carboxamide;
N-[(2Z)-5-methyl-3-(4-phenoxyphenyl)-1,3-thiazol-2(3H)-ylidene]pyrrolidine-1-carboxamide;
N-[(2Z)-3-[4-(benzyloxy)phenyl]-5-methyl-1,3-thiazol-2(3H)-ylidene]pyrrolidine-1-carboxamide;
N-[(2Z)-3-(3,4-dimethylpenyl)-5-methyl-1,3-thiazol-2(3H)-ylidene]pyrrolidine-1-carboxamide;
N-[(2Z)-3-(3,5-dimethylphenyl)-5-methyl-1,3-thiazol-2(3H)-ylidene]pyrrolidine-1-carboxamide;
N-[(2Z)-3-(3,4-dichlorophenyl)-5-methyl-1,3-thiazol-2(3H)-ylidene]pyrrolidine-1-carboxamide;
N-[(2Z)-3-(3,5-dichlorophenyl)-5-methyl-1,3-thiazol-2(3H)-ylidene]pyrrolidine-1-carboxamide;
N-[(2Z)-5-methyl-3-[4-(methylthio)phenyl]-1,3-thiazol-2(3H)-ylidene]pyrrolidine-1-carboxamide;

N-[(2Z)-3-(3-methoxyphenyl)-5-methyl-1,3-thiazol-2(3H)-ylidene]pyrrolidine-1-carboxamide;
N-[(2Z)-3-(4-chloro-3-methylphenyl)-5-methyl-1,3-thiazol-2(3H)-ylidene]pyrrolidine-1-carboxamide;
N-[(2Z)-3-(4-benzylphenyl)-5-methyl-1,3-thiazol-2(3H)-ylidene]pyrrolidine-1-carboxamide;
N-[(2Z)-3-(1-benzothien-5-yl)-5-methyl-1,3-thiazol-2(3H)-ylidene]pyrrolidine-1-carboxamide;
N-[(2Z)-3-[4-(methylthio)phenyl]-1,3-thiazol-2(3H)-ylidene]pyrrolidine-1-carboxamide;
N-[(2Z)-3-phenyl-1,3-thiazol-2(3H)-ylidene]pyrrolidine-1-carboxamide;
N-[(2Z)-3-(3-chlorophenyl)-1,3-thiazol-2(3H)-ylidene]pyrrolidine-1-carboxamide;
N-[(2Z)-3-[3-(trifluoromethyl)phenyl]-1,3-thiazol-2(3H)-ylidene]pyrrolidine-1-carboxamide;
N-[(2Z)-3-(4-chlorophenyl)-1,3-thiazol-2(3H)-ylidene]pyrrolidine-1-carboxamide;
N-[(2Z)-3-(4-methylphenyl)-1,3-thiazol-2(3H)-ylidene]pyrrolidine-1-carboxamide;
N-[(2Z)-3-(4-chloro-3-methylphenyl)-1,3-thiazol-2(3H)-ylidene]pyrrolidine-1-carboxamide;
N-[(2Z)-3-(3,4-dichlorophenyl)-1,3-thiazol-2(3H)-ylidene]pyrrolidine-1-carboxamide;
N-[(2Z)-3-(3,4-dimethylphenyl)-1,3-thiazol-2(3H)-ylidene]pyrrolidine-1-carboxamide;
N-[(2Z)-3-(4-cyanophenyl)-1,3-thiazol-2(3H)-ylidene]pyrrolidine-1-carboxamide;
N-[(2Z)-3-(3-chloro-4-methylphenyl)-1,3-thiazol-2(3H)-ylidene]pyrrolidine-1-carboxamide;
N-[(2Z)-3-[4-(difluoromethoxy)phenyl]-1,3-thiazol-2(3H)-ylidene]pyrrolidine-1-carboxamide;
N-[(2Z)-3-[3-fluoro-4-(trifluoromethyl)phenyl]-1,3-thiazol-2(3H)-ylidene]pyrrolidine-1-carboxamide;
(3R)-N-[(2Z)-3-(3-bromophenyl)-5-methyl-1,3-thiazol-2(3H)-ylidene]-3-fluoropyrrolidine-1-carboxamide;
(3R)-N-[(2Z)-3-(4-cyano-3-methylphenyl)-5-methyl-1,3-thiazol-2(3H)-ylidene]-3-fluoropyrrolidine-1-carboxamide;
(3R)-3-fluoro-N-[(2Z)-5-methyl-3-(3-methylphenyl)-1,3-thiazol-2(3H)-ylidene]pyrrolidine-1-carboxamide;
(3R)-N-[(2Z)-3-(4-bromophenyl)-5-methyl-1,3-thiazol-2(3H)-ylidene]-3-fluoropyrrolidine-1-carboxamide;
(3R)-3-fluoro-N-[(2Z)-5-methyl-3-(4-phenoxyphenyl)-1,3-thiazol-2(3H)-ylidene]pyrrolidine-1-carboxamide;
(3R)-3-fluoro-N-[(2Z)-5-methyl-3-(4-methylphenyl)-1,3-thiazol-2(3H)-ylidene]pyrrolidine-1-carboxamide;
(3R)-N-[(2Z)-3-(4-ethylphenyl)-5-methyl-1,3-thiazol-2(3H)-ylidene]-3-fluoropyrrolidine-1-carboxamide;
(3R)-3-fluoro-N-[(2Z)-3-(3-fluorophenyl)-5-methyl-1,3-thiazol-2(3H)-ylidene]pyrrolidine-1-carboxamide;
(3R)-3-fluoro-N-[(2Z)-3-(4-fluorophenyl)-5-methyl-1,3-thiazol-2(3H)-ylidene]pyrrolidine-1-carboxamide;
(3R)-3-fluoro-N-[(2Z)-5-methyl-3-[3-(trifluoromethyl)phenyl]-1,3-thiazol-2(3H)-ylidene]pyrrolidine-1-carboxamide;
(3R)-3-fluoro-N-[(2Z)-5-methyl-3-[4-(trifluoromethyl)phenyl]-1,3-thiazol-2(3H)-ylidene]pyrrolidine-1-carboxamide;
(3R)-N-[(2Z)-3-(4-chlorophenyl)-5-methyl-1,3-thiazol-2(3H)-ylidene]-3-fluoropyrrolidine-1-carboxamide;
(3R)-3-fluoro-N-[(2Z)-3-(4-iodophenyl)-5-methyl-1,3-thiazol-2(3H)-ylidene]pyrrolidine-1-carboxamide;
(3R)-N-[(2Z)-3-(3-cyanophenyl)-5-methyl-1,3-thiazol-2(3H)-ylidene]3-fluoropyrrolidine-1-carboxamide;
(3R)-3-fluoro-N-[(2Z)-5-methyl-3-(2-naphthyl)-1,3-thiazol-2(3H)-ylidene]pyrrolidine-1-carboxamide;
(3R)-N-[(2Z)-3-(3,4-dichlorophenyl)-5-methyl-1,3-thiazol-2(3H)-ylidene]-3-fluoropyrrolidine-1-carboxamide;
(3R)-3-fluoro-N-[(2Z)-3-(3-iodophenyl)-5-methyl-1,3-thiazol-2(3H)-ylidene]pyrrolidine-1-carboxamide;
(3R)-N-[(2Z)-3-(3-chloro-4-methylphenyl)-5-methyl-1,3-thiazol-2(3H)-ylidene]-3-fluoropyrrolidine-1-carboxamide;
N-[(2Z)-3-(2-naphthyl)-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]indoline-1-carboxamide;
2,5-dimethyl-N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]piperidine-1-carboxamide;
4-benzyl-N-[(2Z)-5-methyl-3-[4-(trifluoromethyl)phenyl]-1,3-thiazol-2(3H)-ylidene]piperidine-1-carboxamide;
(3R)-N-[(2Z)-3-(3,5-dichlorophenyl)-5-(hydroxymethyl)-1,3-thiazol-2(3H)-ylidene]-3-fluoropyrrolidine-1-carboxamide;
(3R)-N-[(2Z)-3-(3-chlorophenyl)-5-(hydroxymethyl)-1,3-thiazol-2(3H)-ylidene]-3-fluoropyrrolidine-1-carboxamide;
(3R)-N-[(2Z)-3-(3,4-dimethylphenyl)-5-(hydroxymethyl)-1,3-thiazol-2(3H)-ylidene]-3-fluoropyrrolidine-1-carboxamide;
(3R)-N-[(2Z)-3-(3,5-dimethylphenyl)-5-(hydroxymethyl)-1,3-thiazol-2(3H)-ylidene]-3-fluoropyrrolidine-1-carboxamide;
(3R)-N-[(2Z)-3-(4-chloro-3-methylphenyl)-5-(hydroxymethyl)-1,3-thiazol-2(3H)-ylidene]-3-fluoropyrrolidine-1-carboxamide;
(3R)-3-fluoro-N-[(2Z)-5-(hydroxymethyl)-3-[4-(trifluoromethoxy)phenyl]-1,3-thiazol-2(3H)-ylidene]pyrrolidine-1-carboxamide;
(3R)-N-[(2Z)-3-(3,4-dichlorophenyl)-5-(hydroxymethyl)-1,3-thiazol-2(3H)-ylidene]-3-fluoropyrrolidine-1-carboxamide;
(3R)-3-fluoro-N-[(2Z)-3-[3-fluoro-4-(trifluoromethyl)phenyl]-5-(hydroxymethyl)-1,3-thiazol-2(3H)-ylidene]pyrrolidine-1-carboxamide;
N-[(2Z)-3-(4-chlorophenyl)-4,5-dimethyl-1,3-thiazol-2(3H)-ylidene]pyrrolidine-1-carboxamide;
N-[(2Z)-4,5-dimethyl-3-[4-(trifluoromethyl)phenyl]-1,3-thiazol-2(3H)-ylidene]pyrrolidine-1-carboxamide;
4-acetyl-N-[(2Z)-5-methyl-3-[4-(trifluoromethyl)phenyl]-1,3-thiazol-2(3H)-ylidene]piperazine-1-carboxamide;
N-[(2Z)-3-(4-fluorophenyl)-1,3-thiazol-2(3H)-ylidene]pyrrolidine-1-carboxamide;
(3R)-N-[(2Z)-3-(4-cyanophenyl)-5-(hydroxymethyl)-1,3-thiazol-2(3H)-ylidene]-3-fluoropyrrolidine-1-carboxamide;
(3R)-3-fluoro-N-[(2Z)-5-(hydroxymethyl)-3-(5,6,8-trifluoro-2-naphthyl)-1,3-thiazol-2(3H)-ylidene]pyrrolidine-1-carboxamide;
N-[(2Z)-5-methyl-3-[4-(trifluoromethoxy)phenyl]-1,3-thiazol-2(3H)-ylidene]piperidine-1-carboxamide;
N-[(2Z)-3-[4-(cyanomethyl)phenyl]-5-methyl-1,3-thiazol-2(3H)-ylidene]pyrrolidine-1-carboxamide;
N-[(2Z)-3-[4-(cyanomethyl)phenyl]-5-methyl-1,3-thiazol-2(3H)-ylidene]piperidine-1-carboxamide;

N-[(2Z)-5-methyl-3-[4-(trifluoromethyl)phenyl]-1,3-thiazol-2(3H)-ylidene]piperidine-1-carboxamide;

tert-butyl (2R,3S)-2-methyl-1-({[(2Z)-5-methyl-3-[4-(trifluoromethyhphenyl]-1,3-thiazol-2(3H)-ylidene]amino}carbonyl) pyrrolidin-3-ylcarbamate;

2-isopropyl-N-[(2Z)-5-methyl-3-[4-(trifluoromethyl)phenyl]-1,3-thiazol-2(3H)-ylidene]pyrrolidine-1-carboxamide;

2-isobutyl-N-[(2Z)-5-methyl-3-[4-(trifluoromethyl)phenyl]-1,3-thiazol-2(3H)-ylidene]pyrrolidine-1-carboxamide;

(3R)-3-(dimethylamino)-N-[(2Z)-5-methyl-3- [4-(trifluoromethyl)phenyl]-1,3-thiazol-2(3H)-ylidene]pyrrolidine-1-carboxamide;

tert-butyl (3S)-1-(1[(2Z)-5-methyl-3-[4-(trifluoromethyhphenyl]-1,3-thiazol-2(3H)-ylidene]amino}carbonyl) pyrrolidin-3-ylcarbamate;

tert-butyl 5-({[(2Z)-5-methyl-3-[4-(trifluoromethyl)phenyl]-1,3-thiazol-2(3H)-ylidene]amino}carbonyl) hexahydropyrrolo [3,4-c]pyrrole-2(1H)-carboxylate;

tert-butyl (1S,5R)-3-(1 [(2Z)-5-methyl-3-[4-(trifluoromethyhphenyl]-1,3-thiazol-2(3H)-ylidene]amino}carbonyl)-3,6-diazabicyclo [3.2.0]heptane-6-carboxylate;

tert-butyl (3R)-3-methyl-1-(1 [(2Z)-5-methyl-3-[4-(trifluoromethyl)phenyl]-1,3-thiazol-2(3H)-ylidene]amino}carbonyl) pyrrolidin-3-ylcarbamate;

tert-butyl 6-({[(2Z)-5-methyl-3-[4-(trifluoromethyl)phenyl]-1,3-thiazol-2(3H)-ylidene]amino}carbonyl)octahydro-1 H-pyrrolo [3,4-b]pyridine-1-carboxylate;

tert-butyl (1S,4S)-5-({[(2Z)-5-methyl-3-[4-(trifluoromethyl)phenyl]-1,3-thiazol-2(3H)-ylidene]amino}carbonyl)-2,5-diazabicyclo [2.2.1]heptane-2-carboxylate;

(3S)-3-amino-N-[(2Z)-5-methyl-3-[4-(trifluoromethyl)phenyl]-1,3-thiazol-2 (3H)-ylidene]pyrrolidine-1-carboxamide;

(2R,3S) -3-amino-2-methyl-N- [(2Z)-5-methyl-3-[4-(trifluoromethyhphenyl]-1,3-thiazol-2(3H)-ylidene]pyrrolidine-1-carboxamide;

N-[(2Z)-5-methyl-3-[4-(trifluoromethyl)phenyl]-1,3-thiazol-2(3H)-ylidene]hexahydropyrrolo [3,4-c]pyrrole-2(1H) -carboxamide;

(3R)-3-amino-3-methyl-N-[(2Z)-5-methyl-3-[4-(trifluoromethyl)phenyl]-1,3-thiazol-2(3H)-ylidene]pyrrolidine-1-carboxamide;

(1R,5R)-N-[(2Z)-5-methyl-3-[4-(trifluoromethyl)phenyl]-1,3-thiazol-2(3H)-ylidene]-3,6-diazabicyclo[3.2.0]heptane-3-carboxamide;

(4aS,7aS)-N-[(2Z)-5-methyl-3-[4-(trifluoromethyl)phenyl]-1,3-thiazol-2(3H)-ylidene]octahydro-6H-pyrrolo[3,4-b]pyridine-6-carboxamide;

(1S,4S)-N-[(2Z)-5-methyl-3-[4-(trifluoromethyl)phenyl]-1,3-thiazol-2(3H)-ylidene]-2,5-diazabicyclo [2.2.1] heptane-2-carboxamide;

N-[(2Z)-3-(3-ethoxyphenyl)-4,5-dimethyl-1,3-thiazol-2 (3H)-ylidene]pyrrolidine-1-carboxamide;

3-methyl-N-[(2Z)-5-methyl-3-[4-(trifluoromethyl)phenyl]-1,3-thiazol-2(3H)-ylidene]piperidine-1-carboxamide;

4-methyl-N-[(2Z)-5-methyl-3-[4-(trifluoromethyl)phenyl]-1,3-thiazol-2(3H)-ylidene]piperidine-1-carboxamide;

2-ethyl-N-[(2Z)-5-methyl-3-[4-(trifluoromethyl)phenyl]-1,3-thiazol-2(3H)-ylidene]piperidine-1-carboxamide;

N-[(2Z)-5-methyl-3-[4-(trifluoromethyl)phenyl]-1,3-thiazol-2(3H)-ylidene]-4-propylpiperidine-1-carboxamide;

N-[(2Z)-5-methyl-3-[4-(trifluoromethyl)phenyl]-1,3-thiazol-2(3H)-ylidene]azepane-1-carboxamide;

N-[(2Z)-5-methyl-3-[4-(trifluoromethyl)phenyl]-1,3-thiazol-2(3H)-ylidene]morpholine-4-carboxamide;

N-8 (2Z)-5-methyl-3-[4-(trifluoromethyl)phenyl]-1,3-thiazol-2(3H)-ylidene]thiomorpholine-4-carboxamide;

4-hydroxy-N-[(2Z)-5-methyl-3-[4-(trifluoromethyl)phenyl]-1,3-thiazol-2(3H)-ylidene]piperidine-1-carboxamide;

2,6-dimethyl-N-[(2Z)-5-methyl-3-[4-(trifluoromethyl)phenyl]-1,3-thiazol-2(3H)-ylidene]morpholine-4-carboxamide;

4-methyl-N-[(2Z)-5-methyl-3-[4-(trifluoromethyl)phenyl]-1,3-thiazol-2(3H)-ylidene]piperazine-1-carboxamide;

1 4-ethyl-N-[(2Z)-5-methyl-3-[4-(trifluoromethyl)phenyl]-1,3-thiazol-2(3H)-ylidene]piperazine-1-carboxamide;

N-8 (2Z)-5-methyl-3-[4-(trifluoromethyl)phenyl]-1,3-thiazol-2(3H)-ylidene]-4-phenylpiperazine-1-carboxamide;

N-8 (2Z)-5-methyl-3-[4-(trifluoromethyl)phenyl]-1,3-thiazol-2(3H)-ylidene]-4-pyridin-2-ylpiperazine-1-carboxamide;

4-methyl-N-[(2Z)-5-methyl-3-[4-(trifluoromethyl)phenyl]-1,3-thiazol-2(3H)-ylidene]-1,4-diazepane-1-carboxamide;

N-[(2Z)-5-methyl-3-[4-(trifluoromethyl)phenyl]-1,3-thiazol-2(3H)-ylidene]-4-pyrimidin-2-ylpiperazine-1-carboxamide;

N-(2Z)-5-methylene-3-[4-(trifluoromethyl)phenyl]-1,3-thiazolidin-2-ylidene}pyrrolidine-1-carboxamide;

N-(2Z)-4-hydroxy-5-methylene-3-[4-(trifluoromethyl)phenyl]-1,3-thiazolidin-2-ylidene}pyrrolidine-1-carboxamide;

N-[(2Z)-5-methyl-3-(2-methylphenyl)-1,3-thiazol-2(3H)-ylidene]pyrrolidine-1-carboxamide;

N-[(2Z)-3-(2-aminophenyl)-5-methyl-1,3-thiazol-2(3H)-ylidene]pyrrolidine-1-carboxamide;

N-[(2Z)-3-(2-hydroxyphenyl)-5-methyl-1,3-thiazol-2 (3H)-ylidene]pyrrolidine-1-carboxamide;

N-[(2Z)-3-(4-hydroxyphenyl)-5-methyl-1,3-thiazol-2 (3H)-ylidene]pyrrolidine-1-carboxamide;

N-[(2Z)-3-(2-methoxyphenyl)-5-methyl-1,3-thiazol-2 (3H)-ylidene]pyrrolidine-1-carboxamide;

N-[(2Z)-3-(2-fluorophenyl)-5-methyl-1,3-thiazol-2(3H)-ylidene]pyrrolidine-1-carboxamide;

N-[(2Z)-3-(2-chlorophenyl)-5-methyl-1,3-thiazol-2(3H)-ylidene]pyrrolidine-1-carboxamide;

N-[(2Z)-3-[3-(dimethylamino)phenyl]-5-methyl-1,3-thiazol-2(3H)-ylidene]pyrrolidine-1-carboxamide;

N-[(2Z)-3-(2,3-dimethylphenyl)-5-methyl-1,3-thiazol-2 (3H)-ylidene]pyrrolidine-1-carboxamide;

N-[(2Z)-3-(2,4-dimethylphenyl)-5-methyl-1,3-thiazol-2 (3H)-ylidene]pyrrolidine-1-carboxamide;

N-[(2Z)-3-(2,5-dimethylphenyl)-5-methyl-1,3-thiazol-2 (3H)-ylidene]pyrrolidine-1-carboxamide;

N-[(2Z)-3-(2,4-dimethoxyphenyl)-5-methyl-1,3-thiazol-2 (3H)-ylidene]pyrrolidine-1-carboxamide;

N-[(2Z)-3-(2,5-dimethoxyphenyl)-5-methyl-1,3-thiazol-2 (3H)-ylidene]pyrrolidine-1-carboxamide;

N-[(2Z)-3-(3,4-dimethoxyphenyl)-5-methyl-1,3-thiazol-2 (3H)-ylidene]pyrrolidine-1-carboxamide;

N-[(2Z)-5-methyl-3-(3,4,5-trimethoxyphenyl)-1,3-thiazol-2(3H)-ylidene]pyrrolidine-1-carboxamide;

N-[(2Z)-3-(2,3-dichlorophenyl)-5-methyl-1,3-thiazol-2 (3H)-ylidene]pyrrolidine-1-carboxamide;

N-[(2Z)-3-(2,4-dichlorophenyl)-5-methyl-1,3-thiazol-2 (3H)-ylidene]pyrrolidine-1-carboxamide;
N-[(2Z)-3-(2,5-dichlorophenyl)-5-methyl-1,3-thiazol-2 (3H)-ylidene]pyrrolidine-1-carboxamide;
N-[(2Z)-3-(4-aminophenyl)-5-methyl-1,3-thiazol-2(3H)-ylidene]pyrrolidine-1-carboxamide;
N-[(2Z)-5-methyl-3-(3-propionylphenyl)-1,3-thiazol-2 (3H)-ylidene]pyrrolidine-1-carboxamide;
N-[(2Z)-3-(4-tert-butylphenyl)-5-methyl-1,3-thiazol-2 (3H)-ylidene]pyrrolidine-1-carboxamide;
N-[(2Z)-3-(4-ethylphenyl)-5-methyl-1,3-thiazol-2(3H)-ylidene]pyrrolidine-1-carboxamide;
N-[(2Z)-5-methyl-3-(4-propylphenyl)-1,3-thiazol-2(3H)-ylidene]pyrrolidine-1-carboxamide;
N-[(2Z)-3-(4-butylphenyl)-5-methyl-1,3-thiazol-2(3H)-ylidene]pyrrolidine-1-carboxamide;
N-[(2Z)-5-methyl-3-[3-(methylthio)phenyl]-1,3-thiazol-2 (3H)-ylidene]pyrrolidine-1-carboxamide;
N-[(2Z)-5-methyl-3-[2,3,5,6-tetrafluoro-4-(trifluoromethyl)phenyl]-1,3-thiazol-2(3H)-ylidene]pyrrolidine-1-carboxamide;
N-[(2Z)-3-(3-isopropoxyphenyl)-5-methyl-1,3-thiazol-2 (3H)-ylidene]pyrrolidine-1-carboxamide;
N-[(2Z)-3-[2,4-bis(trifluoromethyl)phenyl]-5-methyl-1,3-thiazol-2 (3H)-ylidene]pyrrolidine-1-carboxamide;
N-[(2Z)-3-(4-chloro-3-methoxyphenyl)-5-methyl-1,3-thiazol-2(3H)-ylidene]pyrrolidine-1-carboxamide;
N-[(2Z)-3-(4-methoxy-3-methylphenyl)-5-methyl-1,3-thiazol-2(3H)-ylidene]pyrrolidine-1-carboxamide;
N-[(2Z)-3-(4-cyclohexylphenyl)-5-methyl-1,3-thiazol-2 (3H)-ylidene]pyrrolidine-1-carboxamide;
N-[(2Z)-5-methyl-3-(1-naphthyl)-1,3-thiazol-2(3H)-ylidene]pyrrolidine-1-carboxamide;
N-[(2Z)-3-(4'-fluoro-1,1'-biphenyl-4-yl)-5-methyl-1,3-thiazol-2(3H)-ylidene]pyrrolidine-1-carboxamide;
N-[(2Z)-3-(4-acetylphenyl)-1,3-thiazol-2(3H)-ylidene]pyrrolidine-1-carboxamide;
N-[(2Z)-3-(4-propionylphenyl)-1,3-thiazol-2(3H)-ylidene]pyrrolidine-1-carboxamide;
N-[(2Z)-3-(4-tert-butylphenyl)-1,3-thiazol-2(3H)-ylidene]pyrrolidine-1-carboxamide;
N-[(2Z)-3-(4-ethylphenyl)-1,3-thiazol-2(3H)-ylidene] pyrrolidine-1-carboxamide;
N-[(2Z)-3-(2,4-dichlorophenyl)-1,3-thiazol-2(3H)-ylidene]pyrrolidine-1-carboxamide;
N-[(2Z)-3-(2-methoxyphenyl)-1,3-thiazol-2(3H)-ylidene] pyrrolidine-1-carboxamide;
N-[(2Z)-3-(2-methylphenyl)-1,3-thiazol-2(3H)-ylidene] pyrrolidine-1-carboxamide;
N-[(2Z)-3-(3,5-dichlorophenyl)-1,3-thiazol-2(3H)-ylidene]pyrrolidine-1-carboxamide;
N-[(2Z)-3-(3-methoxyphenyl)-1,3-thiazol-2(3H)-ylidene] pyrrolidine-1-carboxamide;
N-[(2Z)-3-(3-methylphenyl)-1,3-thiazol-2(3H)-ylidene] pyrrolidine-1-carboxamide;
N-[(2Z)-3-(4-methoxyphenyl)-1,3-thiazol-2(3H)-ylidene] pyrrolidine-1-carboxamide;
N-[(2Z)-3-(4-propylphenyl)-1,3-thiazol-2(3H)-ylidene] pyrrolidine-1-carboxamide;
N-[(2Z)-3-(2,4-dimethylphenyl)-1,3-thiazol-2(3H)-ylidene]pyrrolidine-1-carboxamide;
N-[(2Z)-3-pyridin-3-yl-1,3-thiazol-2(3H)-ylidene]pyrrolidine-1-carboxamide;
N-[(2Z)-3-(4-butylphenyl)-1,3-thiazol-2(3H)-ylidene] pyrrolidine-1-carboxamide;
N-[(2Z)-3-[3-(methylthio)phenyl]-1,3-thiazol-2(3H)-ylidene]pyrrolidine-1-carboxamide;
N-[(2Z)-3-(2,3-dichlorophenyl)-1,3-thiazol-2(3H)-ylidene]pyrrolidine-1-carboxamide;
N-[(2Z)-3-(2-chlorophenyl)-1,3-thiazol-2(3H)-ylidene] pyrrolidine-1-carboxamide;
N-[(2Z)-3-[2,3,5,6-tetrafluoro-4-(trifluoromethyl)phenyl]-1,3-thiazol-2(3H)-ylidene]pyrrolidine-1-carboxamide;
N-[(2Z)-3-(3,5-dimethylphenyl)-1,3-thiazol-2(3H)-ylidene]pyrrolidine-1-carboxamide;
N-[(2Z)-3-(3-isopropoxyphenyl)-1,3-thiazol-2(3H)-ylidene]pyrrolidine-1-carboxamide;
N-[(2Z)-3-[2,4-bis(trifluoromethyl)phenyl]-1,3-thiazol-2 (3H)-ylidene]pyrrolidine-1-carboxamide;
N-[(2Z)-3-(3-cyanophenyl)-1,3-thiazol-2(3H)-ylidene] pyrrolidine-1-carboxamide;
N-[(2Z)-3-(4-methoxy-3-methylphenyl)-1,3-thiazol-2 (3H)-ylidene]pyrrolidine-1-carboxamide;
N-[(2Z)-3-(2'-methyl-1,1'-biphenyl-4-yl)-1,3-thiazol-2 (3H)-ylidene]pyrrolidine-1-carboxamide;
N-[(2Z)-3-(3'-methyl-1,1'-biphenyl-4-yl)-1,3-thiazol-2 (3H)-ylidene]pyrrolidine-1-carboxamide;
N-[(2Z)-3-(4'-methyl-1,1'-biphenyl-4-yl)-1,3-thiazol-2 (3H)-ylidene]pyrrolidine-1-carboxamide;
N-[(2Z)-3-(3'-chloro-1,1'-biphenyl-4-yl)-1,3-thiazol-2 (3H)-ylidene]pyrrolidine-1-carboxamide;
N-[(2Z)-3-(4'-chloro-1,1'-biphenyl-4-yl)-1,3-thiazol-2 (3H)-ylidene]pyrrolidine-1-carboxamide;
N-[(2Z)-3-(4'-methoxy-1,1'-biphenyl-4-yl)-1,3-thiazol-2 (3H)-ylidene]pyrrolidine-1-carboxamide;
N-[(2Z)-3-[3'-(trifluoromethyl)-1,1'-biphenyl-4-yl]-1,3-thiazol-2(3H)-ylidene]pyrrolidine-1-carboxamide;
N-[(2Z)-3-(4-thien-3-ylphenyl)-1,3-thiazol-2(3H)-ylidene]pyrrolidine-1-carboxamide;
N-[(2Z)-3-[4'-(trifluoromethyl)-1,1'-biphenyl-4-yl]-1,3-thiazol-2(3H)-ylidene]pyrrolidine-1-carboxamide;
N-[(2Z)-3-(3'-ethoxy-1,1'-biphenyl-4-yl)-1,3-thiazol-2 (3H)-ylidene]pyrrolidine-1-carboxamide;
N-[(2Z)-3-(3'-methoxy-1,1'-biphenyl-4-yl)-1,3-thiazol-2 (3H)-ylidene]pyrrolidine-1-carboxamide;
N-[(2Z)-3-(3',5'-dichloro-1,1'-biphenyl-4-yl)-1,3-thiazol-2(3H)-ylidene]pyrrolidine-1-carboxamide;
N-[(2Z)-3-(2'-chloro-1,1'-biphenyl-4-yl)-1,3-thiazol-2 (3H)-ylidene]pyrrolidine-1-carboxamide;
N-[(2Z)-3-(2'-methoxy-1,1'-biphenyl-4-yl)-1,3-thiazol-2 (3H)-ylidene]pyrrolidine-1-carboxamide;
N-[(2Z)-3-(2'-acetyl-1,1'-biphenyl-4-yl)-1,3-thiazol-2 (3H)-ylidene]pyrrolidine-1-carboxamide;
N-[(2Z)-3-(3'-acetyl-1,1'-biphenyl-4-yl)-1,3-thiazol-2 (3H)-ylidene]pyrrolidine-1-carboxamide;
N-[(2Z)-3-(4'-acetyl-1,1'-biphenyl-4-yl)-1,3-thiazol-2 (3H)-ylidene]pyrrolidine-1-carboxamide;
N-[(2Z)-3-(3',4'-dichloro-1,1'-biphenyl-4-yl)-1,3-thiazol-2(3H)-ylidene]pyrrolidine-1-carboxamide;
N-[(2Z)-3-(4-pyridin-3-ylphenyl)-1,3-thiazol-2(3H)-ylidene]pyrrolidine-1-carboxamide;
N-[(2Z)-3-(2',5'-dichloro-1,1'-biphenyl-4-yl)-1,3-thiazol-2(3H)-ylidene]pyrrolidine-1-carboxamide;
N-[(2Z)-3-(3'-cyano-1,1'-biphenyl-4-yl)-1,3-thiazol-2 (3H)-ylidene]pyrrolidine-1-carboxamide;
N-[(2Z)-3-(2',3'-dichloro-1,'-biphenyl-4-yl)-1,3-thiazol-2(3H)-ylidene]pyrrolidine-1-carboxamide;
N-[(2Z)-3-(2',4'-dichloro-1,1'-biphenyl-4-yl)-1,3-thiazol-2(3H)-ylidene]pyrrolidine-1-carboxamide;
N-[(2Z)-3-(4'-cyano-1,1'-biphenyl-4-yl)-1,3-thiazol-2 (3H)-ylidene]pyrrolidine-1-carboxamide;
N-[(2Z)-3-[4-(1-methyl-1H-pyrazol-4-yl)phenyl]-1,3-thiazol-2(3H)-ylidene]pyrrolidine-1-carboxamide;

N-[(2Z)-3-[4-(6-methoxypyridin-3-yl)phenyl]-1,3-thiazol-2(3H)-ylidene]pyrrolidine-1-carboxamide;
N-[(2Z)-3-(1,1'-biphenyl-4-yl)-1,3-thiazol-2(3H)-ylidene]pyrrolidine-1-carboxamide;
N-[(2Z)-3-[4-(2-methoxypyrimidin-5-yl)phenyl]-1,3-thiazol-2(3H)-ylidene]pyrrolidine-1-carboxamide;
N-[(2Z)-3-[4'-(cyanomethyl)-1,1'-biphenyl-4-yl]-1,3-thiazol-2(3H)-ylidene]pyrrolidine-1-carboxamide;
N-[(2Z)-3-(6-ethoxy-2-naphthyl)-1,3-thiazol-2(3H)-ylidene]pyrrolidine-1-carboxamide;
N-[(2Z)-3-(4-cyclohexylphenyl)-1,3-thiazol-2(3H)-ylidene]pyrrolidine-1-carboxamide;
N-[(2Z)-3-[2-cyano-4-(trifluoromethyl)phenyl]-1,3-thiazol-2(3H)-ylidene]pyrrolidine-1-carboxamide;
(3R)-3-fluoro-N-[(2Z)-3-(4-isopropylphenyl)-5-methyl-1,3-thiazol-2(3H)-ylidene]pyrrolidine-1-carboxamide;
(3R)-N-[(2Z)-3-(3,4-dimethylphenyl)-5-methyl-1,3-thiazol-2(3H)-ylidene]-3-fluoropyrrolidine-1-carboxamide;
(3R)-3-fluoro-N-[(2Z)-3-(4-methoxyphenyl)-5-methyl-1,3-thiazol-2(3H)-ylidene]pyrrolidine-1-carboxamide; and
(3R)-3-fluoro-N-[(2Z)-3-(4'-fluoro-1,1'-biphenyl-4-yl)-5-methyl-1,3-thiazol-2(3H)-ylidene]pyrrolidine-1-carboxamide;
and a pharmaceutically acceptable salt thereof.

7. A compound selected from the group consisting of:
N-[(2Z)-3-[4-(difluoromethoxy)phenyl]-5-methyl-1,3-thiazol-2(3H)-ylidene]pyrrolidine-1-carboxamide;
N-[(2Z)-3-[4-(difluoromethoxy)phenyl]-5-methyl-1,3-thiazol-2(3H)-ylidene]piperidine-1-carboxamide;
N'-[(2Z)-3-[4-(difluoromethoxy)phenyl]-5-methyl-1,3-thiazol-2(3H)-ylidene]-N,N-diethylurea;
N-[(2Z)-5-methyl-3-[4-(trifluoromethoxy)phenyl]-1,3-thiazol-2(3H)-ylidene]pyrrolidine-1-carboxamide;
N-[(2Z)-3-(4-chlorophenyl)-5-methyl-1,3-thiazol-2(3H)-ylidene]pyrrolidine-1-carboxamide;
N-[(2Z)-3-(4-chlorophenyl)-5-methyl-1,3-thiazol-2(3H)-ylidene]piperidine-1-carboxamide;
N-[(2Z)-3-(4-fluorophenyl)-5-methyl-1,3-thiazol-2(3H)-ylidene]pyrrolidine-1-carboxamide;
N-[(2Z)-3-(4-fluorophenyl)-5-methyl-1,3-thiazol-2(3H)-ylidene]piperidine-1-carboxamide;
N-[(2Z)-3-(4-fluorophenyl)-5-methyl-1,3-thiazol-2(3H)-ylidene]cyclobutanecarboxamide;
N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]pyrrolidine-1-carboxamide;
(2R)-2-methyl-N-[(2Z)-5-methyl-3-[4-(trifluoromethyl)phenyl]-1,3-thiazol-2(3H)-ylidene]pyrrolidine-1-carboxamide;
(2S)-2-methyl-N-[(2Z)-5-methyl-3-[4-(trifluoromethyl)phenyl]-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]azetidine-1-carboxamide;
N-[(2Z)-5-methyl-3-(2-naphthyl)-1,3-thiazol-2(3H)-ylidene]pyrrolidine-1-carboxamide;
N-[(2Z)-3-(4-bromophenyl)-1,3-thiazol-2(3H)-ylidene]pyrrolidine-1-carboxamide;
N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-(2-naphthyl)-1,3-thiazol-2(3H)-ylidene]pyrrolidine-1-carboxamide;
(3R)-3-fluoro-N-[(2Z)-5-(hydroxymethyl)-3-[4-(trifluoromethyl)phenyl]-1,3-thiazol-2(3H)-ylidene]pyrrolidine-1-carboxamide;
(3R)-N-[(2Z)-3-(5,6-difluoro-2-naphthyl)-5-(hydroxymethyl)-1,3-thiazol-2(3H)-ylidene]-3-fluoropyrrolidine-1-carboxamide;
N-[(2Z)-5-methyl-3-phenyl-1,3-thiazol-2(3H)-ylidene]pyrrolidine-1-carboxamide;
N-[(2Z)-5-methyl-3-(3-methylphenyl)-1,3-thiazol-2(3H)-ylidene]pyrrolidine-1-carboxamide;
N-[(2Z)-5-methyl-3-(4-methylphenyl)-1,3-thiazol-2(3H)-ylidene]pyrrolidine-1-carboxamide;
N-[(2Z)-3-(3-hydroxyphenyl)-5-methyl-1,3-thiazol-2(3H)-ylidene]pyrrolidine-1-carboxamide;
N-[(2Z)-3-(4-methoxyphenyl)-5-methyl-1,3-thiazol-2(3H)-ylidene]pyrrolidine-1-carboxamide;
N-[(2Z)-3-(3-fluorophenyl)-5-methyl-1,3-thiazol-2(3H)-ylidene]pyrrolidine-1-carboxamide;
N-[(2Z)-3-(3-chlorophenyl)-5-methyl-1,3-thiazol-2(3H)-ylidene]pyrrolidine-1-carboxamide;
N-[(2Z)-3-(3-bromophenyl)-5-methyl-1,3-thiazol-2(3H)-ylidene]pyrrolidine-1-carboxamide;
N-[(2Z)-3-(3-cyanophenyl)-5-methyl-1,3-thiazol-2(3H)-ylidene]pyrrolidine-1-carboxamide;
N-[(2Z)-3-(4-cyanophenyl)-5-methyl-1,3-thiazol-2(3H)-ylidene]pyrrolidine-1-carboxamide;
N-[(2Z)-3-[4-(dimethylamino)phenyl]-5-methyl-1,3-thiazol-2(3H)-ylidene]pyrrolidine-1-carboxamide;
N-[(2Z)-5-methyl-3-[3-(trifluoromethoxy)phenyl]-1,3-thiazol-2(3H)-ylidene]pyrrolidine-1-carboxamide;
N-[(2Z)-5-methyl-3-(4-phenoxyphenyl)-1,3-thiazol-2(3H)-ylidene]pyrrolidine-1-carboxamide;
N-[(2Z)-3-[4-(benzyloxy)phenyl]-5-methyl-1,3-thiazol-2(3H)-ylidene]pyrrolidine-1-carboxamide;
N-[(2Z)-3-(3,4-dimethylphenyl)-5-methyl-1,3-thiazol-2(3H)-ylidene]pyrrolidine-1-carboxamide;
N-[(2Z)-3-(3,5-dimethylphenyl)-5-methyl-1,3-thiazol-2(3H)-ylidene]pyrrolidine-1-carboxamide;
N-[(2Z)-3-(3,4-dichlorophenyl)-5-methyl-1,3-thiazol-2(3H)-ylidene]pyrrolidine-1-carboxamide;
N-[(2Z)-3-(3,5-dichlorophenyl)-5-methyl-1,3-thiazol-2(3H)-ylidene]pyrrolidine-1-carboxamide;
N-[(2Z)-5-methyl-3-[4-(methylthio)phenyl]-1,3-thiazol-2(3H)-ylidene]pyrrolidine-1-carboxamide;
N-[(2Z)-3-(3-methoxyphenyl)-5-methyl-1,3-thiazol-2(3H)-ylidene]pyrrolidine-1-carboxamide;
N-[(2Z)-3-(4-chloro-3-methylphenyl)-5-methyl-1,3-thiazol-2(3H)-ylidene]pyrrolidine-1-carboxamide;
N-[(2Z)-3-(4-benzylphenyl)-5-methyl-1,3-thiazol-2(3H)-ylidene]pyrrolidine-1-carboxamide;
N-[(2Z)-3-[4-(methylthio)phenyl]-1,3-thiazol-2(3H)-ylidene]pyrrolidine-1-carboxamide;
N-[(2Z)-3-phenyl-1,3-thiazol-2(3H)-ylidene]pyrrolidine-1-carboxamide;
N-[(2Z)-3-(3-chlorophenyl)-1,3-thiazol-2(3H)-ylidene]pyrrolidine-1-carboxamide;
N-[(2Z)-3-[3-(trifluoromethyl)phenyl]-1,3-thiazol-2(3H)-ylidene]pyrrolidine-1-carboxamide;
N-[(2Z)-3-(4-chlorophenyl)-1,3-thiazol-2(3H)-ylidene]pyrrolidine-1-carboxamide;
N-[(2Z)-3-(4-methylphenyl)-1,3-thiazol-2(3H)-ylidene]pyrrolidine-1-carboxamide;
N-[(2Z)-3-(4-chloro-3-methylphenyl)-1,3-thiazol-2(3H)-ylidene]pyrrolidine-1-carboxamide;
N-[(2Z)-3-(3,4-dichlorophenyl)-1,3-thiazol-2(3H)-ylidene]pyrrolidine-1-carboxamide;

N-[(2Z)-3-(3,4-dimethylphenyl)-1,3-thiazol-2(3H)-ylidene]pyrrolidine-1-carboxamide;
N-[(2Z)-3-(4-cyanophenyl)-1,3-thiazol-2(3H)-ylidene]pyrrolidine-1-carboxamide;
N-[(2Z)-3-(3-chloro-4-methylphenyl)-1,3-thiazol-2(3H)-ylidene]pyrrolidine-1-carboxamide;
N-[(2Z)-3-[4-(difluoromethoxy)phenyl]-1,3-thiazol-2(3H)-ylidene]pyrrolidine-1-carboxamide;
N-[(2Z)-3-[3-fluoro-4-(trifluoromethyl)phenyl]-1,3-thiazol-2(3H)-ylidene]pyrrolidine-1-carboxamide;
(3R)-N-[(2Z)-3-(3-bromophenyl)-5-methyl-1,3-thiazol-2(3H)-ylidene]-3-fluoropyrrolidine-1-carboxamide;
(3R)-N-[(2Z)-3-(4-cyano-3-methylphenyl)-5-methyl-1,3-thiazol-2(3H)-ylidene]-3-fluoropyrrolidine-1-carboxamide;
(3R)-3-fluoro-N-[(2Z)-5-methyl-3-(3-methylphenyl)-1,3-thiazol-2(3H)-ylidene]pyrrolidine-1-carboxamide;
(3R)-N-[(2Z)-3-(4-bromophenyl)-5-methyl-1,3-thiazol-2(3H)-ylidene]-3-fluoropyrrolidine-1-carboxamide;
(3R)-3-fluoro-N-[(2Z)-5-methyl-3-(4-phenoxyphenyl)-1,3-thiazol-2(3H)-ylidene]pyrrolidine-1-carboxamide;
(3R)-3-fluoro-N-[(2Z)-5-methyl-3-(4-methylphenyl)-1,3-thiazol-2(3H)-ylidene]pyrrolidine-1-carboxamide;
(3R)-N-[(2Z)-3-(4-ethylphenyl)-5-methyl-1,3-thiazol-2(3H)-ylidene]-3-fluoropyrrolidine-1-carboxamide;
(3R)-3-fluoro-N-[(2Z)-3-(3-fluorophenyl)-5-methyl-1,3-thiazol-2(3H)-ylidene]pyrrolidine-1-carboxamide;
(3R)-3-fluoro-N-[(2Z)-3-(4-fluorophenyl)-5-methyl-1,3-thiazol-2(3H)-ylidene]pyrrolidine-1-carboxamide;
(3R)-3-fluoro-N-[(2Z)-5-methyl-3-[4-(trifluoromethyl)phenyl]-1,3-thiazol-2(3H)-ylidene]pyrrolidine-1-carboxamide;
(3R)-N-[(2Z)-3-(4-chlorophenyl)-5-methyl-1,3-thiazol-2(3H)-ylidene]-3-fluoropyrrolidine-1-carboxamide;
(3R)-3-fluoro-N-[(2Z)-3-(4-iodophenyl)-5-methyl-1,3-thiazol-2(3H)-ylidene]pyrrolidine-1-carboxamide;
(3R)-N-[(2Z)-3-(3-cyanophenyl)-5-methyl-1,3-thiazol-2(3H)-ylidene]-3-fluoropyrrolidine-1-carboxamide;
(3R)-3-fluoro-N-[(2Z)-5-methyl-3-(2-naphthyl)-1,3-thiazol-2(3H)-ylidene]pyrrolidine-1-carboxamide;
(3R)-N-[(2Z)-3-(3,4-dichlorophenyl)-5-methyl-1,3-thiazol-2(3H)-ylidene]-3-fluoropyrrolidine-1-carboxamide;
(3R)-3-fluoro-N-[(2Z)-3-(3-iodophenyl)-5-methyl-1,3-thiazol-2(3H)-ylidene]pyrrolidine-1-carboxamide;
(3R)-N-[(2Z)-3-(3-chloro-4-methylphenyl)-5-methyl-1,3-thiazol-2(3H)-ylidene]-3-fluoropyrrolidine-1-carboxamide;
N-[(2Z)-3-(2-naphthyl)-1,3-thiazol-2(3H)-ylidene]pyrrolidine-1-carboxamide;
N-[(2Z)-5-methyl-3-[4-(trifluoromethyl)phenyl]-1,3-thiazol-2(3H)-ylidene]indoline-1-carboxamide;
2,5-dimethyl-N-[(2Z)-5-methyl-3-[4-(trifluoromethyl)phenyl]-1,3-thiazol-2(3H)-ylidene]pyrrolidine-1-carboxamide;
2-methyl-N-[(2Z)-5-methyl-3-[4-(trifluoromethyl)phenyl]-1,3-thiazol-2(3H)-ylidene]piperidine-1-carboxamide;
4-benzyl-N-[(2Z)-5-methyl-3-[4-(trifluoromethyl)phenyl]-1,3-thiazol-2(3H)-ylidene]piperidine-1-carboxamide;
N-[(2Z)-3-(4-chlorophenyl)-4,5-dimethyl-1,3-thiazol-2(3H)-ylidene]pyrrolidine-1-carboxamide;
N-[(2Z)-4,5-dimethyl-3-[4-(trifluoromethyl)phenyl]-1,3-thiazol-2(3H)-ylidene]pyrrolidine-1-carboxamide; and
N-[(2Z)-3-(4-fluorophenyl)-1,3-thiazol-2(3H)-ylidene]pyrrolidine-1-carboxamide;
and a pharmaceutically acceptable salt thereof.

* * * * *